US012017997B2

(12) United States Patent
Lingappa et al.

(10) Patent No.: US 12,017,997 B2
(45) Date of Patent: Jun. 25, 2024

(54) HOST-TARGETED PAN-RESPIRATORY ANTIVIRAL SMALL MOLECULE THERAPEUTICS

(71) Applicant: Prosetta Biosciences, Inc., San Francisco, CA (US)

(72) Inventors: Vishwanath R. Lingappa, San Francisco, CA (US); Kumarapandian Paulvannan, San Jose, CA (US)

(73) Assignee: Prosetta Biosciences, Inc., San Francisco, CA (US)

( * ) Notice: Subject to any disclaimer, the term of this patent is extended or adjusted under 35 U.S.C. 154(b) by 0 days.

(21) Appl. No.: 17/971,804

(22) Filed: Oct. 24, 2022

(65) Prior Publication Data

US 2023/0147603 A1    May 11, 2023

Related U.S. Application Data

(60) Provisional application No. 63/270,918, filed on Oct. 22, 2021.

(51) Int. Cl.
| | | |
|---|---|---|
| C07D 231/14 | (2006.01) |
| A61P 31/00 | (2006.01) |
| C07D 403/12 | (2006.01) |
| C07D 487/04 | (2006.01) |
| C07D 487/08 | (2006.01) |

(52) U.S. Cl.
CPC .......... *C07D 231/14* (2013.01); *A61P 31/00* (2018.01); *C07D 403/12* (2013.01); *C07D 487/04* (2013.01); *C07D 487/08* (2013.01)

(58) Field of Classification Search
CPC .................................................. C07D 231/14
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,710,795 A | 1/1973 | Higuchi et al. |
| 3,845,770 A | 11/1974 | Theeuwes et al. |
| 3,916,899 A | 11/1975 | Theeuwes et al. |
| RE28,819 E | 5/1976 | Thompson |
| 4,008,719 A | 2/1977 | Theeuwes et al. |
| 4,044,126 A | 8/1977 | Cook et al. |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,522,811 A | 6/1985 | Eppstein et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,323,907 A | 6/1994 | Kalvelage |
| 5,354,556 A | 10/1994 | Sparks et al. |
| 5,591,767 A | 1/1997 | Mohr et al. |
| 5,639,476 A | 6/1997 | Oshlack et al. |
| 5,639,480 A | 6/1997 | Bodmer et al. |
| 5,674,533 A | 10/1997 | Santus et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,840,674 A | 11/1998 | Yatvin et al. |
| 5,860,957 A | 1/1999 | Jacobsen et al. |
| 5,891,474 A | 4/1999 | Busetti et al. |
| 5,900,252 A | 5/1999 | Calanchi et al. |
| 5,922,356 A | 7/1999 | Koseki et al. |
| 5,948,433 A | 9/1999 | Burton et al. |
| 5,972,366 A | 10/1999 | Haynes et al. |
| 5,972,891 A | 10/1999 | Kamei et al. |
| 5,980,945 A | 11/1999 | Ruiz |
| 5,983,134 A | 11/1999 | Ostrow |
| 5,985,307 A | 11/1999 | Hanson et al. |
| 5,985,317 A | 11/1999 | Venkateshwaran et al. |
| 5,993,855 A | 11/1999 | Yoshimoto et al. |
| 6,004,534 A | 12/1999 | Langer et al. |
| 6,010,715 A | 1/2000 | Wick et al. |
| 6,024,975 A | 2/2000 | D'Angelo et al. |
| 6,039,975 A | 3/2000 | Shah et al. |
| 6,045,830 A | 4/2000 | Igari et al. |
| 6,048,736 A | 4/2000 | Kosak |

(Continued)

FOREIGN PATENT DOCUMENTS

| | | | | |
|---|---|---|---|---|
| WO | 2005/025506 A2 | 3/2005 | | |
| WO | WO-2016161021 A1 * | 10/2016 | ............. | A61P 31/12 |

OTHER PUBLICATIONS

STN Chemical Database Registry entry for RN 1385362-04-8, 1-ethyl-N-[2-(3-methoxy-4-methylphenyl)ethyl]-3-methyl-1H-pyrazole-5-carboxamide, ED Entered STN: Aug. 2, 2012.*
Online "http://web.archive.org/web/20090428093726/http://www.ukrorgsynth.com/bb.php" dated to Apr. 28, 2009 accessed Nov. 22, 2016.*
Online: "http://web.archive.org/web/20090405123528/http://www.ukrorgsynth.com/screening.php" dated to Apr. 5, 2009 accessed Nov. 22, 2016.*
Pubchem, Substance Record for SID 280614968, Avallable Date: Jan. 13, 2016 [retrieved on Dec. 30, 2022J. Retrieved from the Internet: <URL:https://pubchem.ncbl.n!m.nih.gov/substance/280614968>. entire document.

(Continued)

*Primary Examiner* — David K O'Dell
(74) *Attorney, Agent, or Firm* — Young Basile Hanlon & MacFarlane, P.C.

(57) ABSTRACT

Described herein are compounds, pharmaceutical compositions and methods of using these compounds and pharmaceutical compositions for treating and/or preventing conditions such as, for example, those caused by any viral family causing respiratory viral disease, including specifically coronaviruses and influenza viruses.

6 Claims, No Drawings

(56) References Cited

U.S. PATENT DOCUMENTS

| | | | |
|---|---|---|---|
| 6,060,082 | A | 5/2000 | Chen et al. |
| 6,071,495 | A | 6/2000 | Unger et al. |
| 6,087,324 | A | 7/2000 | Igari et al. |
| 6,113,943 | A | 9/2000 | Okada et al. |
| 6,120,751 | A | 9/2000 | Unger |
| 6,131,570 | A | 10/2000 | Schuster et al. |
| 6,139,865 | A | 10/2000 | Friend et al. |
| 6,167,301 | A | 12/2000 | Flower et al. |
| 6,197,350 | B1 | 3/2001 | Yamagata et al. |
| 6,248,363 | B1 | 6/2001 | Patel et al. |
| 6,253,872 | B1 | 7/2001 | Neumann |
| 6,256,533 | B1 | 7/2001 | Yuzhakov et al. |
| 6,261,595 | B1 | 7/2001 | Stanley et al. |
| 6,264,970 | B1 | 7/2001 | Hata et al. |
| 6,267,981 | B1 | 7/2001 | Okamoto et al. |
| 6,267,983 | B1 | 7/2001 | Fujii et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,376,461 | B1 | 4/2002 | Igari et al. |
| 6,419,961 | B1 | 7/2002 | Igari et al. |
| 6,589,548 | B1 | 7/2003 | Oh et al. |
| 6,613,358 | B2 | 9/2003 | Randolph et al. |
| 6,699,500 | B2 | 3/2004 | Okada et al. |
| 6,740,634 | B1 | 5/2004 | Saikawa et al. |
| 10,532,980 | B2 * | 1/2020 | Selvarajah ............... A61P 31/16 |
| 2018/0118679 | A1 | 5/2018 | Selvarajah et al. |

OTHER PUBLICATIONS

Pubchem, Substance Record for SID 67745764, Modify Date: Aug. 25, 2017 [retrieved .on Dec. 27, 2022]. Retrieved from the Internet: <URL:hltps :I/pubchem,nc bL n Im. nih.gov /s ubstance/67 7 4 5 764>, entire document.

Pubchem, Substance Record for SID 290882390, Avallable Date: Jan. 18, 2016 [retrieved~ on Dec. 27, 2022]. Retrieved from the Internet: <URL:hltps://pubchem.ncbi.nlm.nlh,govfsubstance/ 290882390> entire document.

Pubchem, Substance Record for SID 295853831, Available Date: Jan. 27, 2016 {retrieved on Dec. 27, 2022}. Retrieved from the Internet: <URL:https://pubchem.ncbi.nlm.nih.gov/substance/ 295853831>, entire document.

Muller-Schiffmann et al., A Pan-resplratory Antiviral Chemotype Targeting a Transient Host Mult!protein Complex, bloRxiv, Jul. 19, 2022, pp. 1-21, 32-51.

Suganya Selvarajah et al., From COVID-19 to the Common Cold: Novel Host-Targeted, Pan-Respiratory Antiviral Small Molecule Therapeutics; bioRxiv 2021.01.17.426875; doi: https://doi.org/10.1101/2021.01.17.426875.

Brittain, H., Chapter 6, pp. 205-208 in Polymorphism in Pharmaceutical Solids, (Brittain, H. ed.), Marcel Dekker, Inc. New York, 1999.

Buchwald, Henry, et al. "Long-term, continuous intravenous heparin administration by an implantable infusion pump in ambulatory patients with recurrent venous thrombosis." Surgery 88.4 (1980): 507-516.

Goodson, Medical Applications of Controlled Release, vol. 2, pp. 115?138 (1984).

Guillory, K., Chapter 5, pp. 202-205 in Polymorphism in Pharmaceutical Solids, (Brittain, H. ed.), Marcel Dekker, Inc., New York, NY, 1999).

Holodiag, Pharmaparc II, Voie de l'Innovation, 27 100 Val de Reuil, France; accessed Jun. 29, 2023 http://www.holodiag.com.

Jens T. Carstensen, Drug Stability: Principles & Practice, 2d. Ed., Marcel Dekker, NY, NY, 1995, pp. 379-380.

Langer, Robert. "New methods of drug delivery." Science 249.4976 (1990): 1527-1533.

Saudek CD, Selam JL, Pitt HA, Waxman K, Rubio M, Jeandidier N, Turner D, Fischell RE, Charles MA. A preliminary trial of the programmable implantable medication system for insulin delivery. N Engl J Med. Aug. 31, 1989;321(9):574-9.

Sefton, CRC Crit. Ref. Biomed. Eng. 14:201 (1987.

* cited by examiner

HOST-TARGETED PAN-RESPIRATORY ANTIVIRAL SMALL MOLECULE THERAPEUTICS

CROSS REFERENCE TO RELATED APPLICATION

This application claims priority to U.S. Provisional Application Ser. No. 63/270,918 filed Oct. 22, 2021, under 35 U.S.C. § 119 (e) which is incorporated by reference in its entirety.

BACKGROUND

There is a need for compounds useful as host targeted pan respiratory antiviral compounds.

It has now been discovered that certain compounds described herein are effective pan respiratory antiviral small molecule therapeutics. These compounds may be used to inhibit pan-respiratory viral family antiviral activity, including specifically coronaviruses and influenza viruses and diseases caused by these viral families and are described herein.

Earlier compounds of this chemotype have shown a striking barrier to development of viral resistance mutants. Furthermore, a novel molecular basis for targeting the host without host toxicity has been demonstrated (https://www.biorxiv.org/content/10.1101/2021.01.17.426875v1).

SUMMARY

In one aspect, a compound of Formula (I) is provided:

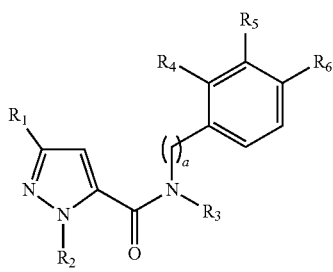

(I)

or pharmaceutically acceptable salts, hydrates or solvates thereof, where: $R_1$ and $R_2$ are independently alkyl, alkenyl, cycloalkyl or cycloalkenyl; $R_3$ is —H or alkyl; a is 1, 2 or 3; $R_4$ is —H, halo, alkyl, or —$OR_7$; $R_5$ is —H, halo, alkyl, substituted alkyl,

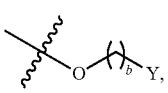

—C(O)$NR_{76}R_{77}$, —$NR_{78}R_{79}$, —NHC(O)$R_{80}$,

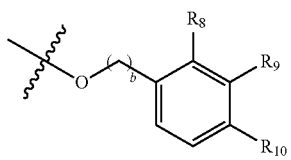

or —$OR_{11}$; b is 0, 1, 2 or 3; $R_6$ is —H, alkyl,

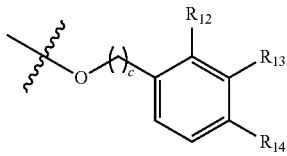

or —$OR_{15}$; c is 1, 2 or 3; Y is

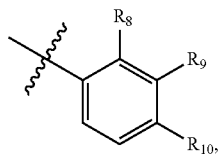

substituted aryl, heteroaryl, substituted heteroaryl;
$R_8$ is —H, —C(O)$NR_{16}R_{17}$, —$CH_2OC(O)NR_{18}R_{19}$, —$NR_{20}R_{21}$, —$CH_2NR_{22}R_{23}$ or —$SO_2R_{24}R_{25}$; $R_9$ is —H, —C(O)$NR_{26}R_{27}$, —$CH_2OC(O)NR_{28}R_{29}$, —$NR_{30}R_{31}$, —$CH_2NR_{32}R_{33}$ or —$SO_2R_{34}R_{35}$; $R_{10}$ is —H, —C(O)$NR_{36}R_{37}$, —$CH_2OC(O)NR_{38}R_{39}$, —$NR_{40}R_{41}$, —$CH_2NR_{42}R_{43}$ or —$SO_2R_{44}R_{45}$; $R_{12}$ is —H, —C(O)$NR_{46}R_{47}$, —$CH_2OC(O)NR_{48}R_{49}$, —$NR_{50}R_{51}$, —$CH_2NR_{52}R_{53}$ or —$SO_2R_{54}R_{55}$; $R_{13}$ is —H, substituted alkyl, —C(O)$NR_{56}R_{57}$, —$CH_2OC(O)NR_{58}R_{59}$, —$NR_{60}R_{61}$ or —$CH_2NR_{62}R_{63}$ or —$SO_2R_{64}R_{65}$; $R_{14}$ is —H, —C(O)$N_{66}R_{67}$, —$CH_2OC(O)NR_{68}R_{69}$, —$NR_{70}R_{71}$ or —$CH_2NR_{72}R_{73}$ or —$SO_2R_{74}R_{75}$; $R_7$, $R_{11}$ and $R_{15}$ are independently alkyl, substituted alkyl, alkenyl, substituted alkenyl, heteroalkyl, substituted heteroalkyl, heteroalkenyl or substituted heteroalkenyl; $R_{16}$ and $R_{17}$ together with the atoms to which they are attached form a heterocyclic or substituted heterocyclic ring; $R_{18}$ and $R_{19}$ together with the atoms to which they are attached form a heterocyclic or substituted heterocyclic ring; $R_{20}$ and $R_{21}$ together with the atoms to which they are attached form a heterocyclic or substituted heterocyclic ring; $R_{22}$ and $R_{23}$ together with the atoms to which they are attached form a heterocyclic or substituted heterocyclic ring; $R_{24}$ and $R_{25}$ together with the atoms to which they are attached form a heterocyclic or substituted heterocyclic ring; $R_{26}$ and $R_{27}$ together with the atoms to which they are attached form a heterocyclic or substituted heterocyclic ring; $R_{28}$ and $R_{29}$ together with the atoms to which they are attached form a heterocyclic or substituted heterocyclic ring; $R_{30}$ and $R_{31}$ together with the atoms to which they are attached form a heterocyclic or substituted heterocyclic ring; $R_{32}$ and $R_{33}$ together with the atoms to which they are attached form a heterocyclic or substituted heterocyclic ring; $R_{34}$ and $R_{35}$ together with the atoms to which they are attached form a heterocyclic or substituted heterocyclic ring; $R_{36}$ and $R_{37}$ together with the atoms to which they are attached form a heterocyclic or substituted heterocyclic ring; $R_{38}$ and $R_{39}$ together with the atoms to which they are attached form a heterocyclic or substituted heterocyclic ring; $R_{40}$ and $R_{41}$ together with the atoms to which they are attached form a heterocyclic or substituted heterocyclic ring; $R_{42}$ and $R_{43}$ together with the atoms to which they are attached form a heterocyclic or substituted heterocyclic ring; $R_{44}$ and $R_{45}$ together with the atoms to which they are attached form a heterocyclic or substituted heterocyclic ring; $R_{46}$ and $R_{47}$ together with the atoms to which they are attached form a heterocyclic or substituted heterocyclic ring; $R_{48}$ and $R_{49}$ together with the atoms to which they are attached form a heterocyclic or substituted heterocyclic ring; $R_{50}$ and $R_{51}$ together with the atoms to which they are attached form a heterocyclic or substituted heterocyclic ring; $R_{52}$ and $R_{53}$ together with the atoms to which they are attached form a heterocyclic or substituted heterocyclic ring; $R_{54}$ and $R_{15}$ together with the atoms to which they are attached form a heterocyclic or substituted heterocyclic ring; $R_{56}$ and $R_{57}$ together with the atoms to which they are attached form a heterocyclic or substituted heterocyclic ring; $R_{58}$ and $R_{59}$ together with the atoms to which they are attached form a heterocyclic or substituted heterocyclic ring; $R_{60}$ and $R_{61}$ together with the atoms to which they are attached form a heterocyclic or substituted heterocyclic ring; $R_{62}$ and $R_{63}$ together with the atoms to which they are attached form a heterocyclic or substituted heterocyclic ring; $R_{64}$ and $R_{65}$ together with the atoms to which they are attached form a heterocyclic or substituted heterocyclic ring; $R_{66}$ and $R_{67}$ together with the atoms to which they are attached form a heterocyclic or substituted heterocyclic ring; $R_{68}$ and $R_{69}$ together with the atoms to which they are attached form a heterocyclic or substituted heterocyclic ring; $R_{70}$ and $R_{71}$ together with the atoms to which they are attached form a heterocyclic or substituted heterocyclic ring; $R_{72}$ and $R_{73}$ together with the atoms to which they are attached form a heterocyclic or substituted heterocyclic ring; $R_{74}$ and $R_{75}$ together with the atoms to which they are attached form a heterocyclic or substituted heterocyclic ring; $R_{76}$, $R_{77}$, $R_{78}$, or $R_{79}$ are independently alkyl, substituted alkyl alkenyl, substituted alkenyl, heteroalkyl, substituted heteroalkyl, heteroalkenyl or substituted heteroalkenyl or alternatively, $R_{76}$ and $R_{77}$ together with the atoms to which they are attached form a heterocyclic or substituted heterocyclic ring and/or $R_{78}$, or $R_{79}$ together with the atoms to which they are attached form a heterocyclic or substituted heterocyclic ring; and $R_{80}$ is alkyl, substituted alkyl, alkenyl, substituted alkenyl, aryl, substituted aryl, heteroalkyl, substituted heteroalkyl, heteroalkenyl, substituted heteroalkenyl, aryl or substituted aryl; provided that at least one of $R_5$ or $R_6$ is not —H; provided that at least one of $R_8$-$R_{10}$ is not —H; and provided that at least one of $R_{12}$-$R_{14}$ is not —H.

Also provided are derivatives, including salts, esters, enol ethers, enol esters, solvates, hydrates, metabolites and prodrugs of the compounds described herein. Further provided are pharmaceutical compositions which include the compounds provided herein and a pharmaceutically acceptable vehicle. Methods of treating, preventing, or ameliorating symptoms of medical disorders such as, for example, a variety of pan respiratory antiviral infections and diseases are also provided herein.

DETAILED DESCRIPTION

Definitions

Unless defined otherwise, all technical and scientific terms used herein have the same meaning as is commonly understood by one of ordinary skill in the art to which this invention belongs. If a plurality of definitions for a term exist herein, those in this section prevail unless stated otherwise.

As used herein, and unless otherwise specified, the terms "about" and "approximately," when used in connection with a property with a numeric value or range of values indicate that the value or range of values may deviate to an extent deemed reasonable to one of ordinary skill in the art while still describing the particular property. Specifically, the terms "about" and "approximately," when used in this context, indicate that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values. Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

A dash ("—") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u\text{-}v}$," indicates that the following group has from u to v carbon atoms. It should be understood that u to v carbons includes u+1 to v, u+2 to v, u+3+v, etc. carbons, u+1 to u+3 to v, u+1 to u+4 to v, u+2 to u+4 to v, etc. and cover all possible permutation of u and v.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane. Typical alkyl groups include, but are not limited to, methyl; ethyl; propyls such as propan-1-yl, propan-2-yl, etc.; butyls such as butan-1-yl, butan-2-yl, 2-methyl-propan-1-yl, 2-methyl-propan-2-yl, etc.; and the like. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl).

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In some embodiments, an alkenyl group comprises from 1 to 20 carbon atoms ($C_1$-$C_{20}$ alkenyl). Inn other embodiments, an alkenyl group comprises from 1 to 10 carbon atoms ($C_1$-$C_{10}$ alkenyl). In still other embodiments, an alkenyl group comprises from 1 to 6 carbon atoms ($C_1$-$C_6$ alkenyl).

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In some embodiments, an alkynyl group comprises from 1 to 20 carbon atoms ($C_1$-$C_{20}$ alkynyl). In other embodiments, an alkynyl group comprises from 1 to 10 carbon atoms ($C_1$-$C_{10}$ alkynyl). In still other embodiments, an alkynyl group comprises from 1 to 6 carbon atoms ($C_1$-$C_6$ alkynyl).

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 10 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. In some embodiments, an arylalkyl group is ($C_6$-$C_{30}$) arylalkyl, e.g., the alkyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkyl moiety of the arylalkyl group is ($C_1$-$C_5$) alkyl and the aryl moiety is ($C_6$-$C_{10}$) aryl.

"Arylalkenyl," by itself or as part of another substituent, refers to an acyclic alkenyl group in which one of the hydrogen atoms bonded to a carbon atom, is replaced with an aryl group as, as defined herein. In some embodiments, an arylalkenyl group is ($C_6$-$C_{30}$) arylalkenyl, e.g., the alkenyl moiety of the arylalkenyl group is ($C_1$-$C_{10}$) alkenyl and the aryl moiety is ($C_6$-$C_{20}$) aryl. In other embodiments, an arylalkenyl group is ($C_6$-$C_{20}$) arylalkenyl, e.g., the alkenyl moiety of the arylalkenyl group is ($C_1$-$C_8$) alkenyl and the aryl moiety is ($C_6$-$C_{12}$) aryl. In still other embodiments, an arylalkenyl group is ($C_6$-$C_{15}$) arylalkenyl, e.g., the alkenyl moiety of the arylalkenyl group is ($C_1$-$C_5$) alkenyl and the aryl moiety is ($C_6$-$C_{10}$) aryl.

"Arylalkynyl," by itself or as part of another substituent, refers to an acyclic alkynyl group in which one of the hydrogen atoms bonded to a carbon atom, is replaced with an aryl group as, as defined herein. In some embodiments, an arylalkynyl group is ($C_6$-$C_{3M}$) arylalkynyl, e.g., the alkynyl moiety of the arylalkynyl group is ($C_1$-$C_{10}$) alkynyl and the aryl moiety is ($C_6$-$C_{20}$) aryl. In other embodiments, an arylalkynyl group is ($C_6$-$C_{20}$) arylalkynyl, e.g., the alkynyl moiety of the arylalkynyl group is ($C_1$-$C_8$) alkynyl and the aryl moiety is ($C_6$-$C_{12}$) aryl. In still other embodiments, an arylalkynyl group is ($C_6$-$C_{15}$) arylalkynyl, e.g., the alkynyl moiety of the arylalkynyl group is ($C_1$-$C_5$) alkynyl and the aryl moiety is ($C_6$-$C_{10}$) aryl.

"Cycloalkyl," by itself or as part of another substituent, refers to a saturated cyclic monovalent hydrocarbon radical derived by the removal of one hydrogen atom from a single carbon atom of a parent cycloalkane. Typical cycloalkyl groups include, but are not limited to, cyclopropyl, cyclobutyl, cyclopentyl cycopentenyl; etc.; and the like. In some embodiments, a cycloalkyl group comprises from 3 to 20 carbon atoms ($C_1$-$C_{15}$ cycloalkyl). In other embodiments, a cycloalkyl group comprises from 3 to 10 carbon atoms ($C_1$-$C_{10}$ cycloalkyl). In still other embodiments, a cycloalkyl group comprises from 3 to 8 carbon atoms ($C_1$-$C_8$ cycloalkyl). The term "cyclic monovalent hydrocarbon radical" also includes multicyclic hydrocarbon ring systems having a single radical and between 3 and 12 carbon atoms. Exemplary multicyclic cycloalkyl rings include, for example, norbornyl, pinyl, and adamantyl.

"Cycloalkenyl," by itself or as part of another substituent, refers to an unsaturated cyclic monovalent hydrocarbon radical derived by the removal of one hydrogen atom from a single carbon atom of a parent cycloalkene. Typical cycloalkenyl groups include, but are not limited to, cyclopropene, cyclobutene cyclopentene; etc.; and the like. In some embodiments, a cycloalkenyl group comprises from 3 to 20 carbon atoms ($C_1$-$C_{20}$ cycloalkenyl). In other embodiments, a cycloalkenyl group comprises from 3 to 10 carbon atoms ($C_1$-$C_{10}$ cycloalkenyl). In still other embodiments, a cycloalkenyl group comprises from 3 to 8 carbon atoms ($C_1$-$C_5$ cycloalkenyl). The term 'cyclic monovalent hydrocarbon radical" also includes multicyclic hydrocarbon ring systems having a single radical and between 3 and 12 carbon atoms.

"Cycloheteroalkyl," by itself or as part of another substituent, refers to a cycloalkyl group as defined herein in which one or more one or more of the carbon atoms (and optionally any associated hydrogen atoms), are each, independently of one another, replaced with the same or different heteroatoms or heteroatomic groups as defined in "heteroalkyl" below. In some embodiments, a cycloheteroalkyl group comprises from 3 to 20 carbon and hetero atoms (1-20 cycloheteroalkyl). In other embodiments, a cycloheteroalkyl group comprises from 3 to 10 carbon and hetero atoms ($_{1-10}$ cycloheteroalkyl). In still other embodiments, a cycloheteroalkyl group comprises from 3 to 8 carbon and hetero atoms (1.8 cycloheteroalkyl). The term "cyclic monovalent heteroalkyl radical" also includes multicyclic heteroalkyl ring systems having a single radical and between 3 and 12 carbon and at least one hetero atom.

"Cycloheteroalkenyl," by itself or as part of another substituent, refers to a cycloalkenyl group as defined herein in which one or more one or more of the carbon atoms (and optionally any associated hydrogen atoms), are each, independently of one another, replaced with the same or different heteroatoms or heteroatomic groups as defined in "heteroalkenyl" below. In some embodiments, a cycloheteroalkenyl group comprises from 3 to 20 carbon and hetero atoms (1-20 cycloheteroalkenyl). In other embodiments, a cycloheteroalkenyl group comprises from 3 to 10 carbon and hetero atoms ($_{1-10}$) cycloheteroalkenyl). In still other embodiments, a cycloheteroalkenyl group comprises from 3 to 8 carbon and heteroatoms ($_1$-8 cycloheteroalkenyl). The term "cyclic monovalent heteroalkenyl radical" also includes multicyclic heteroalkenyl ring systems having a single radical and between 3 and 12 carbon and at least one hetero atoms.

"Compounds," refers to compounds encompassed by structural formulae disclosed herein and includes any specific compounds within these formulae whose structure is disclosed herein. Compounds may be identified either by their chemical structure and/or chemical name. The chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass the stereoisomerically pure form depicted in the structure (e.g., geometrically pure, enantiomerically pure or diastereomerically pure). The chemical structures depicted herein also encompass the enantiomeric and stereoisomeric derivatives of the compound depicted. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds may exist in unsolvated forms as well as solvated forms, including hydrated forms. In general, compounds may be hydrated or solvated. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that brackets indicate the point of attachment of the partial structure to the rest of the molecule.

"Halo," by itself or as part of another substituent refers to a radical —F, —Cl, —Br or —I.

"Heteroalkyl," refer to an alkyl, group, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{501}$R$^{502}$, =N—N=, —N=N—, —N=N—NR$^{503}$R$^{404}$, —PR$^{505}$-, —P(O)$_2$—, —POR$^{506}$-, —O—P(O)$_2$—, —SO—, —SO$_2$—, —SnR$^{507}$R$^{508}$ and the like, where R$^{501}$, R$^{502}$, R$^{503}$, R$^{504}$, R$^{505}$, R$^{506}$, R$^{507}$ and R$^{508}$ are independently hydrogen, alkyl, aryl, substituted aryl, heteroalkyl, heteroaryl or substituted heteroaryl. In some embodiments, an heteroalkyl group comprises from 1 to 20 carbon and hetero atoms (1-20 heteroalkyl). In other embodiments, an heteroalkyl group comprises from 1 to 10 carbon and hetero atoms ($_{1-10}$ heteroalkyl). In still other embodiments, an heteroalkyl group comprises from 1 to 6 carbon and hetero atoms ($_{1-6}$ heteroalkyl).

"Heteroalkenyl," refers to an alkenyl group in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{501}$R$^{502}$, =N—N=, —N=N—, —N=N—NR$^{503}$R$^{404}$, —PR$^{505}$-, —P(O)$_2$—, —POR$^{506}$-, —O—P(O)$_2$—, —SO—, —SO$_2$—, —SnR$^{507}$R$^{508}$ and the like, where R$^{501}$, R$^{502}$, R$^{503}$, R$^{504}$, R$^{505}$, R$^{506}$, R$^{507}$ and R$^{508}$ are independently hydrogen, alkyl, aryl, substituted aryl, heteroalkyl, heteroaryl or substituted heteroaryl. In some embodiments, an heteroalkenyl group comprises from 1 to 20 carbon and hetero atoms ($_{1-20}$ heteroalkenyl). In other embodiments, an heteroalkenyl group comprises from 1 to 10 carbon and hetero atoms ($_{1-10}$ heteroalkenyl). In still other embodiments, an heteroalkenyl group comprises from 1 to 6 carbon and hetero atoms ($_{1-6}$ heteroalkenyl).

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl," by itself or as part of another substituent refers to an acyclic alkyl group in which one of the hydrogen atoms bonded to a carbon atom, typically a terminal or sp$^3$ carbon atom, is replaced with a heteroaryl group. In some embodiments, the heteroarylalkyl group is a 6-21 membered heteroarylalkyl, e.g., the alkyl moiety of the heteroarylalkyl is (C$_1$-C$_6$) alkyl and the heteroaryl moiety is a 5-15-membered heteroaryl. In other embodiments, the heteroarylalkyl is a 6-13 membered heteroarylalkyl, e.g., the alkyl moiety is (C$_1$-C$_3$) alkyl and the heteroaryl moiety is a 5-10 membered heteroaryl.

"Heteroarylalkenyl," by itself or as part of another substituent refers to an acyclic alkenyl group in which one of the hydrogen atoms bonded to a carbon atom, is replaced with a heteroaryl group. In some embodiments, the heteroarylalkenyl group is a 6-21 membered heteroarylalkenyl, e.g., the alkenyl moiety of the heteroarylalkenyl is (C$_1$-C$_6$) alkenyl and the heteroaryl moiety is a 5-15-membered heteroaryl. In other embodiments, the heteroarylalkenyl is a 6-13 membered heteroarylalkenyl, e.g., the alkenyl moiety is (C$_1$-C$_3$) alkyl and the heteroaryl moiety is a 5-10 membered heteroaryl.

"Heteroarylalkynyl," by itself or as part of another substituent refers to an acyclic alkenyl group in which one of the hydrogen atoms bonded to a carbon atom, is replaced with a heteroaryl group. In some embodiments, the heteroarylalkynyl group is a 6-21 membered heteroarylalkyl, e.g., the alkynyl moiety of the heteroarylalkynyl is (C$_1$-C$_6$) alkynyl and the heteroaryl moiety is a 5-15-membered heteroaryl. In other embodiments, the heteroarylalkynyl is a 6-13 membered heteroarylalkynyl, e.g., the alkynyl moiety is (C$_1$-C$_3$) alkyl and the heteroaryl moiety is a 5-10 membered heteroaryl.

"Hydrates," refers to incorporation of water into to the crystal lattice of a compound described herein, in stoichiometric proportions, resulting in the formation of an addict. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism. See e.g., (Guillory, K., Chapter 5, pp. 202205 in *Polymorphism in Pharmaceutical Solids*, (Brittain, H. ed.), Marcel Dekker, Inc., New York, NY, 1999). The above methods for preparing hydrates are well within the ambit of those of skill in the art, are completely conventional and do not require any experimentation beyond what is typical in the art. Hydrates may be characterized and/or analyzed by methods well known to those of skill in the art such as, for example, single crystal X-ray diffraction, X-ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205208 in *Polymorphism in Pharmaceutical Solids*, (Brittain, H. ed.), Marcel Dekker, Inc. New York, 1999). In addition, many commercial companies routine offer services that include preparation and/or characterization of hydrates such as, for example, HOLODIAG, Pharmaparc II, Voie de l'Innovation, 27 100 Val de Reuil, France (www.holodiag.com).

"Parent Aromatic Ring System," refers to an unsaturated cyclic or polycyclic ring system having a conjugated p electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System," refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, b-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Pharmaceutically acceptable salt," refers to a salt of a compound which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Preventing," or "prevention," refers to a reduction in risk of acquiring a disease or disorder (i.e., causing at least one of the clinical symptoms of the disease not to develop in a patient that may be exposed to or predisposed to the disease but does not yet experience or display symptoms of the disease). The application of a therapeutic for preventing or prevention of a disease or disorder is known as 'prophylaxis.' In some embodiments, the compounds provided herein provide superior prophylaxis because of lower long term side effects over long time periods.

"Prodrug" as used herein, refers to a derivative of a drug molecule that requires a transformation within the body to release the active drug. Prodrugs are frequently, although not necessarily, pharmacologically inactive until converted to the parent drug.

"Promoiety" as used herein, refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group," refers to a grouping of atoms that when attached to a reactive functional group in a molecule masks, reduces or prevents reactivity of the functional group during chemical synthesis. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Solvates," refers to incorporation of solvents into to the crystal lattice of a compound described herein, in stoichiometric proportions, resulting in the formation of an adduct. Methods of making solvates include, but are not limited to, storage in an atmosphere containing a solvent, dosage forms that include the solvent, or routine pharmaceutical processing steps such as, for example, crystallization (i.e., from solvent or mixed solvents) vapor diffusion, etc. Solvates may also be formed, under certain circumstances, from other crystalline solvates or hydrates upon exposure to the solvent or upon suspension material in solvent. Solvates may crystallize in more than one form resulting in solvate polymorphism. See e.g., (Guillory, K., Chapter 5, pp. 205208 in *Polymorphism in Pharmaceutical Solids*, (Brittain, H. ed.), Marcel Dekker, Inc., New York, NY, 1999)). The above methods for preparing solvates are well within the ambit of those of skill in the art, are completely conventional do not require any experimentation beyond what is typical in the art. Solvates may be characterized and/or analyzed by methods well known to those of skill in the art such as, for example, single crystal X-ray diffraction, X-ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205208 in *Polymorphism in Pharmaceutical Solids*, (Brittain, H. ed.), Marcel Dekker, Inc. New York, 1999). In addition, many commercial companies routine offer services that include preparation and/or characterization of solvates such as, for example, HOLODIAG, Pharmaparc II, Voie de l'Innovation, 27 100 Val de Reuil, France (www.holodiag.com).

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include $R^a$, halo, —O—, =O, —$OR^b$, —$SR^b$, —S—, =S, —$NR^cR^c$, =$NR^b$, =N—$OR^b$, trihalomethyl, —$CF_3$, —CN, —OCN, —SCN, —NO, —$NO_2$, —N—$OR^b$, —N—$NR^cR^c$, —$NR^bS(O)_2R^b$, =$N_2$, —$N_3$, —$S(O)_2R^b$, —$S(O)_2NR^bR^b$, —$S(O)_2O$—, —$S(O)_2OR^b$, —$OS(O)_2R^b$, —$OS(O)_2O$, —$OS(O)_2OR^b$, —$OS(O)_2NR^cNR^c$, —$P(O)(O^-)_2$, —$P(O)(OR^b)(O^-)$, —$P(O)(OR^b)(OR^b)$, —$C(O)R^b$, —$C(O)NR^b$—$OR^b$—C(S) $R^b$, —$C(NR^b)R^b$, —C(O)O—, —$C(O)OR^b$, —$C(S)OR^b$, —$C(O)NR^cR^c$, —$C(NR^b)NR^cR^c$, —$OC(O)R^b$, —OC(S) $R^b$, —OC(O) O—, —$OC(O)OR^b$, —$OC(O)NR^cR^c$, —OC(NCN) $NR^cR^c$—$OC(S)OR^b$, —$NR^bC(O)R^b$, —$NR^bC(S)R^b$, —$NR^bC(O)O^-$, —$NR^bC(O)OR^b$, —$NR^bC(NCN)OR^b$, —$NR^bS(O)_2NR^cR^c$, —$NR^bC(S)NR^cR^c$, —$NR^bC(S)$ $NR^cR^c$, —$NR^bC(S)NR^cR^c$, —$NR^bC(S)NR^bC(O)R^a$, —$NR^bS(O)_2OR^b$, —$NR^bS(O)_2R^b$, —$NR^bC(NCN)$ $NR^cR^c$, —$NR^bC(NR^b)R^b$ and —$NR^bC(NR^b)NR^cR^c$, where each $R^a$ is independently, aryl, substituted aryl, heteroalkyl, substituted heteroalkyl, heteroaryl or substituted heteroaryl; each $R^b$ is independently hydrogen, alkyl, heteroalkyl, substituted heteroalkyl, arylalkyl, substituted arylalkyl, heteroarylalkyl or substituted heteroarylalkyl; and each $R^c$ is independently $R^b$ or alternatively, the two $R^c$s taken together with the nitrogen atom to which they are bonded form a 4-, 5-, 6- or 7 membered-cycloheteroalkyl, substituted cycloheteroalkyl or a cycloheteroalkyl fused with an aryl group which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl. In other embodiments, substituent groups useful for substituting saturated carbon atoms in the specified group or radical include $R^a$, halo, —$OR^b$, —$NR^cR^c$, trihalomethyl, —CN, —$NR^bS(O)_2R^b$, —$C(O)R^b$, —$C(O)NR^b$—$OR^b$, —$C(O)OR^b$, —$C(O)NR^cR^c$, —$OC(O)R^b$, —OC(O) $OR^b$, —$OS(O)_2NR^cNR^c$, —$OC(O)NR^cR^c$, and —$NR^bC(O)OR^b$, where each $R^a$ is independently alkyl, aryl, heteroaryl, each $R^b$ is independently hydrogen, $R^a$, heteroalkyl, arylalkyl, heteroarylalkyl; and each $R^c$ is independently $R^b$ or alternatively, the two $R^c$s taken together with the nitrogen atom to which they are bonded form a 4-, 5-, 6 or −7 membered-cycloheteroalkyl ring.

Substituent groups useful for substituting unsaturated carbon atoms in the specified group or radical include —$R^a$, halo, —O—, —$OR^b$, —$SR^b$, —S—, —$NR^cR^c$, trihalomethyl, —$CF_3$, —CN, —OCN, —SCN, —NO, —$NO_2$, —$N_3$, —$S(O)_2O$—, —$S(O)_2OR^b$, —$OS(O)_2R^b$, —$OS(O)_2OR^b$, —$OS(O)_2O$—, —$P(O)$ $(O^-)_2$, —$P(O)(OR^b)(O^-)$, —$P(O)(OR^b)(OR^b)$, —C(O) $R^b$, —$C(S)R^b$, —$C(NR^b)$ $R^b$, —C(O)O—, —C(O) $OR^b$, —$C(S)OR^b$, —$C(O)NR^cR^c$, —$C(NR^b)NR^cR^c$, —$OC(O)R^b$, —$OC(S)R^b$, —OC(O) O—, —$OC(O)OR^b$, —$OC(S)OR^b$, —$OC(O)NR^cR^c$, —$OS(O)_2NR^cNR^c$, —$NR^bC(O)R^b$, —$NR^bC(S)R^b$, —$NR^bC(O)O^-$, —$NR^bC(O)OR^b$, —$NR^bS(O)_2OR^a$, —$NR^bS(O)_2R^a$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined. In other embodiments, substituent groups useful for substituting unsaturated carbon atoms in the specified group or radical include —$R^a$, halo, —$OR^b$, —$SR^b$, —$NR^cR^c$, trihalomethyl, —CN, —$S(O)_2OR^b$, —$C(O)R^b$, —C(O) $OR^b$, —$C(O)NR^cR^c$, —$OC(O)R^b$, —$OC(O)OR^b$, —$OS(O)_2NR^cNR^c$, —$NR^bC(O)R^b$ and —$NR^bC(O)$ $OR^b$, where $R^a$, $R^b$ and $R^c$ are as previously defined.

Substituent groups useful for substituting nitrogen atoms in heteroalkyl and cycloheteroalkyl groups include, but are not limited to, —$R^a$, —O—, —$OR^b$, —$SR^b$, —S—, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O$—, —$OS(O)_2OR^b$, —$P(O)(O^-)_2$, —$P(O)$ $(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —OC (S)$R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC$ $(NR^b)NR^cR^c$, where $R^a$, $R^b$ and $R^c$ are as previously defined. In some embodiments, substituent groups useful for substituting nitrogen atoms in heteroalkyl and cycloheteroalkyl groups include, $R^a$, halo, —$OR^b$, —$NR^cR^c$, trihalomethyl, —CN, —$S(O)_2R^b$, —OS $(O)_2R^b$, —$OS(O)_2OR^b$, —$C(O)R^b$, —$C(NR^b)R^b$, —$C(O)OR^b$, —$C(O)NR^cR^c$, —$OC(O)R^b$, —$OC(O)$ $OR^b$, —$OS(O)_2NR^cNR^c$, —$NR^bC(O)R^b$ and —$NR^bC$ $(O)OR^b$, where $R^a$, $R^b$ and $R^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

"Subject," "individual," or "patient," is used interchangeably herein and refers to a vertebrate, preferably a mammal. Mammals include, but are not limited to, murines, rodents, simians, humans, farm animals, sport animals and pets.

"Treating," or "treatment," of any disease or disorder refers, in some embodiments, to ameliorating the disease or disorder (i.e., arresting or reducing the development of the disease or at least one of the clinical symptoms thereof). Treatment may also be considered to include preemptive or prophylactic administration to ameliorate, arrest or prevent the development of the disease or at least one of the clinical symptoms. In a further feature the treatment rendered has lower potential for long-term side effects over multiple years. In other embodiments "treating" or "treatment" refers to ameliorating at least one physical parameter, which may not be discernible by the patient. In yet other embodiments, "treating" or "treatment" refers to inhibiting the disease or disorder, either physically (e.g., stabilization of a discernible symptom), physiologically (e.g., stabilization of a physical parameter) or both. In yet other embodiments, "treating" or "treatment" refers to delaying the onset of the disease or disorder.

"Therapeutically effective amount," means the amount of a compound that, when administered to a patient for treating a disease, is sufficient to treat the disease. The "therapeutically effective amount" will vary depending on the compound, the disease and its severity and the age, weight, adsorption, distribution, metabolism and excretion etc., of the patient to be treated.

"Vehicle," refers to a diluent, excipient or carrier with which a compound is administered to a subject. In some embodiments, the vehicle is pharmaceutically acceptable Provided herein is a compound of Formula (I):

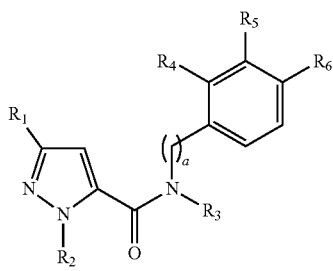

or pharmaceutically acceptable salts, hydrates or solvates thereof, where: $R_1$ and $R_2$ are independently alkyl, alkenyl, cycloalkyl or cycloalkenyl; $R_3$ is —H or alkyl; a is 1, 2 or 3; $R_4$ is —H, halo, alkyl, or —$OR_7$; $R_5$ is —H, halo, alkyl, substituted alkyl,

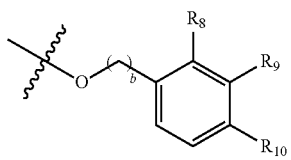

—C(O)$NR_{76}R_{77}$, —$NR_{78}R_{79}$, —NHC(O)$R_{80}$,

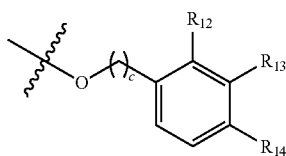

or —$OR_{11}$; b is 0, 1, 2 or 3; $R_6$ is —H, alkyl, or —$OR_{15}$; c is 1, 2 or 3; Y is

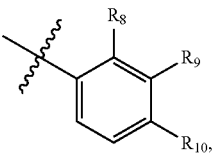

substituted aryl, heteroaryl, substituted heteroaryl;
$R_8$ is —H, —C(O)$NR_{16}R_{17}$, —$CH_2OC(O)NR_{18}R_{19}$, —$NR_{20}R_{21}$, —$CH_2NR_{22}R_{23}$ or —$SO_2R_{24}R_{25}$; $R_9$ is —H, —C(O)$NR_{26}R_{27}$, —$CH_2OC(O)NR_{28}R_{29}$, —$NR_{30}R_{31}$, —$CH_2NR_{32}R_{33}$ or —$SO_2R_{34}R_{35}$; $R_{10}$ is —H, —C(O)$NR_{36}R_{37}$, —$CH_2OC(O)NR_{38}R_{39}$, —$NR_{40}R_{41}$, —$CH_2NR_{42}R_{43}$ or —$SO_2R_{44}R_{45}$; $R_{12}$ is —H, —C(O)$NR_{46}R_{47}$, —$CH_2OC(O)NR_{48}R_{49}$, —$NR_{50}R_{51}$, —$CH_2NR_{52}R_{53}$ or —$SO_2R_{54}R_{55}$; $R_{13}$ is —H, substituted alkyl, —C(O)$NR_{56}R_{57}$, —$CH_2OC(O)NR_{58}R_{59}$, —$NR_{60}R_{61}$ or —$CH_2NR_{62}R_{63}$ or —$SO_2R_{64}R_{65}$; $R_{14}$ is —H, —C(O)$N_{66}R_{67}$, —$CH_2OC(O)NR_{68}R_{69}$, —$NR_{70}R_{71}$ or —$CH_2NR_{72}R_{73}$ or —$SO_2R_{74}R_{75}$; $R_7$, $R_{11}$ and $R_{15}$ are independently alkyl, substituted alkyl, alkenyl, substituted alkenyl, heteroalkyl, substituted heteroalkyl, heteroalkenyl or substituted heteroalkenyl; $R_{16}$ and $R_{17}$ together with the atoms to which they are attached form a heterocyclic or substituted heterocyclic ring; $R_{18}$ and $R_{19}$ together with the atoms to which they are attached form a heterocyclic or substituted heterocyclic ring; $R_{20}$ and $R_{21}$ together with the atoms to which they are attached form a heterocyclic or substituted heterocyclic ring; $R_{22}$ and $R_{23}$ together with the atoms to which they are attached form a heterocyclic or substituted heterocyclic ring; $R_{24}$ and $R_{25}$ together with the atoms to which they are attached form a heterocyclic or substituted heterocyclic ring; $R_{26}$ and $R_{27}$ together with the atoms to which they are attached form a heterocyclic or substituted heterocyclic ring; $R_{28}$ and $R_{29}$ together with the atoms to which they are attached form a heterocyclic or substituted heterocyclic ring; $R_{30}$ and $R_{31}$ together with the atoms to which they are attached form a heterocyclic or substituted heterocyclic ring; $R_{32}$ and $R_{33}$ together with the atoms to which they are attached form a heterocyclic or substituted heterocyclic ring; $R_{34}$ and $R_{35}$ together with the atoms to which they are attached form a heterocyclic or substituted heterocyclic ring; $R_{36}$ and $R_{37}$ together with the atoms to which they are attached form a heterocyclic or substituted heterocyclic ring; $R_{38}$ and $R_{39}$ together with the atoms to which they are attached form a heterocyclic or substituted heterocyclic ring; $R_{40}$ and $R_{41}$ together with the atoms to which they are attached form a heterocyclic or substituted heterocyclic ring; $R_{42}$ and $R_{43}$ together with the atoms to which they are attached form a heterocyclic or substituted heterocyclic ring; $R_{44}$ and $R_{45}$ together with the atoms to which they are attached form a heterocyclic or substituted heterocyclic ring; $R_{46}$ and $R_{47}$ together with the atoms to which they are attached form a heterocyclic or substituted heterocyclic ring; $R_{48}$ and $R_{49}$ together with the atoms to which they are attached form a heterocyclic or substituted heterocyclic ring; $R_{50}$ and $R_{51}$ together with the atoms to which they are attached form a heterocyclic or substituted heterocyclic ring; $R_{52}$ and $R_{53}$ together with the atoms to which they are attached form a heterocyclic or substituted heterocyclic ring; $R_{54}$ and $R_{15}$ together with the atoms to which they are attached form a heterocyclic or substituted heterocyclic ring; $R_{56}$ and $R_{57}$ together with the atoms to which they are attached form a heterocyclic or substituted heterocyclic ring; $R_{58}$ and $R_{59}$ together with the atoms to which they are attached form a heterocyclic or substituted heterocyclic ring; $R_{60}$ and $R_{61}$ together with the atoms to which they are attached form a heterocyclic or substituted heterocyclic ring; $R_{62}$ and $R_{63}$ together with the atoms to which they are attached form a heterocyclic or substituted heterocyclic ring; $R_{64}$ and $R_{65}$ together with the atoms to which they are attached form a heterocyclic or substituted heterocyclic ring; $R_{66}$ and $R_{67}$ together with the atoms to which they are attached form a heterocyclic or substituted heterocyclic ring; $R_{68}$ and $R_{69}$ together with the atoms to which they are attached form a heterocyclic or substituted heterocyclic ring; $R_{70}$ and $R_{71}$ together with the atoms to which they are attached form a heterocyclic or substituted heterocyclic ring; $R_{72}$ and $R_{73}$ together with the atoms to which they are attached form a heterocyclic or substituted heterocyclic ring; $R_{74}$ and $R_{75}$ together with the atoms to which they are attached form a heterocyclic or substituted heterocyclic ring; $R_{76}$, $R_{77}$, $R_{78}$, or $R_{79}$ are independently alkyl, substituted alkyl alkenyl, substituted alkenyl, heteroalkyl, substituted heteroalkyl, heteroalkenyl or substituted heteroalkenyl or alternatively, $R_{76}$ and $R_{77}$ together with the atoms to which they are attached form a heterocyclic or substituted heterocyclic ring and/or $R_{78}$, or $R_{79}$ together with the atoms to which they are attached form a heterocyclic or substituted heterocyclic ring; and $R_{80}$ is alkyl, substituted alkyl, alkenyl, substituted alkenyl, aryl, substituted aryl, heteroalkyl, substituted heteroalkyl, heteroalkenyl, substituted heteroalkenyl, aryl or substituted aryl; provided that at least one of $R_5$ or $R_6$ is not —H; provided that at least one of $R_8$-$R_{10}$ is not —H; and provided that at least one of $R_{12}$-$R_{14}$ is not —H.

In some embodiments, a compound of Formula (II)

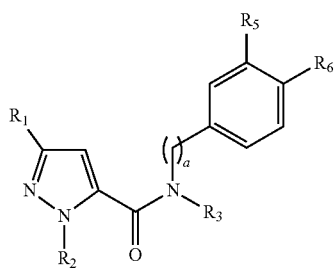

(II)

is provided.

In some embodiments, a compound of Formula (III)

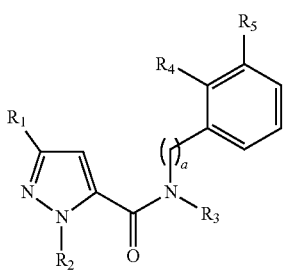

(III)

is provided.

In some embodiments, a compound of Formula (IV)

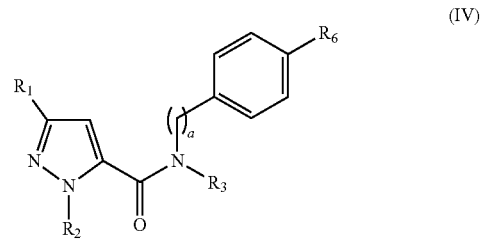

(IV)

is provided.

In some embodiments a compound of Formula (V)

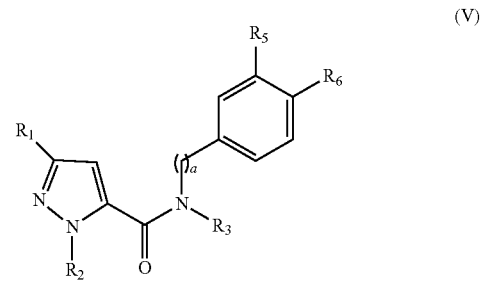

(V)

is provided.

In some embodiments, $R_1$ and $R_2$ are independently alkyl or cycloalkyl.

In some embodiments, a, b and c are 1.

In some embodiments, $R_7$ is alkyl or substituted alkyl.

In some embodiments, $R_9$ is alkyl substituted with a heterocyclic or substituted heterocyclic ring or haloalkyl.

In some embodiments, $R_{11}$ is alkyl substituted with a heterocyclic or substituted heterocyclic ring or haloalkyl.

In some embodiments, $R_1$ and $R_2$ are independently alkyl or cycloalkyl, a, b and c are 1, $R_7$ is alkyl or substituted alkyl, $R_1$ is alkyl substituted with a heterocyclic or substituted heterocyclic ring, or haloalkyl and $R_{15}$ is alkyl substituted with a heterocyclic or substituted heterocyclic ring, or haloalkyl.

In some embodiments of Formula (II), $R_5$ is —H, halo or —$OR_9$. In other embodiments o Formula (II), $R_9$ is alkyl substituted with a heterocyclic or substituted heterocyclic ring or haloalkyl. In still other embodiments of Formula (II), $R_6$ is

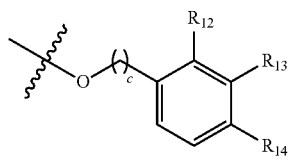

or —$OR_{15}$. In still other embodiments of Formula (II), $R_{11}$ is alkyl substituted with a heterocyclic or substituted heterocyclic ring or haloalkyl.

In some embodiments of Formula (II), $R_5$ is —H or halo. In other embodiments of Formula (II), $R_5$ is

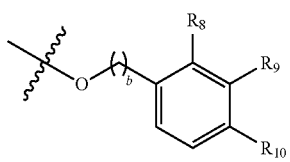

or —OR$_{11}$. In still other embodiments of Formula (II), R$_1$ and R$_2$ are independently alkyl or cycloalkyl and a is 1.

In some embodiments of Formula (III), R$_6$ is

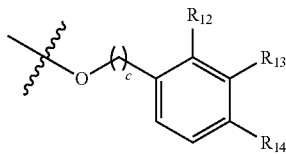

or —OR$_{15}$. R$_9$ is alkyl substituted with a heterocyclic or substituted heterocyclic ring or haloalkyl. In other embodiments of Formula (III), R$_1$ and R$_2$ are independently alkyl or cycloalkyl and a is 1. In still other embodiments of Formula (III), R$_6$ is

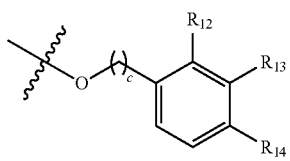

or —OR$_{15}$. In still other embodiments of Formula (III), R$_u$ is alkyl substituted with a heterocyclic or substituted heterocyclic ring or haloalkyl. In still other embodiments of Formula (III), R$_1$ and R$_2$ are independently alkyl or cycloalkyl and a is 1.

In some embodiments of Formula (V), R$_5$ is

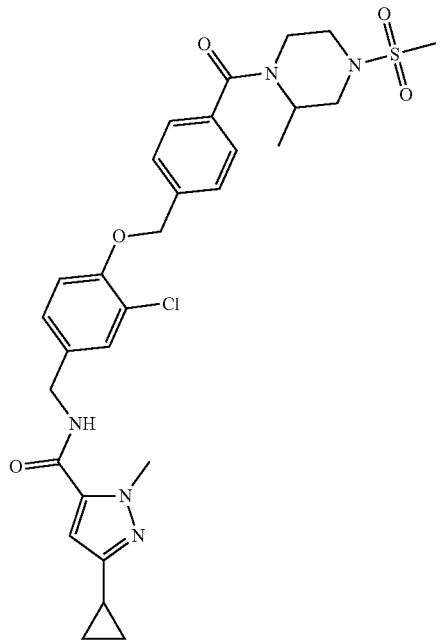 [SMILES: CC1CN(S(C)(=O)=O)CCN1C(=O)c1ccc(COc2ccc(CNC(=O)c3cc(C4CC4)nn3C)cc2Cl)cc1]

or —OR$_{11}$. In other embodiments of Formula (V), R$_9$ is alkyl substituted with a heterocyclic or substituted heterocyclic ring or haloalkyl. In still other embodiments, R$_1$ and R$_2$ are independently alkyl or cycloalkyl and a is 1.

In some of the above embodiments, R$_{12}$ and R$_{13}$ are hydrogen. In some of the above embodiments, R$_8$ and R$_9$ are hydrogen.

Exemplary compounds are illustrated in Table 1 below.

TABLE 1

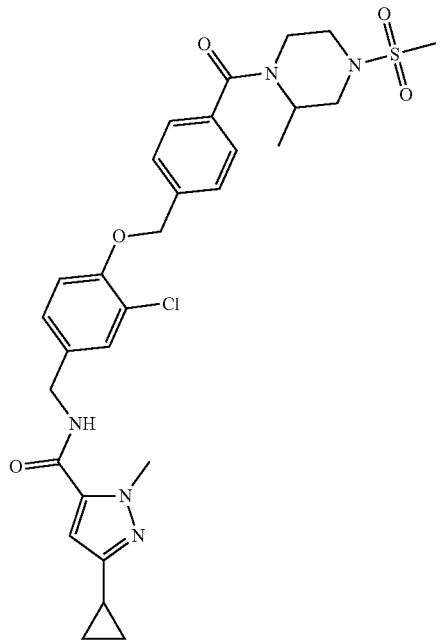 [SMILES: CC1CN(S(C)(=O)=O)CCN1C(=O)c1ccc(COc2ccc(CNC(=O)c3cc(C4CC4)nn3C)cc2Cl)cc1]

TABLE 1-continued
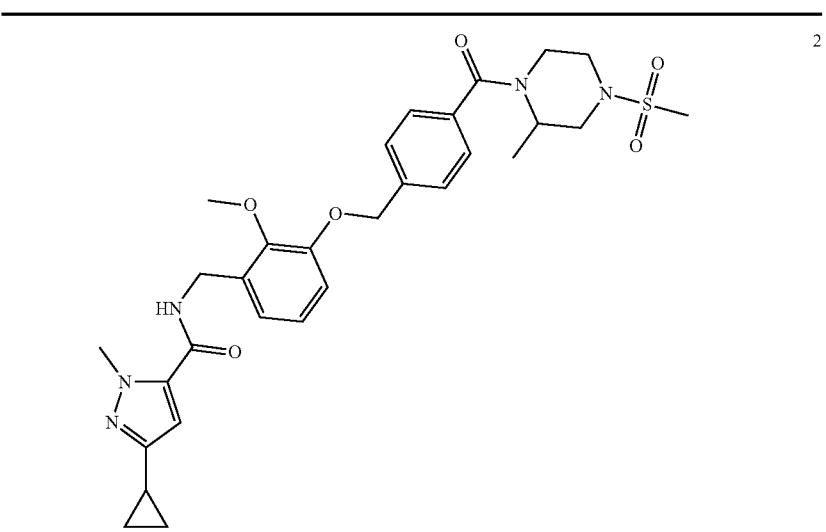
2
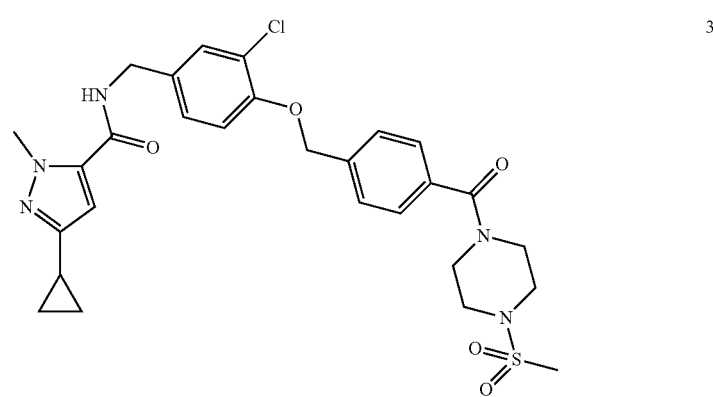
3
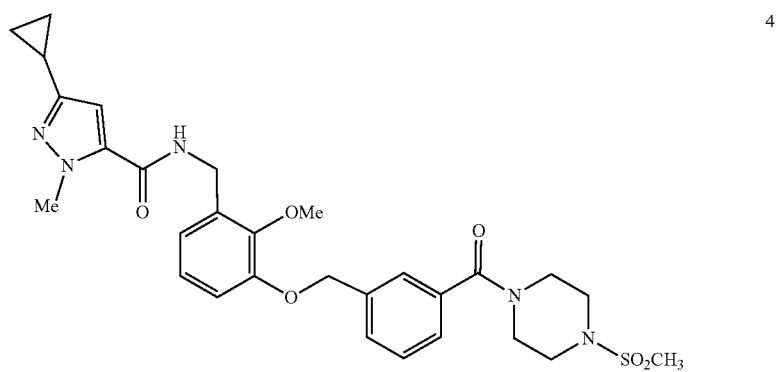
4

TABLE 1-continued
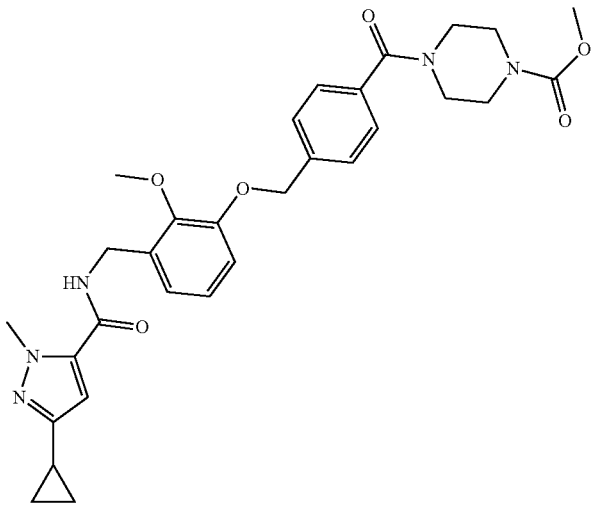 [SMILES: COC(=O)N1CCN(C(=O)c2ccc(COc3cccc(CNC(=O)c4cc(C5CC5)nn4C)c3OC)cc2)CC1]
5
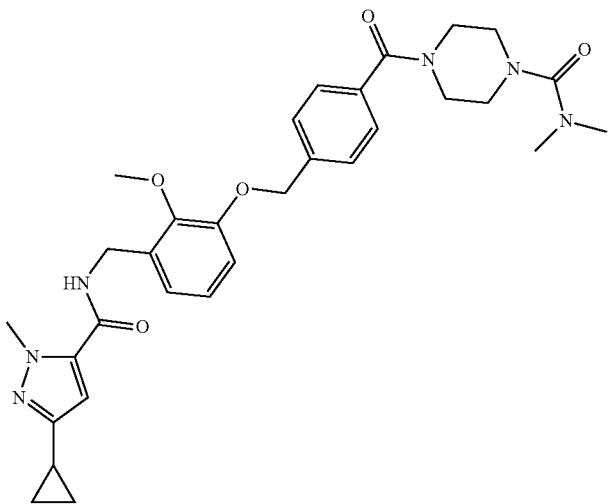
6
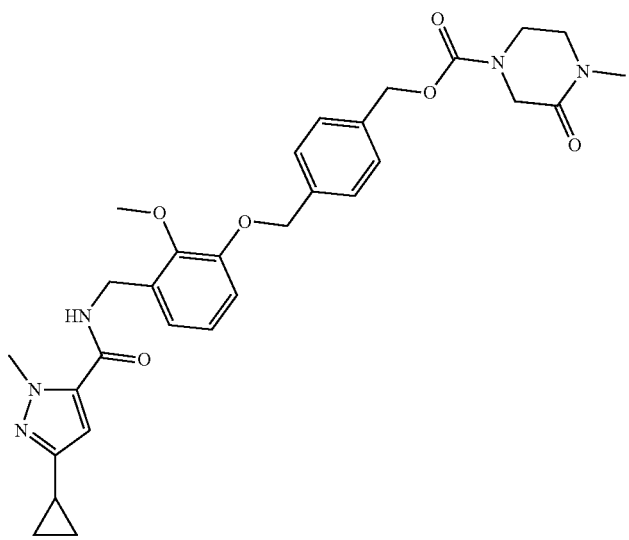
7

TABLE 1-continued
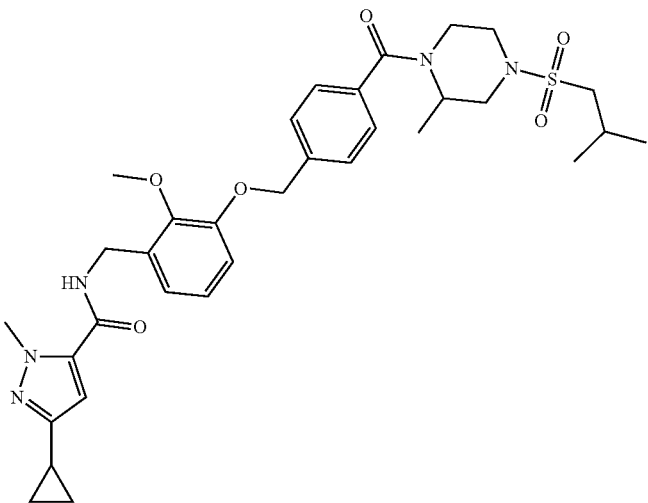 [SMILES: COc1c(CNC(=O)c2cc(C3CC3)nn2C)cccc1OCc1ccc(C(=O)N2CCN(S(=O)(=O)CC(C)C)CC2C)cc1]
8
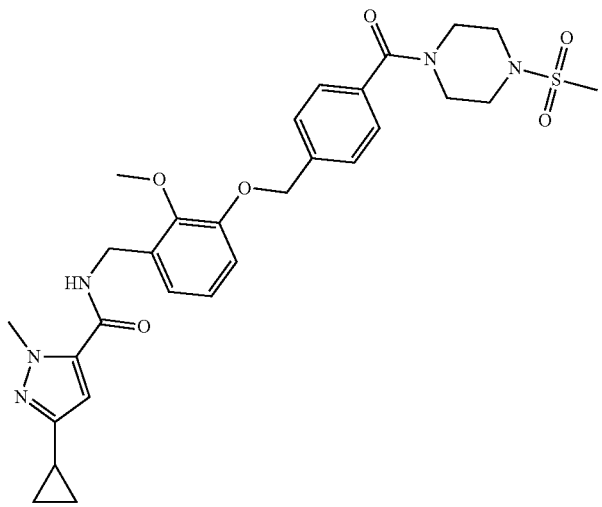
9
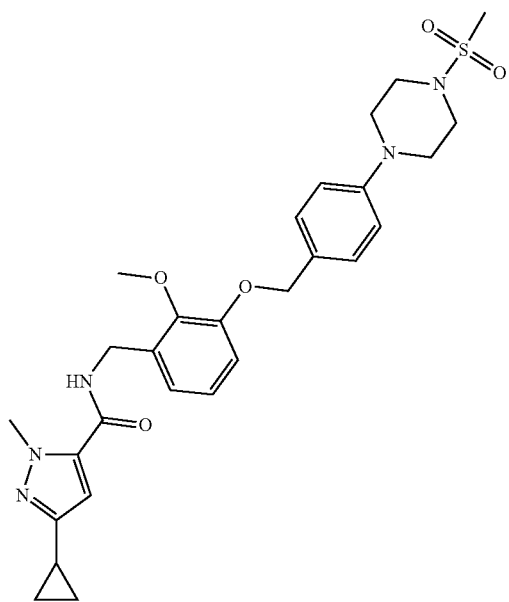 [SMILES: COc1c(CNC(=O)c2cc(C3CC3)nn2C)cccc1OCc1ccc(N2CCN(S(C)(=O)=O)CC2)cc1]
10

TABLE 1-continued
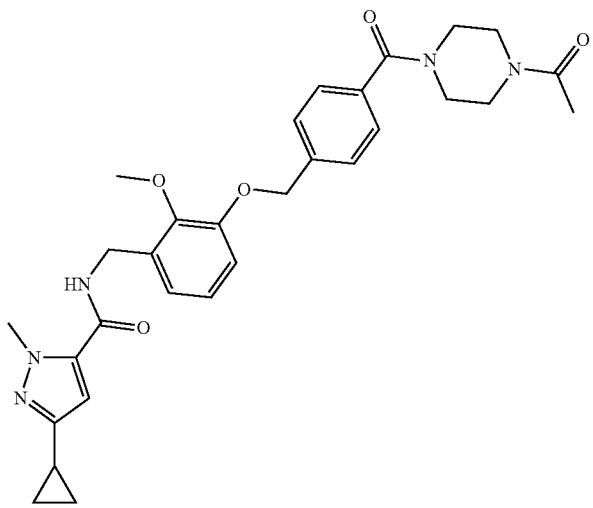 [SMILES: COc1c(CNC(=O)c2cc(C3CC3)nn2C)cccc1OCc1ccc(C(=O)N2CCN(C(C)=O)CC2)cc1]
11
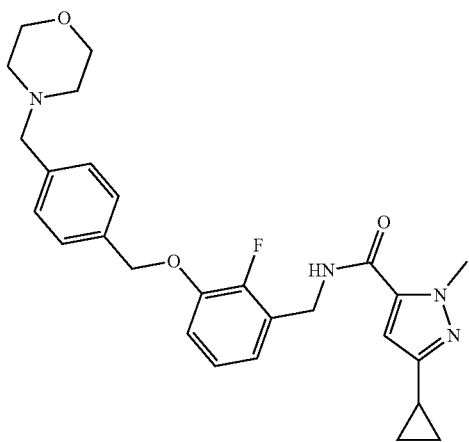 [SMILES: Cn1nc(C2CC2)cc1C(=O)NCc1cccc(OCc2ccc(CN3CCOCC3)cc2)c1F]
12
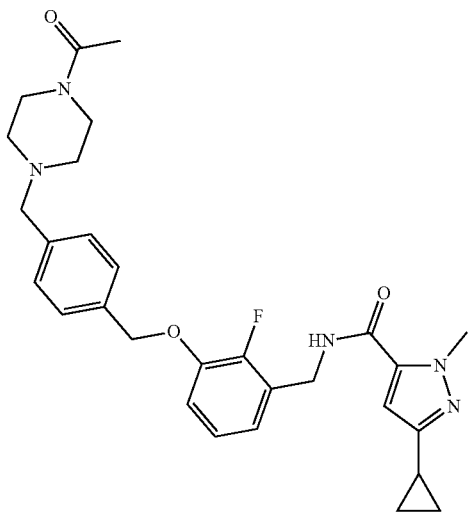 [SMILES: CC(=O)N1CCN(Cc2ccc(COc3cccc(CNC(=O)c4cc(C5CC5)nn4C)c3F)cc2)CC1]
13

TABLE 1-continued
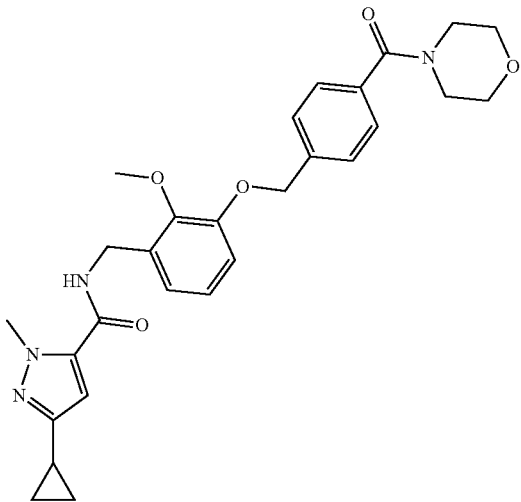 [SMILES: COc1c(CNC(=O)c2cc(C3CC3)nn2C)cccc1OCc1ccc(C(=O)N2CCOCC2)cc1]
14
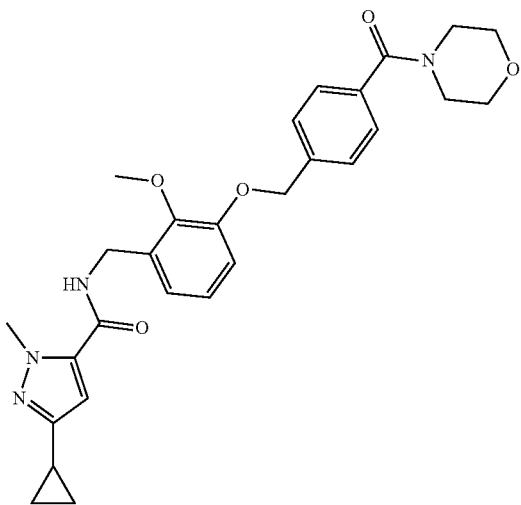 [SMILES: COc1c(CNC(=O)c2cc(C3CC3)nn2C)cccc1OCc1ccc(C(=O)N2CCOCC2)cc1]
15
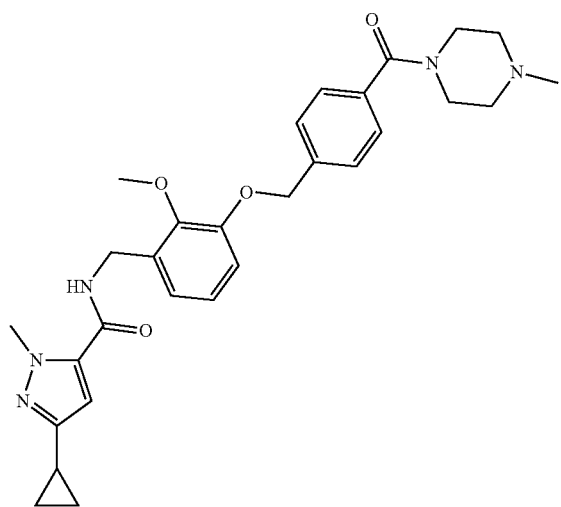
16

TABLE 1-continued
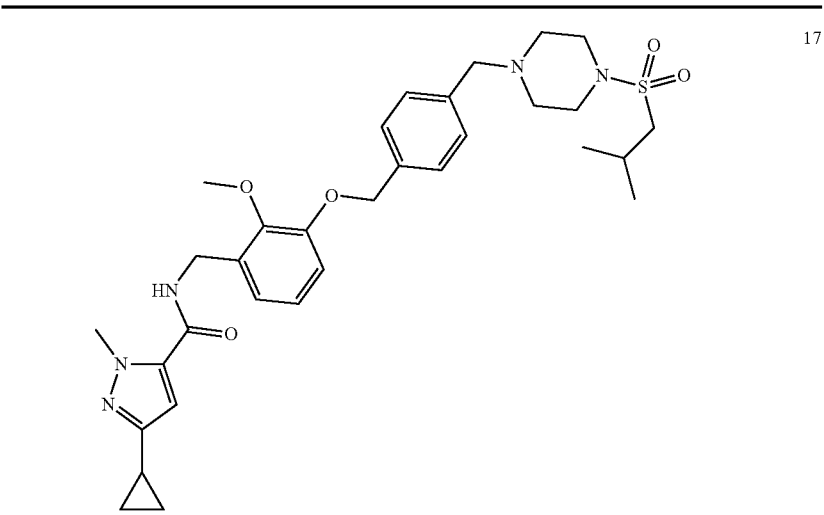
17
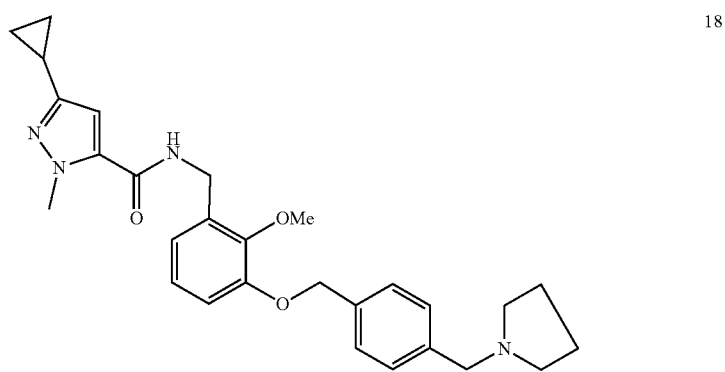
18
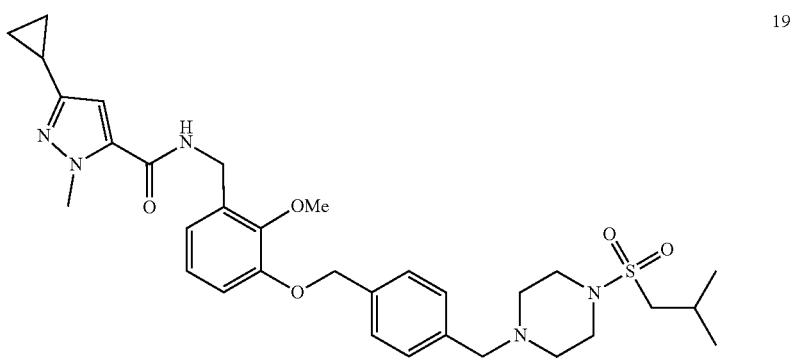
19

TABLE 1-continued
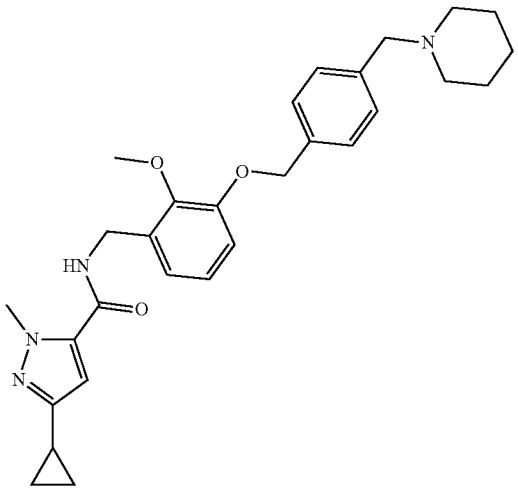 [SMILES: COc1c(CNC(=O)c2cc(C3CC3)nn2C)cccc1OCc1ccc(CN2CCCCC2)cc1]
20
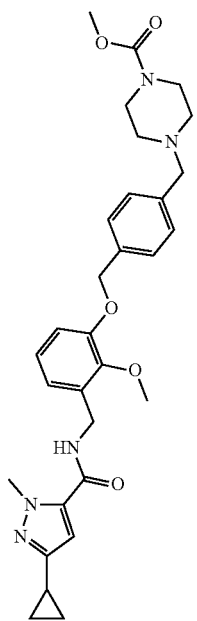 [SMILES: COC(=O)N1CCN(Cc2ccc(COc3cccc(CNC(=O)c4cc(C5CC5)nn4C)c3OC)cc2)CC1]
21
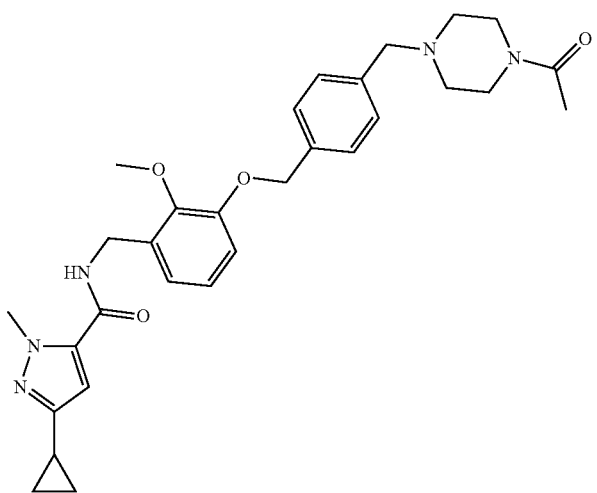 [SMILES: COc1c(CNC(=O)c2cc(C3CC3)nn2C)cccc1OCc1ccc(CN2CCN(C(C)=O)CC2)cc1]
22

TABLE 1-continued
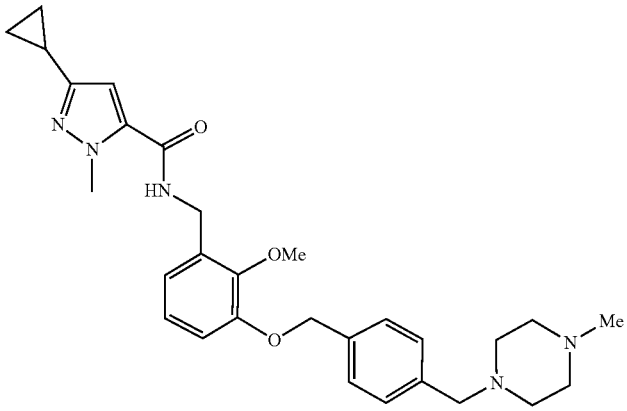 [SMILES: COc1c(CNC(=O)c2cc(C3CC3)nn2C)cccc1OCc1ccc(CN2CCN(C)CC2)cc1]
23
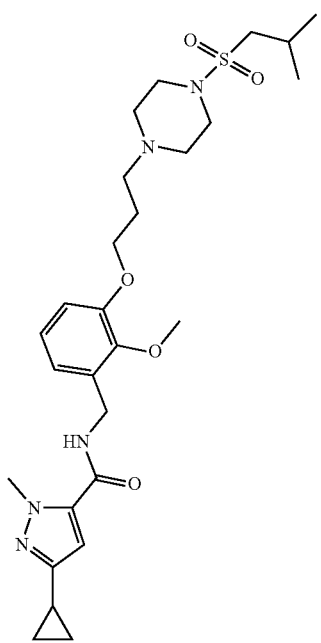 [SMILES: COc1c(CNC(=O)c2cc(C3CC3)nn2C)cccc1OCCCN1CCN(S(=O)(=O)CC(C)C)CC1]
24
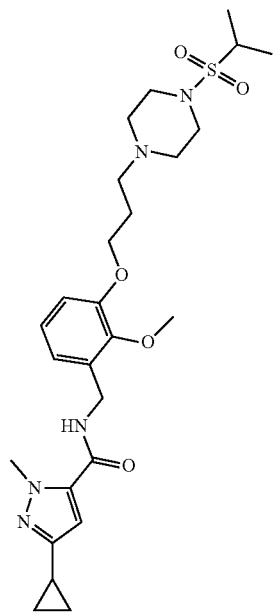 [SMILES: COc1c(CNC(=O)c2cc(C3CC3)nn2C)cccc1OCCCN1CCN(S(=O)(=O)C(C)C)CC1]
25

TABLE 1-continued
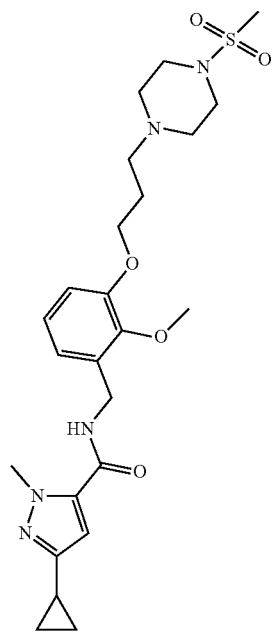 [SMILES: COc1c(CNC(=O)c2cc(C3CC3)nn2C)cccc1OCCCN1CCN(S(C)(=O)=O)CC1]
26
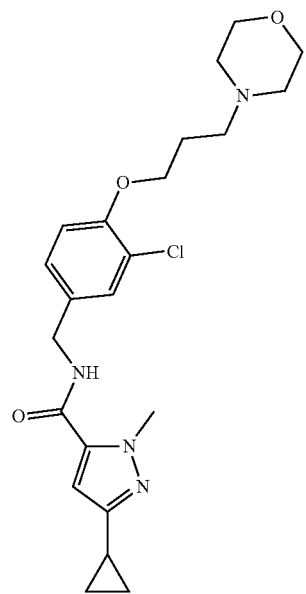 [SMILES: Cn1nc(C2CC2)cc1C(=O)NCc1ccc(OCCCN2CCOCC2)c(Cl)c1]
27

TABLE 1-continued
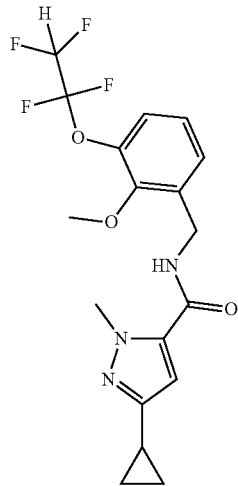 [SMILES: COc1c(CNC(=O)c2cc(C3CC3)nn2C)cccc1OC(F)(F)C(F)F]
28
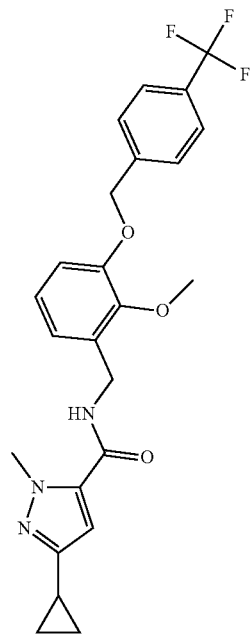 [SMILES: COc1c(CNC(=O)c2cc(C3CC3)nn2C)cccc1OCc1ccc(C(F)(F)F)cc1]
29
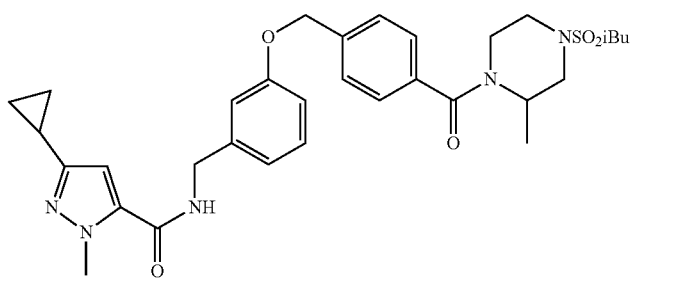
30

TABLE 1-continued
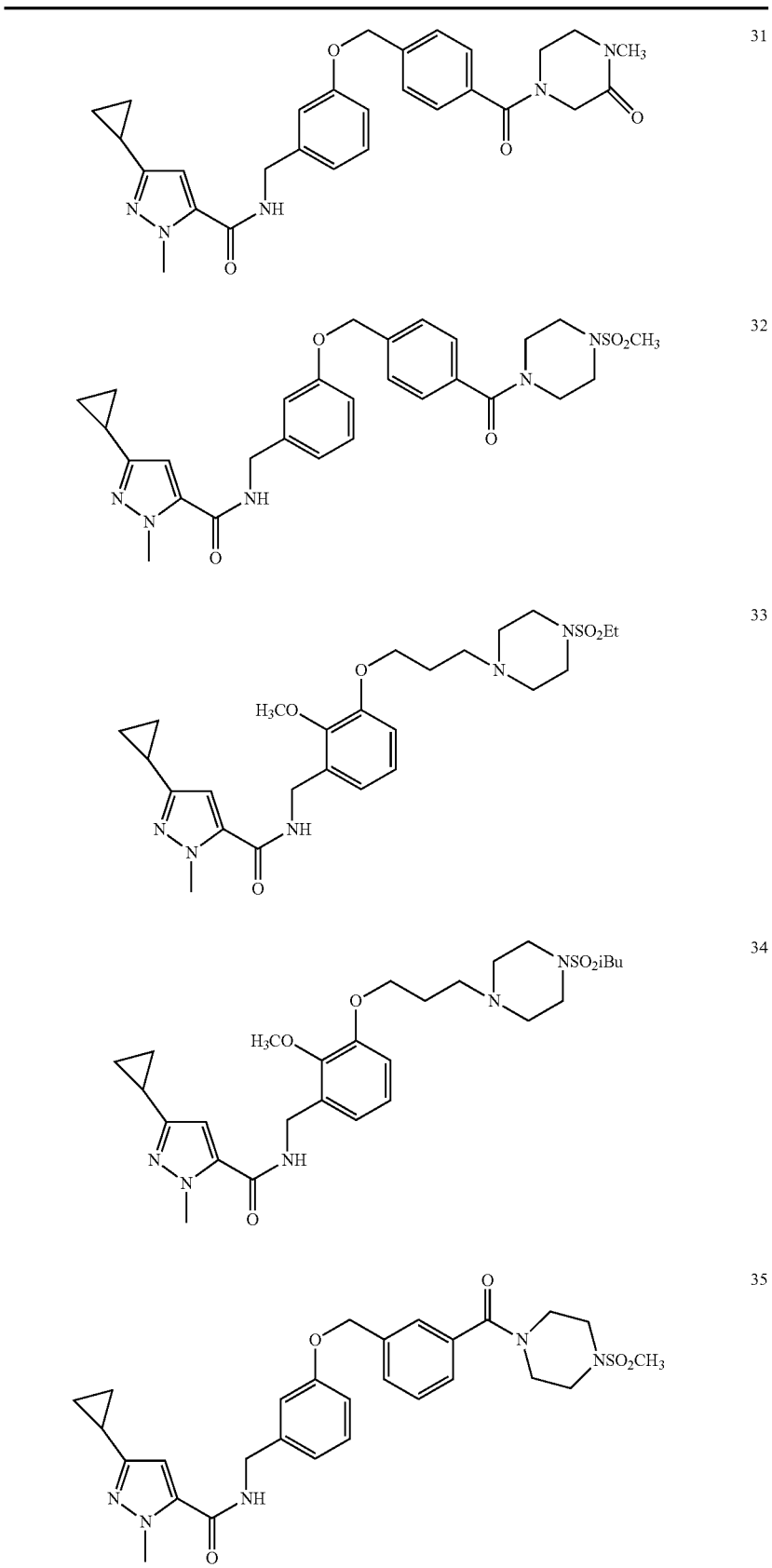

TABLE 1-continued
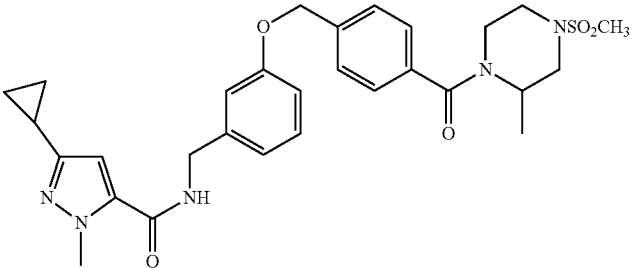
36
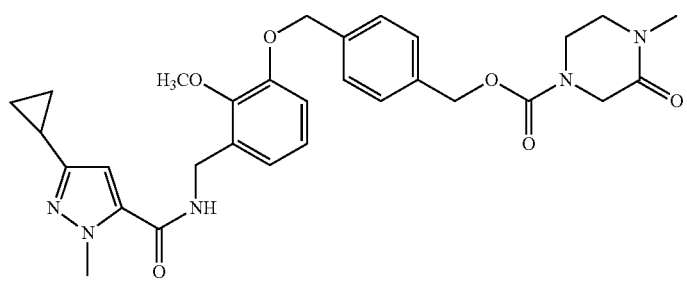 [SMILES: COc1c(CNC(=O)c2cc(C3CC3)nn2C)cccc1OCc1ccc(COC(=O)N2CCN(C)C(=O)C2)cc1]
37
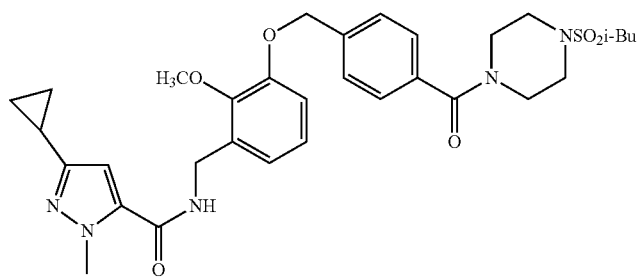
38
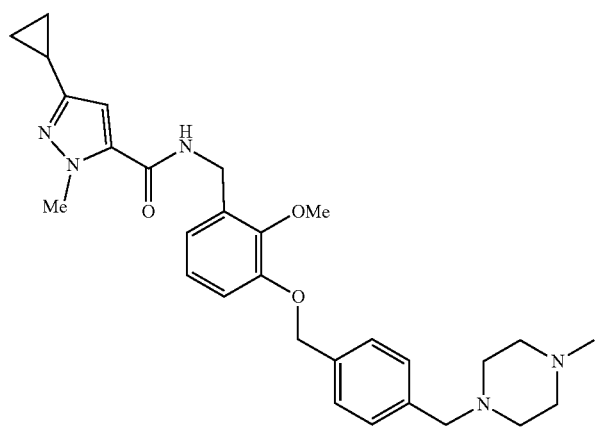 [SMILES: COc1c(CNC(=O)c2cc(C3CC3)nn2C)cccc1OCc1ccc(CN2CCN(C)CC2)cc1]
39

TABLE 1-continued
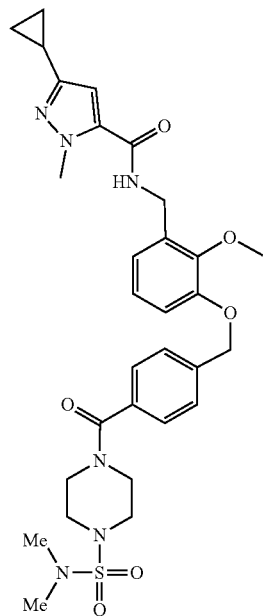 [SMILES: COc1c(CNC(=O)c2cc(C3CC3)nn2C)cccc1OCc1ccc(C(=O)N2CCN(S(=O)(=O)N(C)C)CC2)cc1]
40
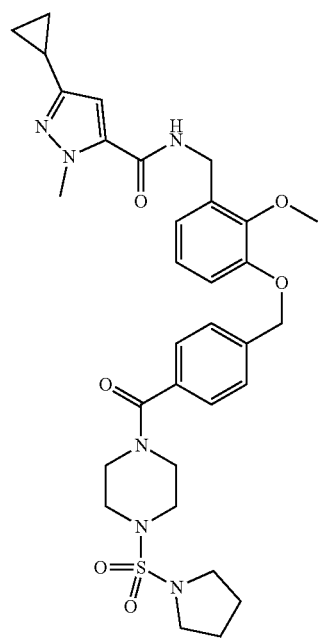 [SMILES: COc1c(CNC(=O)c2cc(C3CC3)nn2C)cccc1OCc1ccc(C(=O)N2CCN(S(=O)(=O)N3CCCC3)CC2)cc1]
41

TABLE 1-continued
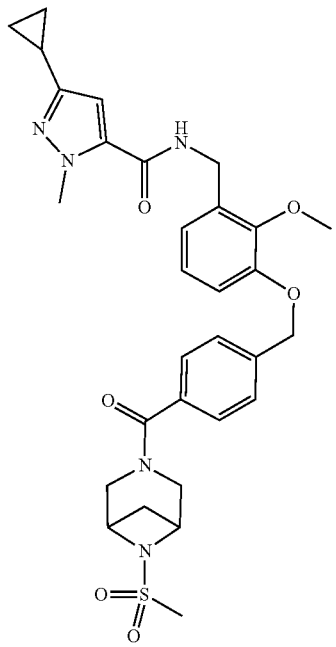 [SMILES: COc1c(CNC(=O)c2cc(C3CC3)nn2C)cccc1OCc1ccc(C(=O)N2CC3CC(C2)N3S(C)(=O)=O)cc1]
42
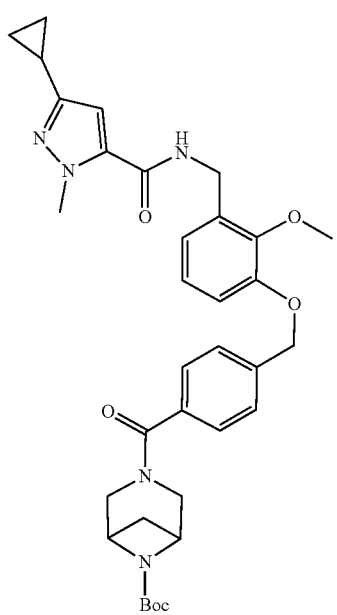 [SMILES: COc1c(CNC(=O)c2cc(C3CC3)nn2C)cccc1OCc1ccc(C(=O)N2CC3CC(C2)N3C(=O)OC(C)(C)C)cc1]
43

TABLE 1-continued
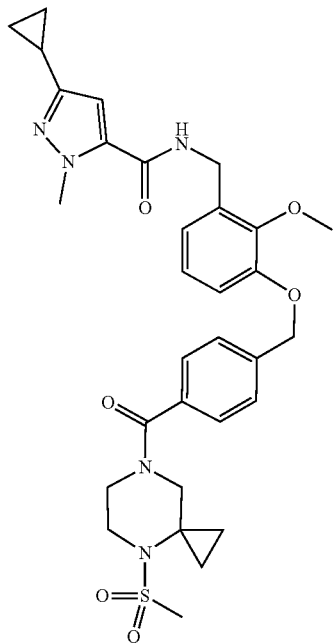 [SMILES: COc1c(CNC(=O)c2cc(C3CC3)nn2C)cccc1OCc1ccc(C(=O)N2CCN(S(C)(=O)=O)C3(CC3)C2)cc1]
44
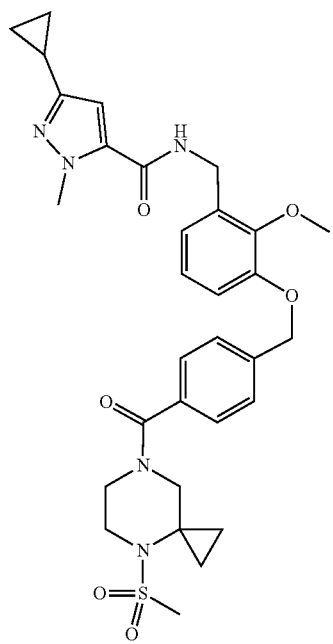 [SMILES: COc1c(CNC(=O)c2cc(C3CC3)nn2C)cccc1OCc1ccc(C(=O)N2CCN(S(C)(=O)=O)C3(CC3)C2)cc1]
45

TABLE 1-continued
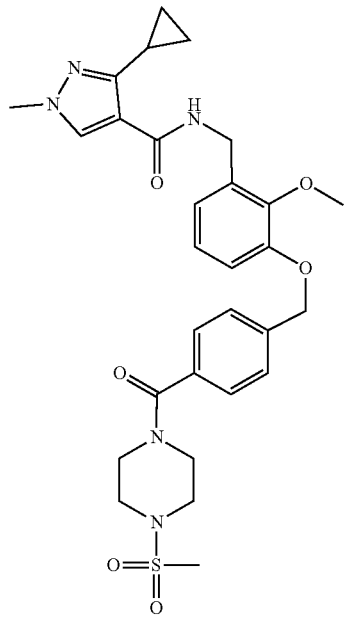
46
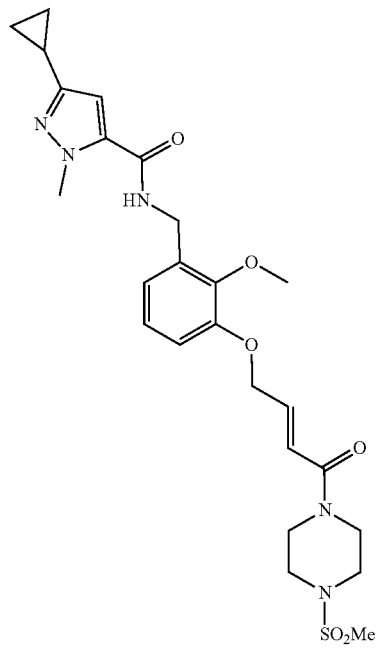 [SMILES: COc1c(CNC(=O)c2cc(C3CC3)nn2C)cccc1OC/C=C/C(=O)N1CCN(S(C)(=O)=O)CC1]
47

TABLE 1-continued
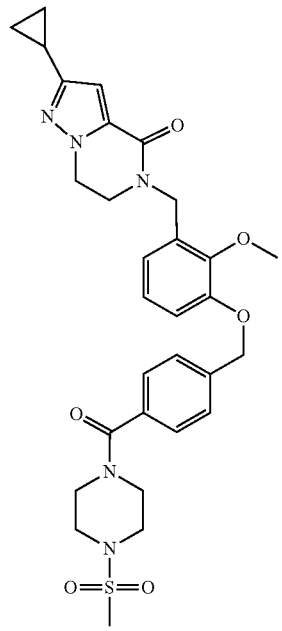 [SMILES: COc1c(CN2CCn3nc(C4CC4)cc3C2=O)cccc1OCc1ccc(C(=O)N2CCN(S(C)(=O)=O)CC2)cc1]
48
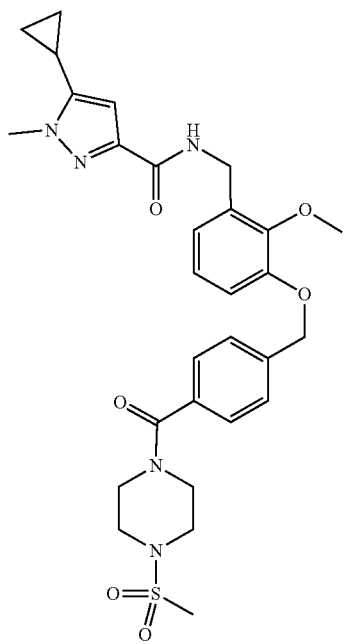
49

TABLE 1-continued
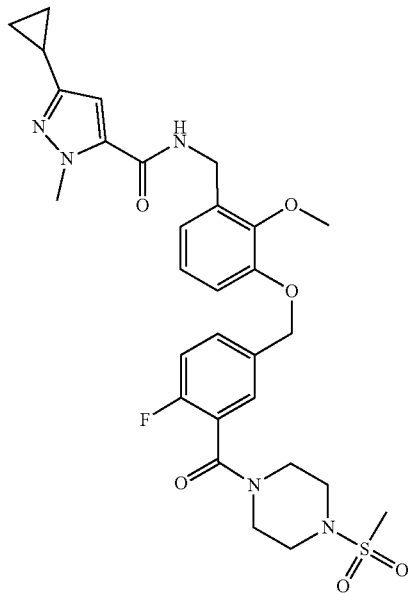 [SMILES: COc1c(CNC(=O)c2cc(C3CC3)nn2C)cccc1OCc1ccc(F)c(C(=O)N2CCN(S(C)(=O)=O)CC2)c1]
50
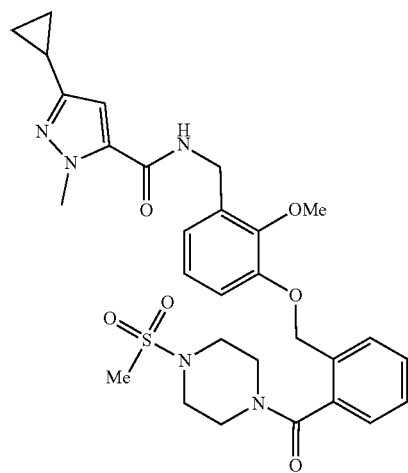 [SMILES: COc1c(CNC(=O)c2cc(C3CC3)nn2C)cccc1OCc1ccccc1C(=O)N1CCN(S(C)(=O)=O)CC1]
51

TABLE 1-continued
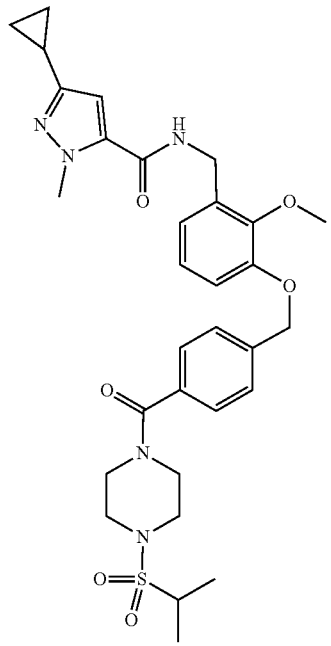 [SMILES: COc1c(CNC(=O)c2cc(C3CC3)nn2C)cccc1OCc1ccc(C(=O)N2CCN(S(=O)(=O)C(C)C)CC2)cc1]
52
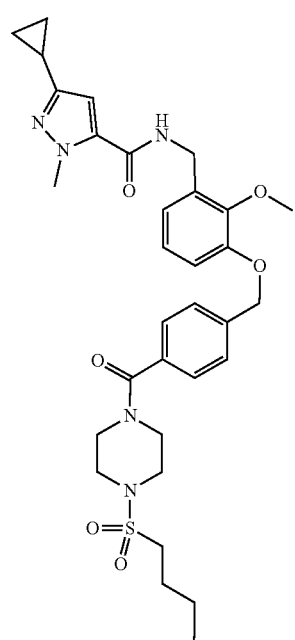 [SMILES: CCCCS(=O)(=O)N1CCN(C(=O)c2ccc(COc3cccc(CNC(=O)c4cc(C5CC5)nn4C)c3OC)cc2)CC1]
53

TABLE 1-continued
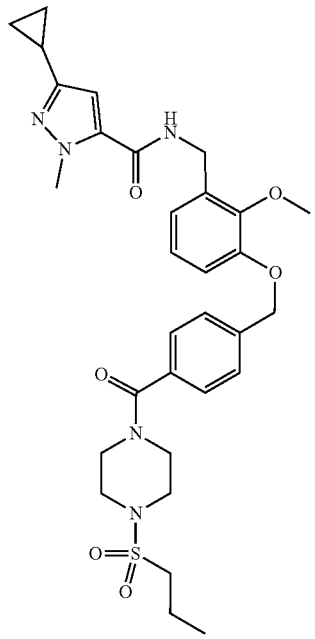 [SMILES: CCCS(=O)(=O)N1CCN(C(=O)c2ccc(COc3cccc(CNC(=O)c4cc(C5CC5)nn4C)c3OC)cc2)CC1]
54
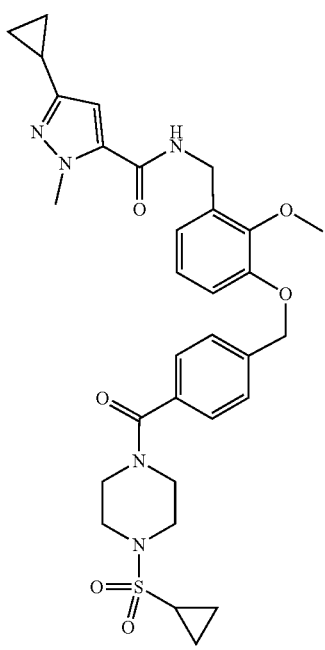 [SMILES: COc1c(CNC(=O)c2cc(C3CC3)nn2C)cccc1OCc1ccc(C(=O)N2CCN(S(=O)(=O)C3CC3)CC2)cc1]
55

TABLE 1-continued
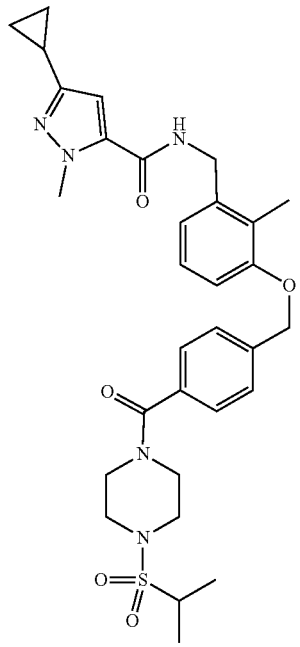 [SMILES: Cc1c(CNC(=O)c2cc(C3CC3)nn2C)cccc1OCc1ccc(C(=O)N2CCN(S(=O)(=O)C(C)C)CC2)cc1]
56
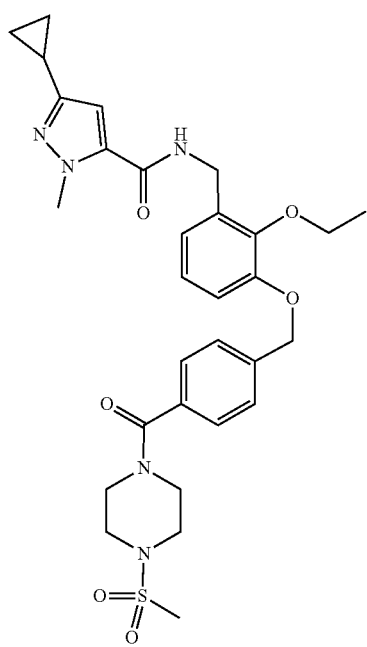 [SMILES: CCOc1c(CNC(=O)c2cc(C3CC3)nn2C)cccc1OCc1ccc(C(=O)N2CCN(S(C)(=O)=O)CC2)cc1]
57

TABLE 1-continued
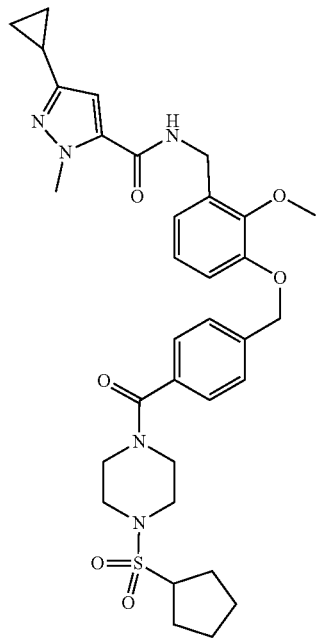 [SMILES: COc1c(CNC(=O)c2cc(C3CC3)nn2C)cccc1OCc1ccc(C(=O)N2CCN(S(=O)(=O)C3CCCC3)CC2)cc1]
58
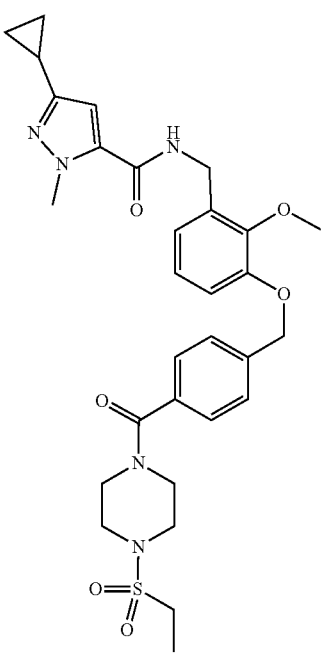 [SMILES: CCS(=O)(=O)N1CCN(C(=O)c2ccc(COc3cccc(CNC(=O)c4cc(C5CC5)nn4C)c3OC)cc2)CC1]
59

TABLE 1-continued
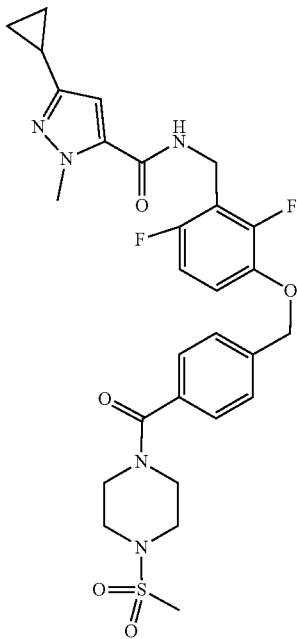 [SMILES: Cn1nc(C2CC2)cc1C(=O)NCc1c(F)ccc(OCc2ccc(C(=O)N3CCN(S(C)(=O)=O)CC3)cc2)c1F]
60
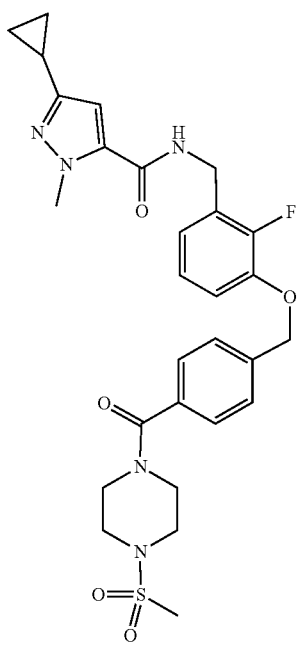 [SMILES: Cn1nc(C2CC2)cc1C(=O)NCc1cccc(OCc2ccc(C(=O)N3CCN(S(C)(=O)=O)CC3)cc2)c1F]
61

TABLE 1-continued
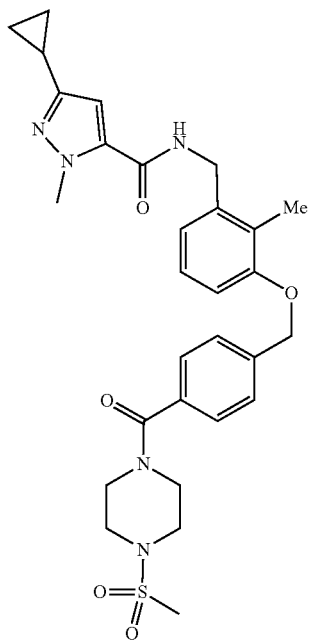 [SMILES: Cc1c(CNC(=O)c2cc(C3CC3)nn2C)cccc1OCc1ccc(C(=O)N2CCN(S(C)(=O)=O)CC2)cc1]
62
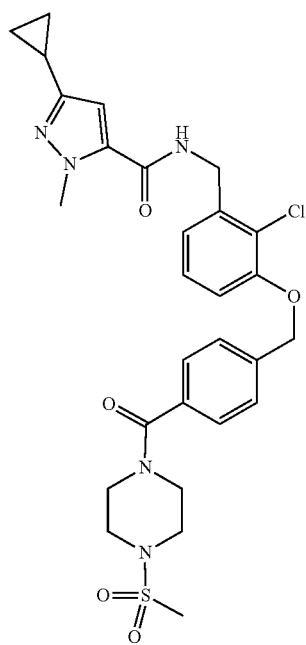 [SMILES: Cn1nc(C2CC2)cc1C(=O)NCc1cccc(OCc2ccc(C(=O)N3CCN(S(C)(=O)=O)CC3)cc2)c1Cl]
63

TABLE 1-continued
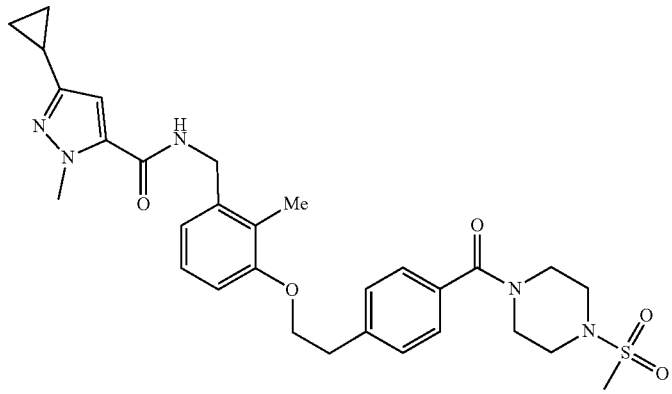 [SMILES: Cc1c(CNC(=O)c2cc(C3CC3)nn2C)cccc1OCCc1ccc(C(=O)N2CCN(S(C)(=O)=O)CC2)cc1]
64
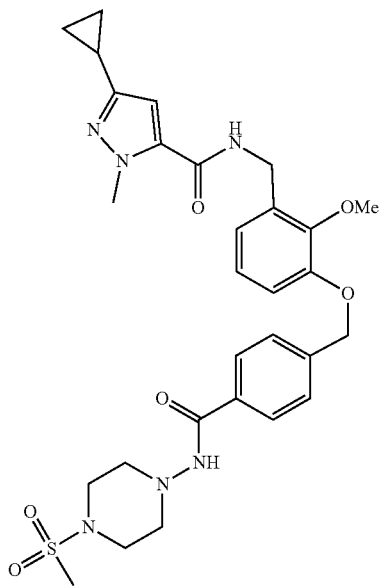 [SMILES: COc1c(CNC(=O)c2cc(C3CC3)nn2C)cccc1OCc1ccc(C(=O)NN2CCN(S(C)(=O)=O)CC2)cc1]
65
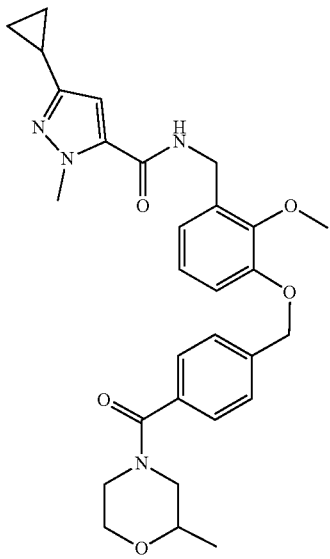 [SMILES: COc1c(CNC(=O)c2cc(C3CC3)nn2C)cccc1OCc1ccc(C(=O)N2CCOC(C)C2)cc1]
66

TABLE 1-continued
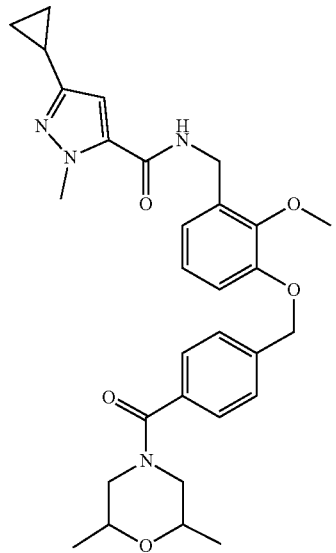 [SMILES: COc1c(CNC(=O)c2cc(C3CC3)nn2C)cccc1OCc1ccc(C(=O)N2CC(C)OC(C)C2)cc1]
67
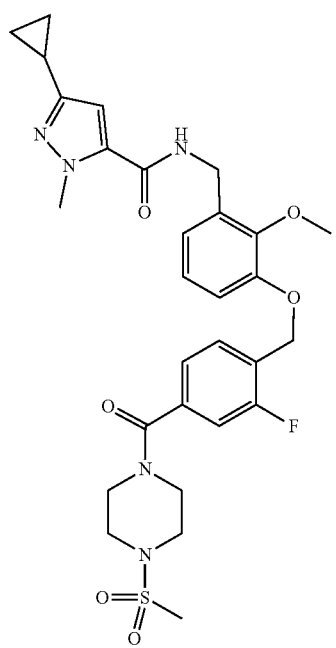 [SMILES: COc1c(CNC(=O)c2cc(C3CC3)nn2C)cccc1OCc1ccc(C(=O)N2CCN(S(C)(=O)=O)CC2)cc1F]
68

TABLE 1-continued
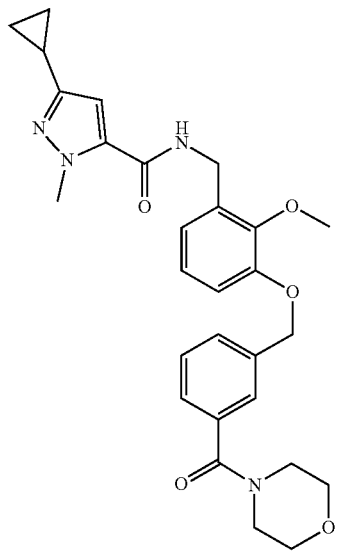 [SMILES: COc1c(CNC(=O)c2cc(C3CC3)nn2C)cccc1OCc1cccc(C(=O)N2CCOCC2)c1]
69
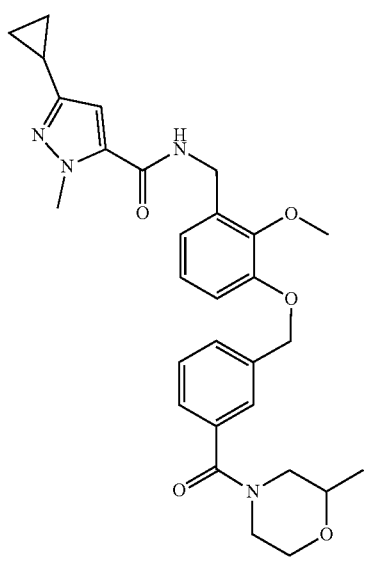 [SMILES: COc1c(CNC(=O)c2cc(C3CC3)nn2C)cccc1OCc1cccc(C(=O)N2CCOC(C)C2)c1]
70

TABLE 1-continued
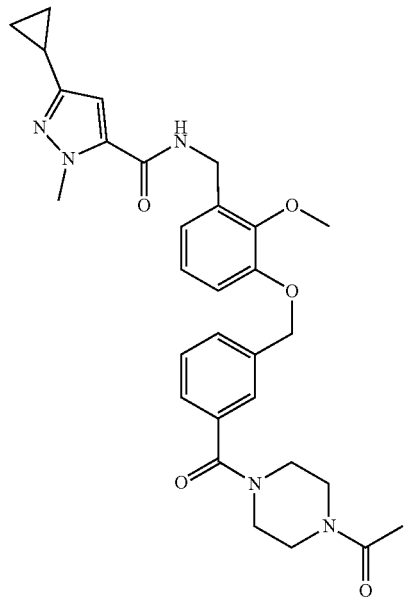 [SMILES: COc1c(CNC(=O)c2cc(C3CC3)nn2C)cccc1OCc1cccc(C(=O)N2CCN(C(C)=O)CC2)c1]
71
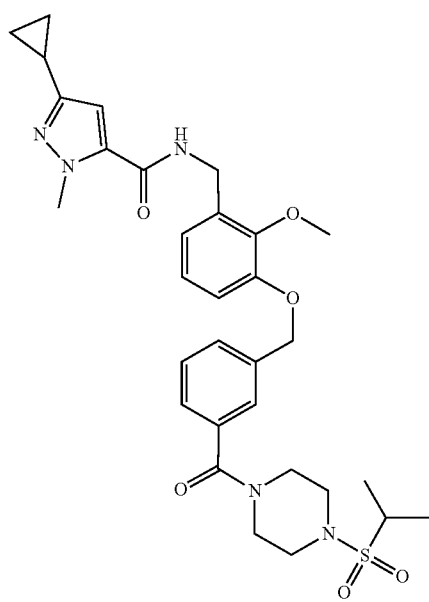 [SMILES: COc1c(CNC(=O)c2cc(C3CC3)nn2C)cccc1OCc1cccc(C(=O)N2CCN(S(=O)(=O)C(C)C)CC2)c1]
72

TABLE 1-continued
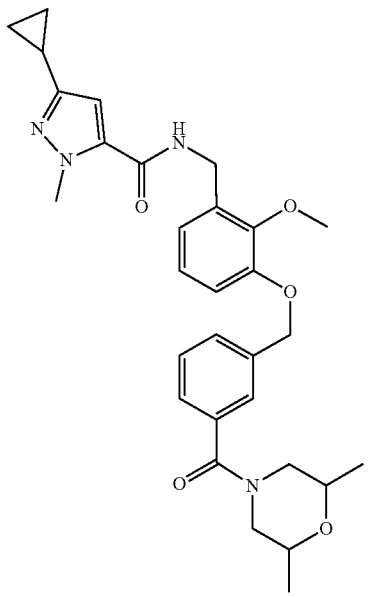 [SMILES: COc1c(CNC(=O)c2cc(C3CC3)nn2C)cccc1OCc1cccc(C(=O)N2CC(C)OC(C)C2)c1]
73
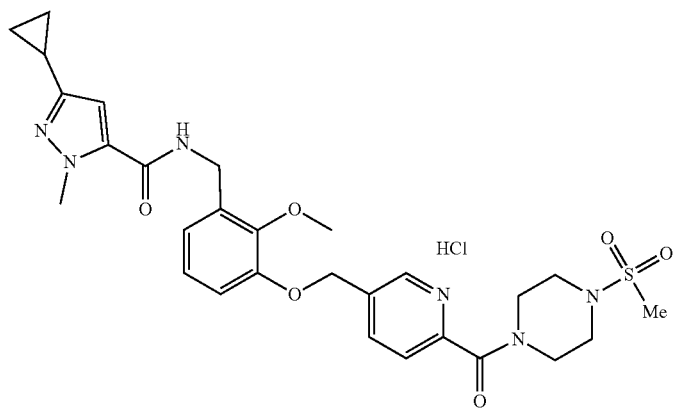 [SMILES: COc1c(CNC(=O)c2cc(C3CC3)nn2C)cccc1OCc1ccc(C(=O)N2CCN(S(C)(=O)=O)CC2)nc1 ; Cl]
74
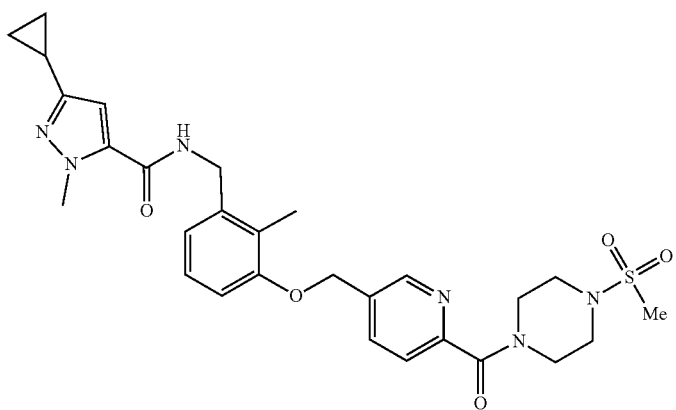 [SMILES: Cc1c(CNC(=O)c2cc(C3CC3)nn2C)cccc1OCc1ccc(C(=O)N2CCN(S(C)(=O)=O)CC2)nc1]
75

TABLE 1-continued
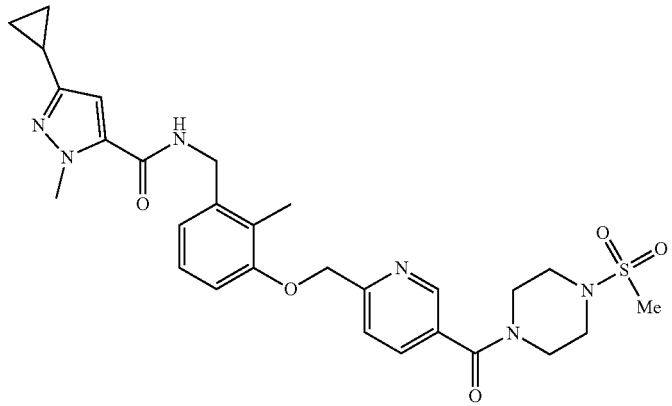 [SMILES: Cc1c(CNC(=O)c2cc(C3CC3)nn2C)cccc1OCc1ccc(C(=O)N2CCN(S(C)(=O)=O)CC2)cn1]
76
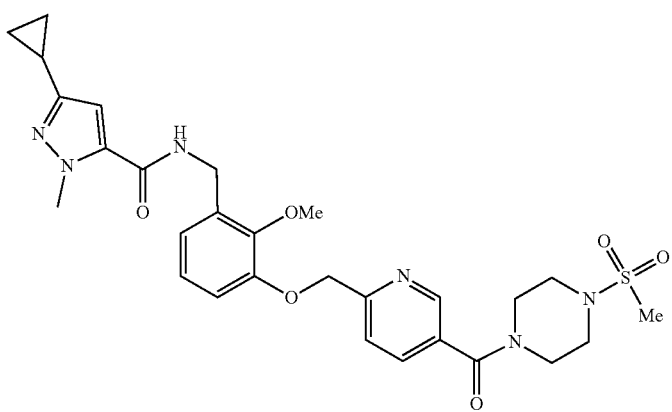 [SMILES: COc1c(CNC(=O)c2cc(C3CC3)nn2C)cccc1OCc1ccc(C(=O)N2CCN(S(C)(=O)=O)CC2)cn1]
77
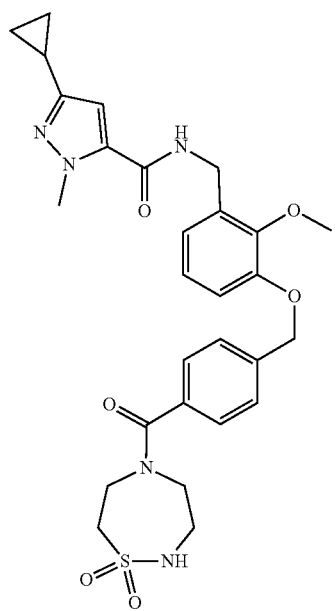 [SMILES: COc1c(CNC(=O)c2cc(C3CC3)nn2C)cccc1OCc1ccc(C(=O)N2CCNS(=O)(=O)CC2)cc1]
78

TABLE 1-continued
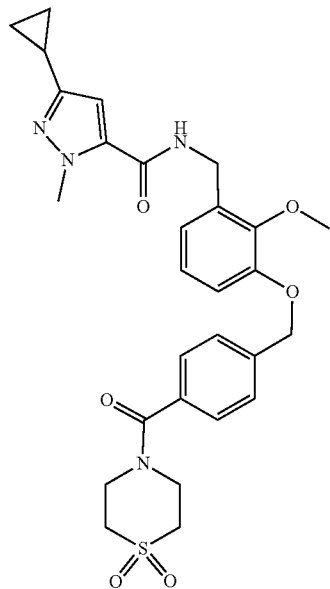 [SMILES: COc1c(CNC(=O)c2cc(C3CC3)nn2C)cccc1OCc1ccc(C(=O)N2CCS(=O)(=O)CC2)cc1]
79
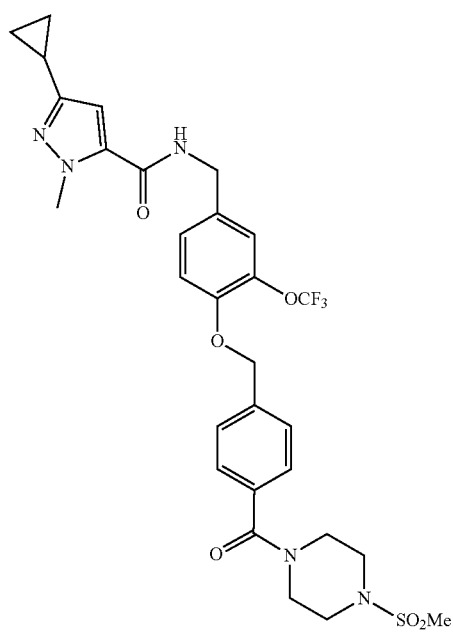 [SMILES: Cn1nc(C2CC2)cc1C(=O)NCc1ccc(OCc2ccc(C(=O)N3CCN(S(C)(=O)=O)CC3)cc2)c(OC(F)(F)F)c1]
80

TABLE 1-continued
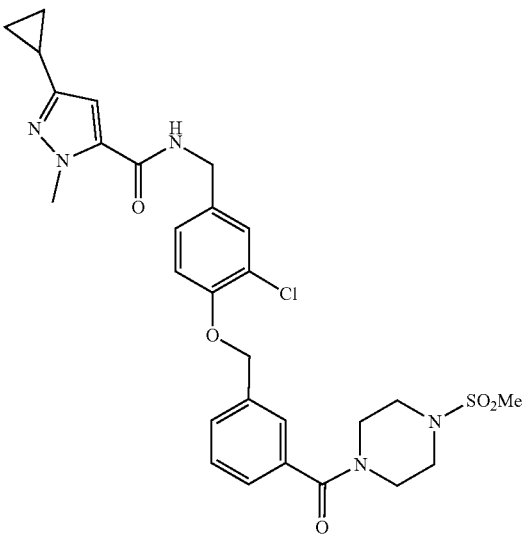 [SMILES: Cn1nc(C2CC2)cc1C(=O)NCc1ccc(OCc2cccc(C(=O)N3CCN(S(C)(=O)=O)CC3)c2)c(Cl)c1]
81
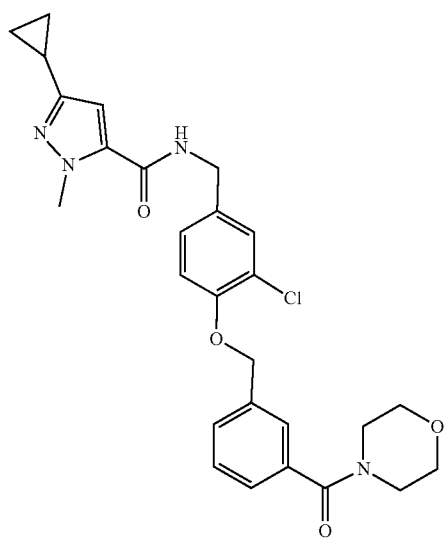 [SMILES: Cn1nc(C2CC2)cc1C(=O)NCc1ccc(OCc2cccc(C(=O)N3CCOCC3)c2)c(Cl)c1]
82

TABLE 1-continued
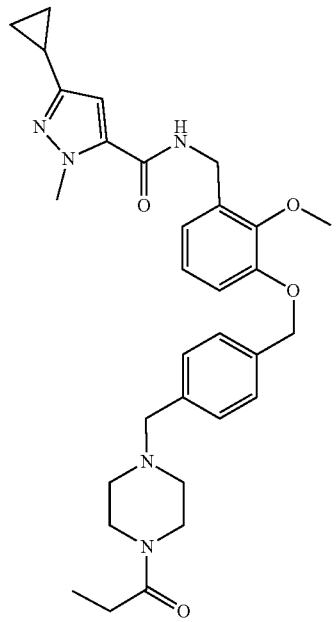 [SMILES: CCC(=O)N1CCN(Cc2ccc(COc3cccc(CNC(=O)c4cc(C5CC5)nn4C)c3OC)cc2)CC1]
83
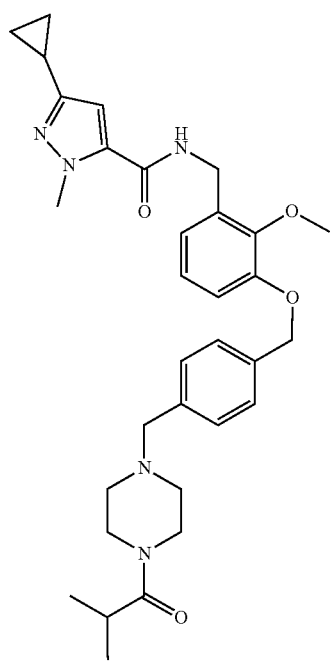 [SMILES: COc1c(CNC(=O)c2cc(C3CC3)nn2C)cccc1OCc1ccc(CN2CCN(C(=O)C(C)C)CC2)cc1]
84

TABLE 1-continued
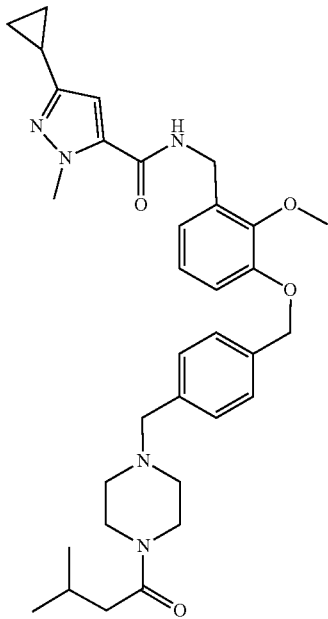 [SMILES: COc1c(CNC(=O)c2cc(C3CC3)nn2C)cccc1OCc1ccc(CN2CCN(C(=O)CC(C)C)CC2)cc1]
85
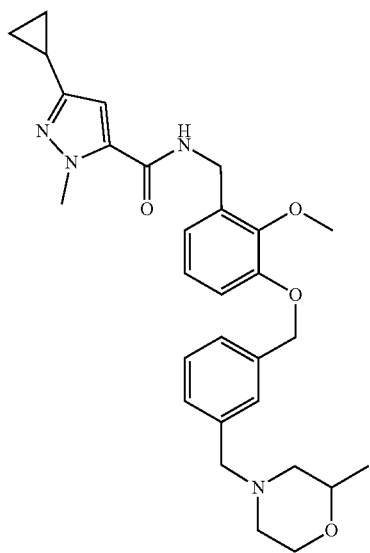 [SMILES: COc1c(CNC(=O)c2cc(C3CC3)nn2C)cccc1OCc1cccc(CN2CCOC(C)C2)c1]
86

TABLE 1-continued
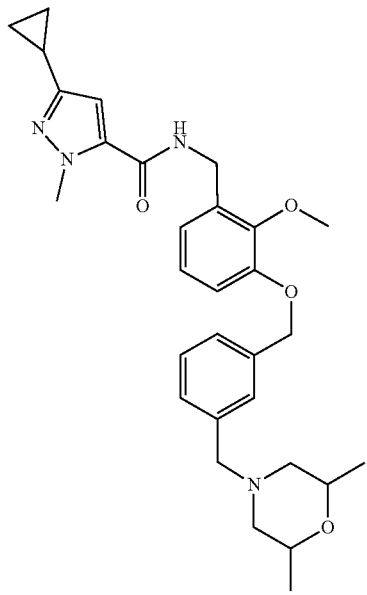 [SMILES: COc1c(CNC(=O)c2cc(C3CC3)nn2C)cccc1OCc1cccc(CN2CC(C)OC(C)C2)c1]
87
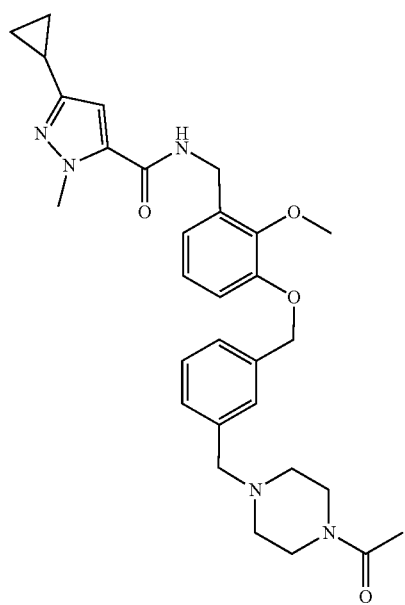 [SMILES: COc1c(CNC(=O)c2cc(C3CC3)nn2C)cccc1OCc1cccc(CN2CCN(C(C)=O)CC2)c1]
88

TABLE 1-continued
| | |
|---|---|
| 89 | 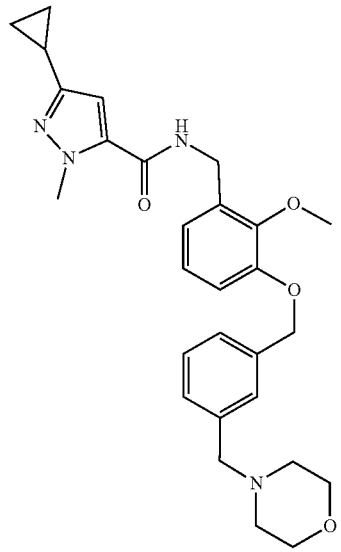 [SMILES: COc1c(CNC(=O)c2cc(C3CC3)nn2C)cccc1OCc1cccc(CN2CCOCC2)c1] |
| 90 | 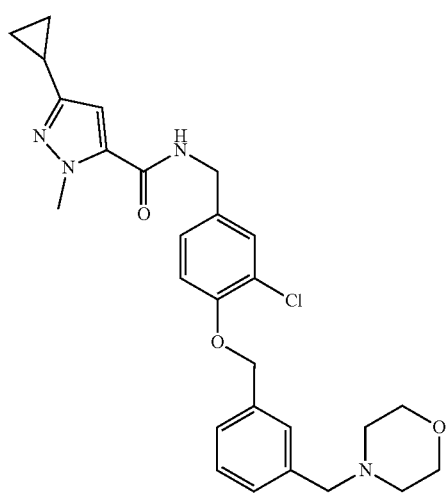 [SMILES: Cn1nc(C2CC2)cc1C(=O)NCc1ccc(OCc2cccc(CN3CCOCC3)c2)c(Cl)c1] |

TABLE 1-continued
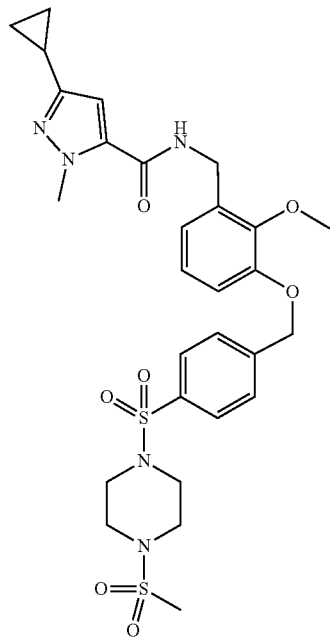 [SMILES: COc1c(CNC(=O)c2cc(C3CC3)nn2C)cccc1OCc1ccc(S(=O)(=O)N2CCN(S(C)(=O)=O)CC2)cc1]
91
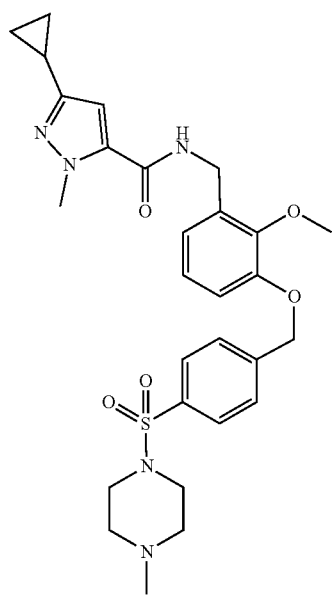 [SMILES: COc1c(CNC(=O)c2cc(C3CC3)nn2C)cccc1OCc1ccc(S(=O)(=O)N2CCN(C)CC2)cc1]
92

TABLE 1-continued
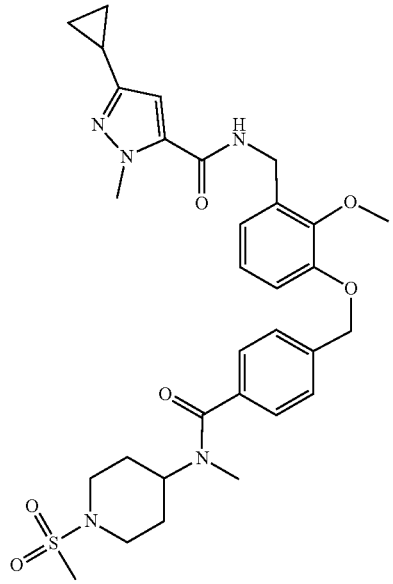 [SMILES: COc1c(CNC(=O)c2cc(C3CC3)nn2C)cccc1OCc1ccc(C(=O)N(C)C2CCN(S(C)(=O)=O)CC2)cc1]
93
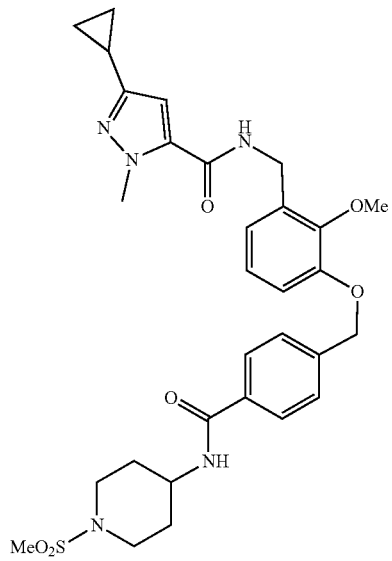 [SMILES: COc1c(CNC(=O)c2cc(C3CC3)nn2C)cccc1OCc1ccc(C(=O)NC2CCN(S(C)(=O)=O)CC2)cc1]
94

TABLE 1-continued
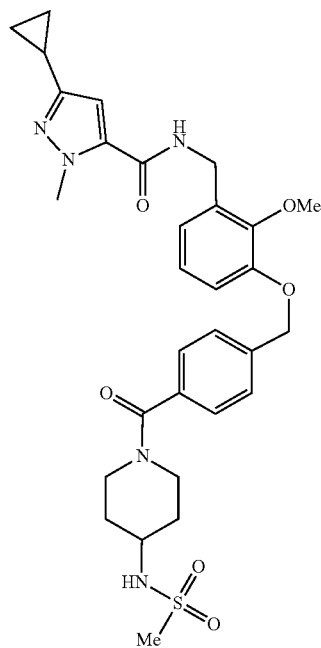 [SMILES: COc1c(CNC(=O)c2cc(C3CC3)nn2C)cccc1OCc1ccc(C(=O)N2CCC(NS(C)(=O)=O)CC2)cc1]
95
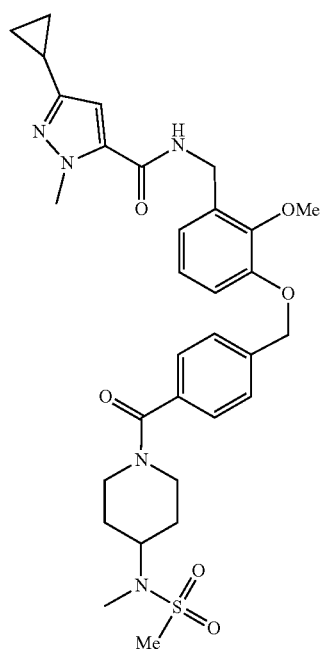 [SMILES: COc1c(CNC(=O)c2cc(C3CC3)nn2C)cccc1OCc1ccc(C(=O)N2CCC(N(C)S(C)(=O)=O)CC2)cc1]
96

TABLE 1-continued
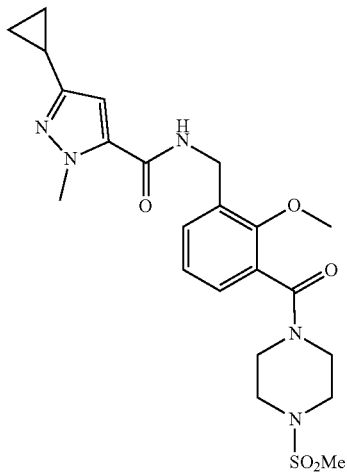 [SMILES: COc1c(CNC(=O)c2cc(C3CC3)nn2C)cccc1C(=O)N1CCN(S(C)(=O)=O)CC1]
97
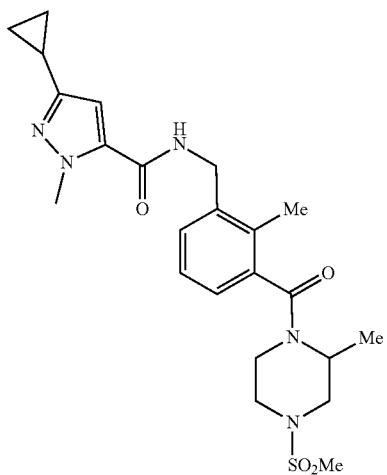 [SMILES: Cc1c(CNC(=O)c2cc(C3CC3)nn2C)cccc1C(=O)N1CCN(S(C)(=O)=O)CC1C]
98
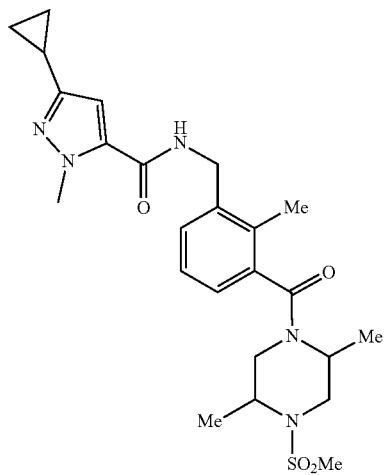 [SMILES: Cc1c(CNC(=O)c2cc(C3CC3)nn2C)cccc1C(=O)N1CC(C)N(S(C)(=O)=O)CC1C]
99

TABLE 1-continued
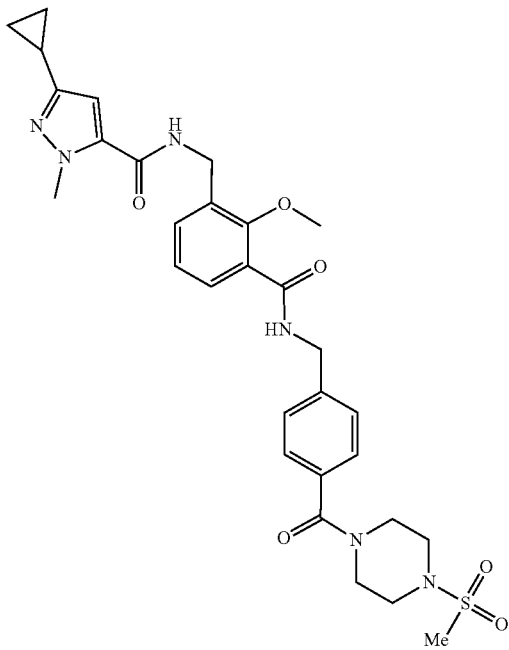 [SMILES: COc1c(CNC(=O)c2cc(C3CC3)nn2C)cccc1C(=O)NCc1ccc(C(=O)N2CCN(S(C)(=O)=O)CC2)cc1]
100
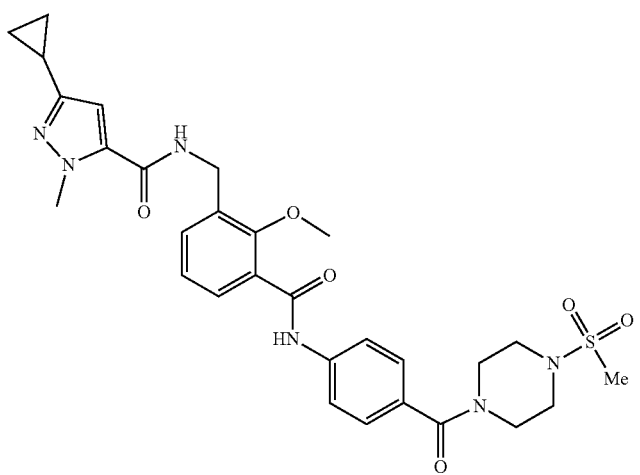 [SMILES: COc1c(CNC(=O)c2cc(C3CC3)nn2C)cccc1C(=O)Nc1ccc(C(=O)N2CCN(S(C)(=O)=O)CC2)cc1]
101
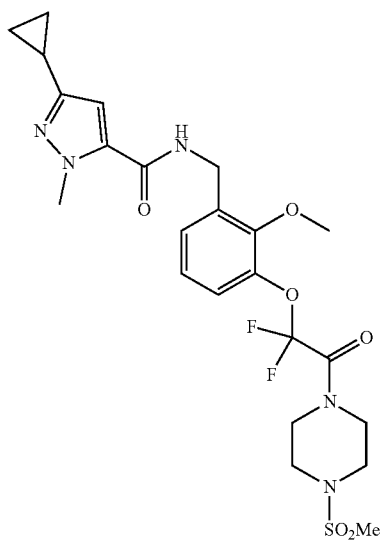 [SMILES: COc1c(CNC(=O)c2cc(C3CC3)nn2C)cccc1OC(F)(F)C(=O)N1CCN(S(C)(=O)=O)CC1]
102

TABLE 1-continued
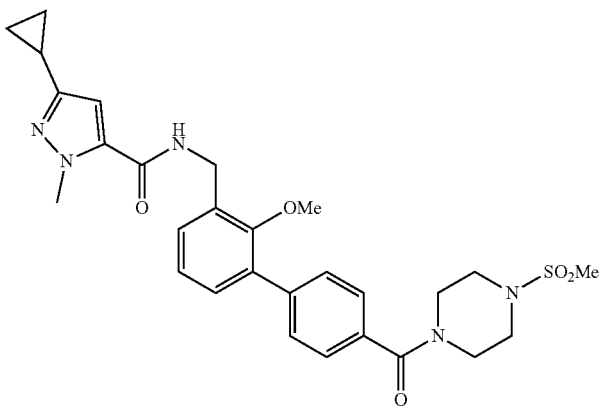 [SMILES: COc1c(CNC(=O)c2cc(C3CC3)nn2C)cccc1-c1ccc(C(=O)N2CCN(S(C)(=O)=O)CC2)cc1]
103
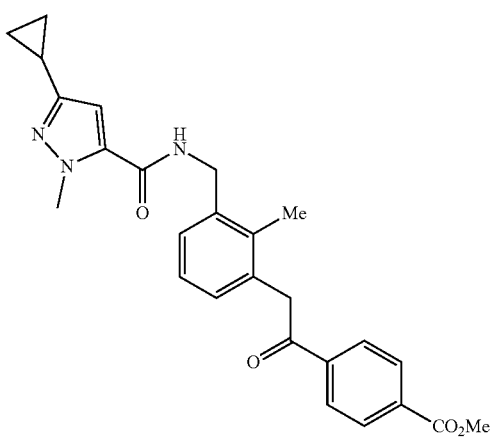 [SMILES: COC(=O)c1ccc(C(=O)Cc2cccc(CNC(=O)c3cc(C4CC4)nn3C)c2C)cc1]
104
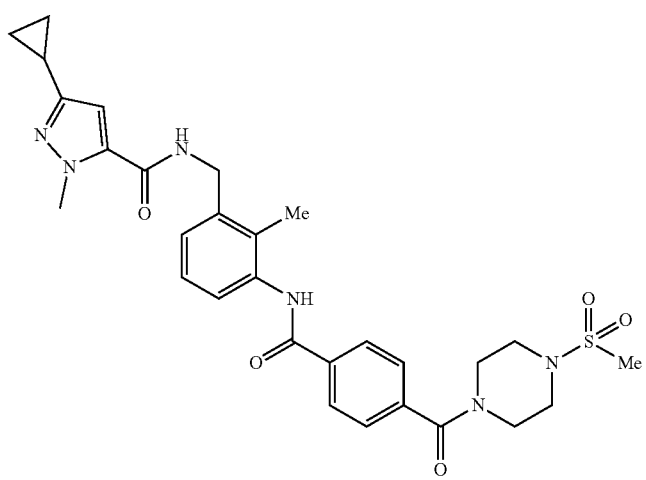 [SMILES: Cc1c(CNC(=O)c2cc(C3CC3)nn2C)cccc1NC(=O)c1ccc(C(=O)N2CCN(S(C)(=O)=O)CC2)cc1]
105

TABLE 1-continued
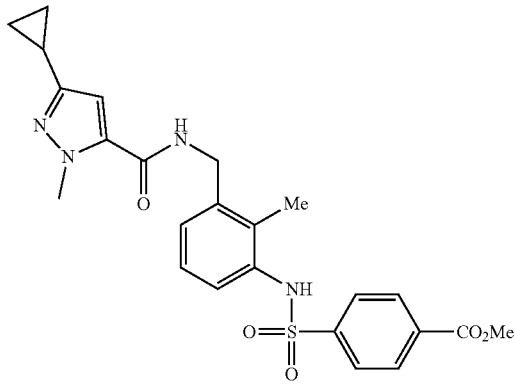 [SMILES: COC(=O)c1ccc(S(=O)(=O)Nc2cccc(CNC(=O)c3cc(C4CC4)nn3C)c2C)cc1]
106
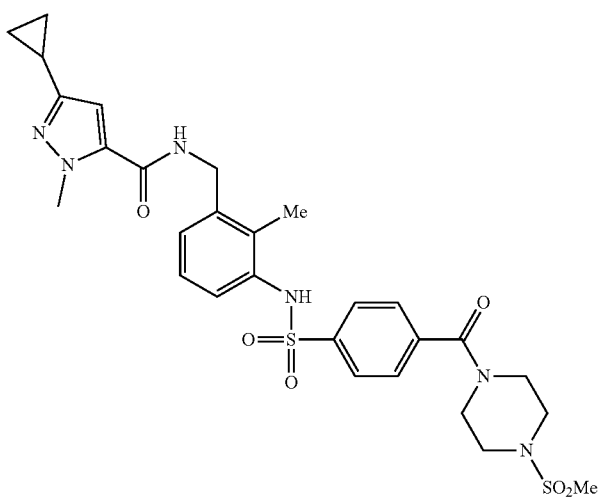 [SMILES: Cc1c(CNC(=O)c2cc(C3CC3)nn2C)cccc1NS(=O)(=O)c1ccc(C(=O)N2CCN(S(C)(=O)=O)CC2)cc1]
107
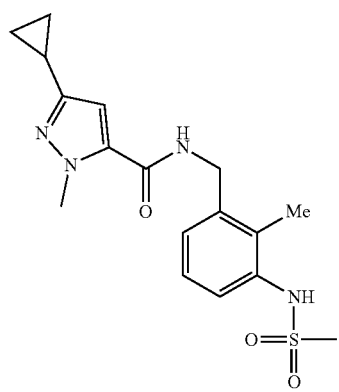 [SMILES: Cc1c(CNC(=O)c2cc(C3CC3)nn2C)cccc1NS(C)(=O)=O]
108

TABLE 1-continued
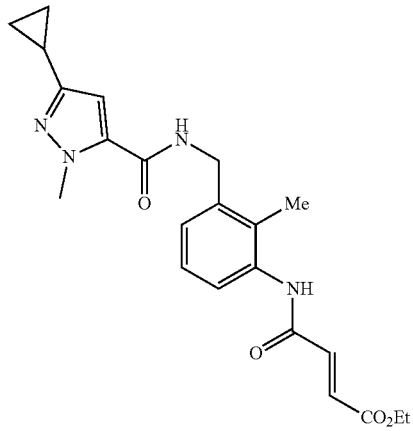 [SMILES: CCOC(=O)/C=C/C(=O)Nc1cccc(CNC(=O)c2cc(C3CC3)nn2C)c1C]
109
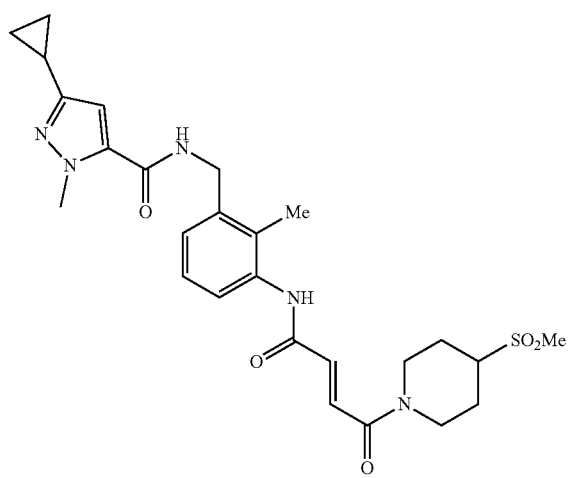 [SMILES: Cc1c(CNC(=O)c2cc(C3CC3)nn2C)cccc1NC(=O)/C=C/C(=O)N1CCC(S(C)(=O)=O)CC1]
110
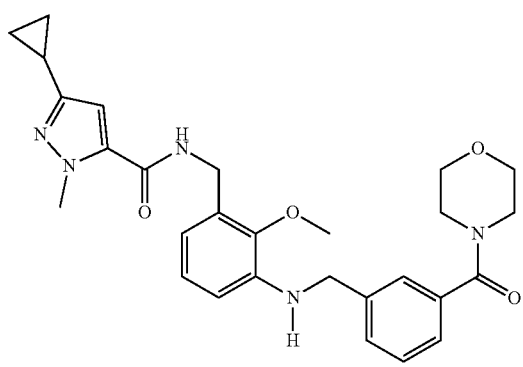 [SMILES: COc1c(CNC(=O)c2cc(C3CC3)nn2C)cccc1NCc1cccc(C(=O)N2CCOCC2)c1]
111

TABLE 1-continued
| | |
|---|---|
| 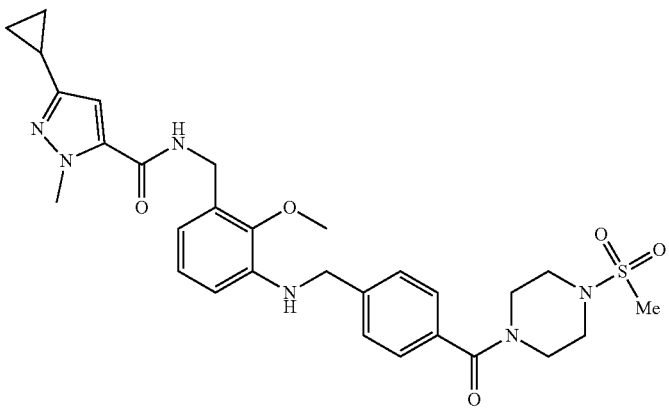 [SMILES: COc1c(CNC(=O)c2cc(C3CC3)nn2C)cccc1NCc1ccc(C(=O)N2CCN(S(C)(=O)=O)CC2)cc1] | 112 |
| 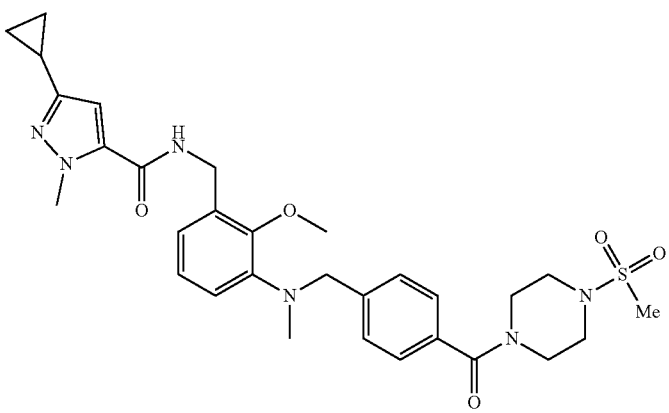 [SMILES: COc1c(CNC(=O)c2cc(C3CC3)nn2C)cccc1N(C)Cc1ccc(C(=O)N2CCN(S(C)(=O)=O)CC2)cc1] | 113 |
| 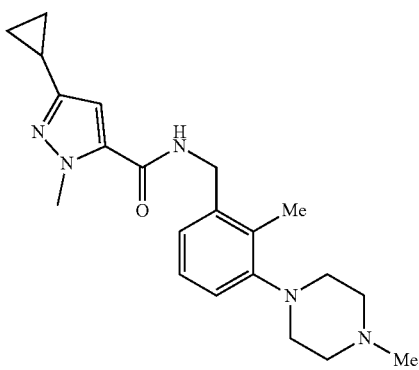 [SMILES: Cc1c(CNC(=O)c2cc(C3CC3)nn2C)cccc1N1CCN(C)CC1] | 114 |
| 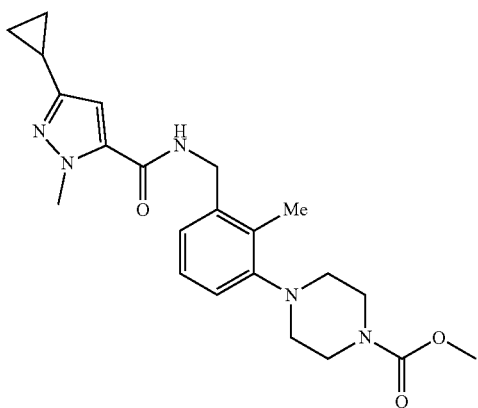 [SMILES: COC(=O)N1CCN(c2cccc(CNC(=O)c3cc(C4CC4)nn3C)c2C)CC1] | 115 |

TABLE 1-continued
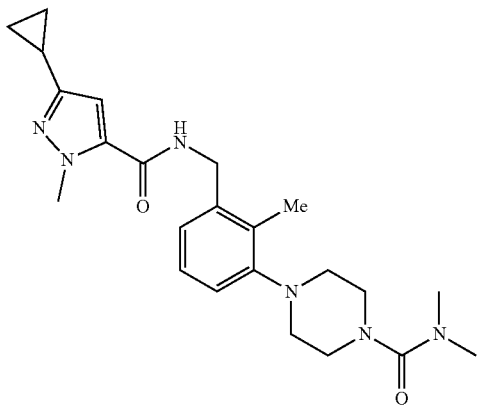 [SMILES: Cc1c(CNC(=O)c2cc(C3CC3)nn2C)cccc1N1CCN(C(=O)N(C)C)CC1]
116
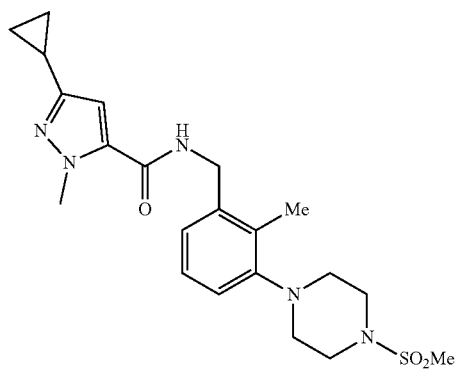 [SMILES: Cc1c(CNC(=O)c2cc(C3CC3)nn2C)cccc1N1CCN(S(C)(=O)=O)CC1]
117
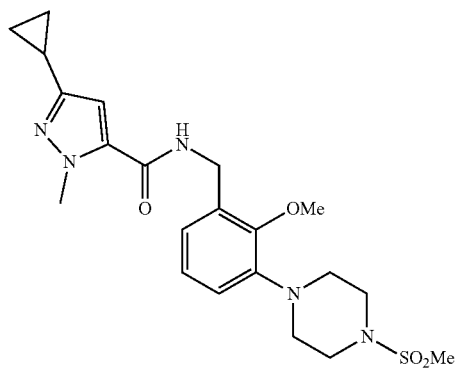 [SMILES: COc1c(CNC(=O)c2cc(C3CC3)nn2C)cccc1N1CCN(S(C)(=O)=O)CC1]
118
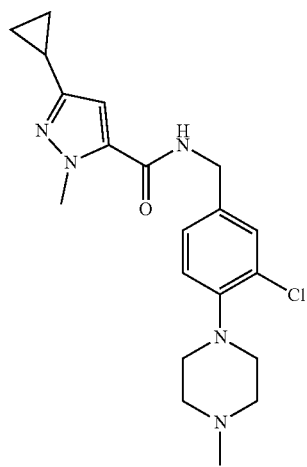 [SMILES: CN1CCN(c2ccc(CNC(=O)c3cc(C4CC4)nn3C)cc2Cl)CC1]
119

TABLE 1-continued
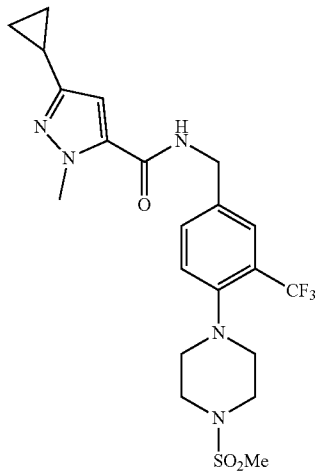 [SMILES: Cn1nc(C2CC2)cc1C(=O)NCc1ccc(N2CCN(S(C)(=O)=O)CC2)c(C(F)(F)F)c1]
120
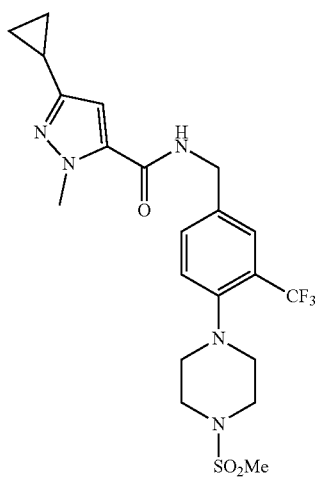 [SMILES: Cn1nc(C2CC2)cc1C(=O)NCc1ccc(N2CCN(S(C)(=O)=O)CC2)c(C(F)(F)F)c1]
121
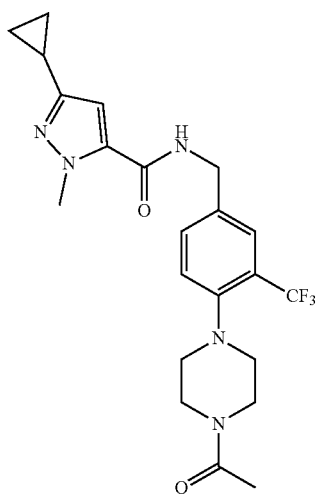 [SMILES: CC(=O)N1CCN(c2ccc(CNC(=O)c3cc(C4CC4)nn3C)cc2C(F)(F)F)CC1]
122

TABLE 1-continued
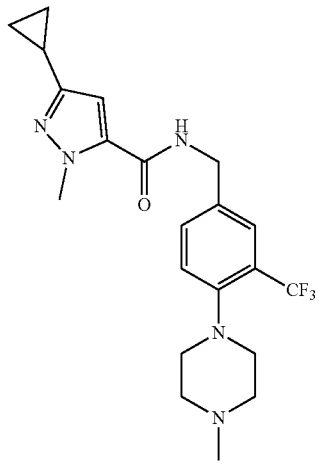 [SMILES: CN1CCN(c2ccc(CNC(=O)c3cc(C4CC4)nn3C)cc2C(F)(F)F)CC1]
123
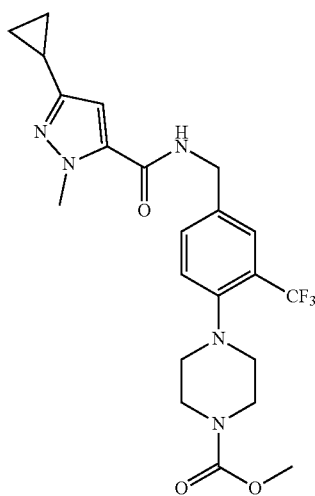 [SMILES: COC(=O)N1CCN(c2ccc(CNC(=O)c3cc(C4CC4)nn3C)cc2C(F)(F)F)CC1]
124
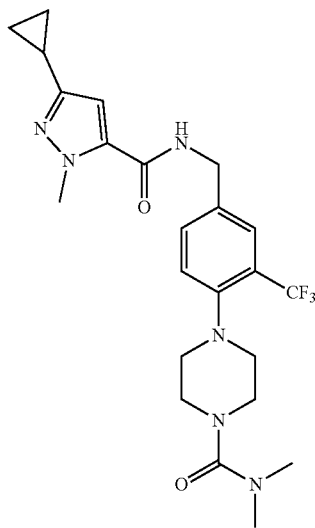 [SMILES: CN(C)C(=O)N1CCN(c2ccc(CNC(=O)c3cc(C4CC4)nn3C)cc2C(F)(F)F)CC1]
125

TABLE 1-continued
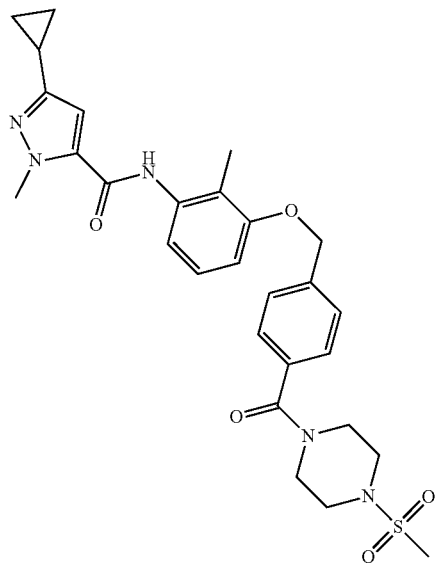 [SMILES: Cc1c(NC(=O)c2cc(C3CC3)nn2C)cccc1OCc1ccc(C(=O)N2CCN(S(C)(=O)=O)CC2)cc1]
126
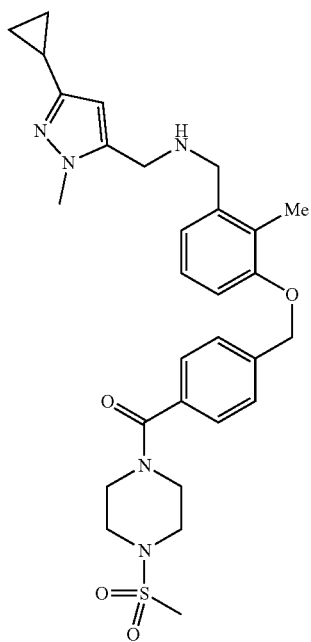 [SMILES: Cc1c(CNCc2cc(C3CC3)nn2C)cccc1OCc1ccc(C(=O)N2CCN(S(C)(=O)=O)CC2)cc1]
127
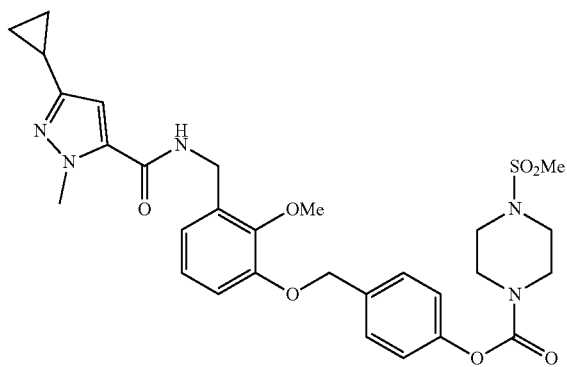 [SMILES: COc1c(CNC(=O)c2cc(C3CC3)nn2C)cccc1OCc1ccc(OC(=O)N2CCN(S(C)(=O)=O)CC2)cc1]
128

TABLE 1-continued
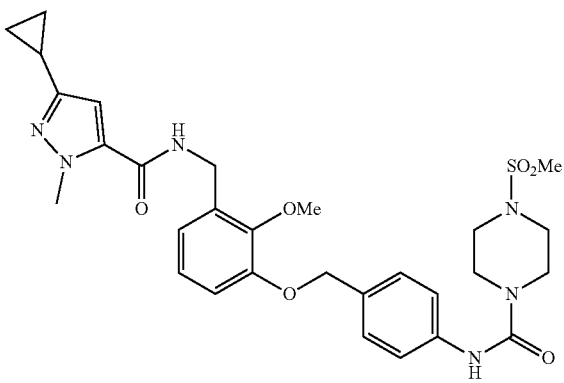 [SMILES: COc1c(CNC(=O)c2cc(C3CC3)nn2C)cccc1OCc1ccc(NC(=O)N2CCN(S(C)(=O)=O)CC2)cc1]
129
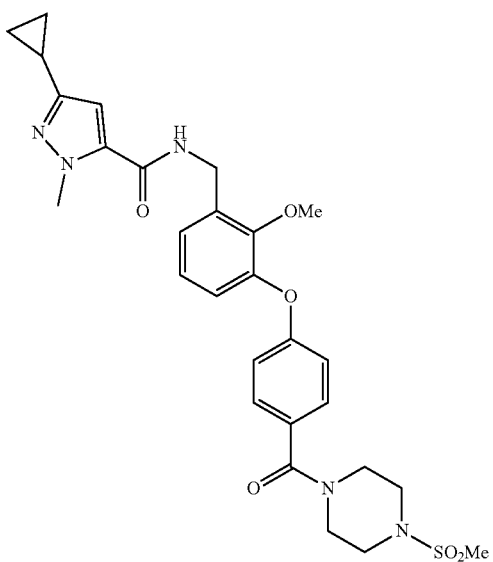 [SMILES: COc1c(CNC(=O)c2cc(C3CC3)nn2C)cccc1Oc1ccc(C(=O)N2CCN(S(C)(=O)=O)CC2)cc1]
130
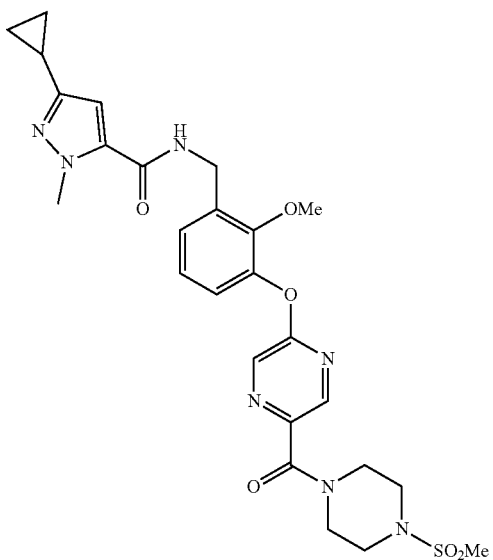 [SMILES: COc1c(CNC(=O)c2cc(C3CC3)nn2C)cccc1Oc1cnc(C(=O)N2CCN(S(C)(=O)=O)CC2)cn1]
131

TABLE 1-continued
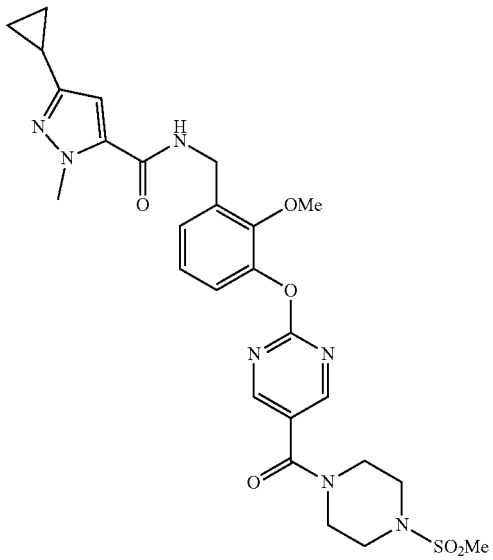 [SMILES: COc1c(CNC(=O)c2cc(C3CC3)nn2C)cccc1Oc1ncc(C(=O)N2CCN(S(C)(=O)=O)CC2)cn1]
132
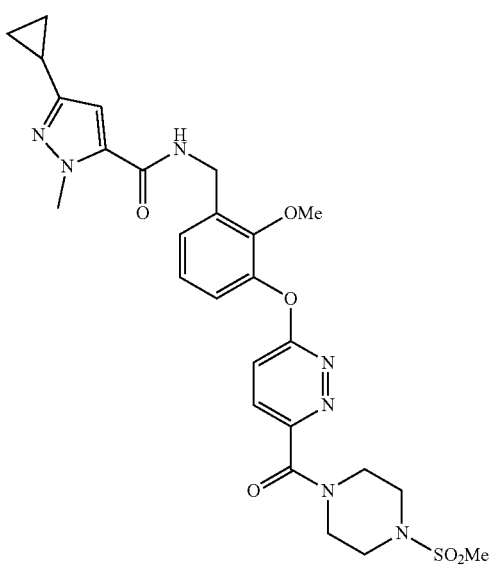 [SMILES: COc1c(CNC(=O)c2cc(C3CC3)nn2C)cccc1Oc1ccc(C(=O)N2CCN(S(C)(=O)=O)CC2)nn1]
133

TABLE 1-continued
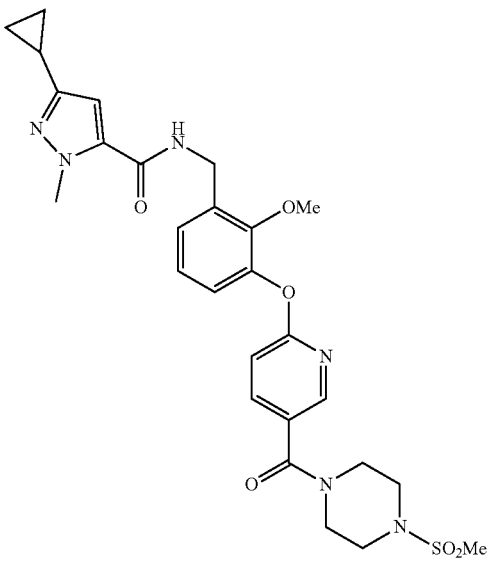
134
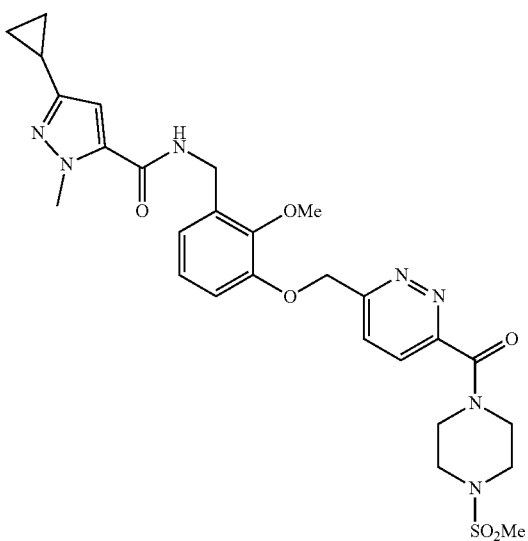 [SMILES: COc1c(CNC(=O)c2cc(C3CC3)nn2C)cccc1OCc1ccc(C(=O)N2CCN(S(C)(=O)=O)CC2)nn1]
135
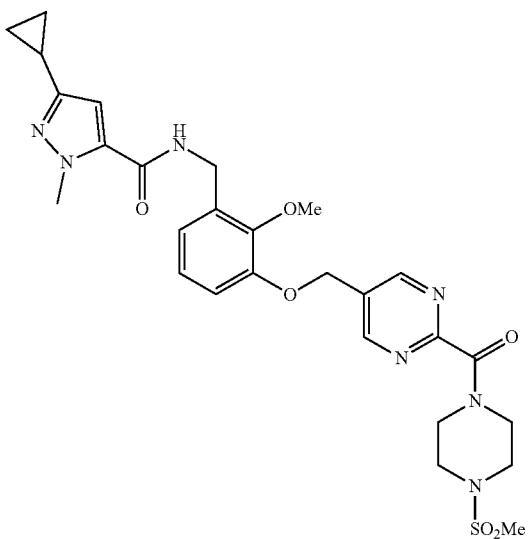 [SMILES: COc1c(CNC(=O)c2cc(C3CC3)nn2C)cccc1OCc1cnc(C(=O)N2CCN(S(C)(=O)=O)CC2)nc1]
136

TABLE 1-continued
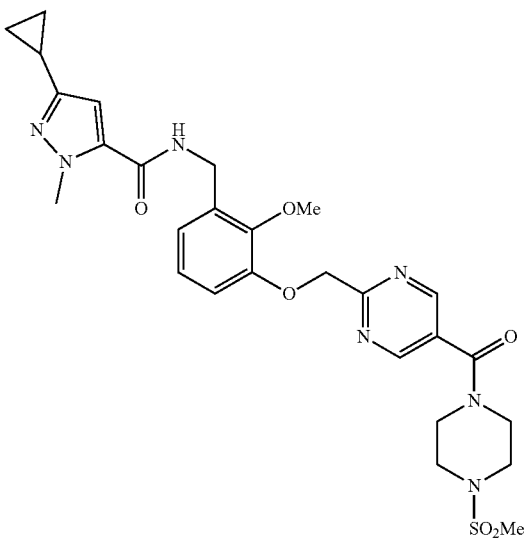 [SMILES: COc1c(CNC(=O)c2cc(C3CC3)nn2C)cccc1OCc1ncc(C(=O)N2CCN(S(C)(=O)=O)CC2)cn1]
137
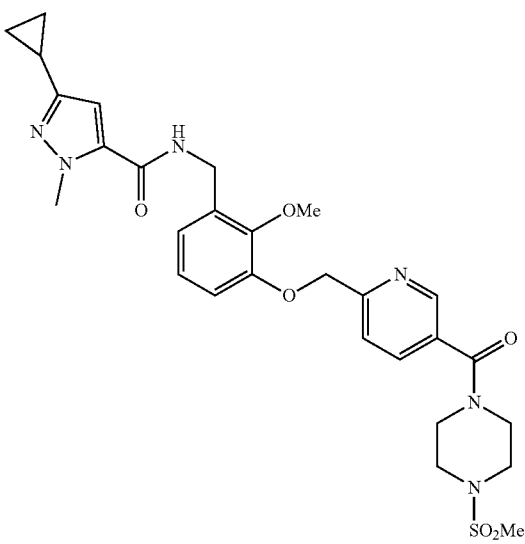 [SMILES: COc1c(CNC(=O)c2cc(C3CC3)nn2C)cccc1OCc1ccc(C(=O)N2CCN(S(C)(=O)=O)CC2)cn1]
138
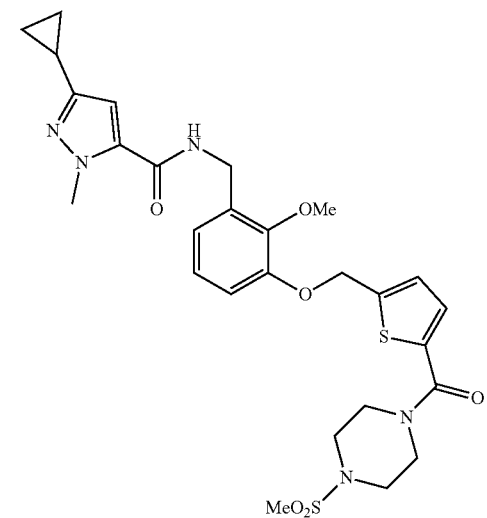 [SMILES: COc1c(CNC(=O)c2cc(C3CC3)nn2C)cccc1OCc1ccc(C(=O)N2CCN(S(C)(=O)=O)CC2)s1]
139

TABLE 1-continued
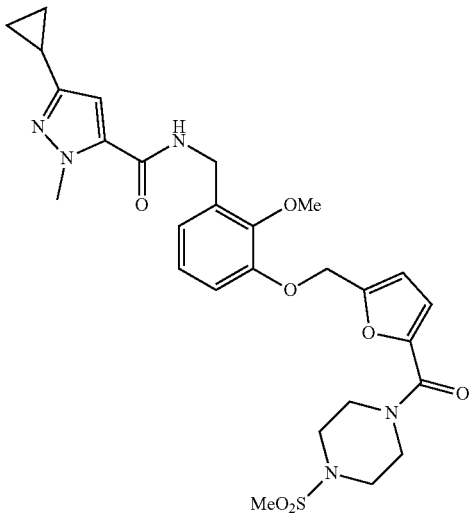 [SMILES: COc1c(CNC(=O)c2cc(C3CC3)nn2C)cccc1OCc1ccc(C(=O)N2CCN(S(C)(=O)=O)CC2)o1]
140
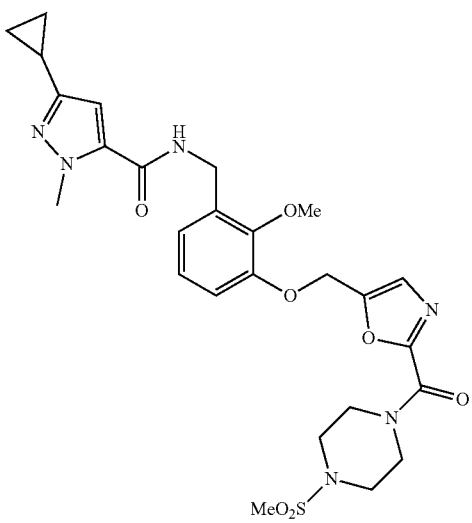 [SMILES: COc1c(CNC(=O)c2cc(C3CC3)nn2C)cccc1OCc1cnc(C(=O)N2CCN(S(C)(=O)=O)CC2)o1]
141
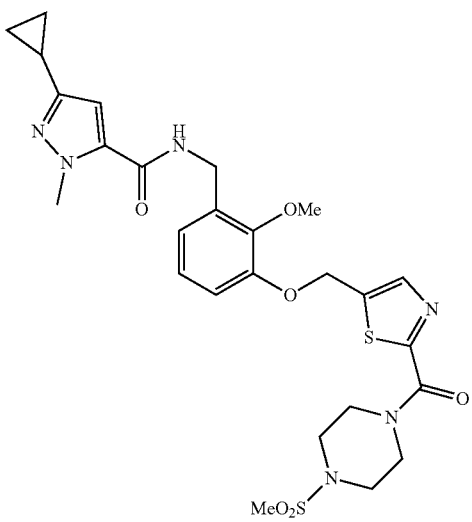 [SMILES: COc1c(CNC(=O)c2cc(C3CC3)nn2C)cccc1OCc1cnc(C(=O)N2CCN(S(C)(=O)=O)CC2)s1]
142

TABLE 1-continued
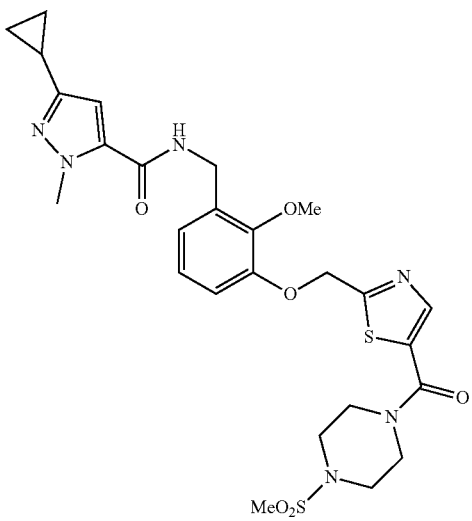
143
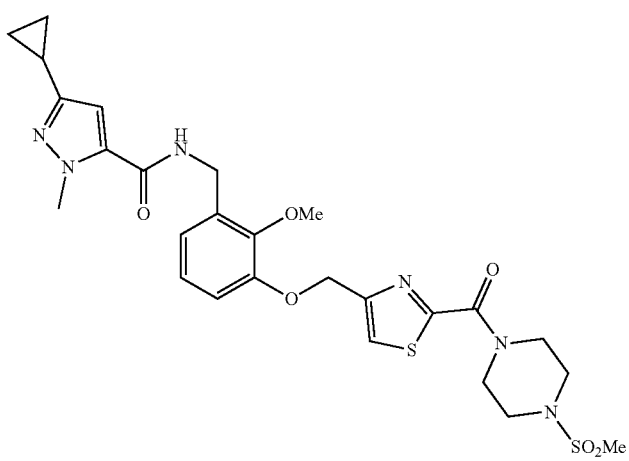 [SMILES: COc1c(CNC(=O)c2cc(C3CC3)nn2C)cccc1OCc1csc(C(=O)N2CCN(S(C)(=O)=O)CC2)n1]
144
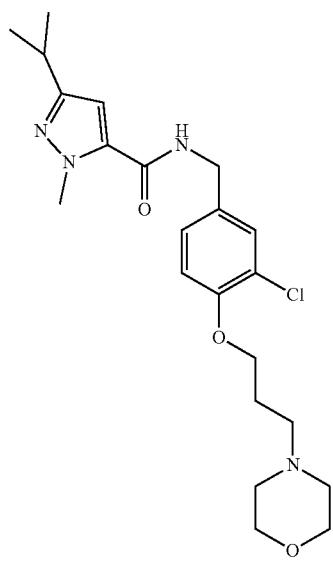 [SMILES: CC(C)c1cc(C(=O)NCc2ccc(OCCCN3CCOCC3)c(Cl)c2)n(C)n1]
145

TABLE 1-continued
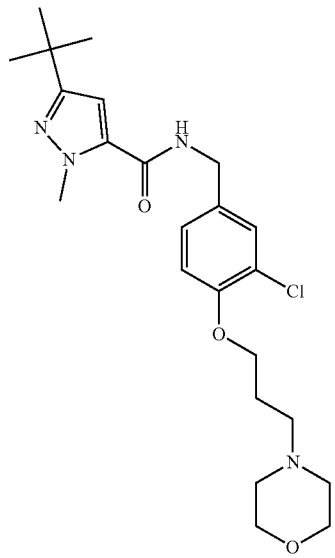 [SMILES: Cn1nc(C(C)(C)C)cc1C(=O)NCc1ccc(OCCCN2CCOCC2)c(Cl)c1]
146
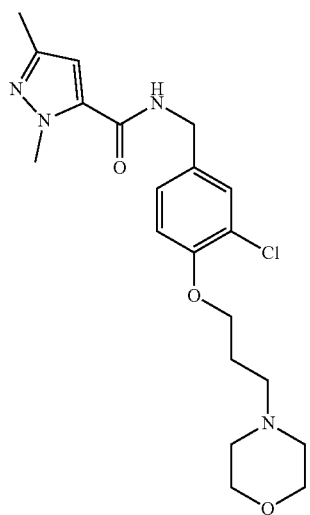 [SMILES: Cc1cc(C(=O)NCc2ccc(OCCCN3CCOCC3)c(Cl)c2)n(C)n1]
147
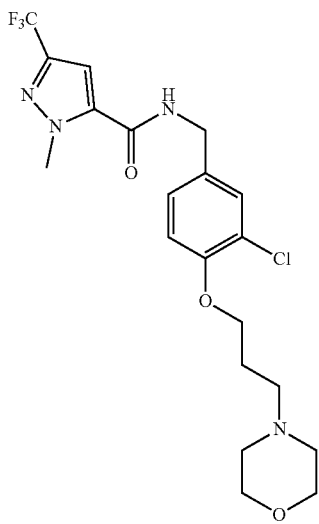 [SMILES: Cn1nc(C(F)(F)F)cc1C(=O)NCc1ccc(OCCCN2CCOCC2)c(Cl)c1]
148

TABLE 1-continued
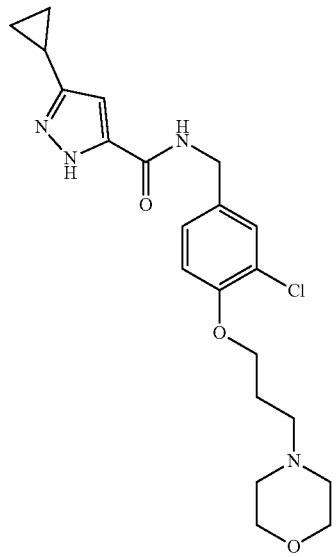 [SMILES: O=C(NCc1ccc(OCCCN2CCOCC2)c(Cl)c1)c1cc(C2CC2)n[nH]1]
149
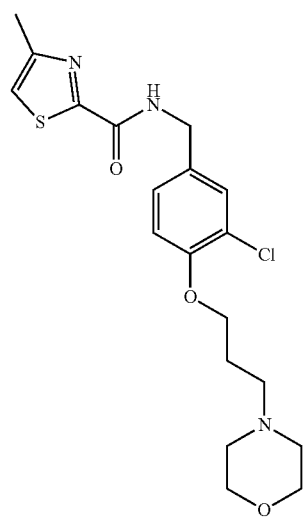 [SMILES: Cc1csc(C(=O)NCc2ccc(OCCCN3CCOCC3)c(Cl)c2)n1]
150
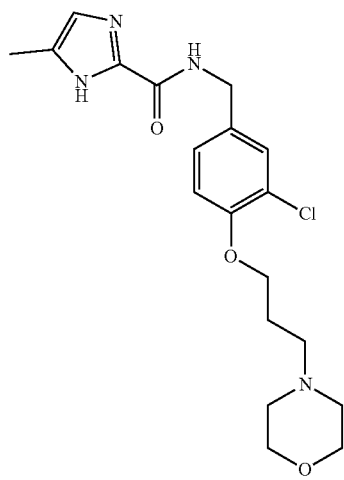 [SMILES: Cc1cnc(C(=O)NCc2ccc(OCCCN3CCOCC3)c(Cl)c2)[nH]1]
151

TABLE 1-continued
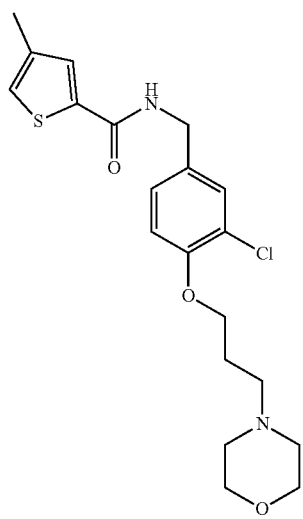 [SMILES: Cc1csc(C(=O)NCc2ccc(OCCCN3CCOCC3)c(Cl)c2)c1]
152
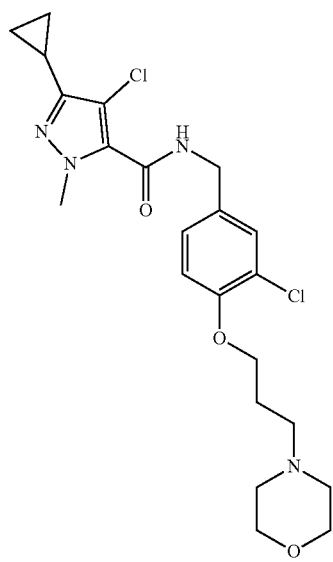 [SMILES: Cn1nc(C2CC2)c(Cl)c1C(=O)NCc1ccc(OCCCN2CCOCC2)c(Cl)c1]
153
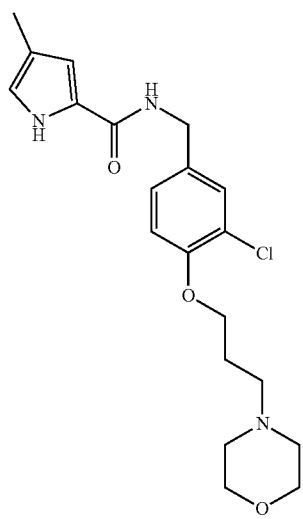 [SMILES: Cc1c[nH]c(C(=O)NCc2ccc(OCCCN3CCOCC3)c(Cl)c2)c1]
154

TABLE 1-continued
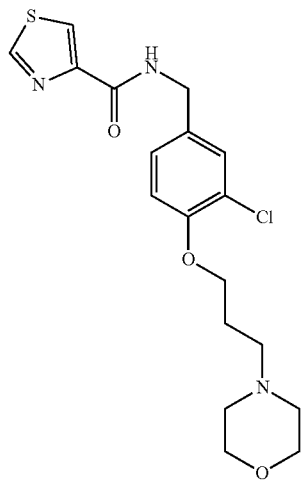 [SMILES: O=C(NCc1ccc(OCCCN2CCOCC2)c(Cl)c1)c1cscn1]
155
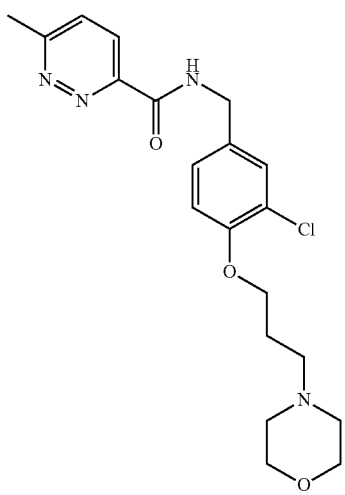 [SMILES: Cc1ccc(C(=O)NCc2ccc(OCCCN3CCOCC3)c(Cl)c2)nn1]
156
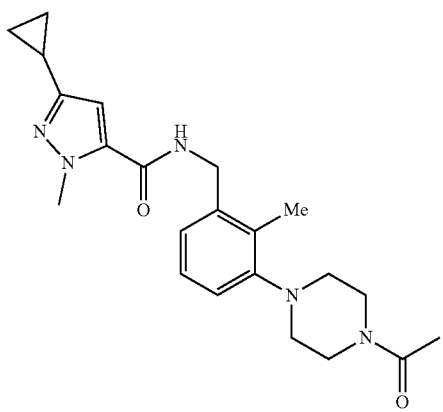 [SMILES: CC(=O)N1CCN(c2cccc(CNC(=O)c3cc(C4CC4)nn3C)c2C)CC1]
156

TABLE 1-continued
| | |
|---|---|
| 157 | 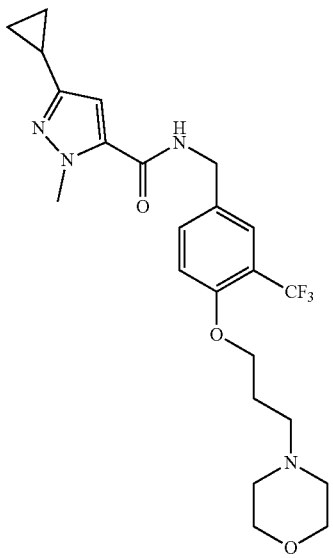 [SMILES: Cn1nc(C2CC2)cc1C(=O)NCc1ccc(OCCCN2CCOCC2)c(C(F)(F)F)c1] |
| 158 | 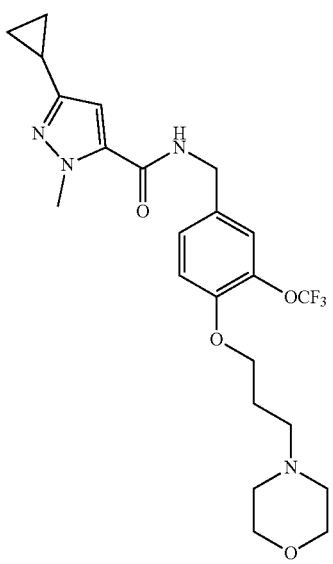 [SMILES: Cn1nc(C2CC2)cc1C(=O)NCc1ccc(OCCCN2CCOCC2)c(OC(F)(F)F)c1] |
| 159 | 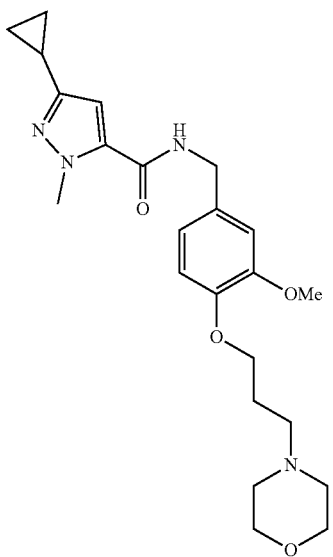 [SMILES: COc1cc(CNC(=O)c2cc(C3CC3)nn2C)ccc1OCCCN1CCOCC1] |

TABLE 1-continued
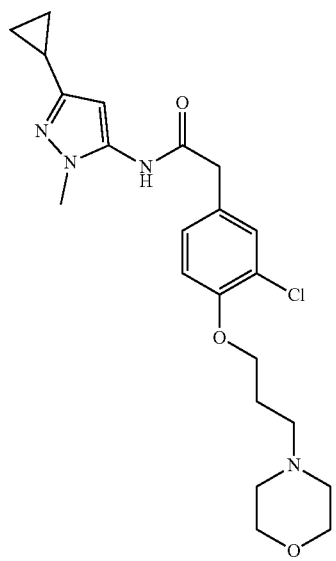 [SMILES: Cn1nc(C2CC2)cc1NC(=O)Cc1ccc(OCCCN2CCOCC2)c(Cl)c1]
160
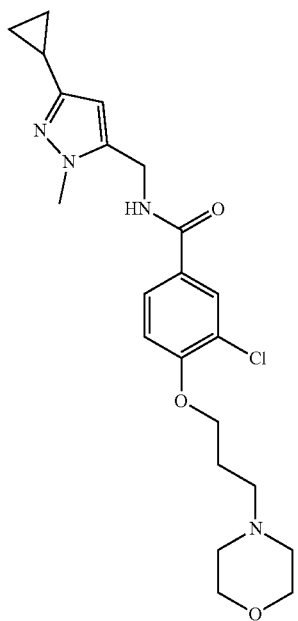 [SMILES: Cn1nc(C2CC2)cc1CNC(=O)c1ccc(OCCCN2CCOCC2)c(Cl)c1]
161

TABLE 1-continued
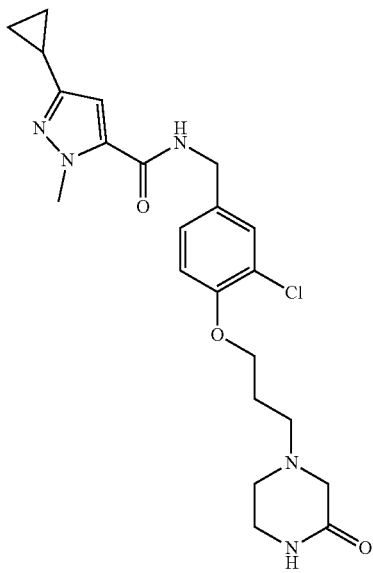 [SMILES: Cn1nc(C2CC2)cc1C(=O)NCc1ccc(OCCCN2CCNC(=O)C2)c(Cl)c1]
162
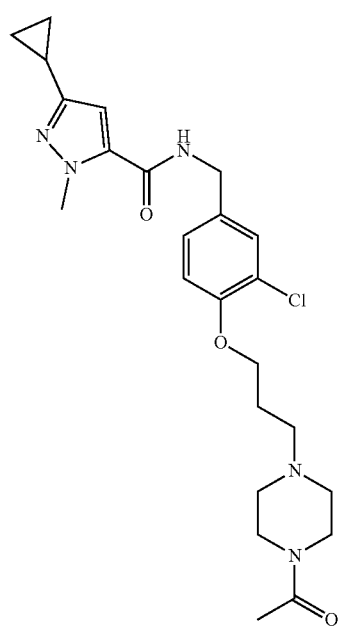 [SMILES: CC(=O)N1CCN(CCCOc2ccc(CNC(=O)c3cc(C4CC4)nn3C)cc2Cl)CC1]
163

TABLE 1-continued
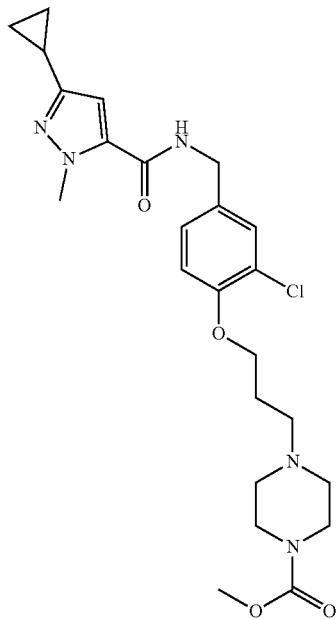 [SMILES: COC(=O)N1CCN(CCCOc2ccc(CNC(=O)c3cc(C4CC4)nn3C)cc2Cl)CC1]
164
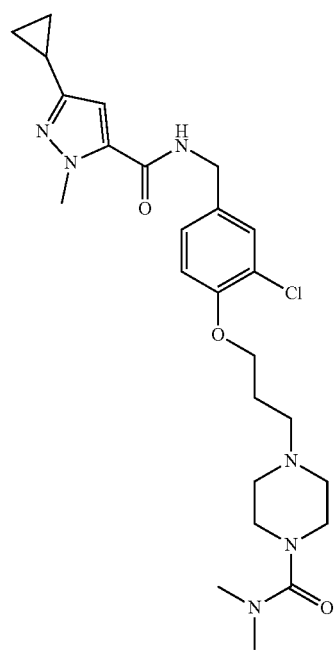 [SMILES: CN(C)C(=O)N1CCN(CCCOc2ccc(CNC(=O)c3cc(C4CC4)nn3C)cc2Cl)CC1]
165

TABLE 1-continued
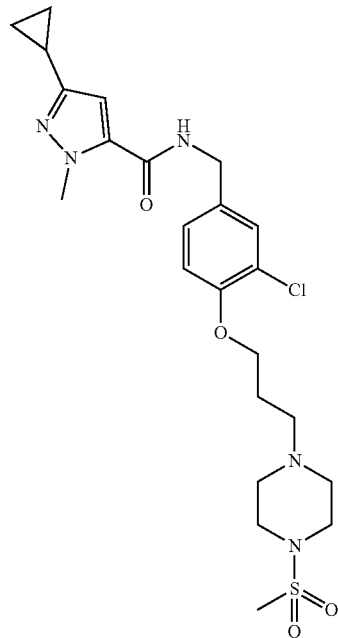 [SMILES: Cn1nc(C2CC2)cc1C(=O)NCc1ccc(OCCCN2CCN(S(C)(=O)=O)CC2)c(Cl)c1]
166
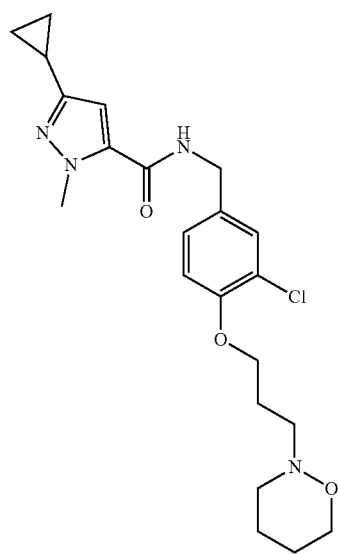 [SMILES: Cn1nc(C2CC2)cc1C(=O)NCc1ccc(OCCCN2CCCCO2)c(Cl)c1]
167

TABLE 1-continued
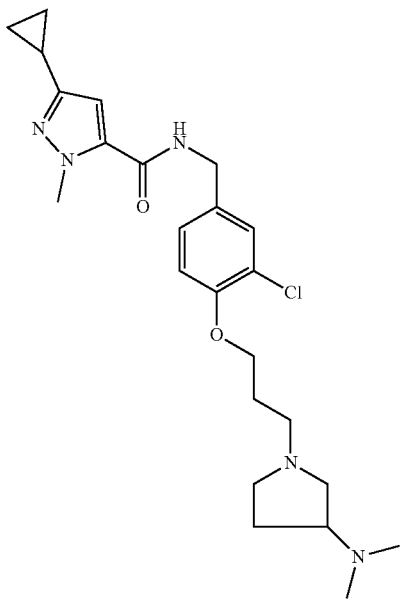 [SMILES: CN(C)C1CCN(CCCOc2ccc(CNC(=O)c3cc(C4CC4)nn3C)cc2Cl)C1]
168
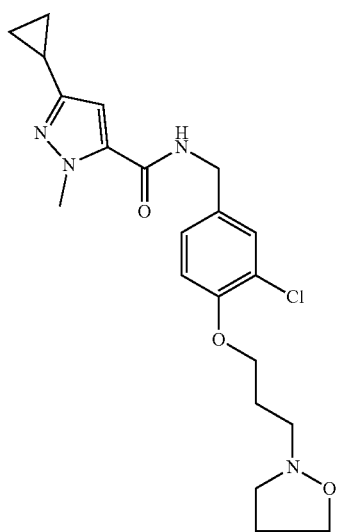 [SMILES: Cn1nc(C2CC2)cc1C(=O)NCc1ccc(OCCCN2CCCO2)c(Cl)c1]
169
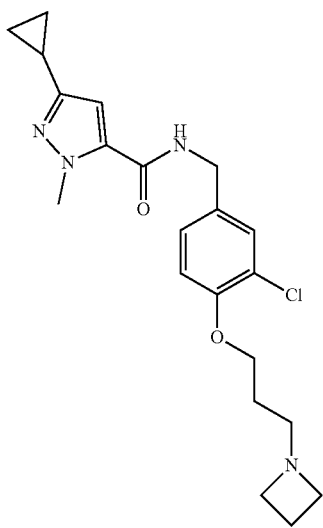 [SMILES: Cn1nc(C2CC2)cc1C(=O)NCc1ccc(OCCCN2CCC2)c(Cl)c1]
170

TABLE 1-continued
171
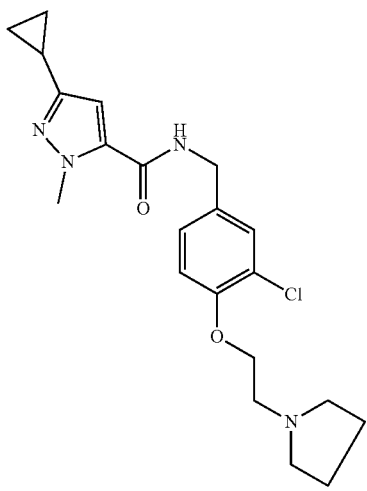 [SMILES: Cn1nc(C2CC2)cc1C(=O)NCc1ccc(OCCN2CCCC2)c(Cl)c1]
172
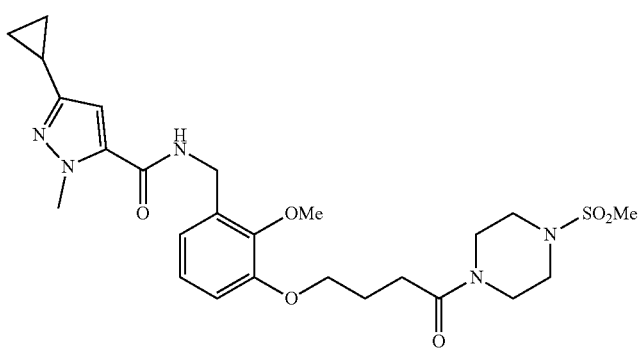 [SMILES: COc1c(CNC(=O)c2cc(C3CC3)nn2C)cccc1OCCCC(=O)N1CCN(S(C)(=O)=O)CC1]
173
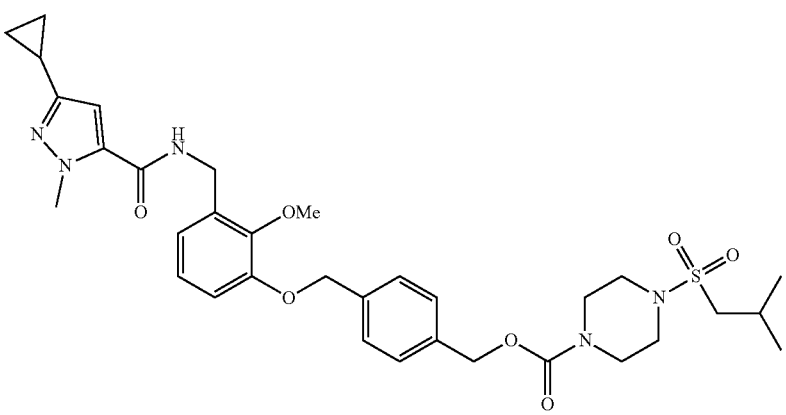 [SMILES: COc1c(CNC(=O)c2cc(C3CC3)nn2C)cccc1OCc1ccc(COC(=O)N2CCN(S(=O)(=O)CC(C)C)CC2)cc1]
174
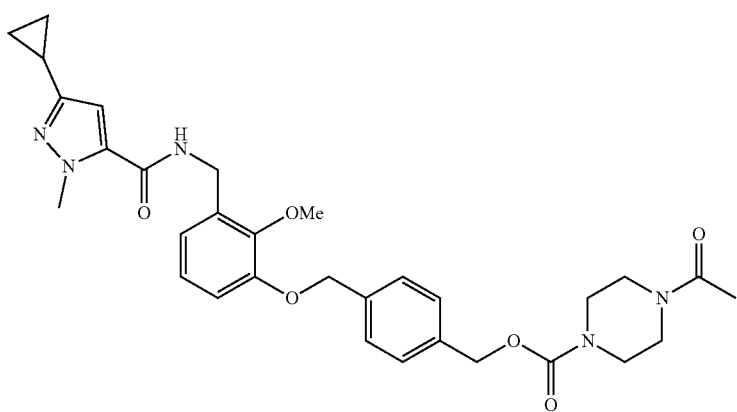 [SMILES: COc1c(CNC(=O)c2cc(C3CC3)nn2C)cccc1OCc1ccc(COC(=O)N2CCN(C(C)=O)CC2)cc1]

TABLE 1-continued

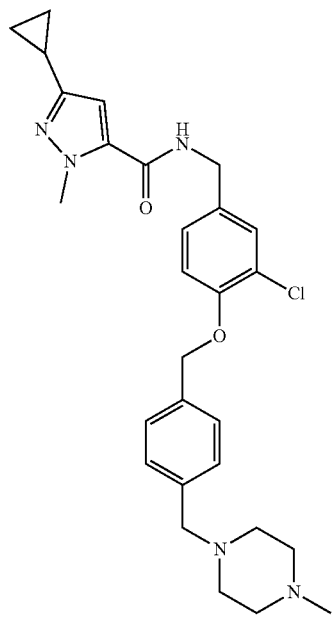 [SMILES: CN1CCN(Cc2ccc(COc3ccc(CNC(=O)c4cc(C5CC5)nn4C)cc3Cl)cc2)CC1]

175

The compounds above can be made by well know procedures some of which are exemplified in the experimental section.

Compositions and Methods of Administration

The compositions provided herein contain therapeutically effective amounts of one or more of the compounds provided herein that are useful in the prevention, treatment, or amelioration of one or more of the symptoms of diseases or disorders described herein and a vehicle. Vehicles suitable for administration of the compounds provided herein include any such carriers known to those skilled in the art to be suitable for the particular mode of administration. In addition, the compounds may be formulated as the sole active ingredient in the composition or may be combined with other active ingredients.

The compositions contain one or more compounds provided herein. The compounds are, in some embodiments, formulated into suitable preparations such as solutions, suspensions, tablets, dispersible tablets, pills, capsules, powders, sustained release formulations or elixirs, for oral administration or in sterile solutions or suspensions for parenteral administration, as well as topical administration, transdermal administration and oral inhalation via nebulizers, pressurized metered dose inhalers and dry powder inhalers. In some embodiments, the compounds described above are formulated into compositions using techniques and procedures well known in the art (see, e.g., Ansel, Introduction to Pharmaceutical Dosage Forms, Seventh Edition (1999)).

In the compositions, effective concentrations of one or more compounds or derivatives thereof is (are) mixed with a suitable vehicle. The compounds may be derivatized as the corresponding salts, esters, enol ethers or esters, acetals, ketals, orthoesters, hemiacetals, hemiketals, acids, bases, solvates, ion-pairs, hydrates or prodrugs prior to formulation, as described above. The concentrations of the compounds in the compositions are effective for delivery of an amount, upon administration that treats, leads to prevention, or amelioration of one or more of the symptoms of diseases or disorders described herein. In some embodiments, the compositions are formulated for single dosage administration. To formulate a composition, the weight fraction of a compound is dissolved, suspended, dispersed or otherwise mixed in a selected vehicle at an effective concentration such that the treated condition is relieved, prevented, or one or more symptoms are ameliorated.

The active compound is included in the vehicle in an amount sufficient to exert a therapeutically useful effect in the absence of undesirable side effects on the patient treated. The therapeutically effective concentration may be predicted empirically by testing the compounds in in vitro and in vivo systems well known to those of skill in the art and then extrapolated therefrom for dosages for humans. Human doses are then typically fine-tuned in clinical trials and titrated to response.

The concentration of active compound in the composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders as described herein.

In instances in which the compounds exhibit insufficient solubility, methods for solubilizing compounds may be used such as use of liposomes, prodrugs, complexation/chelation, nanoparticles, or emulsions or tertiary templating. Such methods are known to those of skill in this art, and include, but are not limited to, using co-solvents, such as dimethylsulfoxide (DMSO), using surfactants or surface modifiers, such as TWEEN®, complexing agents such as cyclodextrin or dissolution by enhanced ionization (i.e., dissolving in aqueous sodium bicarbonate). Derivatives of the compounds, such as prodrugs of the compounds may also be used in formulating effective compositions.

Upon mixing or addition of the compound(s), the resulting mixture may be a solution, suspension, emulsion or the like. The form of the resulting mixture depends upon a number of factors, including the intended mode of administration and the solubility of the compound in the selected vehicle. The effective concentration is sufficient for ameliorating the symptoms of the disease, disorder or condition treated and may be empirically determined.

The compositions are provided for administration to humans and animals in indication appropriate dosage forms, such as dry powder inhalers (DPIs), pressurized metered dose inhalers (pMDIs), nebulizers, tablets, capsules, pills, sublingual tapes/bioerodible strips, tablets or capsules, powders, granules, lozenges, lotions, salves, suppositories, fast melts, transdermal patches or other transdermal application devices/preparations, sterile parenteral solutions or suspensions, and oral solutions or suspensions, and oil-water emulsions containing suitable quantities of the compounds or derivatives thereof. The therapeutically active compounds and derivatives thereof are, in some embodiments, formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required vehicle. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid compositions can, for example, be prepared by dissolving, dispersing, or otherwise mixing an active compound as defined above and optional adjuvants in a vehicle, such as, for example, water, saline, aqueous dextrose, glycerol, glycols, ethanol, and the like, to thereby form a solution or suspension, colloidal dispersion, emulsion or liposomal formulation. If desired, the composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975 or later editions thereof.

Dosage forms or compositions containing active ingredient in the range of 0.005% to 100% with the balance made up from vehicle or carrier may be prepared. Methods for preparation of these compositions are known to those skilled in the art. The contemplated compositions may contain 0.001%-100% active ingredient, in one embodiment 0.1-95%, in another embodiment 0.4-10%.

In certain embodiments, the compositions are lactose-free compositions containing excipients that are well known in the art and are listed, for example, in the U.S. Pharmacopeia (USP) 25-NF20 (2002). In general, lactose-free compositions contain active ingredients, a binder/filler, and a lubricant in compatible amounts. Particular lactose-free dosage forms contain active ingredients, microcrystalline cellulose, pre-gelatinized starch, and magnesium stearate.

Further provided are anhydrous compositions and dosage forms comprising active ingredients, since water can facilitate the degradation of some compounds. For example, the addition of water (e.g., 5%) is widely accepted as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions.

An anhydrous composition should be prepared and stored such that its anhydrous nature is maintained. Accordingly, anhydrous compositions are generally packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Oral dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms such as for example, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an enteric coating; a film coating agent and modified release agent. Examples of binders include microcrystalline cellulose, methyl paraben, polyalkyleneoxides, gum tragacanth, glucose solution, acacia mucilage, gelatin solution, molasses, polyvinylpyrrolidine, povidone, crospovidones, sucrose and starch and starch derivatives. Lubricants include talc, starch, magnesium/calcium stearate, lycopodium and stearic acid. Diluents include, for example, lactose, sucrose, trehalose, lysine, leucine, lecithin, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate and advanced coloring or anti-forgery color/opalescent additives known to those skilled in the art. Sweetening agents include sucrose, lactose, mannitol and artificial sweetening agents such as saccharin and any number of spray dried flavors. Flavoring agents include natural flavors extracted from plants such as fruits and synthetic blends of compounds which produce a pleasant sensation or mask unpleasant taste, such as, but not limited to peppermint and methyl salicylate. Wetting agents include propylene glycol monostearate, sorbitan monooleate, diethylene glycol monolaurate and polyoxyethylene lauryl ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. Modified release agents include polymers such as the Eudragit® series and cellulose esters.

The compound, or derivative thereof, can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, $H_2$ blockers, and diuretics. The active ingredient is a compound or derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Vehicles used in elixirs include solvents. Syrups are concentrated aqueous solutions of a sugar, for example, sucrose, and may contain a preservative. An emulsion is a two-phase system in which one liquid is dispersed in the form of small globules throughout another liquid. Carriers used in emulsions are non-aqueous liquids, emulsifying agents and preservatives. Suspensions use suspending agents and preservatives. Acceptable substances used in non-effervescent granules, to be reconstituted into a liquid oral dosage form, include diluents, sweeteners and wetting agents. Acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example, propylene carbonate, vegetable oils or triglycerides, is in some embodiments encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a liquid vehicle, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or polyalkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including an acetal. Alcohols used in these formulations are any water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in some embodiments characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Vehicles used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (Tween® 80). A sequestering or chelating agent of metal ions includes EDTA. Carriers also include ethyl alcohol, polyethylene glycol and propylene glycol for water miscible vehicles; and sodium hydroxide, hydrochloric acid, citric acid or lactic acid for pH adjustment.

The concentration of compound is adjusted so that an injection provides an effective amount to produce the desired pharmacological effect. The exact dose depends on the age, weight, body surface area and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In some embodiments, a therapeutically effective dosage is formulated to contain a concentration of at least about 0.01% w/w up to about 90% w/w or more, in certain embodiments more than 0.1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 and 6,740,634. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In some embodiments, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In other embodiments, polymeric materials can be used. In other embodiments, a controlled release system can be placed in proximity of the therapeutic target, i.e., thus requiring only a fraction of the systemic dose (see, e.g., Goodson, *Medical Applications of Controlled Release*, vol. 2, pp. 115-138 (1984)). In some embodiments, a controlled release device is introduced into a subject in proximity of the site of inappropriate immune activation or a tumor. Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a derivative thereof, in a suitable solvent. The solvent may contain an excipient which improves the stability or other pharmacological component of the powder or reconstituted solution, prepared from the powder. Excipients that may be used include, but are not limited to, an antioxidant, a buffer and a bulking agent. In some embodiments, the excipient is selected from dextrose, sorbitol, fructose, corn syrup, xylitol, glycerin, glucose, sucrose and other suitable agent. The solvent may contain a buffer, such as citrate, sodium or potassium phosphate or other such buffer known to those of skill in the art at, at about neutral pH. Subsequent sterile filtration of the solution followed by lyophilization under standard conditions known to those of skill in the art provides the desired formulation. In some embodiments, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carriers. The precise amount depends upon the selected compound. Such amount can be empirically determined.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in some embodiments, have mass median geometric diameters of less than 5 microns, in other embodiments less than 10 microns.

Oral inhalation formulations of the compounds or derivatives suitable for inhalation include metered dose inhalers, dry powder inhalers and liquid preparations for administration from a nebulizer or metered dose liquid dispensing system. For both metered dose inhalers and dry powder inhalers, a crystalline form of the compounds or derivatives is the preferred physical form of the drug to confer longer product stability.

In addition to particle size reduction methods known to those skilled in the art, crystalline particles of the compounds or derivatives can be generated using supercritical fluid processing which offers significant advantages in the production of such particles for inhalation delivery by producing respirable particles of the desired size in a single step. (e.g., International Publication No. WO2005/025506). A controlled particle size for the microcrystals can be selected to ensure that a significant fraction of the compounds or derivatives is deposited in the lung. In some embodiments, these particles have a mass median aerodynamic diameter of about 0.1 to about 10 microns, in other embodiments, about 1 to about 5 microns and still other embodiments, about 1.2 to about 3 microns.

Inert and non-flammable HFA propellants are selected from HFA 134a (1,1,1,2-tetrafluoroethane) and HFA 227e (1,1,1,2,3,3,3-heptafluoropropane) and provided either alone or as a ratio to match the density of crystal particles of the compounds or derivatives. A ratio is also selected to ensure that the product suspension avoids detrimental sedimentation or cream (which can precipitate irreversible agglomeration) and instead promote a loosely flocculated system, which is easily dispersed when shaken. Loosely fluctuated systems are well regarded to provide optimal stability for pMDI canisters. As a result of the formulation|s| properties, the formulation contained no ethanol and no surfactants/stabilizing agents.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other excipients can also be administered.

For nasal administration, the preparation may contain an esterified phosphonate compound dissolved or suspended in a liquid carrier, in particular, an aqueous carrier, for aerosol application. The carrier may contain solubilizing or suspending agents such as propylene glycol, surfactants, absorption enhancers such as lecithin or cyclodextrin, or preservatives.

Solutions, particularly those intended for ophthalmic use, may be formulated as 0.01%-10% isotonic solutions, pH about 5-7.4, with appropriate salts.

Other routes of administration, such as transdermal patches, including iontophoretic and electrophoretic devices, and rectal administration, are also contemplated herein.

Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433 and 5,860,957.

For example, dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm. Tablets and capsules for rectal administration are manufactured using the same substance and by the same methods as for formulations for oral administration.

The compounds provided herein, or derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In some embodiments, liposomal suspensions, including tissue-targeted liposomes, such as tumor-targeted liposomes, may also be suitable as carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down phosphatidyl choline and phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The compounds or derivatives may be packaged as articles of manufacture containing packaging material, a compound or derivative thereof provided herein, which is effective for treatment, prevention or amelioration of one or more symptoms of the diseases or disorders, supra, within the packaging material, and a label that indicates that the compound or composition or derivative thereof, is used for the treatment, prevention or amelioration of one or more symptoms of the diseases or disorders, supra.

The articles of manufacture provided herein contain packaging materials. Packaging materials for use in packaging products are well known to those of skill in the art. See, e.g., U.S. Pat. Nos. 5,323,907, 5,052,558 and 5,033,252. Examples of packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder described herein.

Dosages

For use to treat or prevent infectious disease, the compounds described herein, or pharmaceutical compositions thereof, are administered or applied in a therapeutically effective amount. In human therapeutics, the physician will determine the dosage regimen that is most appropriate according to a preventive or curative treatment and according to the age, weight, stage of the disease and other factors specific to the subject to be treated. The amount of active ingredient in the formulations provided herein, which will be effective in the prevention or treatment of an infectious disease will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the infection, the route of administration, as well as age, body, weight, response, and the past medical history of the subject.

Exemplary doses of a formulation include milligram or microgram amounts of the active compound per kilogram of subject (e.g., from about 1 microgram per kilogram to about 50 milligrams per kilogram, from about 10 micrograms per kilogram to about 30 milligrams per kilogram, from about 100 micrograms per kilogram to about 10 milligrams per kilogram, or from about 100 micrograms per kilogram to about 5 milligrams per kilogram).

In some embodiments, a therapeutically effective dosage should produce a serum concentration of active ingredient of from about 0.001 ng/ml to about 50-200 µg/ml. The compositions, in other embodiments, should provide a dosage of from about 0.0001 mg to about 70 mg of compound per kilogram of body weight per day. Dosage unit forms are prepared to provide from about 0.01 mg, 0.1 mg or 1 mg to about 500 mg, 1000 mg or 5000 mg, and in some embodiments from about 10 mg to about 500 mg of the active ingredient or a combination of essential ingredients per dosage unit form.

The active ingredient may be administered at once or may be divided into a number of smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that is lethal to 50% of a cell culture), or the $IC_{100}$ as determined in cell culture (i.e., the concentration of compound that is lethal to 100% of a cell culture). Such information can be used to more accurately determine useful doses in humans.

Initial dosages can also be estimated from in vivo data (e.g., animal models) using techniques that are well known in the art. One of ordinary skill in the art can readily optimize administration to humans based on animal data.

Alternatively, initial dosages can be determined from the dosages administered of known agents by comparing the $IC_{50}$, MIC and/or $I_{100}$ of the specific compound disclosed herein with that of a known agent and adjusting the initial dosages accordingly. The optimal dosage may be obtained from these initial values by routine optimization In cases of local administration or selective uptake, the effective local concentration compound used may not be related to plasma concentration. One of skill in the art will be able to optimize therapeutically effective local dosages without undue experimentation.

Ideally, a therapeutically effective dose of the compounds described herein will provide therapeutic benefit without causing substantial toxicity. Toxicity of compounds can be determined using standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in subjects. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patients condition (See, e.g., Fingl et al., 1975, *In: The Pharmacological Basis of Therapeutics*, Ch. 1, p.1).

The therapy may be repeated intermittently. In certain embodiments, administration of the same formulation provided herein may be repeated and the administrations may be separated by at least 1 day, 2 days, 3 days, 5 days, 10 days, 15 days, 30 days, 45 days, 2 months, 75 days, 3 months, or 6 months.

Methods of Use of the Compounds and Compositions

Methods of treating, preventing, or ameliorating symptoms of medical disorders such as, for example, a variety of pan respiratory antiviral infections including specifically coronaviruses and influenza viruses and associated diseases with the disclosed compounds and pharmaceutical compositions are described herein. Also described herein are methods of using the disclosed compounds and pharmaceutical compositions as antivirals agents. In practicing the methods, therapeutically effective amounts of the compounds or compositions, described herein, supra, are administered to the patient with the disorder or condition.

Combination Therapy

The compounds and compositions disclosed herein may also be used in combination with one or more other active ingredients. In certain embodiments, the compounds may be administered in combination, or sequentially, with another therapeutic agent. Such other therapeutic agents include those known for treatment, prevention, or amelioration of one or more symptoms associated with a variety of pan respiratory antiviral infections and diseases. Other therapeutic agents include those known for treatment, prevention, or amelioration of one or more symptoms of viral infection.

It should be understood that any suitable combination of the compounds and compositions provided herein with one or more of the above therapeutic agents and optionally one or more further pharmacologically active substances are considered to be within the scope of the present disclosure. In some embodiments, the compounds and compositions provided herein are administered prior to or subsequent to the one or more additional active ingredients.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims.

All publications and patents cited herein are incorporated by reference in their entirety.

The following examples are provided for illustrative purposes only and are not intended to limit the scope of the invention.

EXAMPLES

Scheme 1 illustrates the preparation of compound 205.

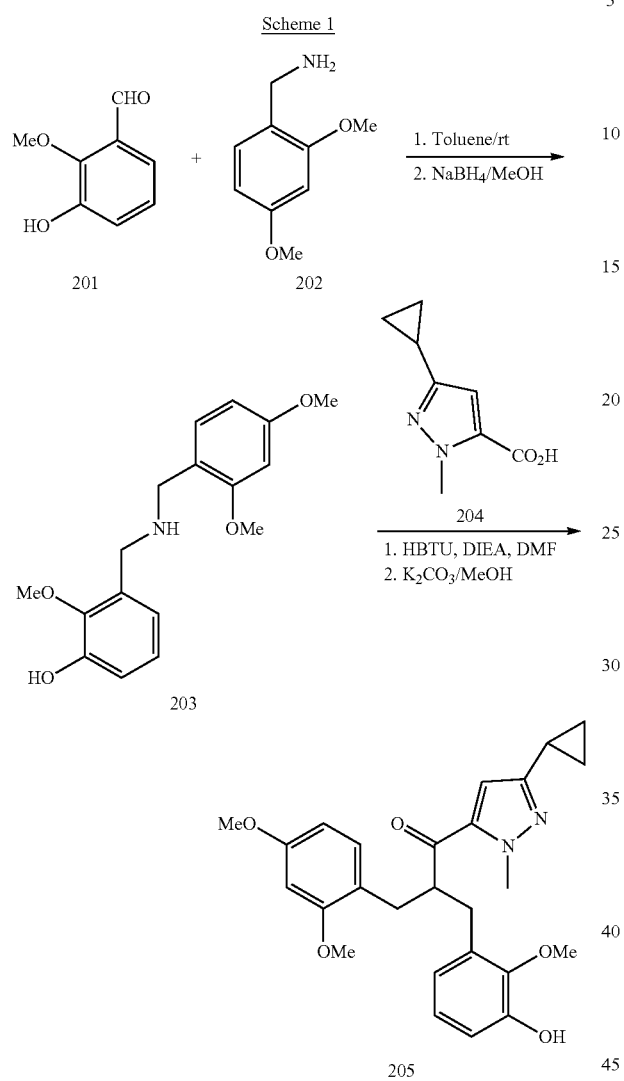

Preparation of Amine 203

To a solution of aldehyde 201 (10 g, 65.79 mmole, 1.0 eq) in toluene was added 2,4-dimethoxybenzyl amine 202 (10.99 g, 65.79 mmol, 1.0 eq) and the reaction mixture was stirred at room temperature for 24 h. Solvent was removed and the residue was taken in MeOH and cooled using an ice bath. Then sodium borohydride (4.97 g, 131.58 mmol, 2.0 eq) was added slowly and the reaction mixture was stirred at room temperature for 12 h. Solvent was removed and residue was taken in ethyl acetate and then saturated NaHCO$_3$ was added and stirred for 1 h. The organic layer was separated, dried (MgSO$_4$) and solvent was removed to give the amine 203, which was used in the next step without further purification.

Preparation of Amide 205

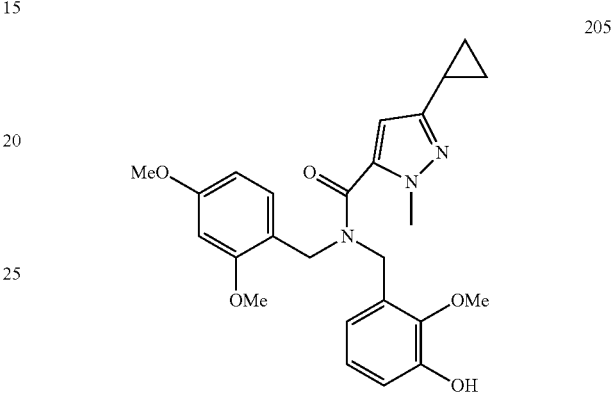

To a solution of the crude amine 203 (5.0 g, 19.1 mmol, 1.0 eq) in DMF (25 mL) was added acid 204 (3.17 g, 19.1 mmol, 1.0 eq), HBTU (8.7 g, 22.92 mmol, 1.2 eq)l, and DIEA (12.32 g, 95.5 mmol, 5.0 eq) and the reaction mixture was stirred at room temperature for 12 h. The reaction mixture was then diluted with EtOAc and washed with 10% aqueous HCl (1×), saturated NaHCO$_3$ (1×) and water (3×). The organic layer was collected, dried (MgSO$_4$) and evaporated to give a residue, which was dissolved in MeOH and then K$_2$CO$_3$ (2.64 g. 19.1 mmol, 1.0 eq) was added and stirred at room temperature for 12 h. The solvent was removed and the residue was dissolved in ethyl acetate and washed with 10% HCl (1×). The organic layer was separated, dried and the solvent was removed to give crude material, which was purified by column chromatography (EtOAc/Hexane) to give compound 205. Mass Spectrum (LCMS, ESI Pos.) Calculated for C$_{25}$H$_{30}$N$_3$O$_5$: 452.0 (M$^+$H), found 452.0.

Scheme 2 illustrate preparation of piperazine 208.

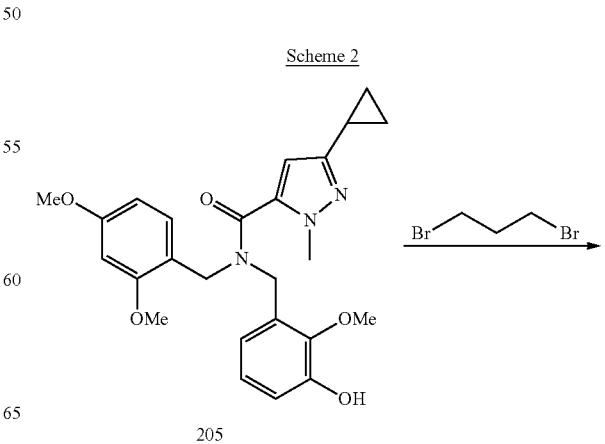

-continued

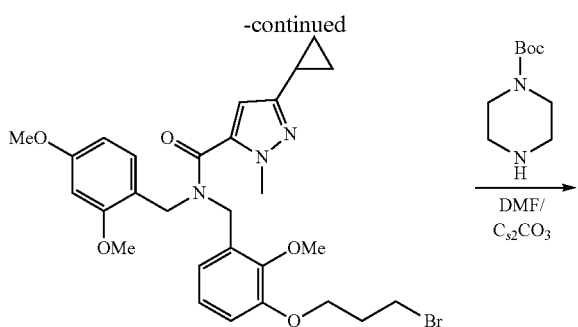

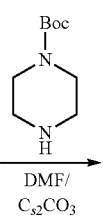

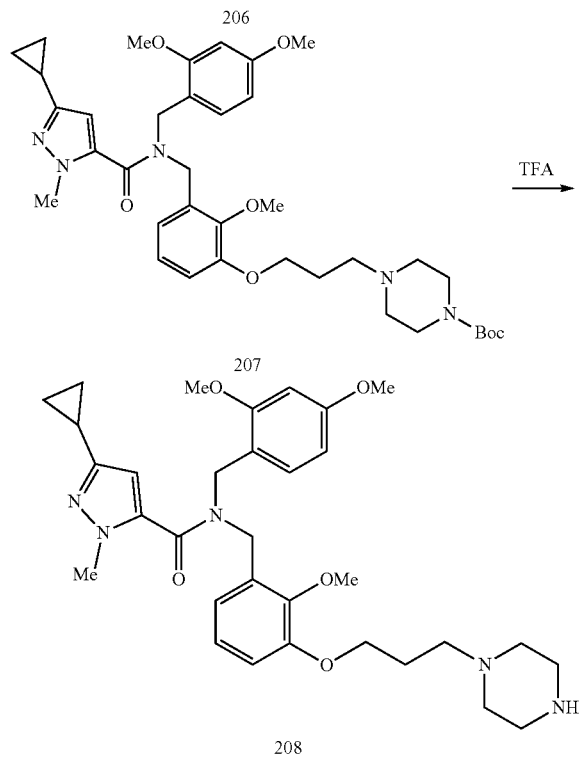

Preparation of Bromide 206

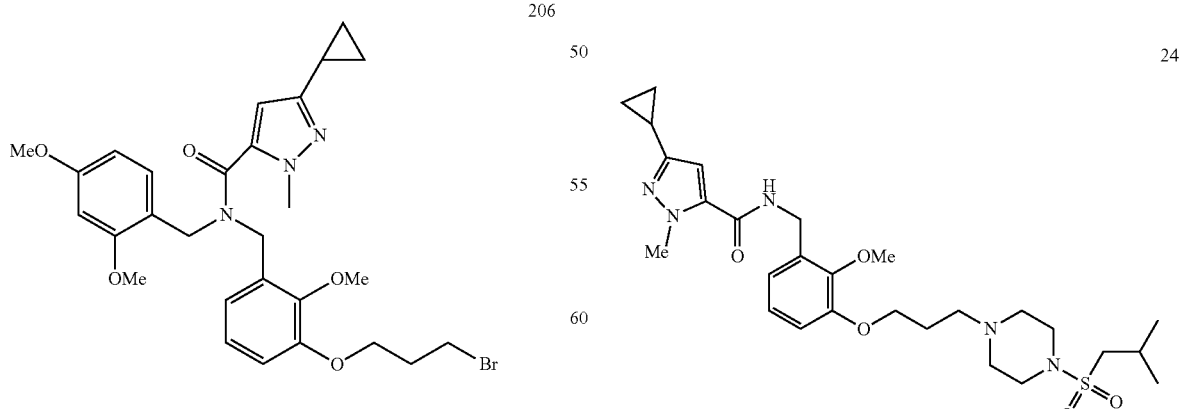

To a solution of compound 205 (5.0 g, 11.0 mmol 1.0 eq) in DMF (25 mL) was added cesium carbonate (7.2 g, 22.0 mmol, 2.0 eq) and the reaction mixture was stirred at room temperature for 10 min. Then, 1.3-dibromopropane (4.44 g, 22.0 mmol, 2.0 eq) was added to the reaction mixture and stirred at room temperature for 24 hours. The reaction mixture was diluted with ethyl acetate and washed with water (3×). The organic layer was dried (MgSO$_4$) and evaporated to give a residue, which was purified by column chromatography (Hexane/EtOAc) to give the bromide 206. Mass Spectrum (LCMS, ESI Pos.): calculated for $C_{28}H_{35}BrN_3O_5$: 572.0 (M$^+$H), found 572.0.

Preparation of Piperazine 208

To a solution of bromide 206 (247 mg, 0.433 mmol, 1.0 eq) in DMF (10 mL) was added Cs$_2$CO$_3$ (211 mg, 0.650 mmol, 1.5 eq) and N-Boc-piperazine (121 mg, 0.650 mmol, 1.5 eq) and the reaction mixture was stirred at room temperature for 24 hours. The reaction mixture was diluted with ethyl acetate and washed with water (3×). The organic layer was collected, dried and solvent was removed to give crude 207 which was immediately treated with 95% TFA and stirred at room temperature for 12 hours. TFA was removed and the crude material was purified by column chromatography (DCM/MeOH) to give the piperazine compound 208. Mass Spectrum (LCMS, ESI Pos.): calculated for $C_{24}H_{38}N_5O_3$: 444.0 (M$^+$H), found 444.0.

Example 1: Preparation of Compound 24

Isobutylsulfonyl chloride (0.024 g, 0.15 mmol, 1.5 eq) was added to a solution of piperazine 208 (0.043 g, 0.1 mmol, 1.0 eq) and DIEA (0.039 mL, 0.3 mmol, 3.0 eq) in DCM (5 mL) at 0° C. The reaction mixture was stirred overnight at room temperature, DCM was added and the organic layer was washed with saturated NaHCO₃ solution, 10% HCl, water, brine, dried and evaporated under vacuum to give a residue, which was purified by column chromatography to provide the desired sulfonamide 24. Mass Spectrum (LCMS, ESI Pos.): calculated for $C_{27}H_{42}N_5O_5S$: 548.0 ($M^+H$), found 548.0.

Scheme 3 illustrate preparation of amide 9

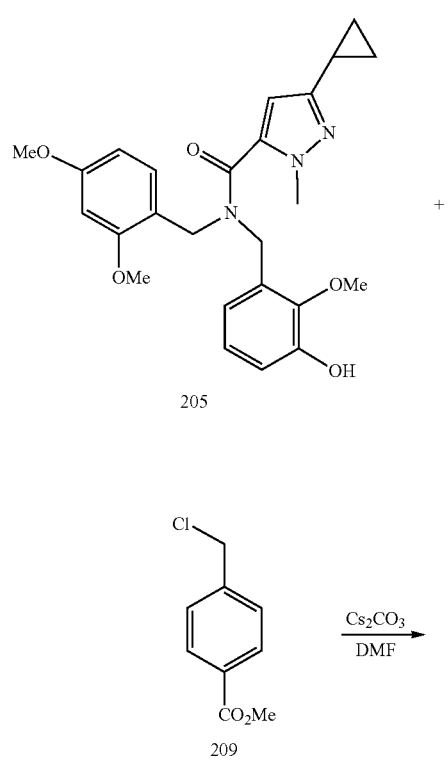
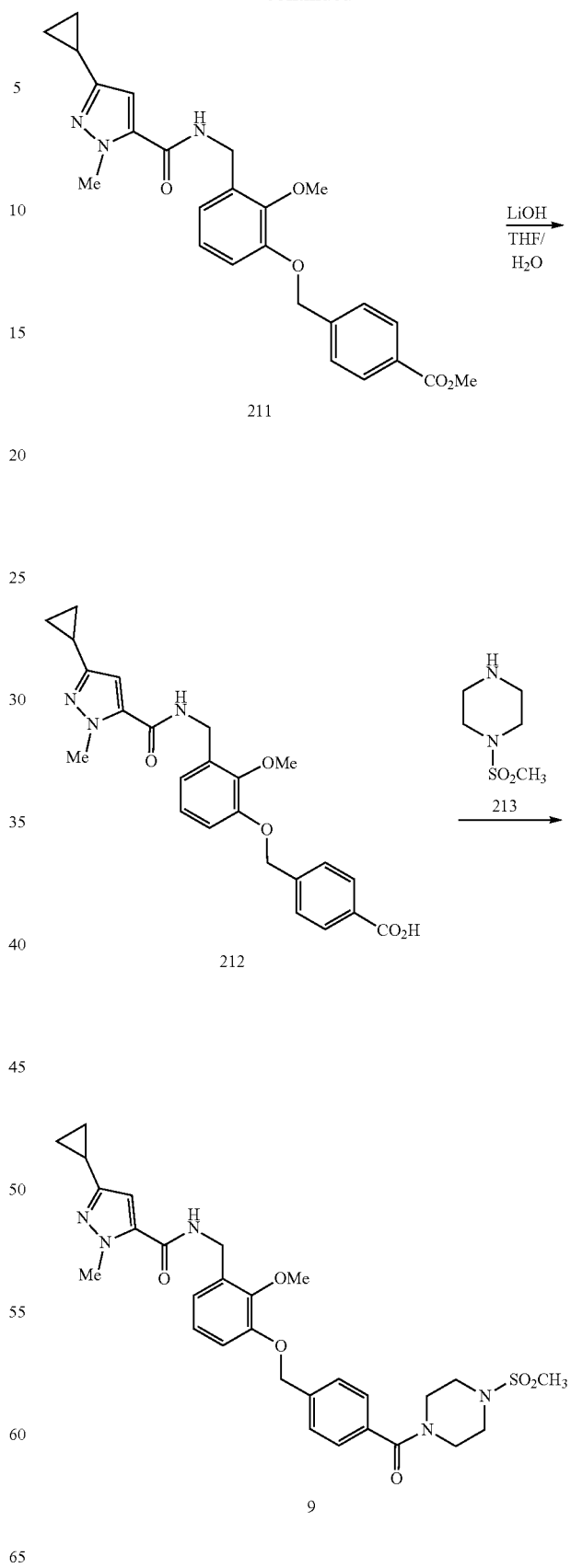

Preparation of Ester 210

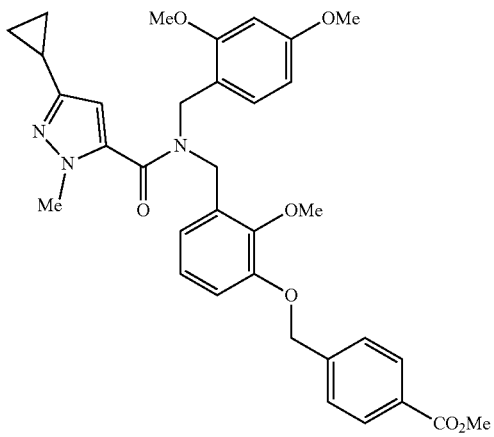

To a stirred solution of amide 205 (1.0 g, 2.22 mmol, 1.0 eq) and cesium carbonate (1.08 g, 3.33 mmol, 1.5 eq) in DMF (15 mL) was added methyl 4-(chloromethyl)benzoate 209 (559 mg, 2.44 mmol, 1.2 eq), the reaction mixture was stirred at room temperature for 18 hours, diluted with ethyl acetate and washed with water (3×). The organic layer was dried and concentrated and the residue was stirred in a 1:1 mixture of TFA: DCM for 12 h. Concentration followed by chromatography purification (Hexane/EtOAc) provided the desired ester 210. Mass Spectrum (LCMS, ESI Pos.): calculated, for $C_{34}H_{37}FN_3O_7$: 600.0 (M$^+$H), found 600.0.

Preparation of Acid 212

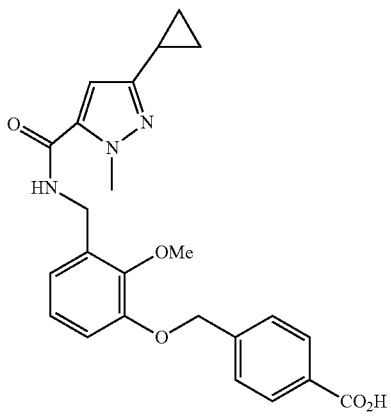

Ester 210 (500 mg, 0.84 mmol) was dissolved in a 1:1 mixture of TFA:DCM (20 mL) and the reaction mixture was stirred at room temperature for 18 hours, evaporated under vacuum to provide a residue, which was dissolved in ethyl acetate and washed with saturated NaHCO$_3$ solution and water (1×). The organic layer was dried and concentrated to give the crude ester 211, which was directly used in the next step. To a stirred solution of ester 211 (0.84 mmol, 1.0 eq) in a 3:1 mixture of THF: H$_2$O (12 mL) was added LiOH (40 mg, 1.68 mmol, 2.0 eq) and the reaction mixture was stirred at room temperature for 12 h. The reaction mixture was evaporated under vacuum to give a residue, which was stirred in a mixture of 10% aqueous HCl and ethyl acetate for 30 minutes. The organic layer was collected, washed with H$_2$O (1×), dried and concentrated to give the crude acid 212. Mass Spectrum (LCMS, ESI Pos.): calculated for $C_{24}H_{25}N_3O_5$: 436.0 (M$^+$H) found 436.0.

Example 2: Preparation of amide 9

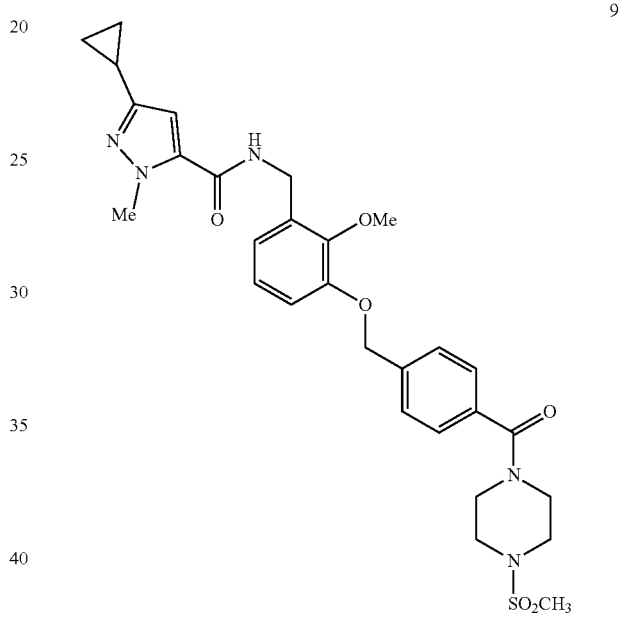

To a solution of the piperazine sulfonamide 213 (68 mg, 0.552 mmol, 1.2 eq) in DMF (25 mL) were added the crude acid 212 (200 mg, 0.46 mmol, 1.0 eq), HATU (210 mg, 0.552 mmol, 1.2 eq, and DIEA (0.300 mg, 2.3 mmol, 5.0 eq) and the reaction mixture was stirred at room temperature for 12 h. The reaction mixture was then diluted with EtOAc and washed with 10% aqueous HCl (1×), saturated NaHCO$_3$ (1×) and water (3×). The organic layer was collected, dried (MgSO$_4$) and evaporated to give a residue, which was purified by column chromatography (EtOAc/Hexane) to give the desired compound 9. Mass Spectrum (LCMS, ESI Pos.): calculated, for $C_{29}H_{35}N_5O_6S$:582.0 (M$^+$H), found 582.0.

Scheme 4 illustrate the preparation of amide 39.

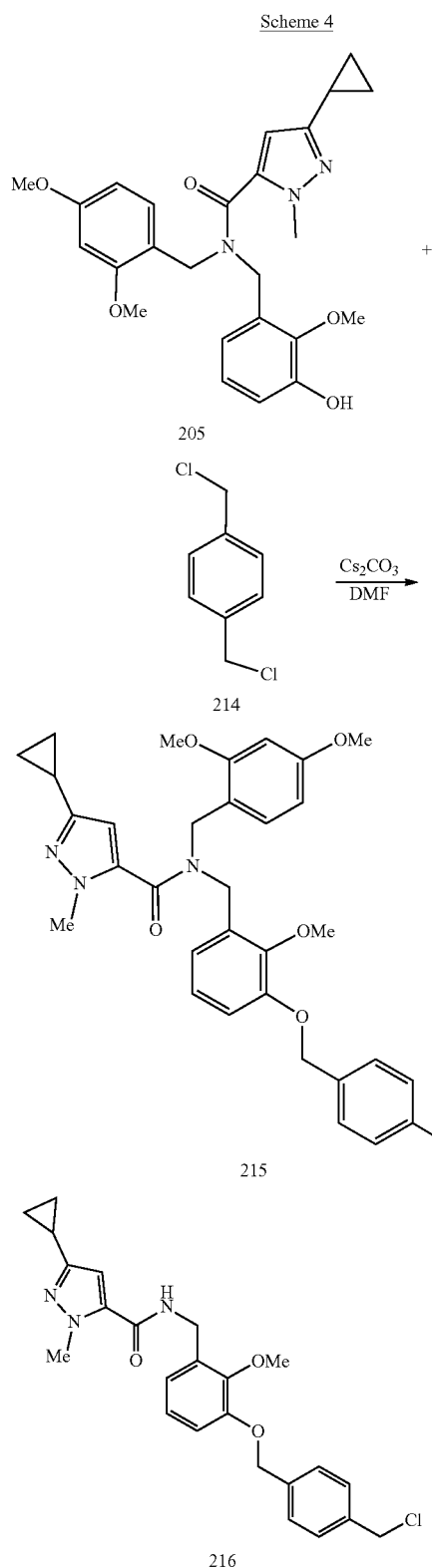

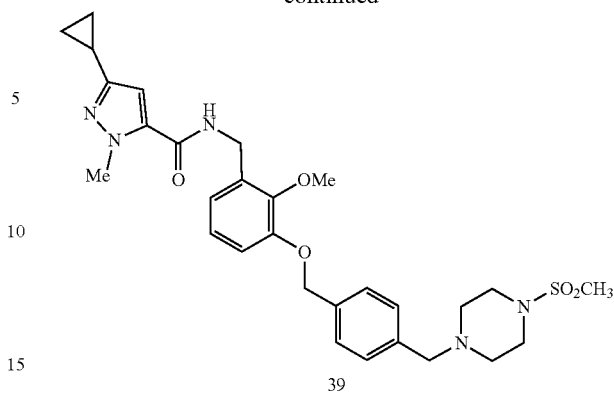

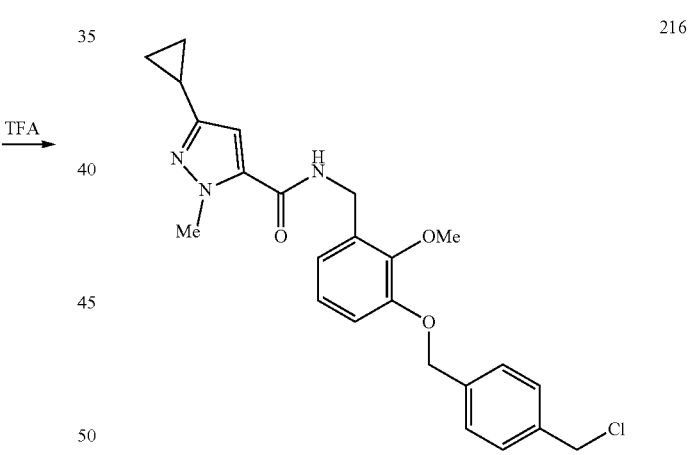

Preparation of Chloride 216

To a stirred solution of compound 205 (0.25 g, 0.55 mmol) and cesium carbonate (0.45 g, 1.37 mmol) in DMF (5 mL) was added 1,4-bis(chloromethyl)benzene 213 (0.14 g, 0.82 mmol) and the reaction mixture was stirred at room temperature for 18 h, diluted with ethyl acetate and washed with water (3×). The organic layer was dried and concentrated to give the crude ether 215, which then was stirred in a 1:1 mixture of TFA: DCM for 12 h. Concentration followed by chromatography purification (Hexane/EtOAc) provided the desired chloride 216.

Example 4: Preparation of Compound 39

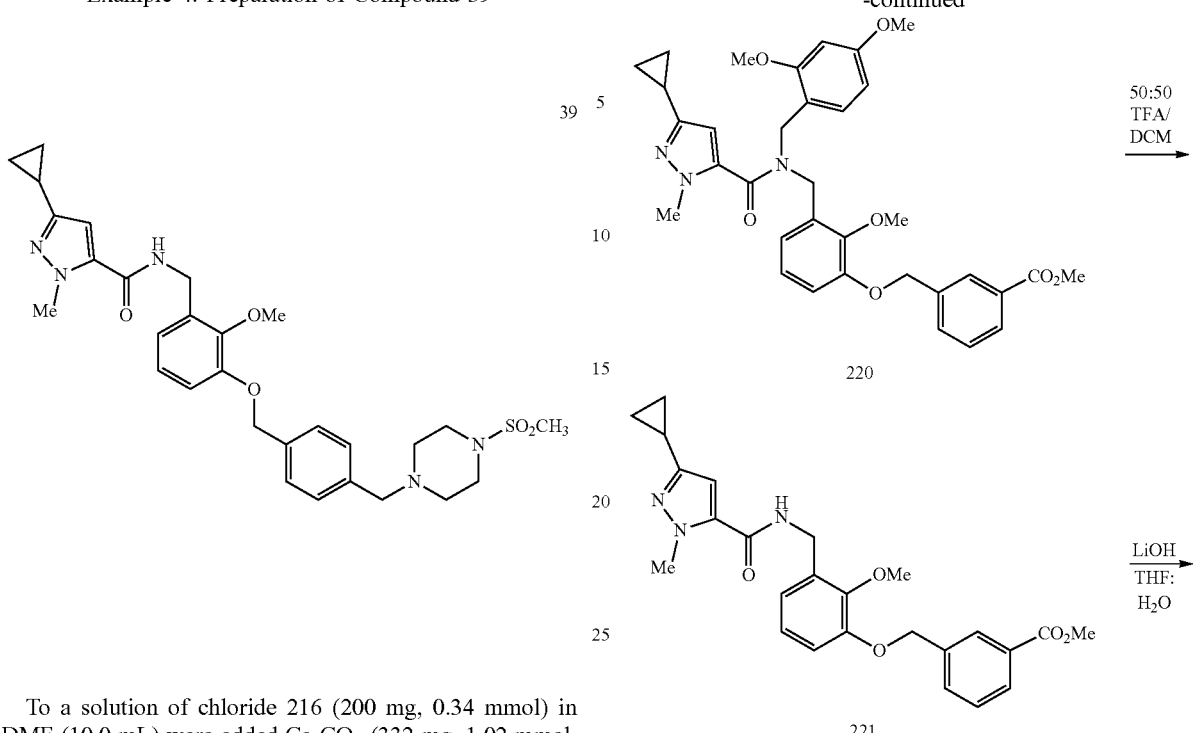

To a solution of chloride 216 (200 mg, 0.34 mmol) in DMF (10.0 mL) were added $Cs_2CO_3$ (332 mg, 1.02 mmol, 3.0 eq) and N-Methyl piperazine 217 (0.68 mmol, 2.0 eq) and the reaction mixture was stirred at 60° C. for 18 hours, diluted with ethyl acetate and washed with water (3×). The organic layer was collected, dried, and evaporated to give a viscous liquid, which was purified by column chromatography to give the desired amine 39.

Scheme 5 illustrates the preparation of compound 4.

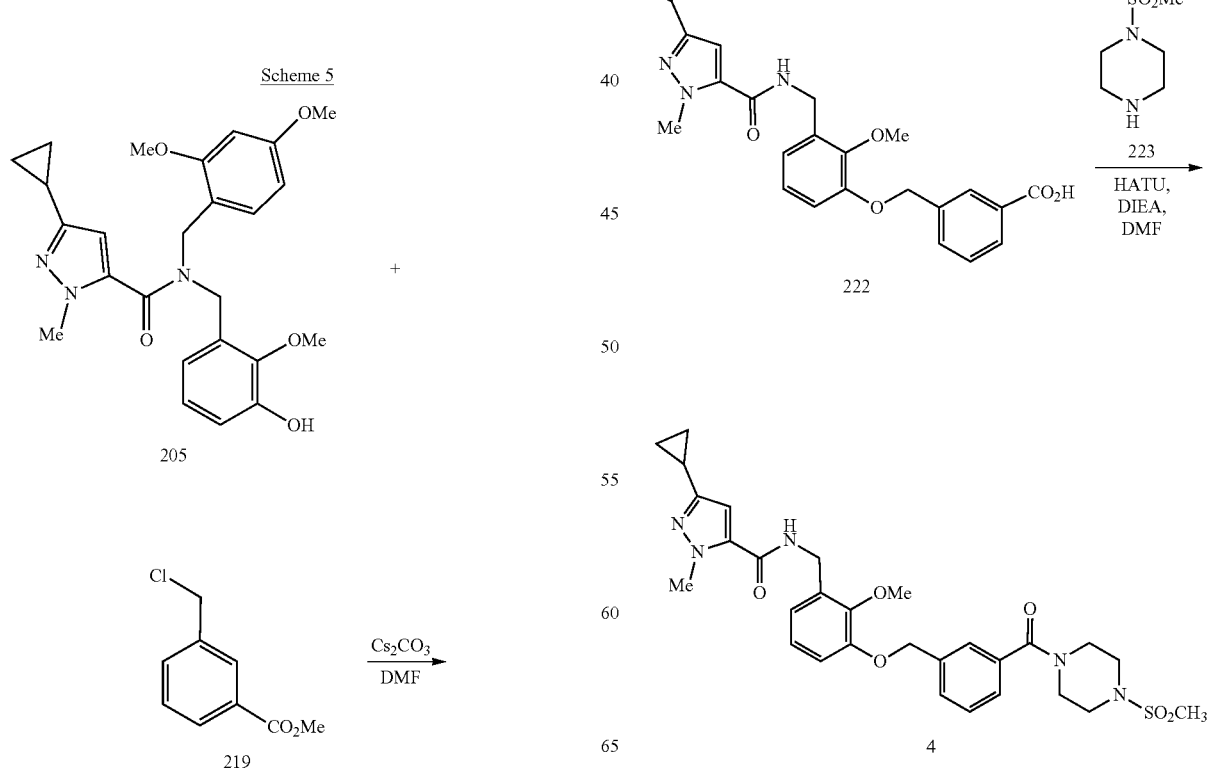

Preparation of Compound 220

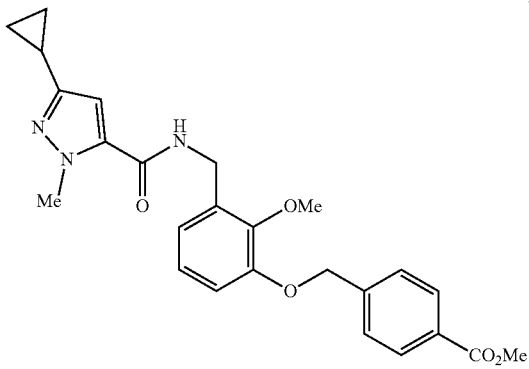

To a stirred solution of compound 205 (1.0 g, 2.22 mmol, 1.0 eq) and cesium carbonate (1.08 g, 3.33 mmol, 1.5 eq) in DMF (15 mL) was added methyl 3-(bromomethyl) benzoate 219 (450 mg, 2.44 mmol, 1.2 eq) and the reaction mixture was stirred at room temperature for 18 hours, diluted with ethyl acetate and washed with water (3×). The organic layer was dried and concentrated to give the crude ether 220 which was stirred in a 1:1 mixture of TFA: DCM for 12 hours. Concentration followed by chromatography purification (Hexane/EtOAc) provided the desired ester 220. Mass Spectrum (LCMS, ESI Pos.): calculated for $C_{34}H_{37}FN_3O_7$: 600.0 (M$^+$H), found 600.0.

Preparation of Compound 222

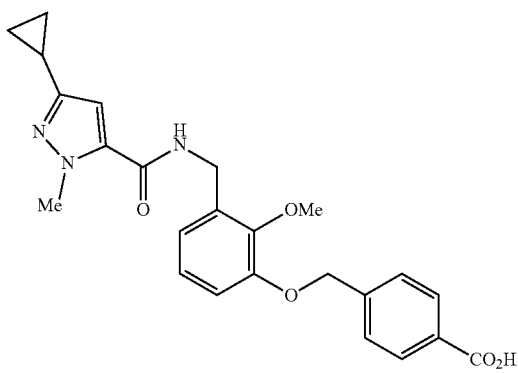

Ester 220 (500 mg, 0.84 mmol) was dissolved in a 1:1 mixture of TFA:DCM (20 mL) and the reaction mixture was stirred at room temperature for 18 hours, evaporated under vacuum to provide a residue, which was dissolved in ethyl acetate and washed with saturated NaHCO$_3$ solution and water (1×). The organic layer was dried and concentrated to give the crude ester 221, which was directly used in the next step. To a stirred solution of ester 221 (0.84 mmol, 1.0 eq) in 3:1 mixture of THF: H$_2$O (12 mL) was added LiOH (40 mg, 1.68 mmol, 2.0 eq) and the reaction mixture was stirred at room temperature for 12 hours. The reaction mixture evaporated under vacuum to give a residue, which was stirred in a mixture of 10% aqueous HCl and ethyl acetate for 30 min. The organic layer was collected, washed with H$_2$O (1×), dried and concentrated to give the crude acid 222. Mass Spectrum (LCMS, ESI Pos.): calculated for $C_{24}H_{25}N_3O_5$: 436.0 (M$^+$H), found 436.0.

Example 5: Preparation of Compound 4

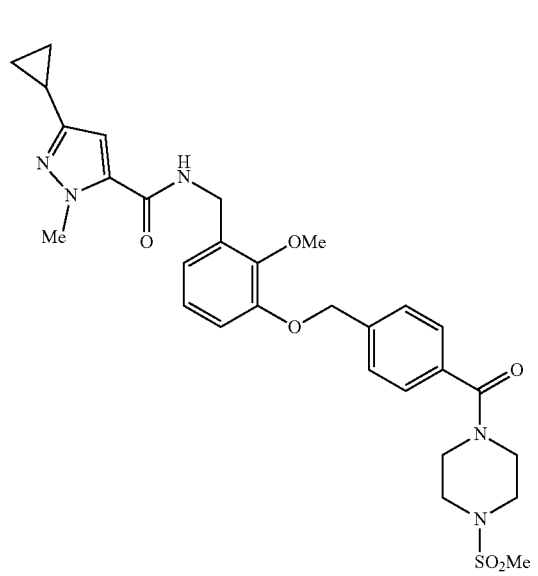

To a solution of the amine 223 (68 mg, 0.552 mmol, 1.2 eq) in DMF (25 mL) was added the crude acid 222 (200 mg, 0.46 mmol, 1.0 eq), HATU (210 mg, 0.552 mmol, 1.2 eq, and DIEA (0.300 mg, 2.3 mmol, 5.0 eq) and the reaction mixture was stirred at RT for 12 hours, was diluted with EtOAc and washed with 10% aqueous HCl (1×), saturated NaHCO$_3$ (IX) and water (3×). The organic layer was collected, dried (MgSO$_4$) and evaporated to give a residue, which was purified by column chromatography (EtOAc/Hexane) to give the desired sulfonamide 4. Mass Spectrum (LCMS, ESI Pos.): calculated for $C_{29}H_{35}N_5O_6S$:582.0 (M$^+$H), found 582.0.

Scheme 6 illustrates a general procedure for the preparation of sulfonamides and specifically the preparation of compound 227.

Scheme 6

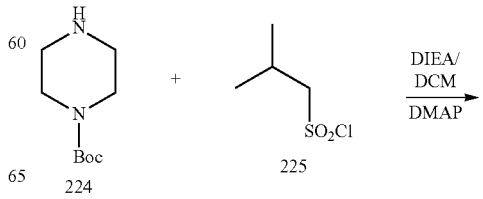

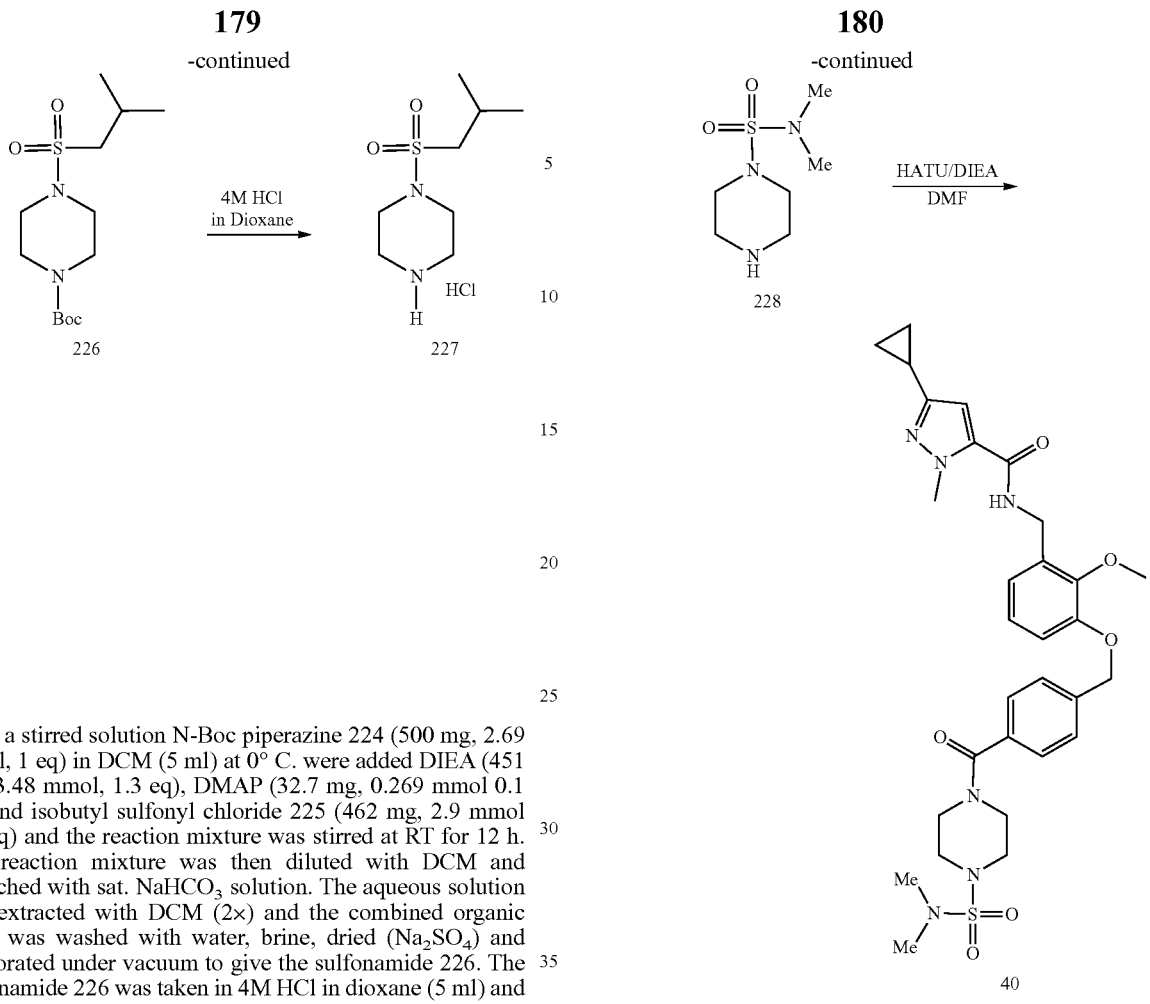

To a stirred solution N-Boc piperazine 224 (500 mg, 2.69 mmol, 1 eq) in DCM (5 ml) at 0° C. were added DIEA (451 mg, 3.48 mmol, 1.3 eq), DMAP (32.7 mg, 0.269 mmol 0.1 eq) and isobutyl sulfonyl chloride 225 (462 mg, 2.9 mmol 1.1 eq) and the reaction mixture was stirred at RT for 12 h. The reaction mixture was then diluted with DCM and quenched with sat. NaHCO₃ solution. The aqueous solution was extracted with DCM (2×) and the combined organic layer was washed with water, brine, dried (Na₂SO₄) and evaporated under vacuum to give the sulfonamide 226. The sulfonamide 226 was taken in 4M HCl in dioxane (5 ml) and the reaction mixture was stirred at RT for 12 hr. The reaction mass was evaporated under vacuum to provide a colorless solid 227, which was used in the next step without further purification.

Scheme 7 illustrates the preparation of compound 40.

Scheme 7

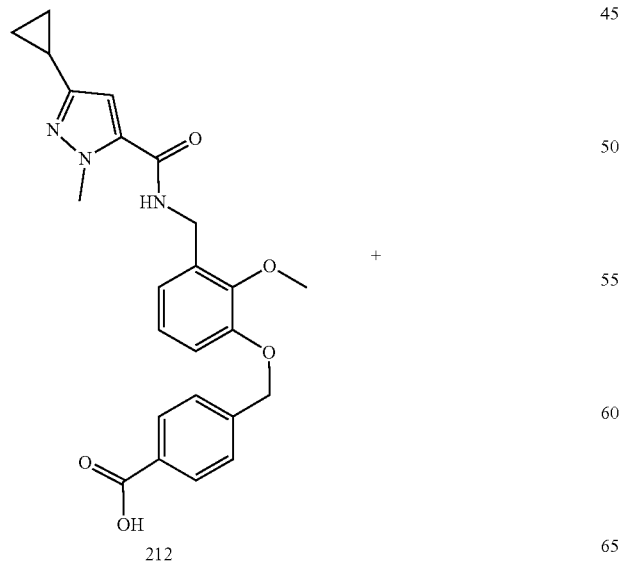

Example 6: Preparation of Compound 40

To a stirred solution of acid 212 (60 mg, 0.137 mmol, 1.2 eq) in DMF (3 mL) were added DIEA (74 mg, 0.57 mmol, 5 eq), piperazine-1-sulfonic acid dimethylamide 228 (22 mg, 0.114 mmol, 1.0 eq) and HTAU (0.065 g, 0.172 mmol, 1.5 eq) and the reaction mixture was stirred at room temperature for 12 h. The reaction mixture was taken in EtOAc and washed with saturated NaHCO₃ solution and 5% HCl solution. The organic layer was then washed with water (2×), brine (1×), dried (Na₂SO₄) and evaporated under vacuum to give a residue, which was purified by column chromatography to give the desired amide 40. Mass Spectrum (LCMS, ESI Pos.) Calcd. For $C_{30}H_{39}N_6O_6S$: 610.0 (M⁺H), Found 610.0

Scheme 8 illustrates the preparation of compound 41.

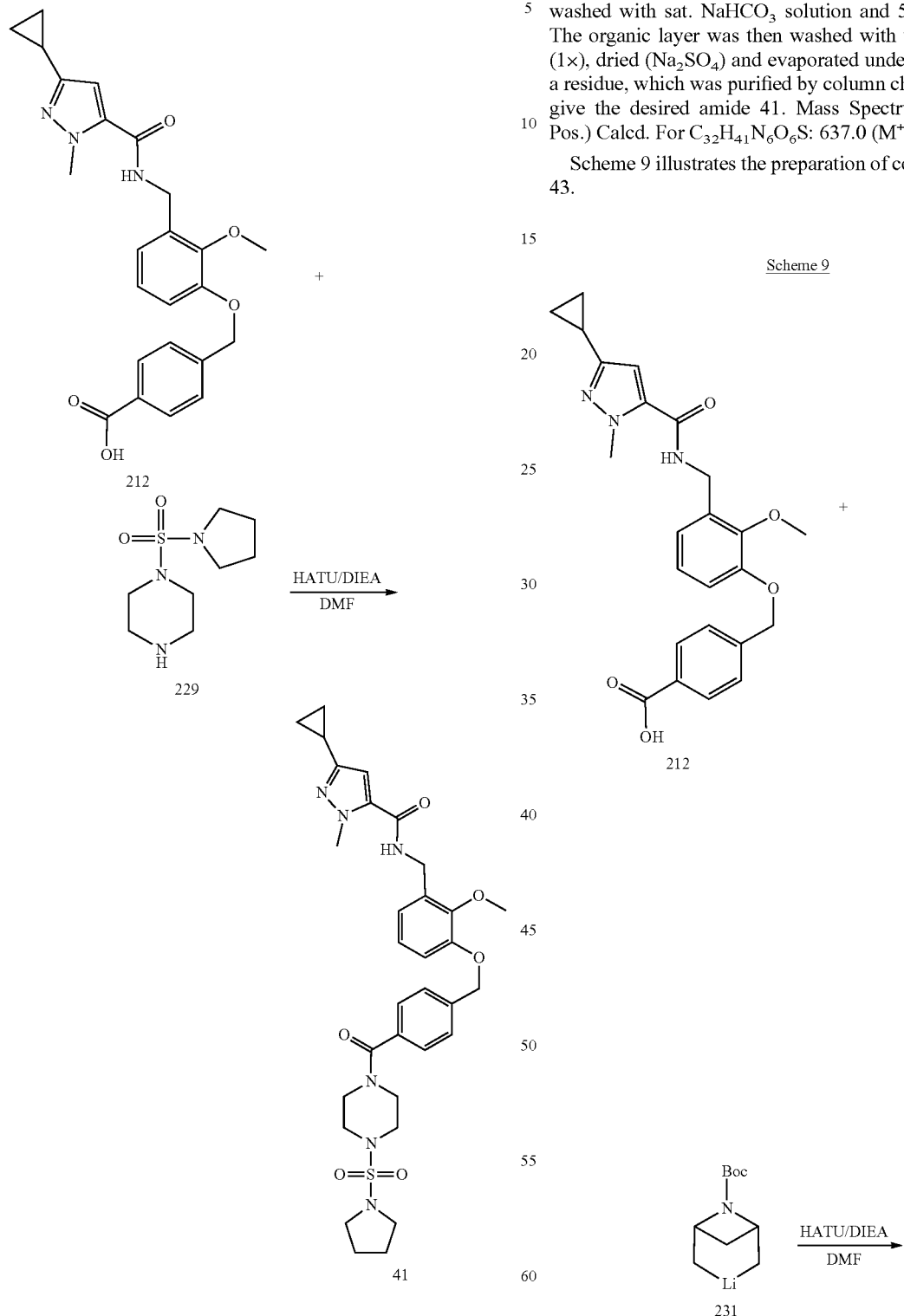

Scheme 9 illustrates the preparation of compounds 42 and 43.

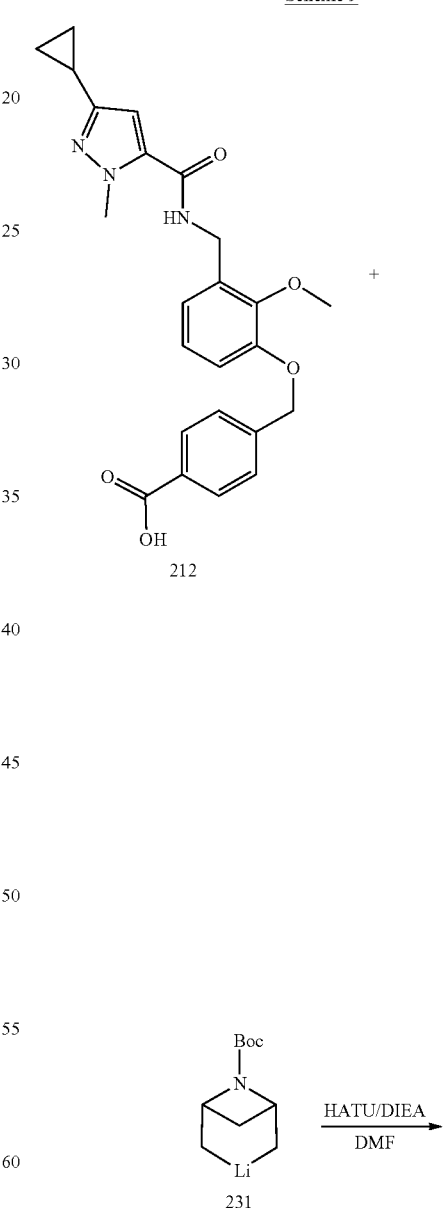

5 eq), 1-(Pyrrolidine-1-sulfonyl)piperazine 229 (25 mg, 0.114 mmol, 1.0 eq) and HATU (0.065 g, 0.172 mmol, 1.5 eq) and the reaction mixture was stirred at room temperature for 12 h. The reaction mixture was taken in EtOAc and washed with sat. NaHCO$_3$ solution and 5% HCl solution. The organic layer was then washed with water (2×), brine (1×), dried (Na$_2$SO$_4$) and evaporated under vacuum to give a residue, which was purified by column chromatography to give the desired amide 41. Mass Spectrum (LCMS, ESI Pos.) Calcd. For C$_{32}$H$_{41}$N$_6$O$_6$S: 637.0 (M$^+$H), Found 637.0.

Example 7: Preparation of Compound 41

To a stirred solution of acid 212 (60 mg, 0.137 mmol, 1.2 eq) in DMF (3 mL) were added DIEA (74 mg, 0.57 mmol,

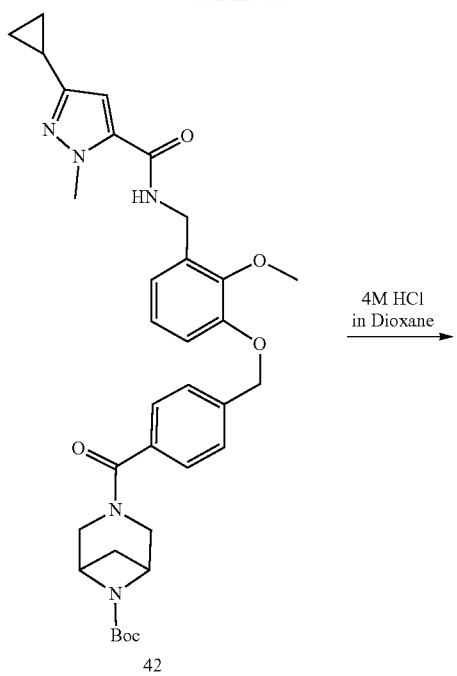

42

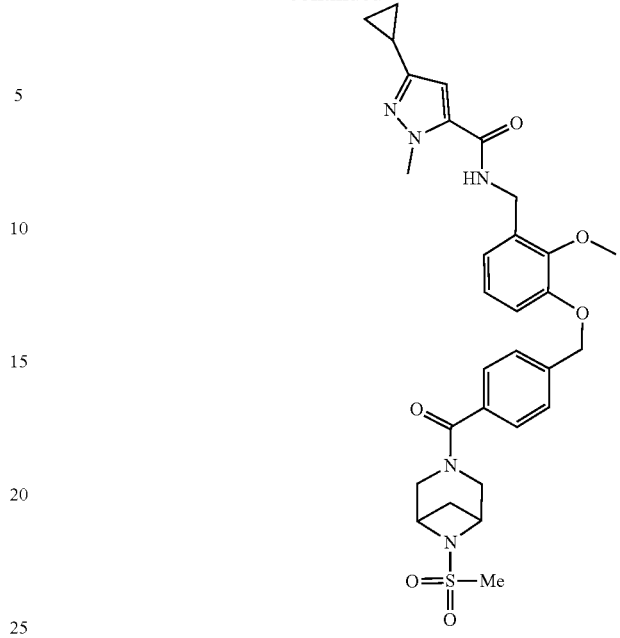

43

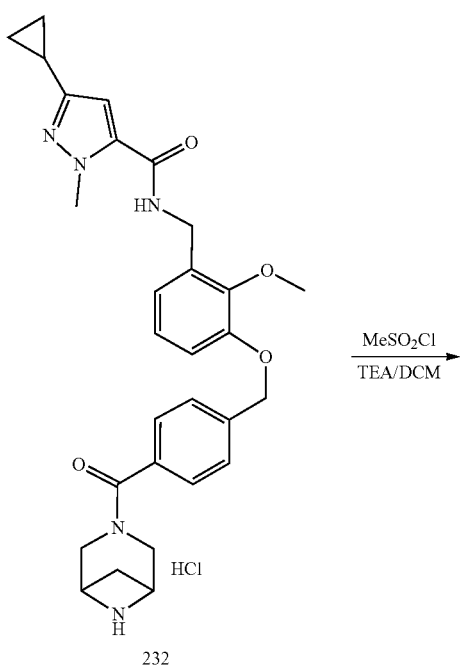

232

Example 8: Preparation of Compound 42

To a stirred solution acid 212 (60 mg, 0.137 mmol, 1.2 eq) in DMF (3 mL) were added DIEA (74 mg, 0.57 mmol, 5 eq), amine 231 (23 mg, 0.114 mmol, 1.0 eq) and HATU (0.065 g, 0.172 mmol, 1.5 eq) and the reaction mixture was stirred at room temperature for 12 h. The reaction mixture was taken in EtOAc and washed with sat. NaHCO$_3$ solution and 5% HCl solution. The organic layer was then washed with water (2×), brine (IX), dried (Na$_2$SO$_4$) and evaporated under vacuum to give a residue, which was purified by column chromatography to give the desired amide 42.

Example 9: Preparation of Compound 43

The amide 42 was dissolved in a minimum amount of DCM and then 4 mL of 4M HCl in dioxane was added and the reaction mixture was stirred for 12 h. Removal of the solvents yielded the amine 232 as a HCl salt, which was directly used in the next step. To a stirred solution of amine 232 (40 mg, 0.073 mmol, 1 eq) and TEA (37 mg, 0.365 mmol, 5 eq) in DCM (5 mL) at 0° C. was dropwise added methanesulfonyl chloride (0.010 g, 0.093 mmol, 1.2 eq) and the reaction mixture was stirred at room temperature for 6 h. The reaction mixture was diluted with DCM and washed with sat. NaHCO$_3$ solution, 10% aq. HCl and brine. The organic layer was dried (NaSO$_4$) and evaporated under vacuum to get a residue, which was purified by column chromatography to provide compound 43. Mass Spectrum (LCMS, ESI Pos.) Calcd. For $C_{30}H_{36}N_5O_6S$: 594.0 (M$^+$H), Found 594.0

Scheme 10 illustrates the preparation of compound 44.

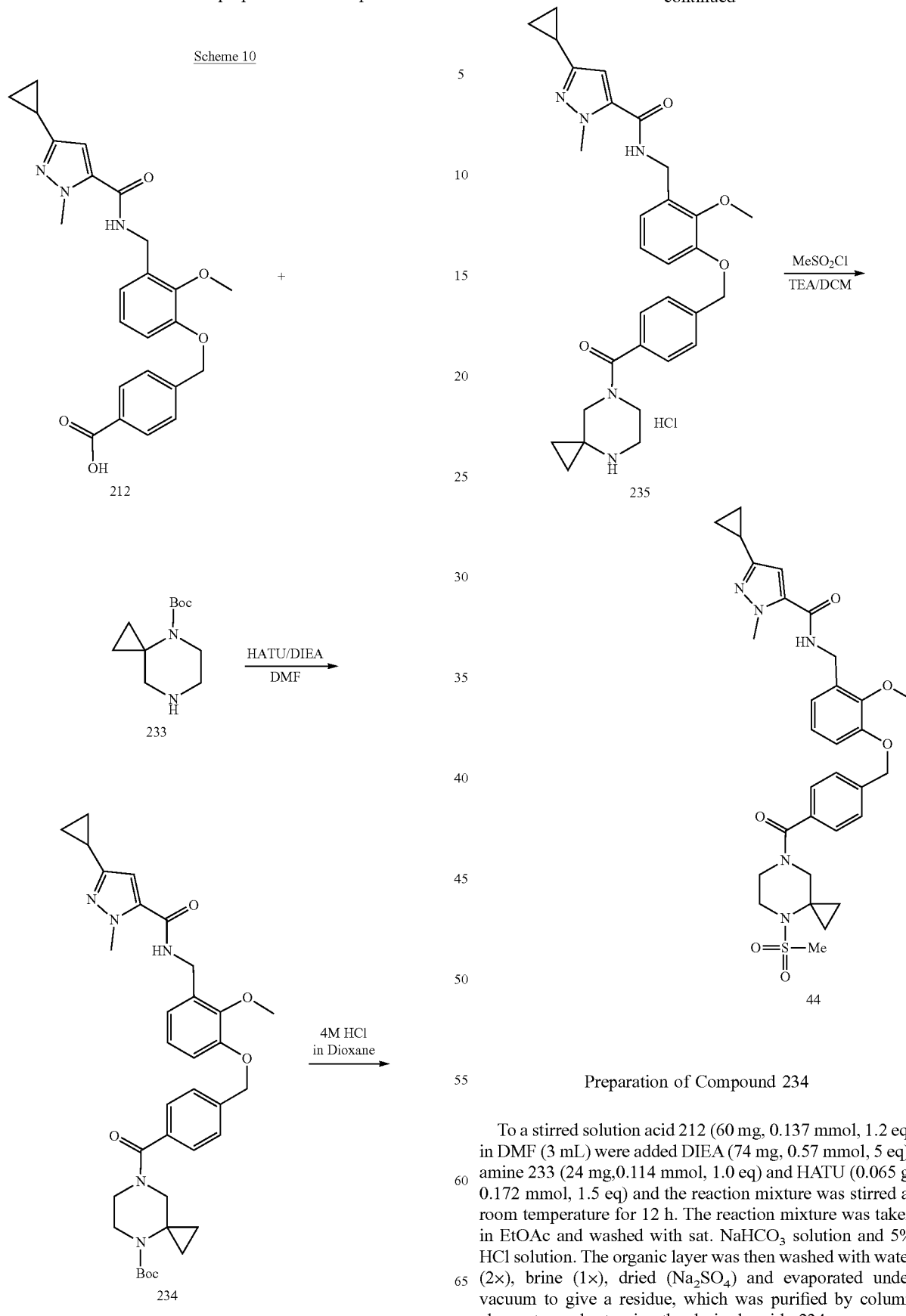

Preparation of Compound 234

To a stirred solution acid 212 (60 mg, 0.137 mmol, 1.2 eq) in DMF (3 mL) were added DIEA (74 mg, 0.57 mmol, 5 eq), amine 233 (24 mg, 0.114 mmol, 1.0 eq) and HATU (0.065 g, 0.172 mmol, 1.5 eq) and the reaction mixture was stirred at room temperature for 12 h. The reaction mixture was taken in EtOAc and washed with sat. NaHCO$_3$ solution and 5% HCl solution. The organic layer was then washed with water (2×), brine (1×), dried (Na$_2$SO$_4$) and evaporated under vacuum to give a residue, which was purified by column chromatography to give the desired amide 234.

Example 10: Preparation of Compound 44

The amide 234 was dissolved in a minimum amount of DCM and then 4 mL of 4M HCl in dioxane was added and the reaction mixture was stirred for 12 h. Removal of the solvents yielded the amine 235 as a HCl salt, which was directly used in the next step. To a stirred solution of amine 235 (44 mg, 0.073 mmol, 1 eq) and TEA (37 mg, 0.365 mmol, 5 eq) in DCM (5 mL) at 0° C. was dropwise added methanesulfonyl chloride (0.010 g, 0.093 mmol, 1.2 eq) and the reaction mixture was stirred at room temperature for 6 h. The reaction mixture was diluted with DCM and washed with sat. NaHCO₃ solution, 10% aq. HCl and brine. The organic layer was dried (NaSO₄) and evaporated under vacuum to get a residue, which was purified by column chromatography to provide compound 44. Mass Spectrum (LCMS, ESI Pos.) Calcd. For $C_{31}H_{38}N_5O_6S$: 608.0 (M⁺H), Found 608.0.

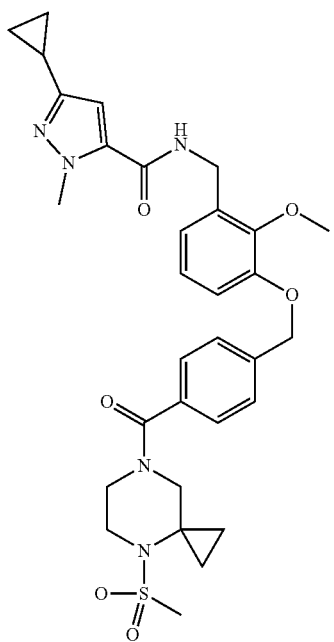

45

Example 11: Preparation of Compound 45

Compound 45 was prepared using the synthetic procedure used to synthesize compound 9. The triazole carboxylic acid was prepared using a literature procedure (*Chemistry of Heterocyclic Compounds* 2022, 58(2/3), 116-128). Mass Spectrum (LCMS, ESI Pos.) Calcd. For $C_{29}H_{35}N_6O_6S$: 583.0 (M+H), Found 583.0

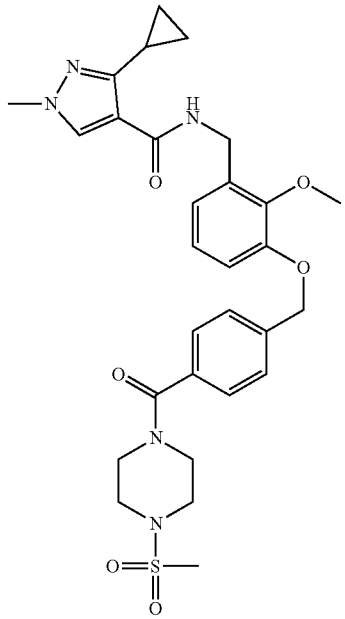

46

Example 12: Preparation of Compound 46

Compound 46 was prepared using the synthetic procedure used to synthesize compound 9. The necessary triazole carboxylic acid, 3-cyclopropyl-1-methyl-1H-pyrazole-4-carboxylic acid is commercially available. Mass Spectrum (LCMS, ESI Pos.) Calcd. For $C_{29}H_{36}N_5O_6S$: 582.0 (M⁺H), Found 582.0.

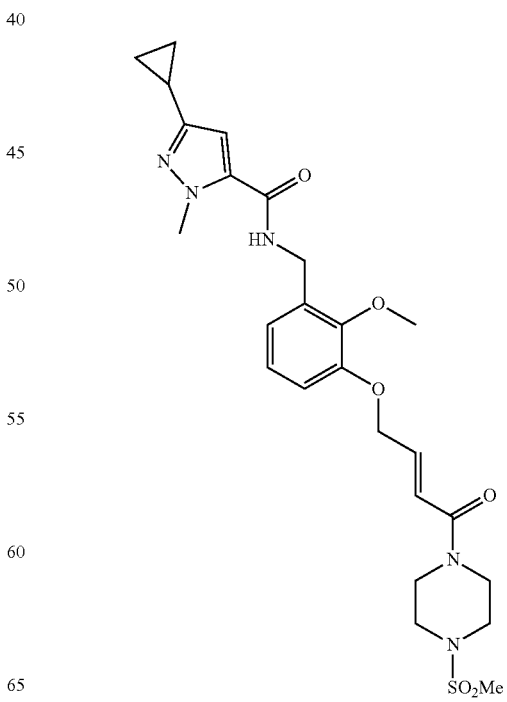

47

Example 13: Preparation of Compound 47

Compound 47 was prepared using the synthetic procedure used to synthesize compound 9. The necessary triazole carboxylic acid, 3-cyclopropyl-1-methyl-1H-pyrazole-4-carboxylic acid is commercially available as is 4 methyl-bromocrotonate. Mass Spectrum (LCMS, ESI Pos.) Calcd. For $C_{25}H_{34}N_5O_6S$: 532.0 (M$^+$H), Found 532.0.

Scheme 11 illustrates the preparation of compound 237.

Scheme 11

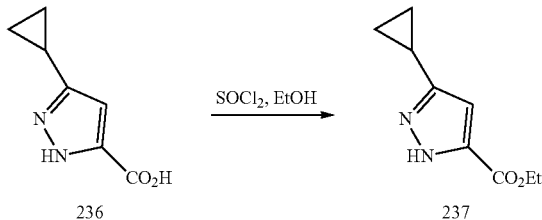

Preparation of Compound 237

To a mixture of 3-cyclopropyl-1H-pyrazole-5-carboxylic acid 236 [1 g (6.5 mmol)] in 30 ml of EtOH was added dropwise thionyl chloride [0.95 ml (13 mmol)]. The resulting mixture was stirred at 60° C. for 3 h, cooled to room temperature and then diluted with 100 ml of ice water. The mixture was extracted with methylene chloride and then the extract was washed with 50 ml of water, 50 ml of sat. NaHCO$_3$, dried (Na$_2$SO$_4$) and the solvent removed affording 1.08 g (91%) of ethyl 3-cyclopropyl-1H-pyrazole-5-carboxylate 237.

Scheme 12 illustrates the preparation of compound 240.

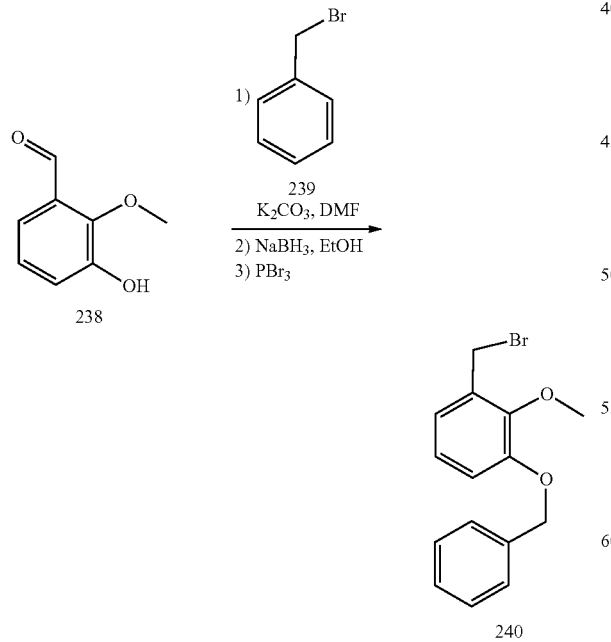

To a solution of 3-hydroxy-2-methoxy-benzaldehyde 238 [500 mg (3.3 mmol)]3 in 5 ml of DMF was added K$_2$CO$_3$ [910 mg (6.6 mmol)]. Next was added benzyl bromide 239 [430 ul (3.6 mmol)]. The resulting mixture was stirred at room temperature for 12 h, then diluted with 30 ml of EtOAc. The reaction was then washed 2× with water (5 ml), the organic layer was dried (Mg$_2$SO$_4$) and the solvent removed via rotary evaporation. The crude material was then taken on to the next step.

The crude benzyl ether from the previous step was dissolved into 10 ml of EtOH to which was added NaBH$_4$ [125 mg (3.3 mmol)]. After stirring at room temperature for 1 h the reaction was quenched with 1N HCl (2 ml) then diluted further with 30 ml of water. The mixture was extracted with 40 ml of EtOAc, dried(Mg$_2$SO$_4$) and the solvent removed via rotary evaporation affording the desired crude benzyl alcohol which was taken on to the next step.

To the crude benzyl alcohol in CH$_2$Cl$_2$ (15 ml) at 0° C. was added dropwise, with stirring, PBr$_3$ [152 ul (1.6 mmol)]. After stirring for 40 min, the reaction was quenched with 10 ml of water. The organic layer was removed and the aqueous was extracted with CH$_2$Cl$_2$ (30 ml) and the combined CH$_2$Cl$_2$ extracts were dried (Na$_2$SO$_4$) and the solvent removed affording 970 mg (97%) 1-benzyloxy-3-(bromomethyl)-2-methoxybenzene 241 after ISCO purification with Hexane/EtOAc.

Scheme 13 illustrates the preparation of compound 243.

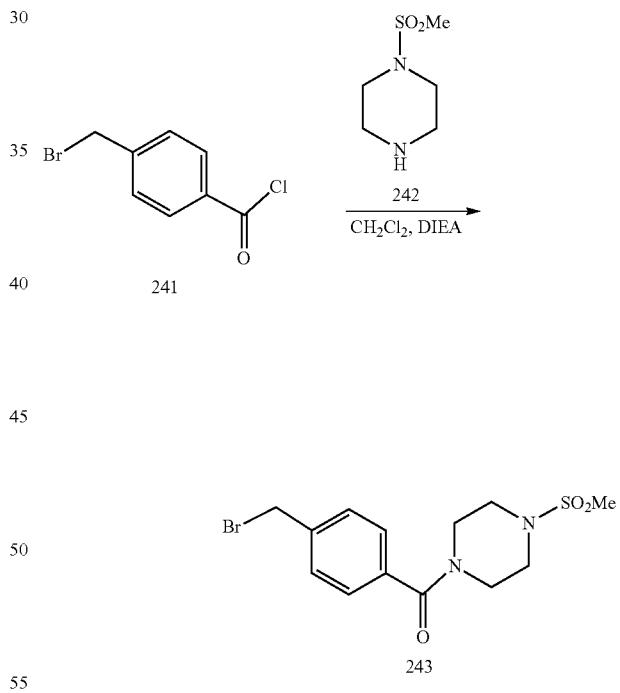

To a solution of 4-(bromomethyl)benzoyl chloride 241 [1 g (4.33 mmol)] in CH$_2$Cl$_2$ (40 ml) at 0° C., with rapid stirring, was slowly added a mixture of DIEA [1.9 ml (10.75 mmol)] and 1-methylsulfonylpiperazine 242 [710 mg (4.3 mmol) dissolved together in a small amount of CH$_2$Cl$_2$. After addition was complete the mixture was stirred at room temperature for 1 h. The reaction was quenched with 20 ml of water, the organic phase removed, dried (Na$_2$SO$_4$) and the solvent removed affording the desired [4-(bromomethyl)phenyl]-(4-methylsulfonylpiperazin-1-yl)methanone 243 774 mg (50%) which was used without further purification.

Scheme 14 illustrates the preparation of compound 48.

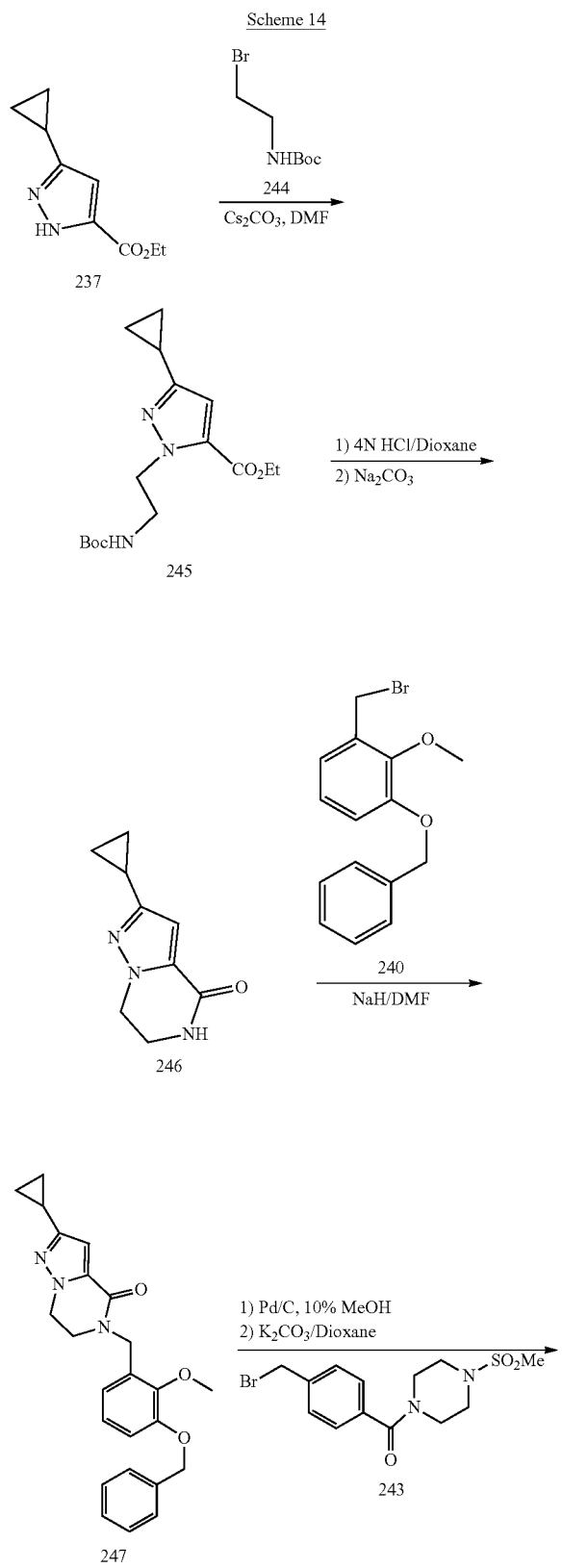

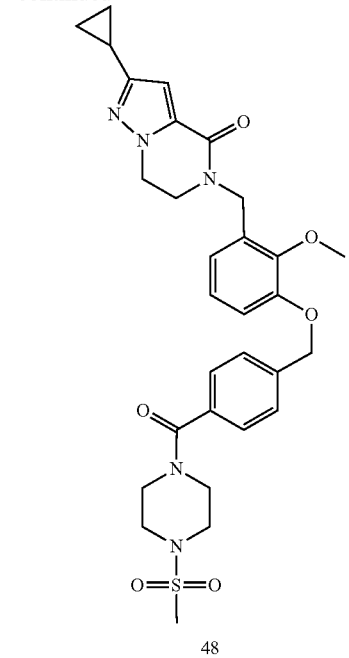 [SMILES: COc1c(CN2CCn3nc(C4CC4)cc3C2=O)cccc1OCc1ccc(C(=O)N2CCN(S(C)(=O)=O)CC2)cc1]

Preparation of Compound 245

To a mixture of ethyl 3-cyclopropyl-1H-pyrazole-5-carboxylate [500 mg (2.7 mmol) 237 in 20 ml of DMF was added 2-(Boc-amino)-ethyl bromide 244 [0.670 g (4.2 mmol)] followed by the addition of $Cs_2CO_3$ [1.1 g (3.4 mmol)]. The mixture was stirred at room temperature for 16 h, filtered through celite and the pad washed with EtOAc (40 ml). The filtrate was then washed 2× with water (50 ml), the organic layer was dried ($Mg_2SO_4$) and the solvent removed via rotary evaporation affording 660 mg (76%) of ethyl 2-[2-(tert-butoxycarbonylamino)ethyl]-5-cyclopropyl-pyrazole-3-carboxylate 245 after ISCO purification with Hexane/EtOAc. The structure was confirmed by LCMS.

Preparation of Compound 246

To ethyl 2-[2-(tert-butoxycarbonylamino)ethyl]-5-cyclopropyl-pyrazole-3-carboxylate 246 [660 mg (2.0 mmol)] was added 8 ml of 4NHCl in dioxane. The mixture was stirred for 1 h at room temperature, then made basic with sat. $Na_2CO_3$, stirred for another 10 min and then diluted with $CH_2Cl_2$ (20 ml). The reaction mixture was dried ($Na_2SO_4$) and the solvent removed affording 322 mg (94%) 2-cyclopropyl-6,7-dihydro-5H-pyrazolo[1,5-a]pyrazin-4-one 246 after ISCO purification with Hexane/EtOAc. The structure was confirmed by LCMS.

Preparation of Compound 247

To a suspension of 60% NaH [48 mg (1.2 mmol)] in DMF (3 ml) at 0° C. was added 2-cyclopropyl-6,7-dihydro-5H-pyrazolo[1,5-a]pyrazin-4-one 246 [150 mg (0.85 mmol)]. After stirring at 0° C. for 1 h 1-benzyloxy-3-(bromomethyl)-2-methoxybenzene 240 [285 mg (0.93 mmol)] was added and the resulting mixture was stirred at room temperature for 3 h. The reaction mixture was then diluted with 10 ml of water and extracted with $CH_2Cl_2$ (2×20 ml). The combined $CH_2Cl_2$ extracts were dried ($Na_2SO_4$) and the solvent Example 14: Preparation of Compound 48

To a mixture of 5-[(3-Benzyloxy-2-methoxy-phenyl)methyl]-2-cyclopropyl-6,7-dihydropyrazolo[1,5-a]pyrazin-4-one 247 [60 mg (0.15 mmol)] in 10 ml of MeOH was added 20 mg of Pd/C 10%. The mixture was aspirated and then filled with $H_2$. After stirring at room temperature for 1 h the removal of the benzyl group was complete. The reaction mixture was filtered through a plug of celite and rotary evaporated to dryness. The residue was then taken up into 3 ml of DMF and to this solution was added [4-(Bromomethyl)phenyl]-(4-methylsulfonylpiperazin-1-yl)methanone 243 [54 mg (0.15 mmol) and $K_2CO_3$ [41 mg (0.3 mmol)]. The reaction was stirred overnight at room temperature then diluted with 20 ml of EtOAc. The mixture was washed with water (10 ml), dried ($Mg_2SO_4$) and the solvent removed via rotary evaporation affording 38 mg (43%) of 2-cyclopropyl-5-[[2-methoxy-3-[[4-(4-methylsulfonylpiperazine-1-carbonyl)phenyl]methoxy]phenyl]methyl]-6,7-dihydropyrazolo[1,5-a]pyrazin-4-one 48 after ISCO purification with Hexane/EtOAc. The structure was confirmed by LCMS.

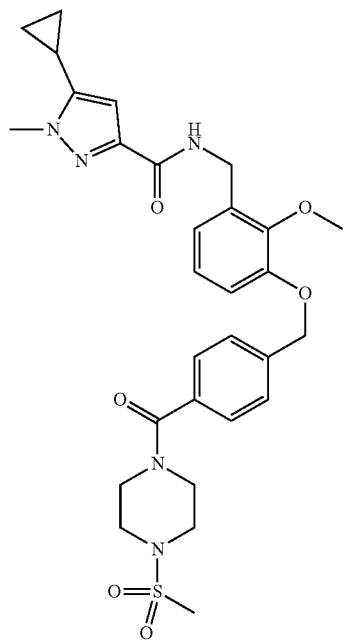

Example 14: Preparation of Compound 49

Compound 49 was prepared using the synthetic procedure used to synthesize compound 9. The necessary triazole carboxylic acid, 3-cyclopropyl-1-methyl-1H-pyrazole-4-carboxylic acid is commercially available. Mass Spectrum (LCMS, ESI Pos.) Calcd. For $C_{29}H_{36}N_5O_6S$: 582.0 ($M^+H$), Found 582.0.

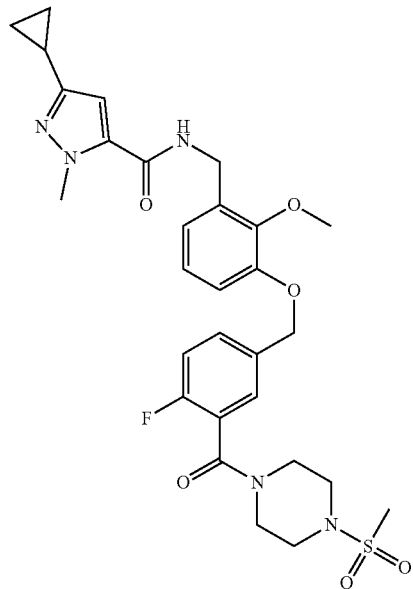

Example 15: Preparation of Compound 50

Compound 50 was prepared using the synthetic procedure used to synthesize compound 9. The necessary triazole carboxylic acid, 3-cyclopropyl-1-methyl-1H-pyrazole-4-carboxylic acid is commercially available as is methyl 5-(bromomethyl)-2-fluorobezoate. Mass Spectrum (LCMS, ESI Pos.) Calcd. For $C_{29}H_{35}FN_5O_6S$: 600.0 ($M^+H$), Found 600.0.

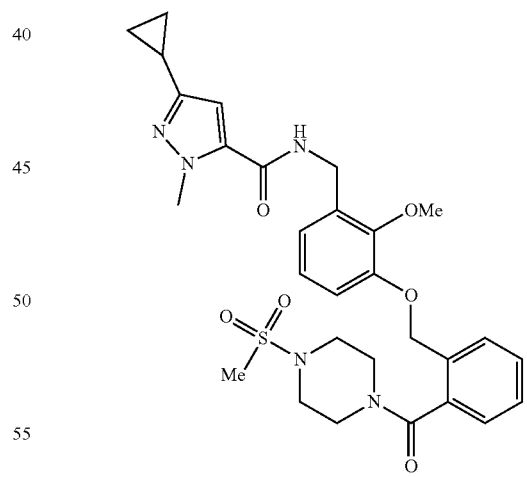

Example 16: Preparation of Compound 51

Compound 51 was prepared using the synthetic procedure used to synthesize compound 9. The necessary triazole carboxylic acid, 3-cyclopropyl-1-methyl-1H-pyrazole-4-carboxylic acid is commercially available as is methyl 2-bromomethylbenzoate. Mass Spectrum (LCMS, ESI Pos.) Calcd. For $C_{29}H_{36}N_5O_6S$: 582.0 ($M^+H$), Found 582.0.

52

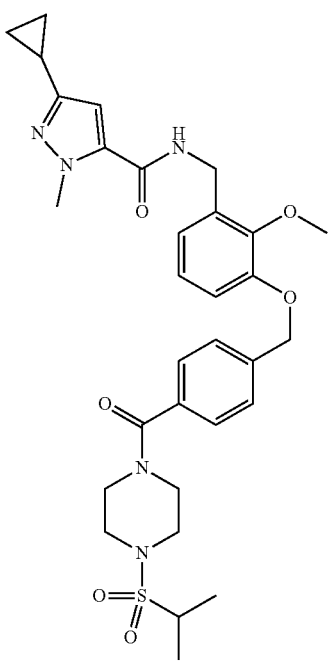

Example 17: Preparation of Compound 52

Compound 52 was prepared using the synthetic procedure used to synthesize compound 9. The necessary triazole carboxylic acid, 3-cyclopropyl-1-methyl-1H-pyrazole-4-carboxylic acid is commercially available. 1-(Isopropylsulfonyl) piperazine was prepared as described in Scheme 6. Mass Spectrum (LCMS, ESI Pos.) Calcd. For $C_{31}H_{40}N_5O_6S$: 610.0 (M$^+$H), Found 610.0.

53

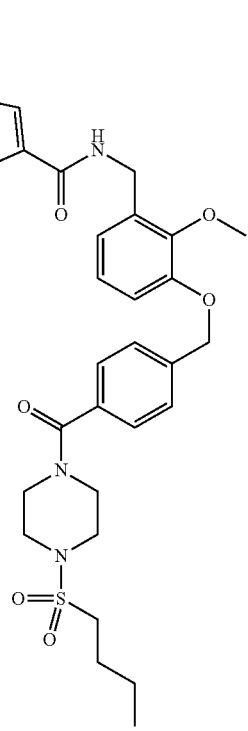

Example 18: Preparation of Compound 53

Compound 53 was prepared using the synthetic procedure used to synthesize compound 9. The necessary triazole carboxylic acid, 3-cyclopropyl-1-methyl-1H-pyrazole-4-carboxylic acid is commercially available. 1-(butylsulfonyl) piperazine was prepared as described in Scheme 6. Mass Spectrum (LCMS, ESI Pos.) Calcd. For $C_{32}H_{42}N_5O_6S$: 624.0 (M$^+$H), Found 624.0.

54

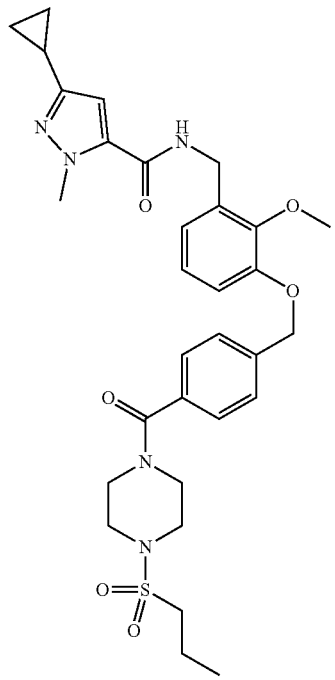

Example 19: Preparation of Compound 54

Compound 54 was prepared using the synthetic procedure used to synthesize compound 9. The necessary triazole carboxylic acid, 3-cyclopropyl-1-methyl-1H-pyrazole-4-carboxylic acid is commercially available. 1-(propane-1-sulfonyl) piperazine was prepared as described in Scheme 6. Mass Spectrum (LCMS, ESI Pos.) Calcd. For $C_{31}H_{40}N_5O_6S$: 610.0 (M$^+$H), Found 610.0.

55

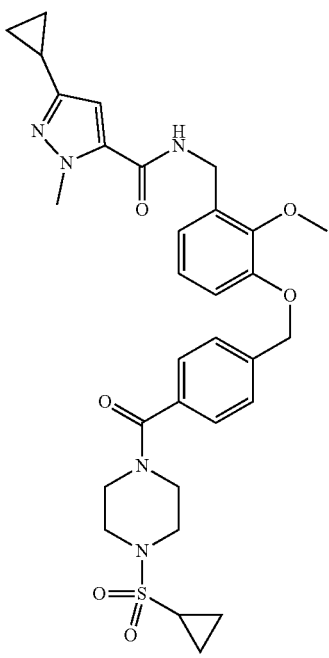

Example 20: Preparation of Compound 55

Compound 55 was prepared using the synthetic procedure used to synthesize compound 9. The necessary triazole carboxylic acid, 3-cyclopropyl-1-methyl-1H-pyrazole-4-carboxylic acid is commercially available. 1-(cyclopropylsulfonyl)piperazine hydrochloride was prepared as described in Scheme 6. Mass Spectrum (LCMS, ESI Pos.) Calcd. For $C_{31}H_{38}N_5O_6S$: 608.0 (M$^+$H), Found 608.0.

56

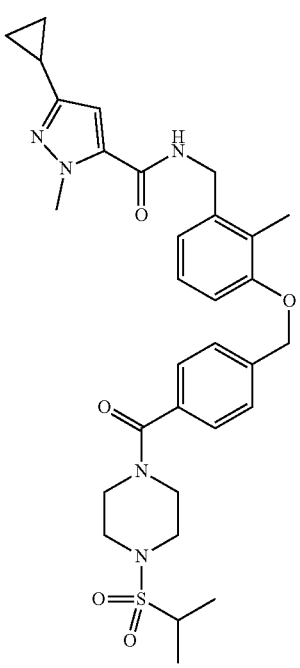

Example 21: Preparation of Compound 56

Compound 56 was prepared using the synthetic procedure used to synthesize compound 9. The necessary triazole carboxylic acid, 3-cyclopropyl-1-methyl-1H-pyrazole-4-carboxylic acid is commercially available as is 3-hydroxy-2-methylbenzaldehyde. 1-(Isopropylsulfonyl) piperazine was prepared as described in Scheme 6. Mass Spectrum (LCMS, ESI Pos.) Calcd. For $C_{31}H_{40}N_5O_5S$: 594.0 (M$^+$H), Found 594.0.

57

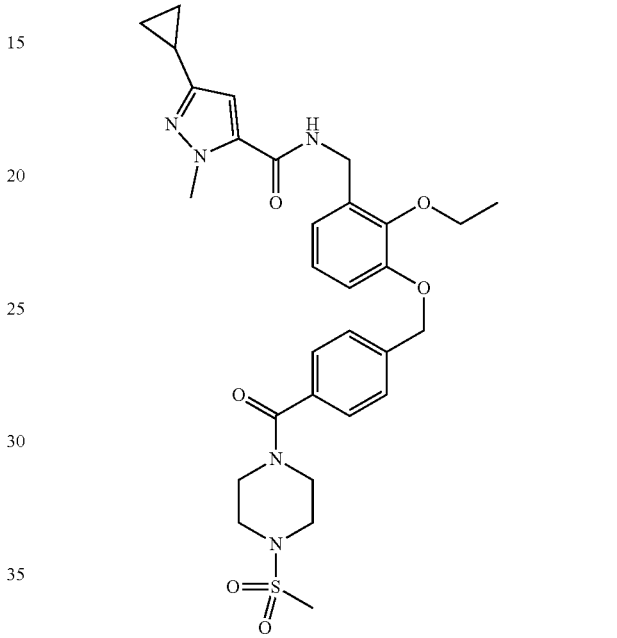

Example 22: Preparation of Compound 57

Compound 57 was prepared using the synthetic procedure used to synthesize compound 9. The necessary triazole carboxylic acid, 3-cyclopropyl-1-methyl-1H-pyrazole-4-carboxylic acid is commercially available as is 2-ethoxy-3-hydroxybenzaldehyde. 1-(methylsulfonyl) piperazine was prepared as described in Scheme 6. Mass Spectrum (LCMS, ESI Pos.) Calcd. For $C_{30}H_{38}N_5O_6S$: 596.0 (M$^+$H), Found 596.0.

58

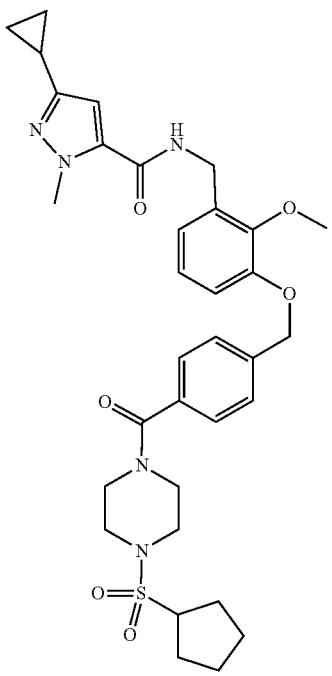

Example 23: Preparation of Compound 58

Compound 58 was prepared using the synthetic procedure used to synthesize compound 9. The necessary triazole carboxylic acid, 3-cyclopropyl-1-methyl-1H-pyrazole-4-carboxylic acid is commercially available. 1-(cyclopentylsulfonyl) piperazine was prepared as described in Scheme 6. Mass Spectrum (LCMS, ESI Pos.) Calcd. For $C_{33}H_{42}N_5O_6S$: 636.0 (M$^+$H), Found 636.0.

59

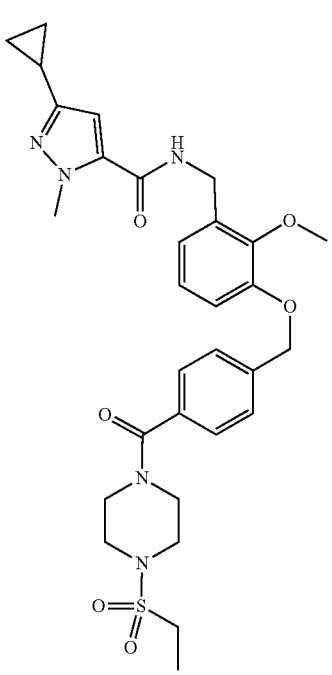

Example 24: Preparation of Compound 59

Compound 59 was prepared using the synthetic procedure used to synthesize compound 9. The necessary triazole carboxylic acid, 3-cyclopropyl-1-methyl-1H-pyrazole-4-carboxylic acid is commercially available. 1-(ethylsulfonyl) piperazine was prepared as described in Scheme 6. Mass Spectrum (LCMS, ESI Pos.) Calcd. For $C_{30}H_{38}N_5O_6S$: 596.0 (M$^+$H), Found 596.0.

60

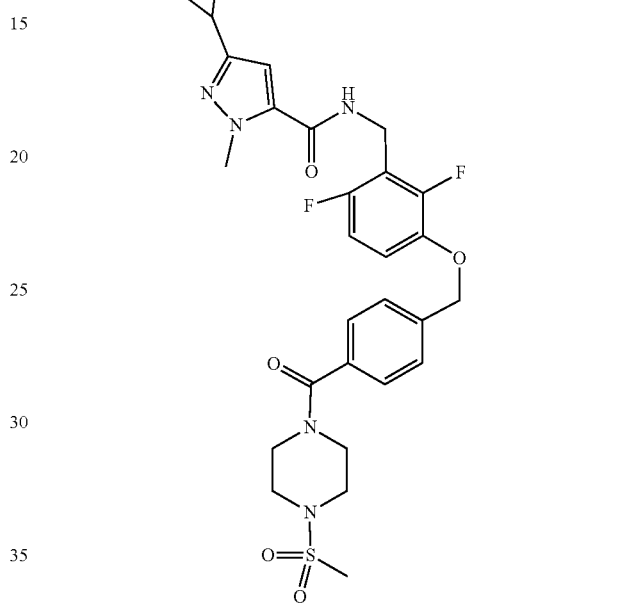

Example 25: Preparation of Compound 60

Compound 60 was prepared using the synthetic procedure used to synthesize compound 9. The necessary triazole carboxylic acid, 3-cyclopropyl-1-methyl-1H-pyrazole-4-carboxylic acid is commercially available as is 2,6-difluoro-3-hydroxybenzaldehyde. 1-(methylsulfonyl) piperazine was prepared as described in Scheme 6. Mass Spectrum (LCMS, ESI Pos.) Calcd. For $C_{28}H_{32}F_2N_5O_5S$: 588.0 (M$^+$H), Found 588.0.

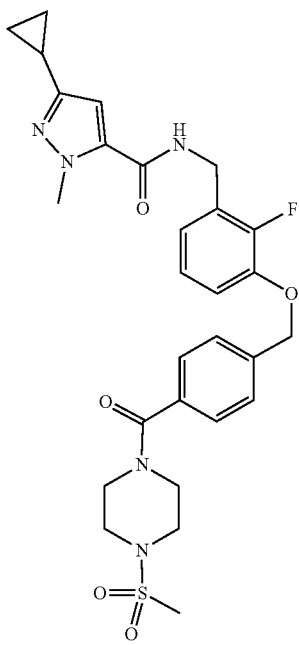

Example 26: Preparation of Compound 61

Compound 61 was prepared using the synthetic procedure used to synthesize compound 9. The necessary triazole carboxylic acid, 3-cyclopropyl-1-methyl-1H-pyrazole-4-carboxylic acid is commercially available as is 2-fluoro-3-hydroxybenzaldehyde. 1-(methylsulfonyl) piperazine was prepared as described in Scheme 6. Mass Spectrum (LCMS, ESI Pos.) Calcd. For $C_{25}H_{33}FN_5O_5S$: 570.0 (M$^+$H), Found 570.0.

Example 27: Preparation of Compound 62

Compound 62 was prepared using the synthetic procedure used to synthesize compound 9. The necessary triazole carboxylic acid, 3-cyclopropyl-1-methyl-1H-pyrazole-4-carboxylic acid is commercially available as is 2-methyl-3-hydroxybenzaldehyde. 1-(methylsulfonyl) piperazine was prepared as described in Scheme 6. Mass Spectrum (LCMS, ESI Pos.) Calcd. For $C_{29}H_{36}N_5O_5S$: 566.0 (M$^+$H), Found 566.0.

Example 28: Preparation of Compound 63

Compound 63 was prepared using the synthetic procedure used to synthesize compound 9. The necessary triazole carboxylic acid, 3-cyclopropyl-1-methyl-1H-pyrazole-4-carboxylic acid is commercially available as is 2-chloro-3-hydroxybenzaldehyde. 1-(methylsulfonyl) piperazine was prepared as described in Scheme 6. Mass Spectrum (LCMS, ESI Pos.) Calcd. For $C_{28}H_{33}ClN_5O_5S$: 587.0 (M$^+$H), Found 587.0.

Example 29: Preparation of Compound 64

Compound 64 was prepared using the synthetic procedure used to synthesize compound 9. The necessary triazole carboxylic acid, 3-cyclopropyl-1-methyl-1H-pyrazole-4-carboxylic acid is commercially available as are methyl 4-(2-bromoethyl)benzoate and 2-methyl-3-hydroxybenzaldehyde. 1-(methylsulfonyl) piperazine was prepared as described in Scheme 6.

Scheme 15 illustrates the preparation of compound 65.

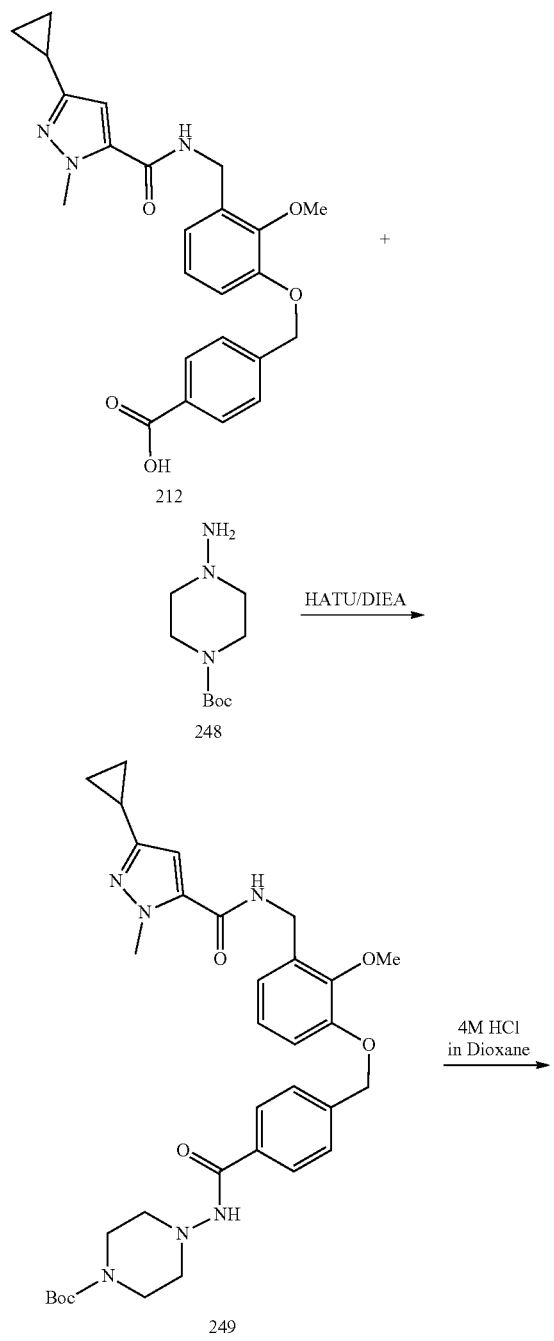

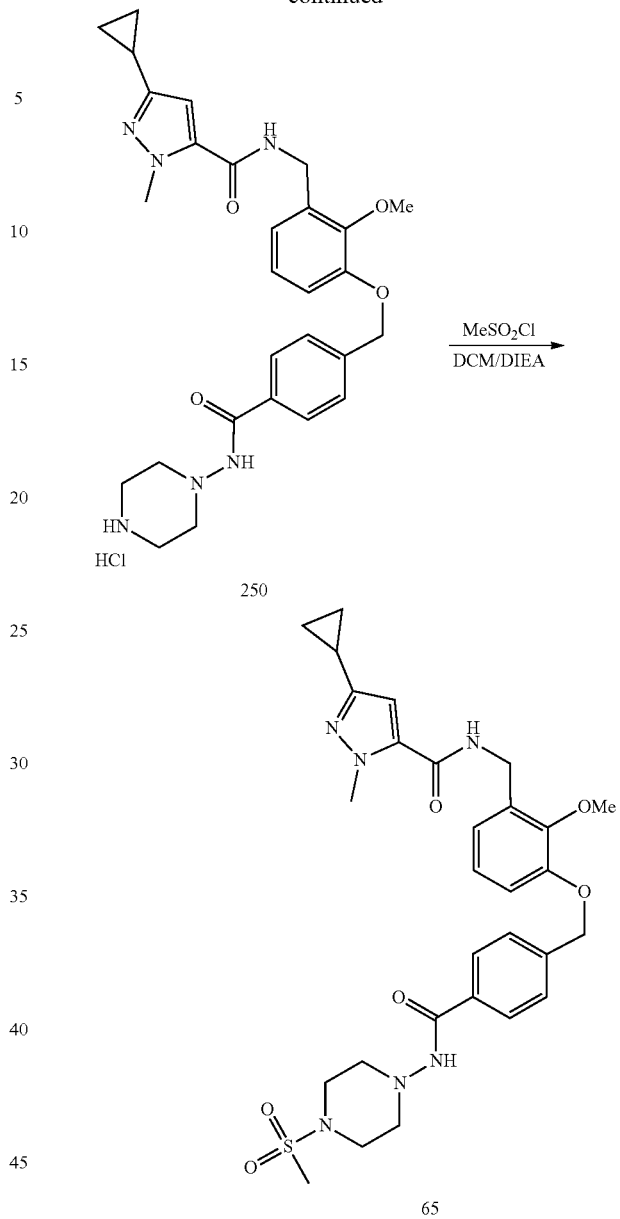

Preparation of Compound 249

To a stirred solution acid 212 (60 mg, 0.137 mmol, 1.2 eq) in DMF (3 mL) were added DIEA (74 mg, 0.57 mmol, 5 eq), tert-butyl 4-aminopiperazine-1-carboxylate 248 (23 mg, 0.114 mmol, 1.0 eq) and HATU (0.065 g, 0.172 mmol, 1.5 eq) and the reaction mixture was stirred at room temperature for 12 h. The reaction mixture was taken in EtOAc and washed with sat. NaHCO$_3$ solution and 5% HCl solution. The organic layer was then washed with water (2×), brine (1×), dried (Na$_2$SO$_4$) and evaporated under vacuum to give a residue, which was purified by column chromatography to give the desired amide 249.

Example 30: Preparation of Compound 65

The amide 249 was dissolved in a minimum amount of DCM and then 4 mL of 4M HCl in dioxane was added and the reaction mixture was stirred for 12 h. Removal of the solvents yielded the amine 250 as a HCl salt, which was directly used in the next step. To a stirred solution of amine 250 (40 mg, 0.073 mmol, 1 eq) and TEA (37 mg, 0.365 mmol, 5 eq) in DCM (5 mL) at 0° C. was dropwise added methanesulfonyl chloride (0.010 g, 0.093 mmol, 1.2 eq) and the reaction mixture was stirred at room temperature for 6 h. The reaction mixture was diluted with DCM and washed with sat. NaHCO₃ solution, 10% aq. HCl and brine. The organic layer was dried (NaSO₄) and evaporated under vacuum to get a residue, which was purified by column chromatography to provide 65. Mass Spectrum (LCMS, ESI Pos.) Calcd. For $C_{29}H_{37}N_6O_6S$: 597.0 (M⁺H), Found 597.0.

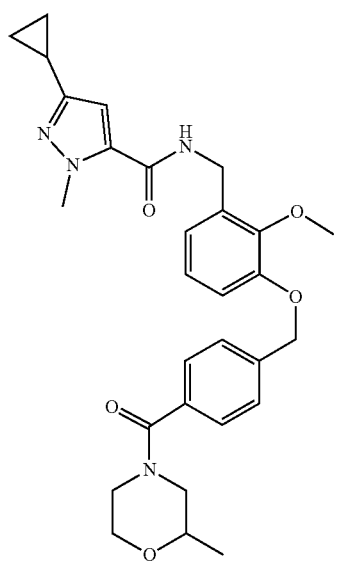

Example 31: Preparation of Compound 66

Compound 66 was prepared using the synthetic procedure used to synthesize compound 9. The necessary triazole carboxylic acid, 3-cyclopropyl-1-methyl-1H-pyrazole-4-carboxylic acid is commercially available as is 2-methyl morpholine. Mass Spectrum (LCMS, ESI Pos.) Calcd. For $C_{29}H_{35}N_4O_5$: 519.0 (M⁺H), Found 519.0.

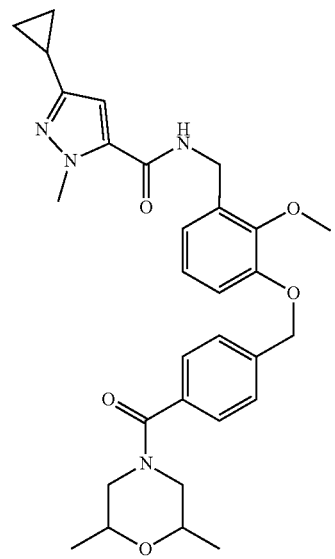

Example 32: Preparation of Compound 67

Compound 67 was prepared using the synthetic procedure used to synthesize compound 9. The necessary triazole carboxylic acid, 3-cyclopropyl-1-methyl-1H-pyrazole-4-carboxylic acid is commercially available as is 2,6-dimethyl morpholine. Mass Spectrum (LCMS, ESI Pos.) Calcd. For $C_{30}H_{37}N_4O_5$: 533.0 (M⁺H), Found 533.0.

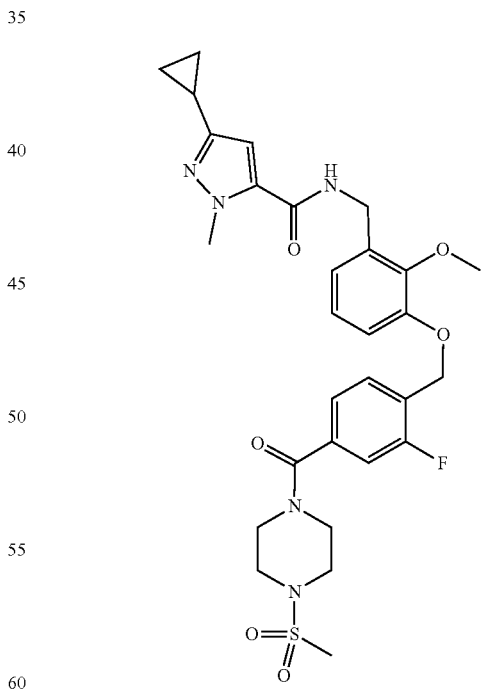

Example 33: Preparation of Compound 68

Compound 68 was prepared using the synthetic procedure used to synthesize compound 9. The necessary triazole carboxylic acid, 3-cyclopropyl-1-methyl-1H-pyrazole-4- carboxylic acid is commercially available as is methyl 4-(bromomethyl)-3-fluorobenzoate. 1-(methylsulfonyl) piperazine was prepared as described in Scheme 6. Mass Spectrum (LCMS, ESI Pos.) Calcd. For $C_{30}H_{38}N_5O_6S$: 596.0 (M+H), Found 596.0.

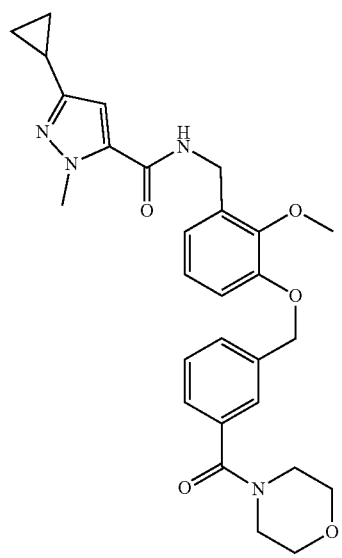

Example 34: Preparation of Compound 69

Compound 69 was prepared using the synthetic procedure used to synthesize compound 4. The necessary triazole carboxylic acid, 3-cyclopropyl-1-methyl-1H-pyrazole-4-carboxylic acid is commercially available as is morpholine. Mass Spectrum (LCMS, ESI Pos.) Calcd. For $C_{28}H_{33}N_4O_5$: 505.0 (M+H), Found 505.0.

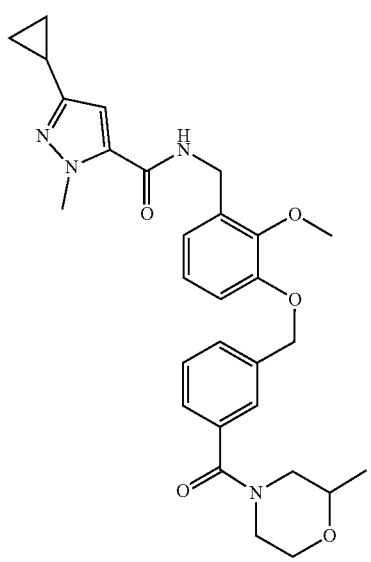

Example 35: Preparation of Compound 70

Compound 70 was prepared using the synthetic procedure used to synthesize compound 4. The necessary triazole carboxylic acid, 3-cyclopropyl-1-methyl-1H-pyrazole-4-carboxylic acid is commercially available as is 2-methyl morpholine. Mass Spectrum (LCMS, ESI Pos.) Calcd. For $C_{29}H_{35}N_4O_5$: 519.0 (M+H), Found 519.0.

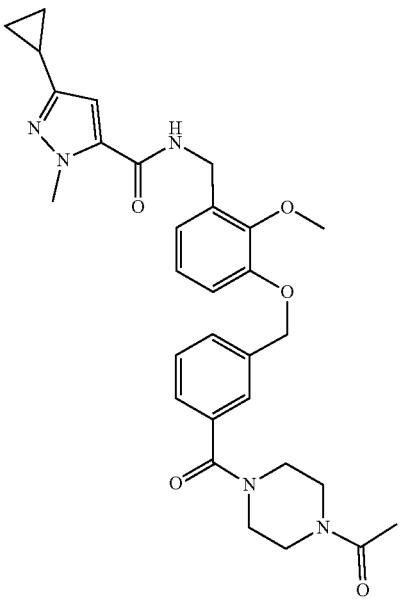

Example 36: Preparation of Compound 71

Compound 71 was prepared using the synthetic procedure used to synthesize compound 4. The necessary triazole carboxylic acid, 3-cyclopropyl-1-methyl-1H-pyrazole-4-carboxylic acid is commercially available as is 1-acetylpiperazine. Mass Spectrum (LCMS, ESI Pos.) Calcd. For $C_{30}H_{36}N_5O_5$: 546.0 (M+H), Found 546.0.

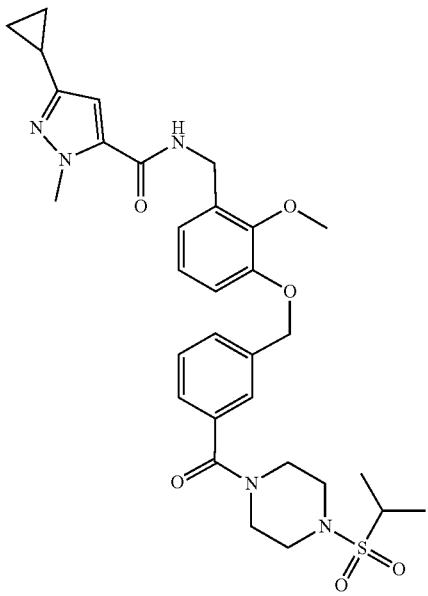

Example 37: Preparation of Compound 72

Compound 72 was prepared using the synthetic procedure used to synthesize compound 4. The necessary triazole carboxylic acid, 3-cyclopropyl-1-methyl-1H-pyrazole-4-carboxylic acid is commercially available. 1-(isopropylsulfonyl) piperazine was prepared as described in Scheme 6. Mass Spectrum (LCMS, ESI Pos.) Calcd. For $C_{31}H_{40}N_5O_6S$: 610.0 (M$^+$H), Found 610.0.

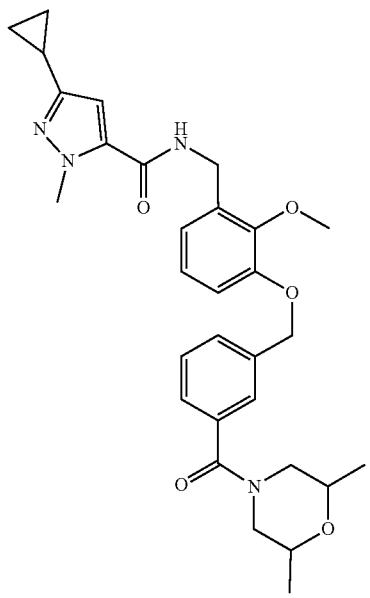

Example 38: Preparation of Compound 73

Compound 73 was prepared using the synthetic procedure used to synthesize compound 4. The necessary triazole carboxylic acid, 3-cyclopropyl-1-methyl-1H-pyrazole-4-carboxylic acid is commercially available as is 2,6-dimethyl morpholine. Mass Spectrum (LCMS, ESI Pos.) Calcd. For $C_{30}H_{37}N_4O_5$: 533.0 (M$^+$H), Found 533.0.

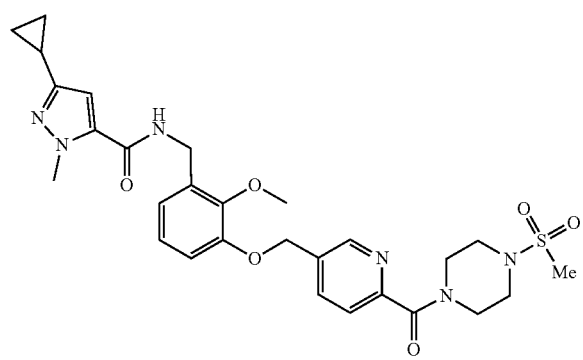

Example 39: Preparation of Compound 74

Compound 74 was prepared using the synthetic procedure used to synthesize compound 9. The necessary triazole carboxylic acid, 3-cyclopropyl-1-methyl-1H-pyrazole-4-carboxylic acid is commercially available as is methyl-5-bromomethylpyridine-2-carboxylate. Mass Spectrum (LCMS, ESI Pos.) Calcd. For $C_{28}H_{35}N_6O_6S$: 583.0 (M$^+$H), Found 583.0.

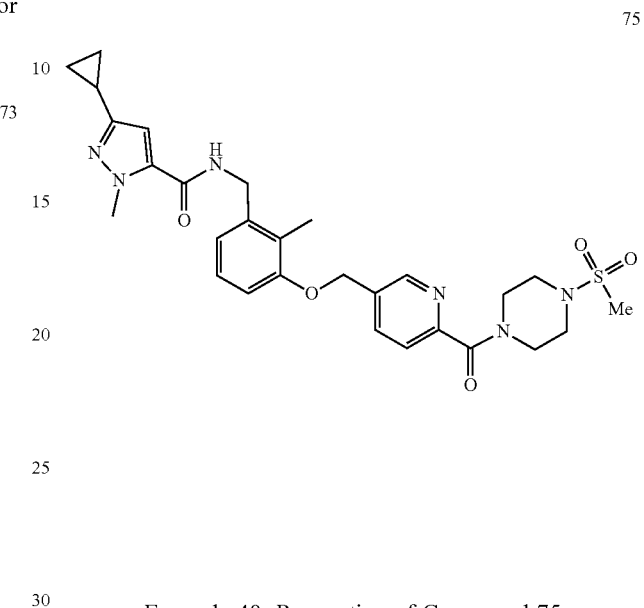

Example 40: Preparation of Compound 75

Compound 75 was prepared using the synthetic procedure used to synthesize compound 9. The necessary triazole carboxylic acid, 3-cyclopropyl-1-methyl-1H-pyrazole-4-carboxylic acid is commercially available as are 3-hydroxy-2-methyl benzaldehyde and methyl-5-bromomethylpyridine-2-carboxylate. Mass Spectrum (LCMS, ESI Pos.) Calcd. For $C_{28}H_{35}N_6O_5S$: 567.0 (M$^+$H), Found 563.0.

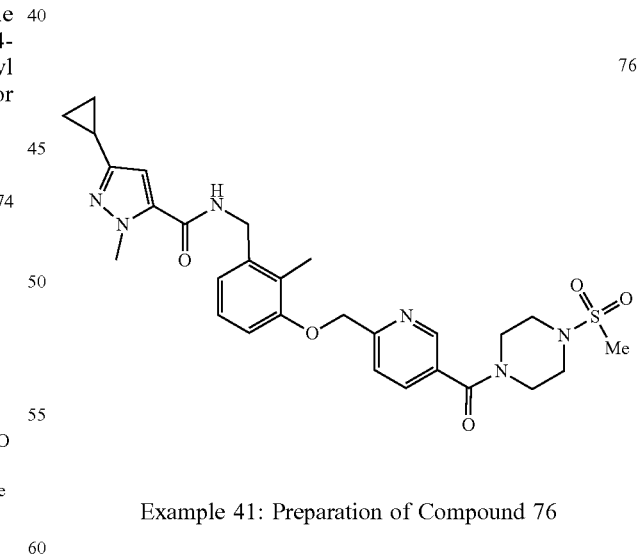

Example 41: Preparation of Compound 76

Compound 76 was prepared using the synthetic procedure used to synthesize compound 9. The necessary triazole carboxylic acid, 3-cyclopropyl-1-methyl-1H-pyrazole-4-carboxylic acid is commercially available as are 3-hydroxy-2-methyl benzaldehyde and methyl 6-(bromomethyl)nicotinate. Mass Spectrum (LCMS, ESI Pos.) Calcd. For $C_{28}H_{35}N_6O_5S$: 567.0 (M$^+$H), Found 563.0.

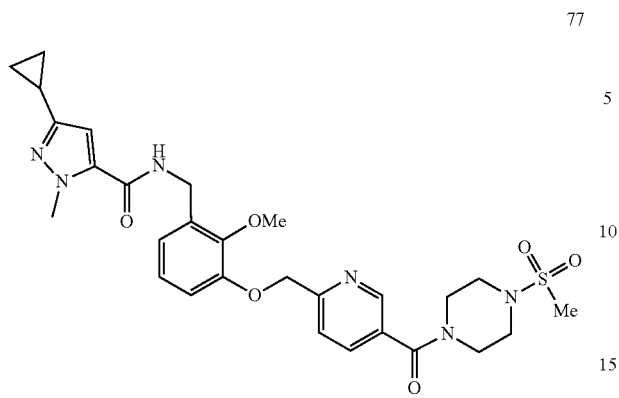

77

Example 42: Preparation of Compound 77

Compound 77 was prepared using the synthetic procedure used to synthesize compound 9. The necessary triazole carboxylic acid, 3-cyclopropyl-1-methyl-1H-pyrazole-4-carboxylic acid is commercially available as is methyl 6-(bromomethyl)nicotinate. Mass Spectrum (LCMS, ESI Pos.) Calcd. For $C_{28}H_{35}N_6O_6S$: 583.0 (M$^+$H), Found 583.0.

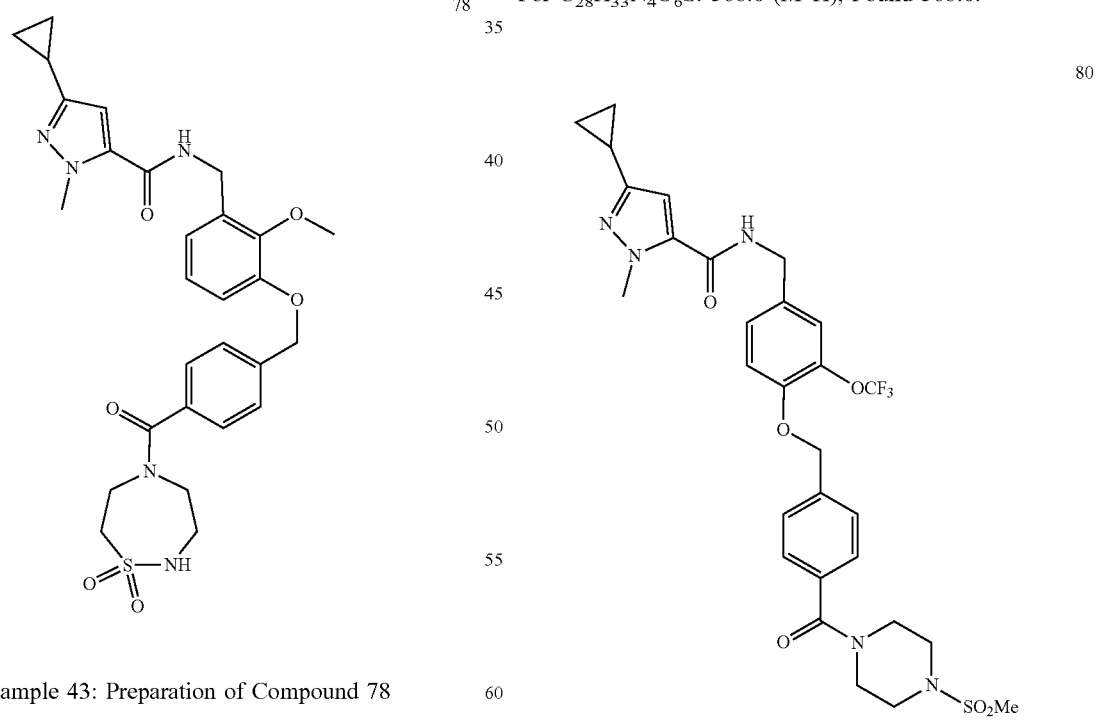

78

Example 43: Preparation of Compound 78

Compound 78 was prepared using the synthetic procedure used to synthesize compound 9. The necessary triazole carboxylic acid, 3-cyclopropyl-1-methyl-1H-pyrazole-4-carboxylic acid is commercially available as is 1-lambda(6),2,5-thiadiazepane-1,1-dione. Mass Spectrum (LCMS, ESI Pos.) Calcd. For $C_{28}H_{34}N_5O_6S$: 568.0 (M$^+$H), Found 568.0.

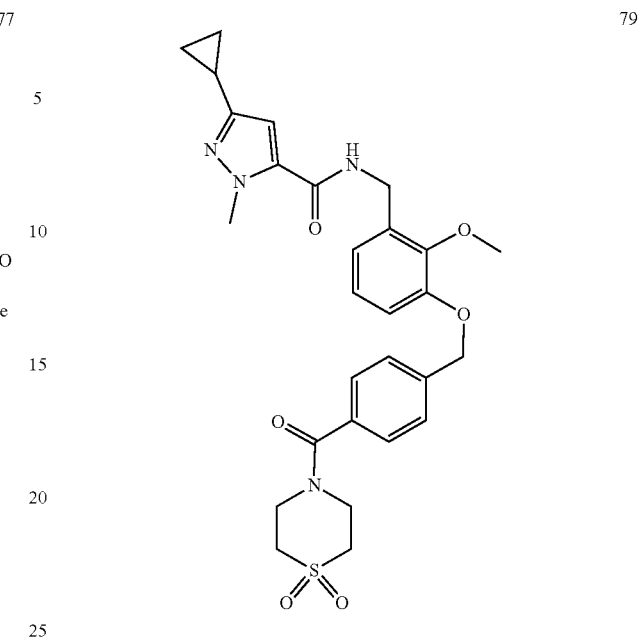

79

Example 44: Preparation of Compound 79

Compound 79 was prepared using the synthetic procedure used to synthesize compound 9. The necessary triazole carboxylic acid, 3-cyclopropyl-1-methyl-1H-pyrazole-4-carboxylic acid is commercially available as is thiomorpholine 1,1 dioxide. Mass Spectrum (LCMS, ESI Pos.) Calcd. For $C_{28}H_{33}N_4O_6S$: 568.0 (M$^+$H), Found 568.0.

80

Example 45: Preparation of Compound 80

Compound 80 was prepared using the synthetic procedure used to synthesize compound 9. The necessary triazole carboxylic acid, 3-cyclopropyl-1-methyl-1H-pyrazole-4-carboxylic acid is commercially available. 1-(methylsulfonyl) piperazine was prepared as described in Scheme 6. Mass Spectrum (LCMS, ESI Pos.) Calcd. For $C_{29}H_{33}F_3N_5O_6S$: 636.0 (M$^+$H), Found 636.0.

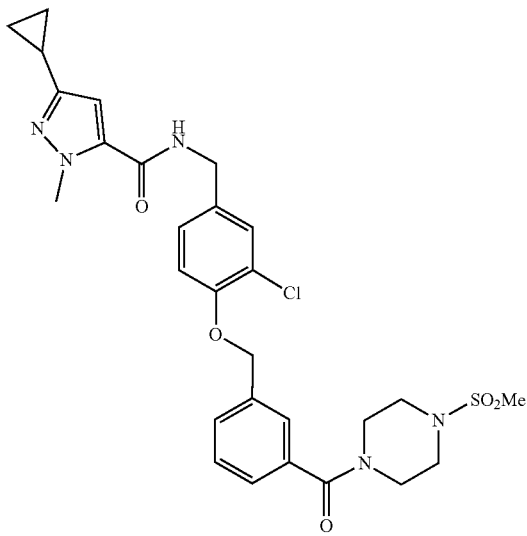

Example 46: Preparation of Compound 81

Compound 81 was prepared using the synthetic procedure used to synthesize compound 9. The necessary triazole carboxylic acid, 3-cyclopropyl-1-methyl-1H-pyrazole-4-carboxylic acid is commercially available. 1-(methylsulfonyl) piperazine was prepared as described in Scheme 6. Mass Spectrum (LCMS, ESI Pos.) Calcd. For $C_{28}H_{33}ClN_5O_5S$: 587.0 (M$^+$H), Found 587.0.

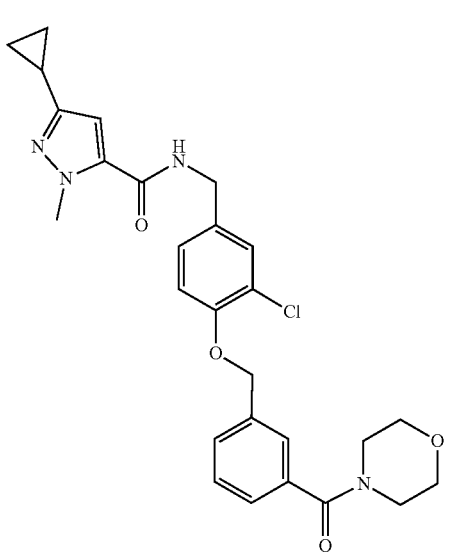

Example 47: Preparation of Compound 82

Compound 82 was prepared using the synthetic procedure used to synthesize compound 9. The necessary triazole carboxylic acid, 3-cyclopropyl-1-methyl-1H-pyrazole-4-carboxylic acid is commercially available as is morpholine. Mass Spectrum (LCMS, ESI Pos.) Calcd. For $C_{27}H_{30}ClN_4O_4$: 510.0 (M$^+$H), Found 510.0.

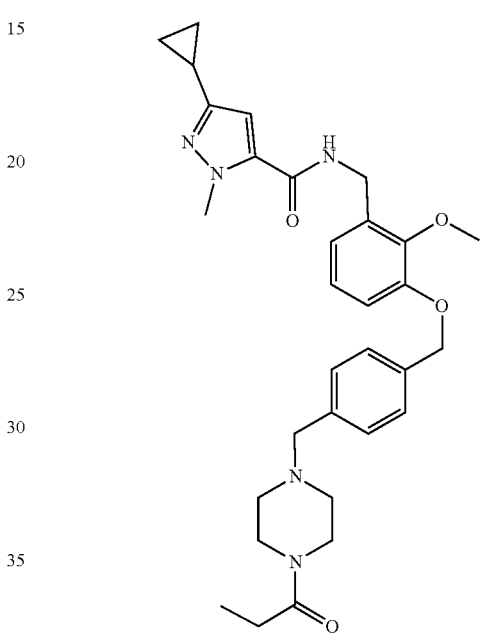

Example 48: Preparation of Compound 83

Compound 83 was prepared using the synthetic procedure used to synthesize compound 39. The necessary triazole carboxylic acid, 3-cyclopropyl-1-methyl-1H-pyrazole-4-carboxylic acid is commercially available as is 1-(piperazin-1-yl)propan-1-one. Mass Spectrum (LCMS, ESI Pos.) Calcd. For $C_{31}H_{40}N_5O_4$: 546.0 (M$^+$H), Found 546.0.

84

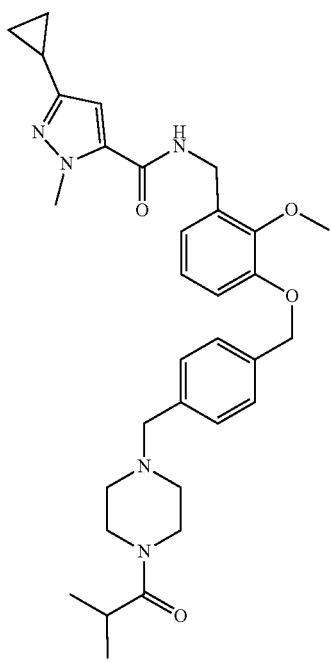

Example 49: Preparation of Compound 84

Compound 84 was prepared using the synthetic procedure used to synthesize compound 39. The necessary triazole carboxylic acid, 3-cyclopropyl-1-methyl-1H-pyrazole-4-carboxylic acid is commercially available as is 2-methyl-1-(piperazin-1-yl)propan-1-one. Mass Spectrum (LCMS, ESI Pos.) Calcd. For $C_{32}H_{42}N_5O_4$: 560.0 ($M^+H$), Found 560.0.

85

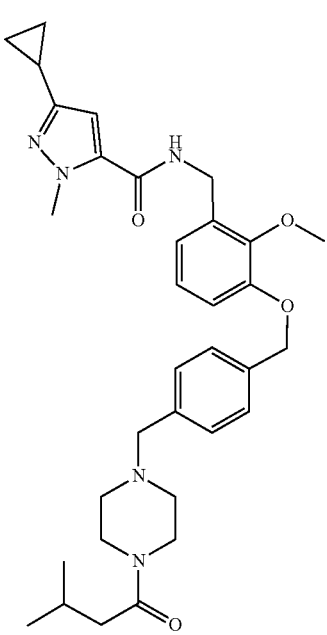

Example 50: Preparation of Compound 85

Compound 85 was prepared using the synthetic procedure used to synthesize compound 39. The necessary triazole carboxylic acid, 3-cyclopropyl-1-methyl-1H-pyrazole-4-carboxylic acid is commercially available as is 1-(3-methylbutanoyl)piperazine. Mass Spectrum (LCMS, ESI Pos.) Calcd. For $C_{33}H_{44}N_5O_4$: 574.0 ($M^+H$), Found 574.0.

86

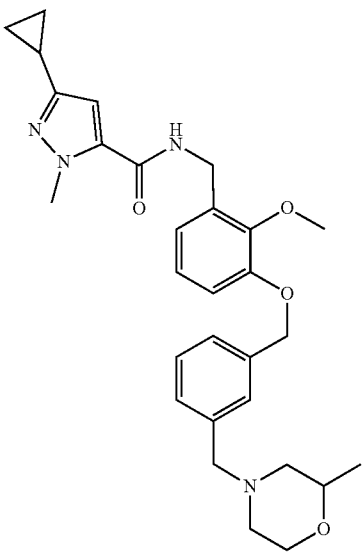

Example 51: Preparation of Compound 86

Compound 86 was prepared using the synthetic procedure used to synthesize compound 39. The necessary triazole carboxylic acid, 3-cyclopropyl-1-methyl-1H-pyrazole-4-carboxylic acid is commercially available as are 1,3-bis(bromomethyl)benzene and 2-methylmorpholine. Mass Spectrum (LCMS, ESI Pos.) Calcd. For $C_{29}H_{37}N_4O_4$: 505.0 ($M^+H$), Found 505.0.

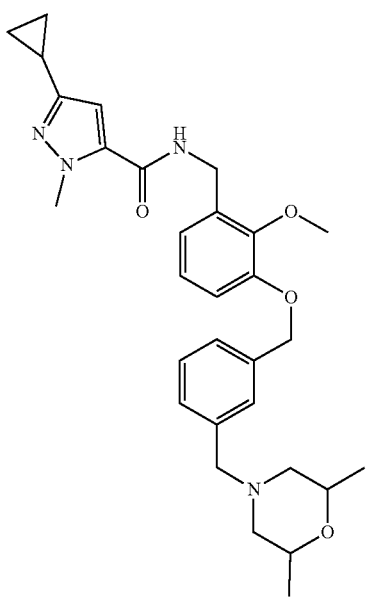 [SMILES: COc1c(CNC(=O)c2cc(C3CC3)nn2C)cccc1OCc1cccc(CN2CC(C)OC(C)C2)c1]

Example 52: Preparation of Compound 87

Compound 87 was prepared using the synthetic procedure used to synthesize compound 39. The necessary triazole carboxylic acid, 3-cyclopropyl-1-methyl-1H-pyrazole-4-carboxylic acid is commercially available as are 1,3-bis(bromomethyl)benzene and 2,6-dimethylmorpholine. Mass Spectrum (LCMS, ESI Pos.) Calcd. For $C_{30}H_{39}N_4O_4$: 519.0 (M$^+$H), Found 519.0.

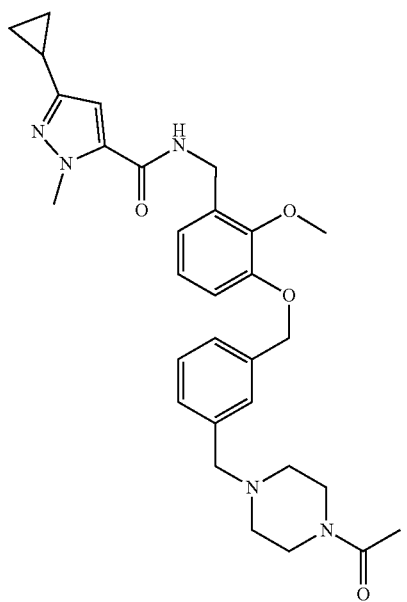

Example 53: Preparation of Compound 88

Compound 88 was prepared using the synthetic procedure used to synthesize compound 39. The necessary triazole carboxylic acid, 3-cyclopropyl-1-methyl-1H-pyrazole-4-carboxylic acid is commercially available as are 1,3-bis(bromomethyl)benzene and 1-acetylpiperazine. Mass Spectrum (LCMS, ESI Pos.) Calcd. For $C_{30}H_{35}N_5O_4$: 532.0 (M$^+$H), Found 532.0.

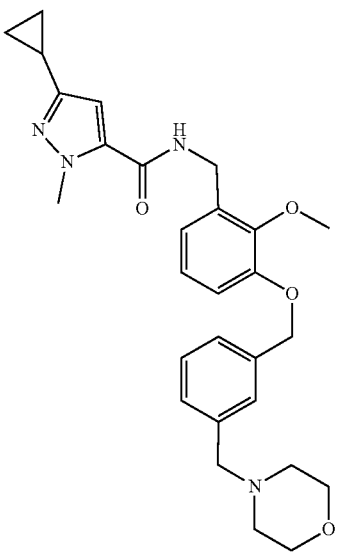

Example 54: Preparation of Compound 89

Compound 89 was prepared using the synthetic procedure used to synthesize compound 39. The necessary triazole carboxylic acid, 3-cyclopropyl-1-methyl-1H-pyrazole-4-carboxylic acid is commercially available as are 1,3-bis(bromomethyl)benzene and morpholine. Mass Spectrum (LCMS, ESI Pos.) Calcd. For $C_{28}H_{35}N_4O_4$: 491.0 (M$^+$H), Found 491.0.

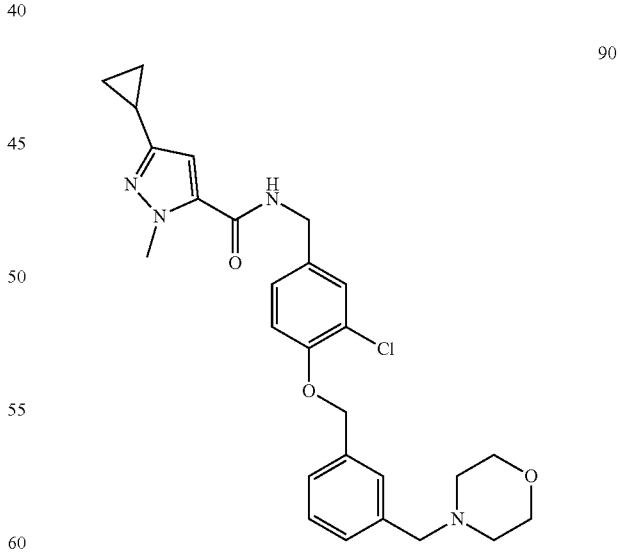

Example 55: Preparation of Compound 90

Compound 90 was prepared using the synthetic procedure used to synthesize compound 39. The necessary triazole carboxylic acid, 3-cyclopropyl-1-methyl-1H-pyrazole-4- carboxylic acid is commercially available as are 1,3-bis (bromomethyl)benzene and morpholine. Mass Spectrum (LCMS, ESI Pos.) Calcd. For $C_{27}H_{32}ClN_4O_3$: 496.0 (M$^+$H), Found 496.0.

Scheme 16 illustrates the preparation of compound 91.

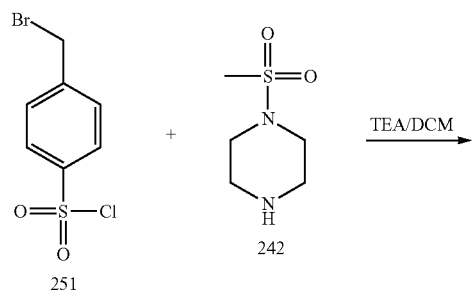

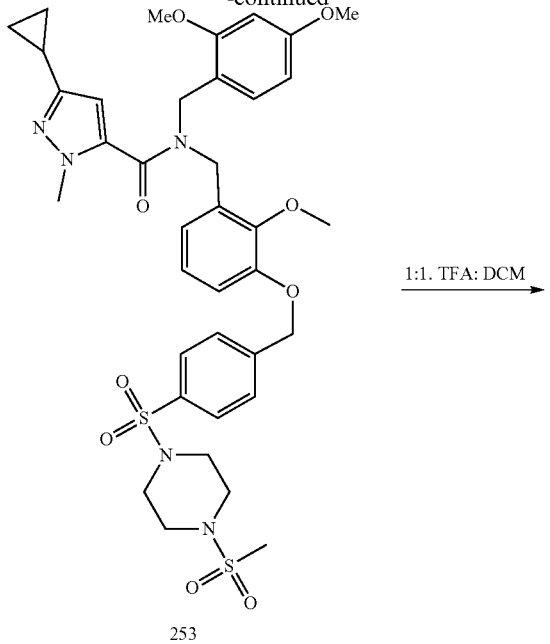

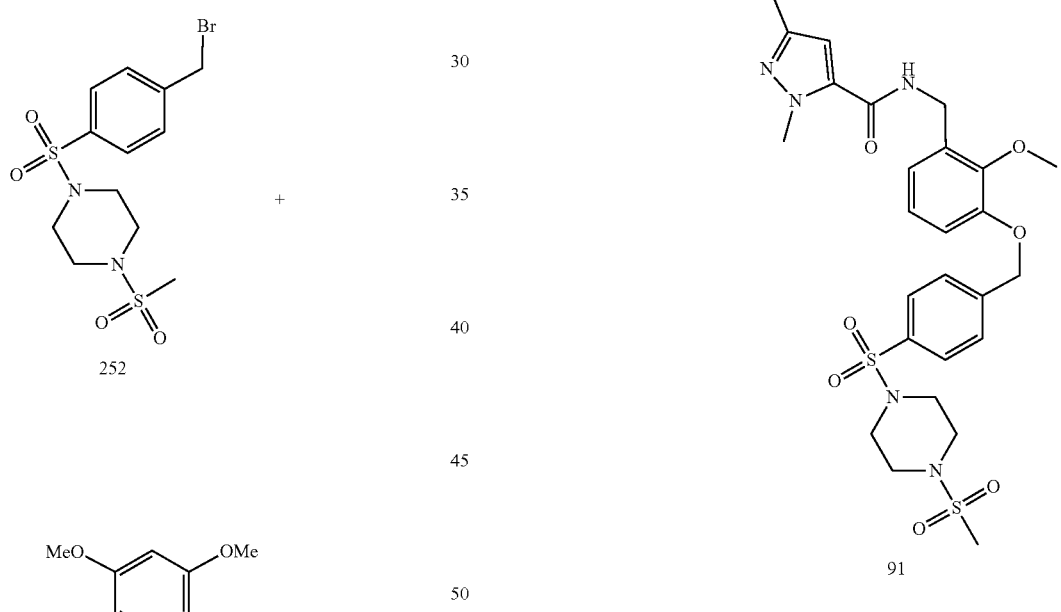

Preparation of Compound 252

To a solution of the sulfonyl chloride 251 (0.244 g, 0.914 mmol, 1.5 eq) in DCM (5 ml) at 0° C. were added TEA (0.123 g, 1.22 mmol, 2.0 eq) and 1-methanesulfonylpiperazine 242 (0.100 g, 0.609 mmol, 1.0 eq). The reaction mixture was stirred at 0° C. for 1 hr and then at RT for 3 h. The reaction mixture was diluted with DCM and then washed with sat. sodium bicarbonate solution. The DCM layer was washed with water, brine and dried over NaSO$_4$ and evaporated under vacuum to give the crude sulfonamide, which was directly used in the next step.

Example 56: Preparation of Compound 91

To a stirred solution of compound 205 (0.315 g, 0.698 mmol, 1.2 eq) in DMF (5 ml) were added Cs$_2$CO$_3$ (0.574 g,1.45 mmol, 2.5 eq) and crude bromide 252 (0.230 g,0.582 mmol, 1.2 eq) and the reaction mixture was stirred at RT for 12 h. The reaction mixture was diluted with water and extracted with ethyl acetate (3×). The combined organic layers were washed with water, brine and dried over NaSO$_4$ and evaporated under vacuum to provide a residue, which was purified by column chromatography to give the desired alkylation product 253. The alkylation product 253 was taken in 1:1 DCM: TFA and stirred at room temperature for 12 h. Then TFA and DCM were removed under vacuum to give a residue, which was purified by column chromatography to give compound 91. Mass Spectrum (LCMS, ESI Pos.)Calcd. For $C_{28}H_{36}N_5O_7S_2$: 618.0 (M$^+$H), Found 618.0

Scheme 17 illustrates the preparation of compound 92.

Scheme 17

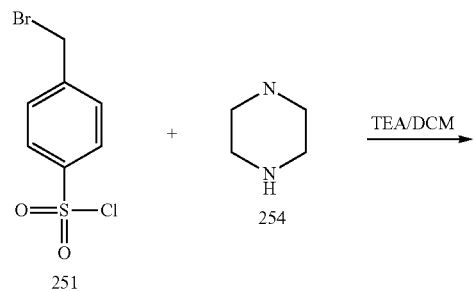

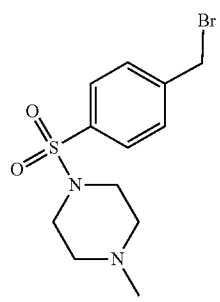

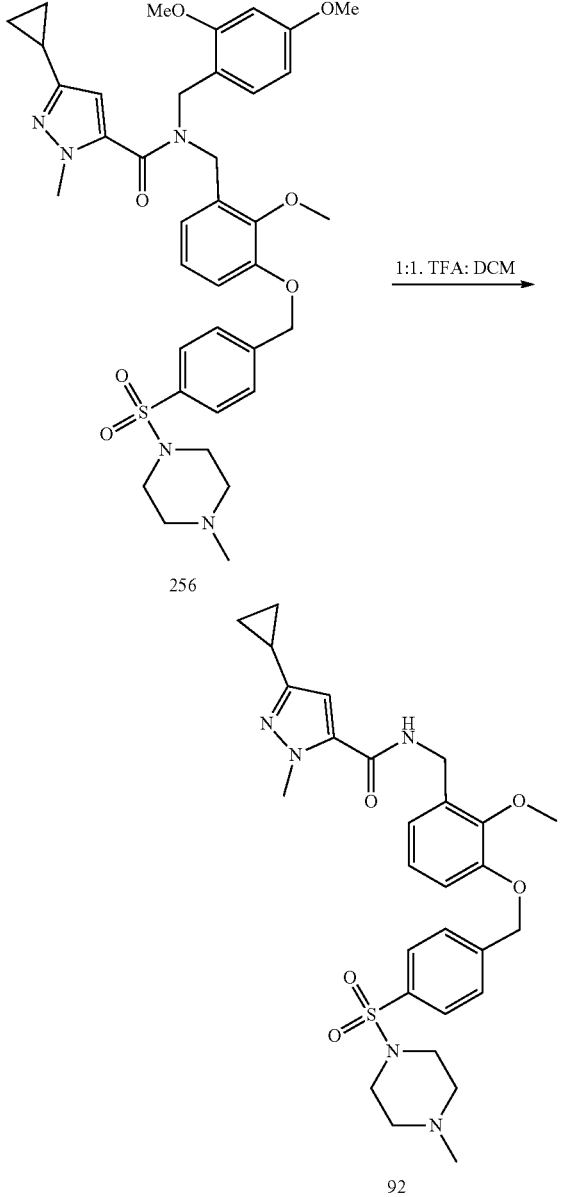

Preparation of Compound 255

To a solution of the sulfonyl chloride 251 (0.244 g, 0.914 mmol, 1.5 eq) in DCM (5 ml) at 0° C. were added TEA (0.123 g, 1.22 mmol, 2.0 eq) and N-methylpiperazine 254 (0.100 g, 0.609 mmol, 1.0 eq). The reaction mixture was stirred at 0° C. for 1 hr and then at RT for 3 h. The reaction mixture was diluted with DCM and then washed with sat. sodium bicarbonate solution. The DCM layer was washed with water, brine and dried over NaSO$_4$ and evaporated under vacuum to give the crude sulfonamide, which was directly used in the next step.

Example 57: Preparation of Compound 92

To a stirred solution of compound 205 (0.315 g, 0.698 mmol, 1.2 eq) in DMF (5 ml) were added Cs$_2$CO$_3$ (0.574 g,1.45 mmol, 2.5 eq) and crude bromide 255 (0.230 g,0.582 mmol, 1.2 eq) and the reaction mixture was stirred at RT for 12 h. The reaction mixture was diluted with water and extracted with ethyl acetate (3×). The combined organic layers were washed with water, brine and dried over NaSO$_4$ and evaporated under vacuum to get a residue, which was purified by column chromatography to give the desired alkylation product 256. The alkylation product 256 was taken in 1:1 DCM:TFA and stirred at RT for 12 h. Then TFA and DCM were removed under vacuum to give a residue. The residue was taken in DCM and carefully neutralized with sat NaHCO$_3$. The DCM layer was collected, dried and evaporated to provide the crude product, which was purified by column chromatography to give compound 92. Mass Spectrum (LCMS, ESI Pos.) Calcd. For C$_{28}$H$_{36}$N$_5$O$_5$S: 554.0 (M$^+$H), Found 554.0

Scheme 18 illustrates the preparation of compound 93.

Scheme 18

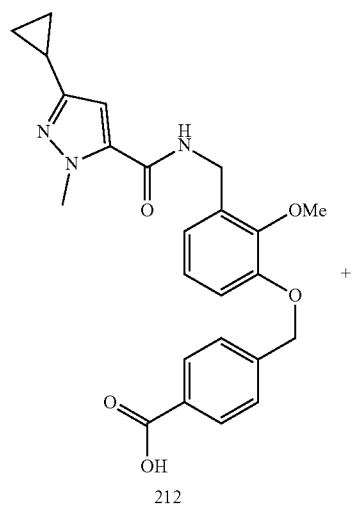

212

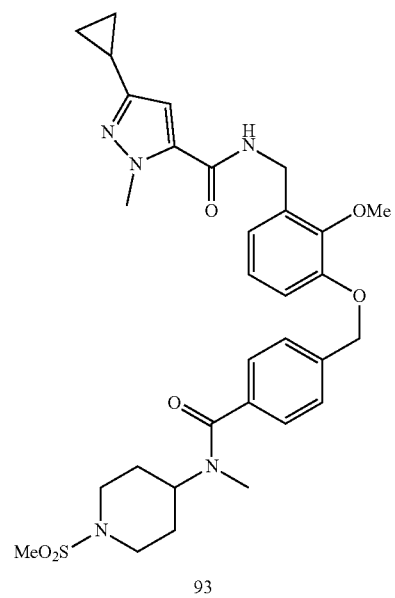

93

Example 58: Preparation of Compound 93

To a stirred solution of acid 212 (60 mg, 0.137 mmol, 1.2 eq) in DMF (3 mL) were added DIEA (74 mg, 0.57 mmol, 5 eq), amine 257 (26 mg, 0.114 mmol, 1.0 eq) and HATU (0.065 g, 0.172 mmol, 1.5 eq) and the reaction mixture was stirred at room temperature for 12 h. The reaction mixture was taken in EtOAc and washed with sat. NaHCO$_3$ solution and 5% HCl solution. The organic layer was then washed with water (2×), brine (1×), dried (Na$_2$SO$_4$) and evaporated under vacuum to give a residue, which was purified by column chromatography to give the desired amide 93. Mass Spectrum (LCMS, ESI Pos.) Calcd. For C$_{31}$H$_{40}$N$_5$O$_6$S: 610.0 (M$^+$H), Found 610.0.

Scheme 19 illustrates the preparation of compound 94.

Scheme 19

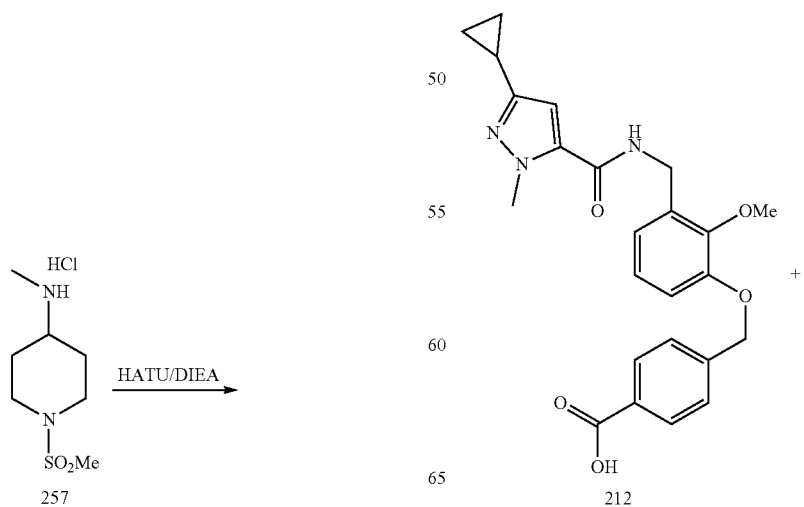

225

-continued

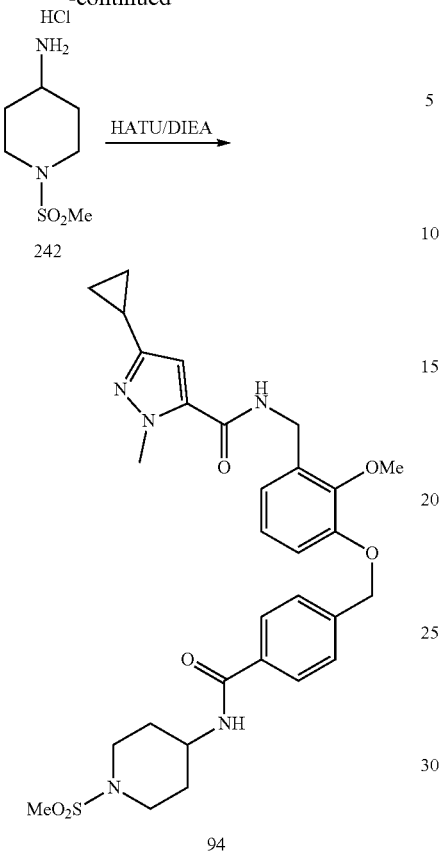

Example 59: Preparation of Compound 94

To a stirred solution of acid 212 (60 mg, 0.137 mmol, 1.2 eq) in DMF (3 mL) were added DIEA (74 mg, 0.57 mmol, 5 eq), amine 242 (24 mg, 0.114 mmol, 1.0 eq) and HATU (0.065 g, 0.172 mmol, 1.5 eq) and the reaction mixture was stirred at room temperature for 12 h. The reaction mixture was taken in EtOAc and washed with sat. NaHCO$_3$ solution and 5% HCl solution. The organic layer was then washed with water (2×), brine (1×), dried (Na$_2$SO$_4$) and evaporated under vacuum to give a residue, which was purified by column chromatography to give the desired amide 94. Mass Spectrum (LCMS, ESI Pos.) Calcd. For $C_{30}H_{38}N_5O_6S$: 596.0 (M$^+$H), Found 596.0

226

Scheme 20 illustrates the preparation of compound 95.

Scheme 20

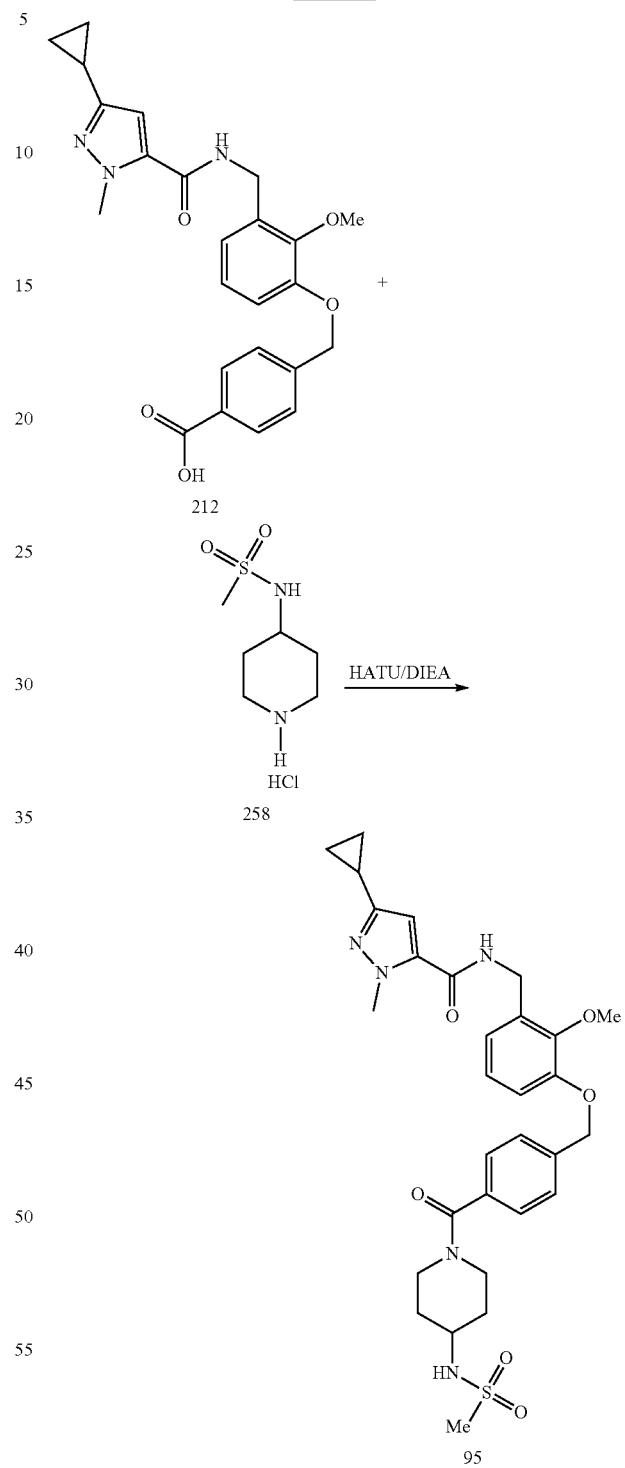

Example 60: Preparation of Compound 95

To a stirred solution of acid 212 (60 mg, 0.137 mmol, 1.2 eq) in DMF (3 mL) were added DIEA (74 mg, 0.57 mmol, 5 eq), amine 258 (24 mg, 0.114 mmol, 1.0 eq) and HATU (0.065 g, 0.172 mmol, 1.5 eq) and the reaction mixture was stirred at room temperature for 12 h. The reaction mixture was taken in EtOAc and washed with sat. NaHCO$_3$ solution and 5% HCl solution. The organic layer was then washed with water (2×), brine (1×), dried (Na$_2$SO$_4$) and evaporated under vacuum to give a residue, which was purified by column chromatography to give the desired amide 95. Mass Spectrum (LCMS, ESI Pos.) Calcd. For C$_{30}$H$_{35}$N$_5$O$_6$S: 596.0 (M$^+$H), Found 596.0.

Scheme 21 illustrates the preparation of compound 96.

Scheme 21

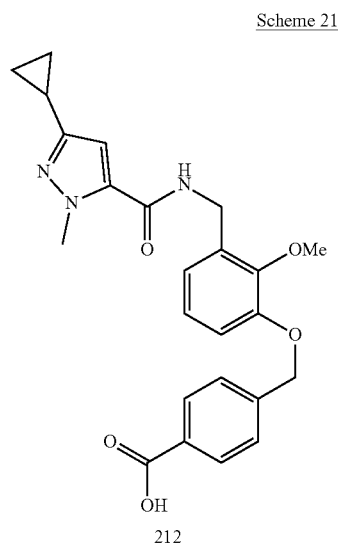

212

-continued

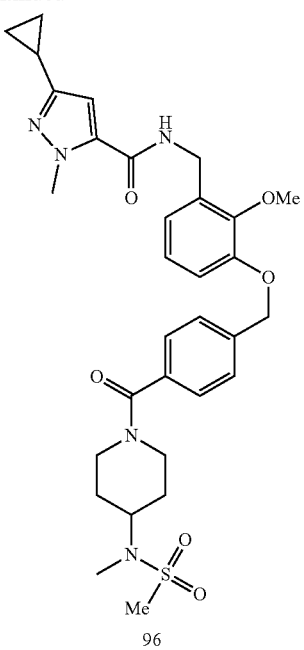

96

Example 61: Preparation of Compound 96

To a stirred solution of acid 212 (60 mg, 0.137 mmol, 1.2 eq) in DMF (3 mL) were added DIEA (74 mg, 0.57 mmol, 5 eq), amine 259 (24 mg, 0.114 mmol, 1.0 eq) and HATU (0.065 g, 0.172 mmol, 1.5 eq) and the reaction mixture was stirred at room temperature for 12 h. The reaction mixture was taken in EtOAc and washed with sat. NaHCO$_3$ solution and 5% HCl solution. The organic layer was then washed with water (2×), brine (1×), dried (Na$_2$SO$_4$) and evaporated under vacuum to give a residue, which was purified by column chromatography to give the desired amide 96. Mass Spectrum (LCMS, ESI Pos.) Calcd. For C$_{31}$H$_{40}$N$_5$O$_6$S: 610.0 (M$^+$H), Found 610.0.

Scheme 22 illustrates the preparation of compound 265.

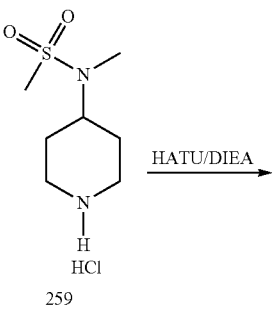

259

Scheme 22

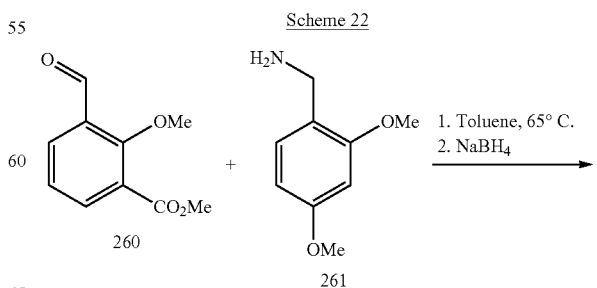

260

261

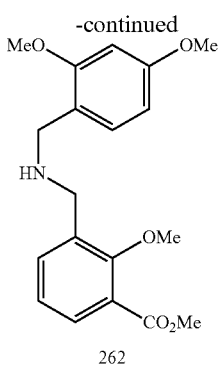

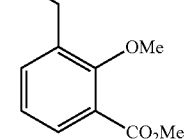

Preparation of Compound 262

To a solution of methyl 3-formyl-2-methoxybenzoate 260 (500 mg, 2.58 mmol, 1.0 eq) in toluene were added 2,4-dimethoxybenzyl amine 261 (430 mg, 2.58 mmol, 1.0 eq) and catalytic amount of p-toluene sulfonic acid. The reaction mixture was stirred at 65° C. for 24 h. Solvent was removed and the residue was taken in MeOH and cooled in an ice bath. Then sodium borohydride (195 mg, 5.16 mmol, 2.0 eq) was added slowly and the reaction mixture was stirred at RT for 12 h. Solvent was removed and residue was taken in ethyl acetate and then sat. NaHCO$_3$ was added and the mixture was stirred for 1 h. The organic layer was separated, dried (MgSO$_4$) and solvent was removed to give the amine 262, which was used in the next step without further purification.

Preparation of Compound 263

To a solution of the crude amine 262 (2.58 mmol, 1.0 eq) in DMF (10 mL) were added 3-cyclopropyl-1-methyl-1H-pyrazole-5-carboxylic acid 204 (477 mg, 2.84 mmol, 1.1 eq), HATU (1.18 g, 3.09 mmol, 1.2 eq), and DIEA (1.67 g, 12.95 mmol, 5.0 eq) and the reaction mixture was stirred at RT for 12 h. The reaction mixture was then diluted with EtOAc and washed with 10% aq. HCl (1×), sat. NaHCO$_3$ (1×) and water (3×). The organic layer was collected, dried (MgSO$_4$) and evaporated to give a residue, which was purified by column chromatography (EtOAc/Hexane) to give the desired amide 263. Mass Spectrum (LCMS, ESI Pos.) Calcd. For C$_{27}$H$_{32}$N$_3$O$_6$: 494.0 (M$^+$H), Found 494.0.

Preparation of Compound 264

The amide 263 (500 mg, 1.01 mmol) was taken in 1:1 mixture of TFA:DCM and stirred at room temperature for 24 h. Solvents were removed to provide a residue, which was purified by column chromatography to give compound 264. Mass Spectrum (LCMS, ESI Pos.)Calcd. For C$_{18}$H$_{22}$N$_3$O$_4$: 344.0 (M$^+$H), Found 344.0.

Preparation of Compound 265

The ester 264 (400 mg, 1.17 mmol, 1.0 eq) was dissolved in a 1:5 mixture of H$_2$O:MeOH (18 mL) and then LiOH (107 mg, 4.66 mmol, 4.0 eq) was added. The reaction mixture was stirred at 65° C. for 12 h. The reaction mixture was evaporated under vacuum to give a residue, which was stirred in a mixture of 10% aq. HCl and ethyl acetate for 30 min. The organic layer was collected, washed with H$_2$O (1×), dried and concentrated to give the crude acid 265, which was used without further purification.

Scheme 23 illustrates the preparation of compound 97.

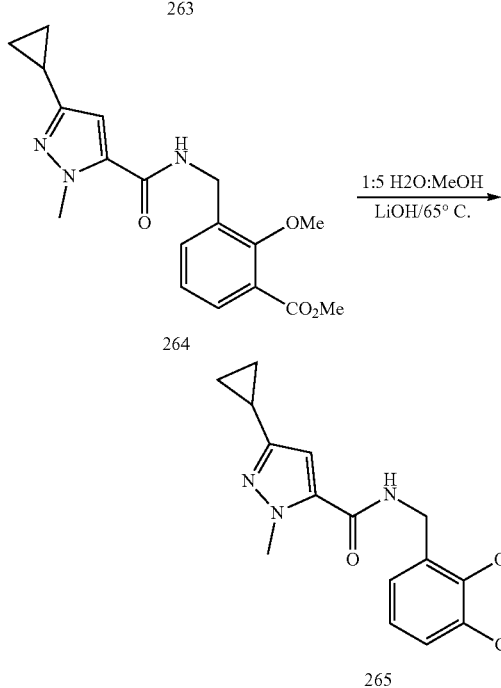

Scheme 23

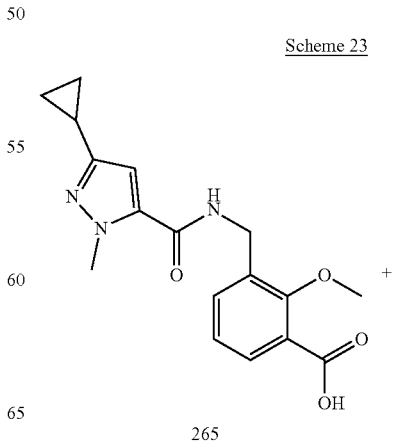

-continued

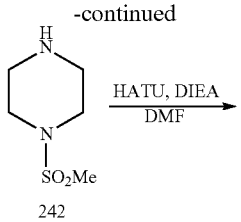
242

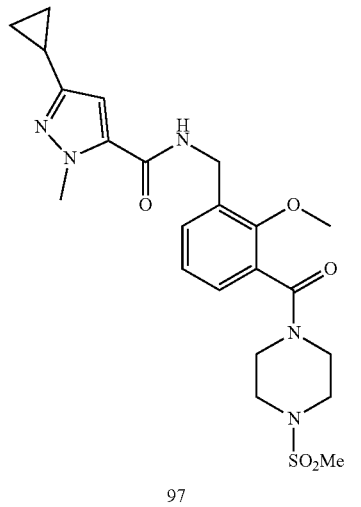
97

Example 62: Preparation of Compound 97

To a solution of the 1-(methylsulfonyl)piperazine 242 (49 mg, 0.299 mmol, 1.2 eq) in DMF (25 mL) were added the crude acid 265 (82 mg, 0.249 mmol, 1.0 eq), HATU (114 mg, 0.299 mmol, 1.2 eq and DIEA (160 mg, 1.245 mmol, 5.0 eq) and the reaction mixture was stirred at RT for 12 h. The reaction mixture was then diluted with EtOAc and washed with 10% aq. HCl (1×), sat. NaHCO$_3$ (1×) and water (3×). The organic layer was collected, dried (MgSO$_4$) and evaporated to give a residue, which was purified by column chromatography (EtOAc/Hexane) to give compound 97. Mass Spectrum (LCMS, ESI Pos.)Calcd. For C$_{22}$H$_{30}$N$_5$O$_5$S: 476.0 (M$^+$H), Found 476.0.

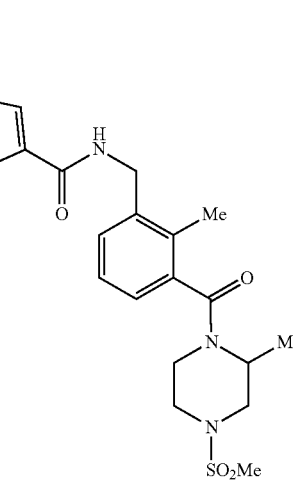
98

Example 63: Preparation of Compound 98

Compound 98 was prepared using the synthetic procedure used to synthesize compound 97. 1-methanesulfonyl-3-methyl-piperazine is commercially available. Mass Spectrum (LCMS, ESI Pos.) Calcd. For C$_{23}$H$_{32}$N$_5$O$_4$S: 474.0 (M$^+$H), Found 474.0.

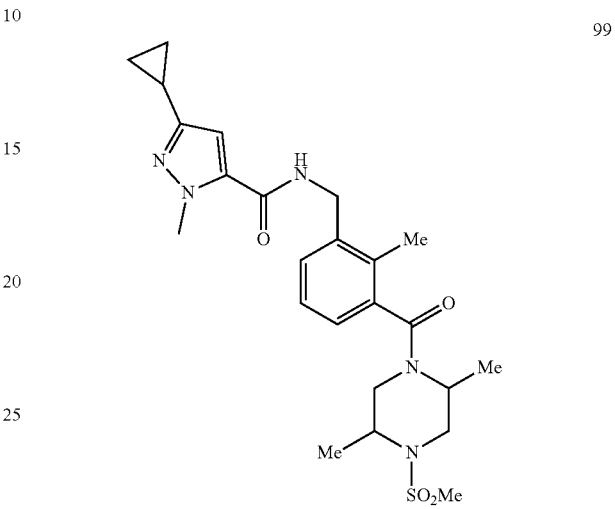
99

Example 64: Preparation of Compound 99

Compound 99 was prepared using the synthetic procedure used to synthesize compound 97. 1-Methanesulfonyl-2,5-dimethyl-piperazine is commercially available. Mass Spectrum (LCMS, ESI Pos.) Calcd. For C$_{24}$H$_{34}$N$_5$O$_4$: 488.0 (M$^+$H), Found 488.0.

Scheme 24 illustrates the preparation of compound 100.

Scheme 24

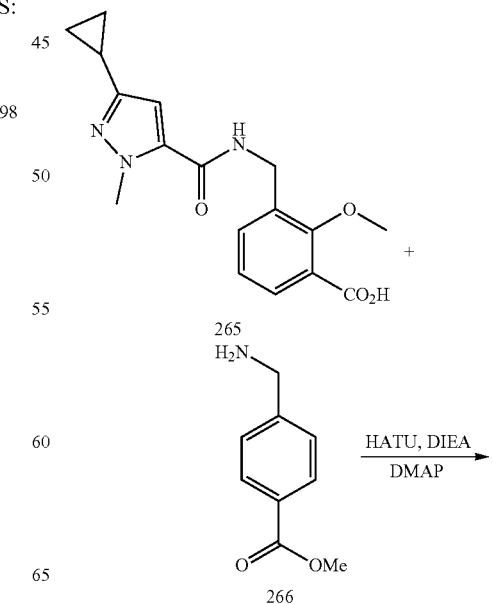

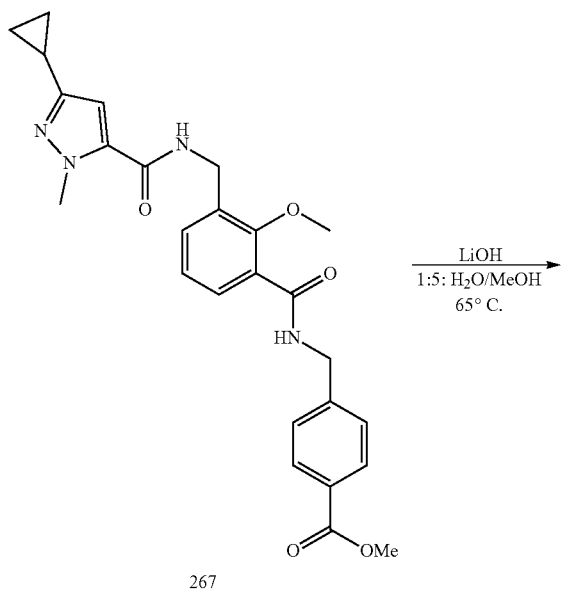

267

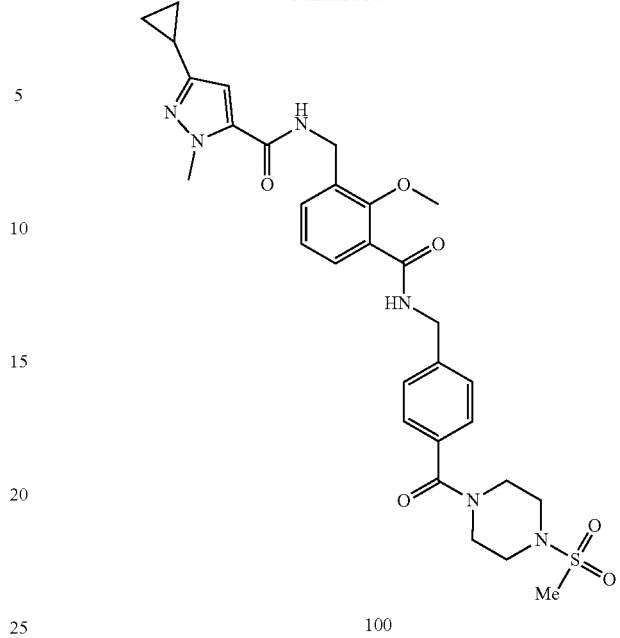

100

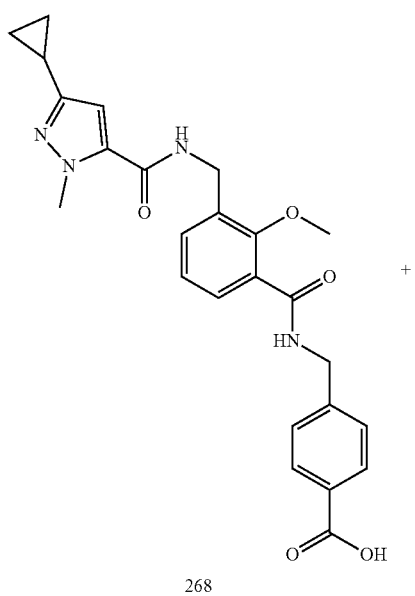

268

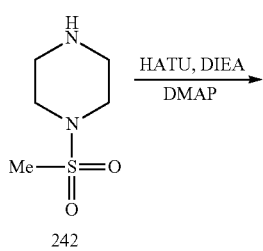

242

Preparation of Compound 267

To a solution of methyl 4-(aminomethyl)benzoate 266 (108 mg, 0.653 mmol, 1.2 eq) in DMF (10 mL) were added crude acid 265 (179 mg, 0.544 mmol, 1.0 eq), HATU (248 mg, 0.653 mmol, 1.2 eq), and DIEA (351 mg, 2.72 mmol, 5.0 eq) and the reaction mixture was stirred at RT for 12 h. The reaction mixture was then diluted with EtOAc and washed with 10% aq. HCl (1×), sat. NaHCO$_3$ (1×) and water (3×). The organic layer was collected, dried (MgSO$_4$) and evaporated to give a residue, which was purified by column chromatography (EtOAc/Hexane) to give the amide 267. Mass Spectrum (LCMS, ESI Pos.) Calcd. For $C_{22}H_{29}N_4O_5$: 477.0 (M$^+$H), Found 477.0.

Preparation of Compound 268

The ester (400 mg, 0.84 mmol, 1.0 eq) was taken in a 1:5 mixture of H$_2$O:MeOH (18 mL) and then LiOH (77 mg, 3.36 mmol, 4.0 eq) was added. The reaction mixture was stirred at 65° C. for 12 h. The reaction mixture evaporated under vacuum to give a residue, which was stirred in a mixture of 10% aq. HCl and ethyl acetate for 30 min. The organic layer was collected, washed with H$_2$O (1×), dried and concentrated to give the crude acid, which was directly used in the next step without further purification.

Example 65: Preparation of Compound 100

To a solution of 1-(methylsulfonyl)piperazine 242 (49 mg, 0.299 mmol, 1.2 eq) in DMF (25 mL) were added the crude acid 268 (115 mg, 0.249 mmol, 1.0 eq), HATU (114 mg, 0.299 mmol, 1.2 eq and DIEA (160 mg, 1.245 mmol, 5.0 eq) and the reaction mixture was stirred at RT for 12 h. The reaction mixture was then diluted with EtOAc and washed with 10% aq. HCl (1×), sat. NaHCO$_3$ (1×) and water (3×). The organic layer was collected, dried (MgSO$_4$) and evaporated to give a residue, which was purified by column chromatography (EtOAc/Hexane) to give the amide 100.

Mass Spectrum (LCMS, ESI Pos.) Calcd. For $C_{30}H_{37}N_6O_6S$:609.0 (M⁺H), Found 609.0.

Scheme 25 illustrates the preparation of compound 101.

Scheme 25

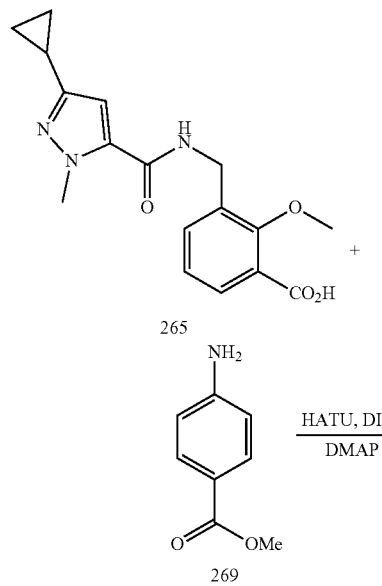

265

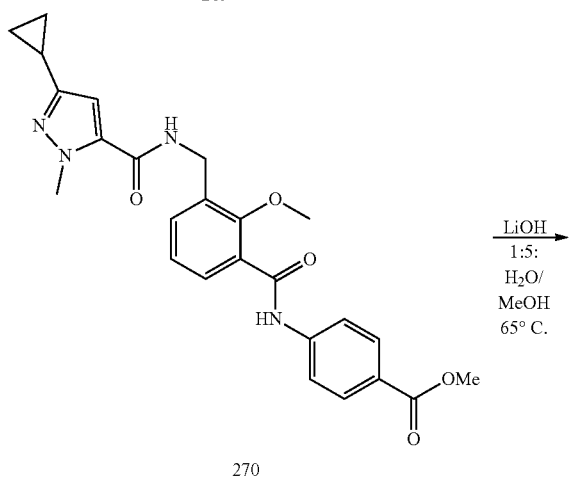

270

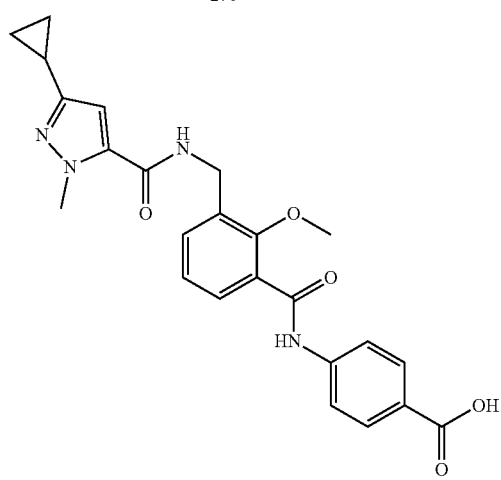

271

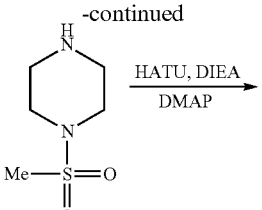

242

-continued

Preparation of Compound 270

To a solution of methyl 4-aminobenzoate 269 (99 mg, 0.653 mmol, 1.2 eq) in DMF (10 mL) were added crude acid 265 (179 mg, 0.544 mmol, 1.0 eq), HATU (248 mg, 0.653 mmol, 1.2 eq), and DIEA (351 mg, 2.72 mmol, 5.0 eq) and the reaction mixture was stirred at RT for 12 h. The reaction mixture was then diluted with EtOAc and washed with 10% aq. HCl (1×), sat. NaHCO₃ (1×) and water (3×). The organic layer was collected, dried (MgSO₄) and evaporated to give a residue, which was purified by column chromatography (EtOAc/Hexane) to give the amide 270. Mass Spectrum (LCMS, ESI Pos.) Calcd. For $C_{25}H_{27}N_4O_5$:463.0 (M⁺H), Found 463.0

Preparation of Compound 271

The ester (388 mg, 0.84 mmol, 1.0 eq) was taken in a 1:5 mixture of H₂O:MeOH (18 mL) and then LiOH (77 mg, 3.36 mmol, 4.0 eq) was added. The reaction mixture was stirred at 65° C. for 12 h. The reaction mixture evaporated under vacuum to give a residue, which was stirred in a mixture of 10% aq. HCl and ethyl acetate for 30 min. The organic layer was collected, washed with H₂O (1×), dried and concentrated to give the crude acid, which was directly used in the next step without further purification.

Example 66: Preparation of Compound 101

To a solution of 1-(methylsulfonyl)piperazine 242 (49 mg, 0.299 mmol, 1.2 eq) in DMF (25 mL) were added the crude acid 271 (112 mg, 0.249 mmol, 1.0 eq), HATU (114 mg, 0.299 mmol, 1.2 eq and DIEA (160 mg, 1.245 mmol, 5.0 eq) and the reaction mixture was stirred at RT for 12 h. The reaction mixture was then diluted with EtOAc and washed with 10% aq. HCL (1×), sat. NaHCO₃ (1×) and water (3×). The organic layer was collected, dried (MgSO₄) and evaporated to give a residue, which was purified by column chromatography (EtOAc/Hexane) to give the amide 101. Mass Spectrum (LCMS, ESI Pos.) Calcd. For $C_{29}H_{35}N_6O_6S$: 595.0 (M⁺H), Found 595.0.

Scheme 26 illustrates the preparation of compound 102.

Scheme 26

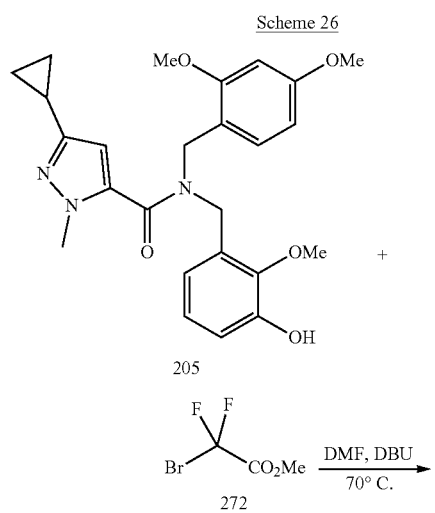

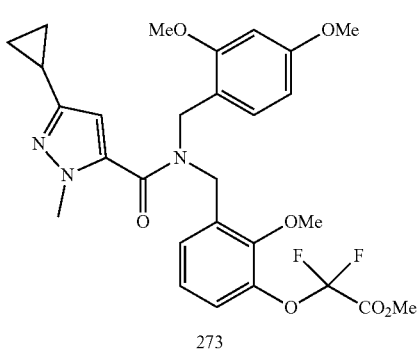

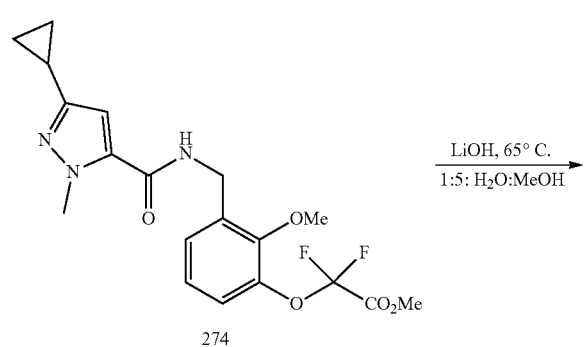

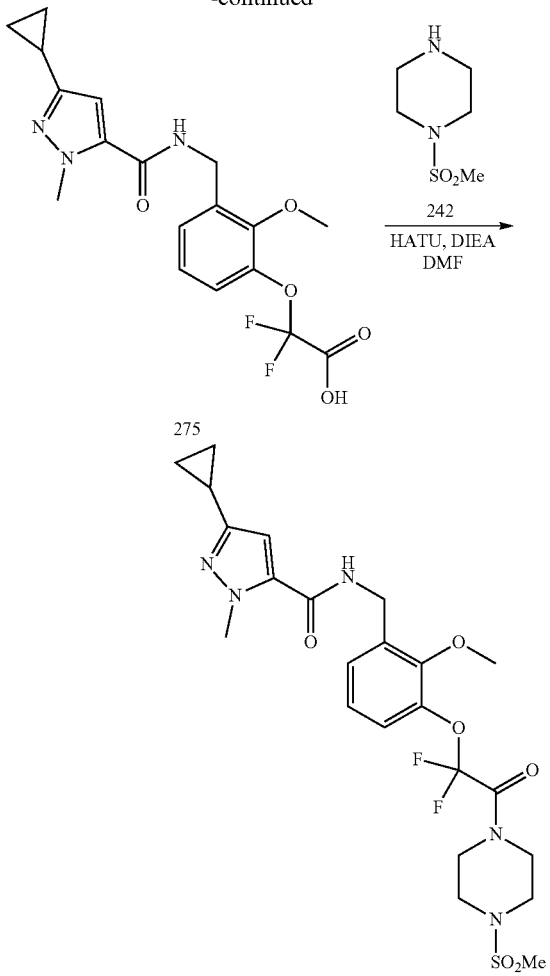

Preparation of Compound 273

To a stirred solution of compound 205 (300 mg, 0.665 mmol) in DMF were added methyl 2-bromo-2,2-difluoroacetate 272 (300 mg) and DBU (300 mg) and the reaction mixture was stirred at 70° C. for 12 h. The reaction mixture was diluted with EtOAc and the reaction mixture was washed with 10% aq. HCl, H₂O and brine. The organic layer was dried and evaporated under vacuum to give a residue, which was purified by column chromatography to give the desired compound 273. Mass Spectrum (LCMS, ESI Pos.) Calcd. For $C_{28}H_{32}F_2N_3O_7$: 560.0 (M⁺H), Found 560.0.

Preparation of Compound 274

The ester 273 was dissolved in a 1:1 mixture of TFA:DCM and the reaction mixture was stirred at room temperature for 25 h. Solvents were removed and the residue was purified by column chromatography to provide 274. Mass Spectrum (LCMS, ESI Pos.) Calcd. For $C_{19}H_{22}F_2N_3O_5$: 410.0 (M⁺H), Found 410.0.

Preparation of Compound 275

The ester 274 (344 mg, 0.84 mmol, 1.0 eq) was dissolved in a 1:5 mixture of H₂O; MeOH (18 mL) and then LiOH (77 mg, 3.36 mmol, 4.0 eq) was added. The reaction mixture was stirred at 65° C. for 12 h. The reaction mixture evaporated under vacuum to give a residue, which was stirred in a mixture of 10% aq. HCl and ethyl acetate for 30 min. The organic layer was collected, washed with $H_2O$ (1×), dried and concentrated to give the crude acid, which was directly used in the next step without further purification.

Example 67: Preparation of Compound 102

To a solution of 1-(methylsulfonyl)piperazine 242 (49 mg, 0.299 mmol, 1.2 eq) in DMF (25 mL) were added the crude acid (98 mg, 0.249 mmol, 1.0 eq), HATU (114 mg, 0.299 mmol, 1.2 eq and DIEA (160 mg, 1.245 mmol, 5.0 eq) and the reaction mixture was stirred at RT for 12 h. The reaction mixture was then diluted with EtOAc and washed with 10% aq. HCl (1×), sat. $NaHCO_3$ (1×) and water (3×). The organic layer was collected, dried ($MgSO_4$) and evaporated to give a residue, which was purified by column chromatography (EtOAc/Hexane) to give the amide 102. Mass Spectrum (LCMS, ESI Pos.) Calcd. For $C_{23}H_{30}F_2N_5O_6S$:542.0 (M⁺H), Found 542.0.

Scheme 27 illustrates the preparation of compound 103.

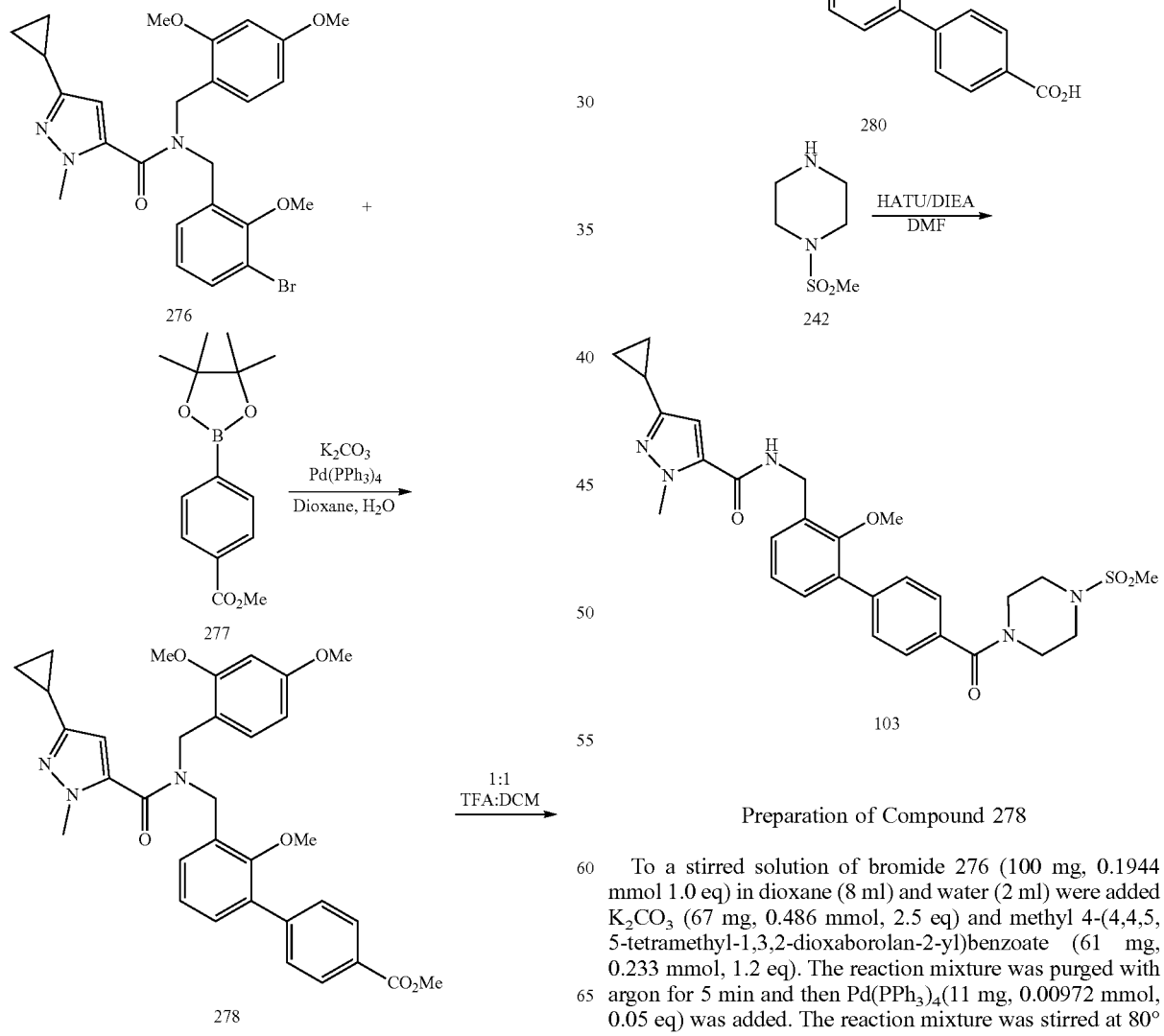

Preparation of Compound 278

To a stirred solution of bromide 276 (100 mg, 0.1944 mmol 1.0 eq) in dioxane (8 ml) and water (2 ml) were added $K_2CO_3$ (67 mg, 0.486 mmol, 2.5 eq) and methyl 4-(4,4,5,5-tetramethyl-1,3,2-dioxaborolan-2-yl)benzoate (61 mg, 0.233 mmol, 1.2 eq). The reaction mixture was purged with argon for 5 min and then $Pd(PPh_3)_4$(11 mg, 0.00972 mmol, 0.05 eq) was added. The reaction mixture was stirred at 80° C. for 6 h. The reaction mixture was taken in EtOAc and washed with water and brine. The combined organic layers were dried and evaporated under vacuum to give a residue, which was purified by column chromatography to provide the desired product 278. Mass Spectrum (LCMS, ESI Pos.) Calcd. For $C_{33}H_{35}N_3O_6$: 570.0 ($M^+H$), Found 570.0.

Preparation of Compound 279

The ester was dissolved in a 1:1 mixture of TFA: DCM and the reaction mixture was stirred at room temperature for 25 h. Solvents were removed and the residue purified by column chromatography to provide ester 279. Mass Spectrum (LCMS, ESI Pos.) Calcd. For $C_{24}H_{26}N_3O_4$: 420.0 ($M^+H$), Found 420.0.

Preparation of Compound 280

The ester (344 mg, 0.84 mmol, 1.0 eq) was dissolved in a 1:5 mixture of $H_2O$; MeOH (18 mL) and then LiOH (77 mg, 3.36 mmol, 4.0 eq) was added. The reaction mixture was stirred at 65° C. for 12 h. The reaction mixture was evaporated under vacuum to give a residue, which was stirred in a mixture of 10% aq. HCl and ethyl acetate for 30 min. The organic layer was collected, washed with $H_2O$ (1×), dried and concentrated to give the crude acid, which was directly used in the next step without further purification.

Example 68: Preparation of Compound 103

To a solution of 1-(methylsulfonyl)piperazine (49 mg, 0.299 mmol, 1.2 eq) in DMF (25 mL) were added the crude acid (98 mg, 0.249 mmol, 1.0 eq), HATU (114 mg, 0.299 mmol, 1.2 eq and DIEA (160 mg, 1.245 mmol, 5.0 eq) and the reaction mixture was stirred at RT for 12 h. The reaction mixture was then diluted with EtOAc and washed with 10% aq. HCl (1×), sat. NaHCO$_3$ (1×) and water (3×). The organic layer was collected, dried (MgSO$_4$) and evaporated to give a residue, which was purified by column chromatography (EtOAc/Hexane) to give the amide 103. Mass Spectrum (LCMS, ESI Pos.) Calcd. For $C_{23}H_{30}F_2N_5O_6S$:542.0 ($M^+H$), Found 542.0.

Scheme 28 illustrates the preparation of compound 104.

Scheme 28

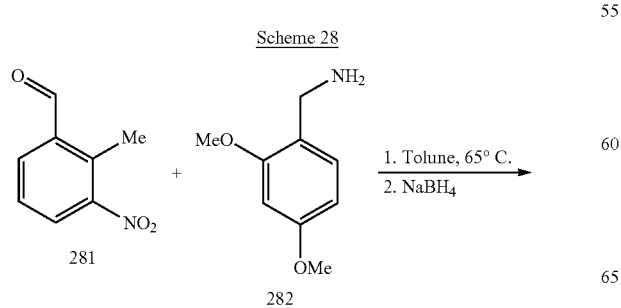

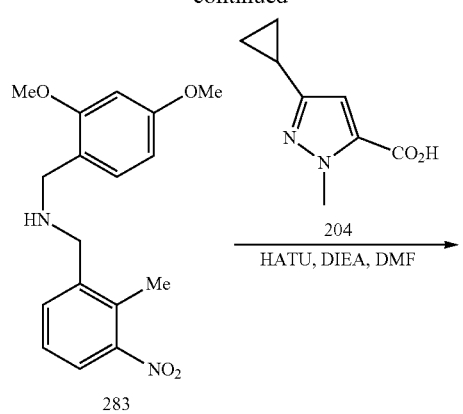

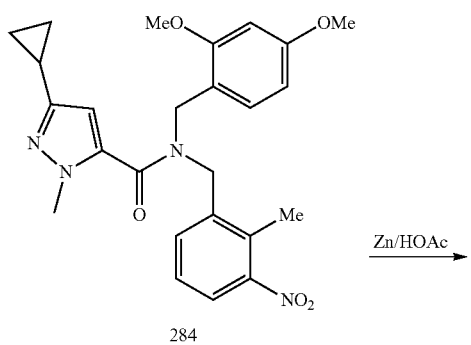

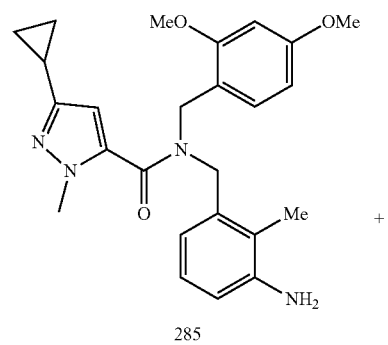

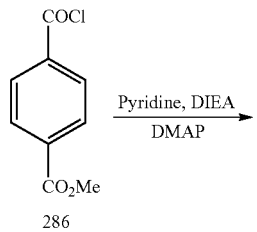

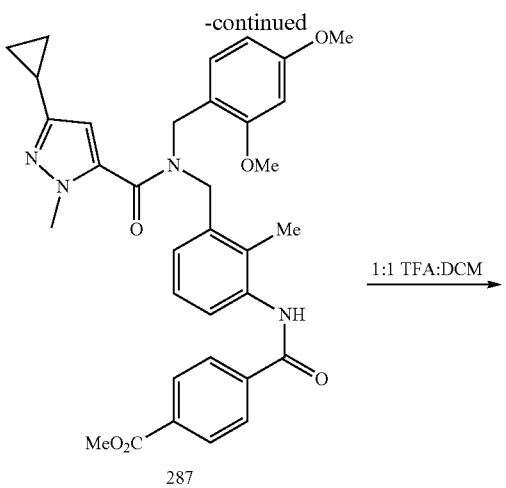

287

104

Preparation of Compound 283

To a solution of 2-methyl-3-nitrobenzaldehyde 281 (426 mg, 2.58 mmol, 1.0 eq) in toluene were added 2,4-dimethoxybenzyl amine 282 (430 mg, 2.58 mmol, 1.0 eq) and catalytic amount of p-toluene sulfonic acid. The reaction mixture was stirred at 65° C. for 24 h. Solvent was removed and the residue was taken in MeOH and cooled in an ice bath. Then sodium borohydride (195 mg, 5.16 mmol, 2.0 eq) was added slowly and the reaction mixture was stirred at RT for 12 h. The solvent was removed and residue was dissolved in ethyl acetate and then sat. NaH—CO₃ was added and the mixture stirred for 1 h. The organic layer was separated, dried (MgSO₄) and the solvent was removed to give the amine, which was used in the next step without further purification.

Preparation of Compound 284

To a solution of the crude amine 283 (2.58 mmol, 1.0 eq) in DMF (10 mL) were added 3-cyclopropyl-1-methyl-1H-pyrazole-5-carboxylic acid (477 mg, 2.84 mmol, 1.1 eq), HATU (1.18 g, 3.09 mmol, 1.2 eq), and DIEA (1.67 g, 12.95 mmol, 5.0 eq) and the reaction mixture was stirred at RT for 12 h. The reaction mixture was then diluted with EtOAc and washed with 10% aq. HCl (1×), sat. NaHCO₃ (1×) and water (3×). The organic layer was collected, dried (MgSO₄) and evaporated to give a residue, which was purified by column chromatography (EtOAc/Hexane) to give compound the desired amide 284. Mass Spectrum (LCMS, ESI Pos.) Calcd. For $C_{27}H_{32}N_3O_6$: 494.0 (M⁺H), Found 494.0.

Preparation of Compound 285

To a stirred solution of the amide 284 (600 mg, 1.25 mmol 1.0 eq) in acetic acid (15 ml) was added zinc powder (0.163 g, 2.5 mmol, 2 eq) and the reaction mixture was stirred at room temperature for 12 hrs. Water was added to the reaction mixture and which was extracted with ethyl acetate (3×). The combined organic layers were washed with water, brine, dried and evaporated under vacuum to provide the crude amine 285, which was used in the next step without further purification.

Preparation of Compound 287

To a stirred solution of the crude amine 285 (398 mg, 0.92 mmol 1.0 eq) in pyridine (15 ml) at 0° C. were added DIEA (178 mg, 1.38 mmol, 1.5 eq), methyl 4-(chlorocarbonyl) benzoate 286 (219 mg, 1.104 mmol, 1.2 eq) and DMAP (11 mg, 0.092 mmol 0.1 eq). The reaction mixture was stirred at room temperature for 12 hours. The reaction mixture was evaporated under vacuum to provide a residue, which was dissolved in ethyl acetate and washed with water, brine, dried and evaporated under vacuum to give the crude amide, which was purified by column chromatography to provide the desired amide 287.

Example 69: Preparation of Compound 104

The ester was dissolved in a 1:1 mixture of TFA: DCM and the reaction mixture was stirred at room temperature for 24 h. Solvents were removed and the residue purified by column chromatography to provide compound 104. Mass Spectrum (LCMS, ESI Pos.) Calcd. For $C_{25}H_{27}N_4O_4$: 446.0 (M+1), Found 447.0

Scheme 29 illustrates the preparation of compound 105.

Scheme 29

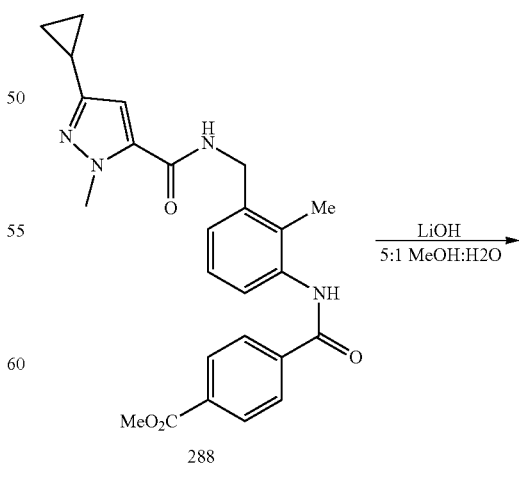

288

-continued

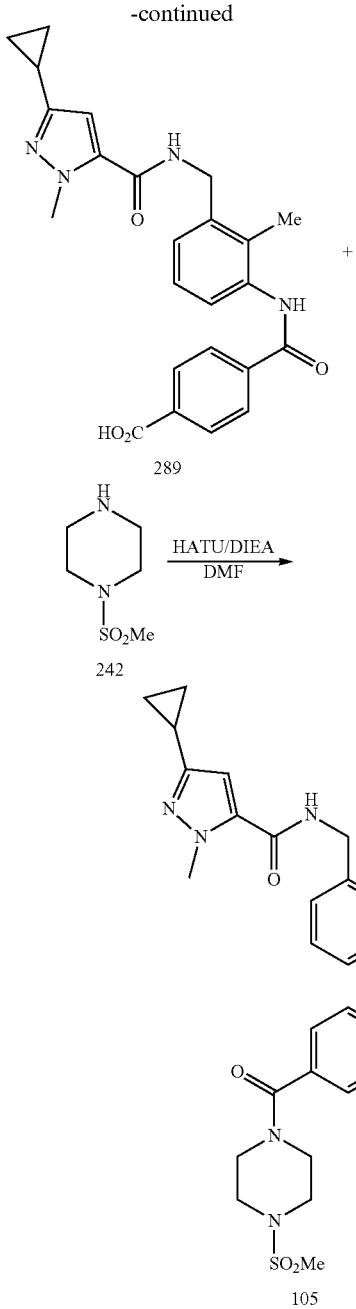

Preparation of Compound 289

The ester 288 (374 mg, 0.84 mmol, 1.0 eq) was dissolved in a 1:5 mixture of H₂O; MeOH (18 mL) and then LiOH (77 mg, 3.36 mmol, 4.0 eq) was added. The reaction mixture was stirred at 65° C. for 12 h. The reaction mixture evaporated under vacuum to give a residue, which was stirred in a mixture of 10% aq. HCl and ethyl acetate for 30 min. The organic layer was collected, washed with H₂O (1×), dried and concentrated to give the crude acid, which was directly used in the next step without further purification.

Example 70: Preparation of Compound 105

To a stirred solution of 1-(methylsulfonyl)piperazine 242 (49 mg, 0.299 mmol, 1.2 eq) in DMF (25 mL) were added the crude acid (107 mg, 0.249 mmol, 1.0 eq), HATU (114 mg, 0.299 mmol, 1.2 eq and DIEA (160 mg, 1.245 mmol, 5.0 eq) and the reaction mixture was stirred at RT for 12 h. The reaction mixture was then diluted with EtOAc and washed with 10% aq. HC (1×), sat. NaHCO₃ (IX) and water (3×). The organic layer was collected, dried (MgSO₄) and evaporated to give a residue, which was purified by column chromatography (EtOAc/Hexane) to give the amide 105. Mass Spectrum (LCMS, ESI Pos.) Calcd. For $C_{29}H_{35}N_6O_5S$:579.0 (M⁺H), Found 579.0.

Scheme 30 illustrates the preparation of compound 106.

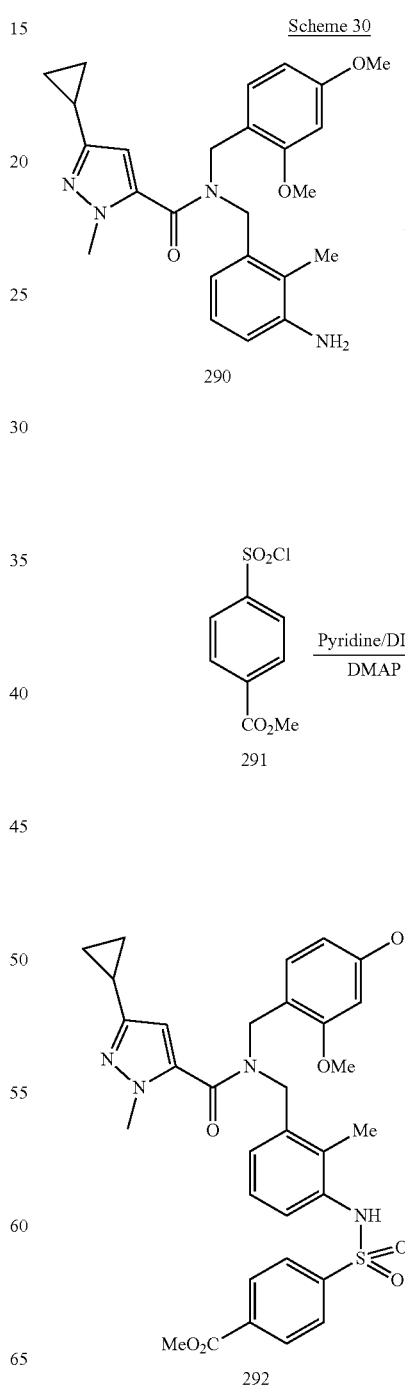

-continued

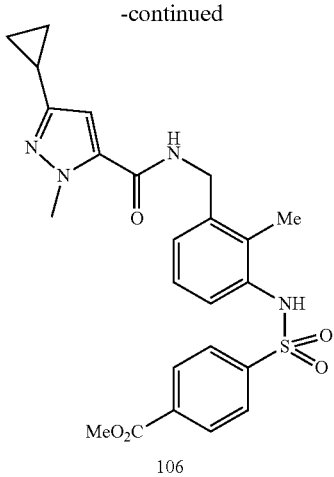

106

Preparation of Compound 292

To a stirred solution of the crude amine 290 (398 mg, 0.92 mmol 1.0 eq) in pyridine (15 ml) at 0° C. were added DIEA (178 mg, 1.38 mmol, 1.5 eq), methyl 4-chlorosulfonylbenzoate 291 (259 mg, 1.104 mmol, 1.2 eq) and DMAP (13 mg, 0.1064 mmol 0.1 eq). The reaction mixture was stirred at room temperature for 12 hours. The reaction mixture was evaporated under vacuum to provide a residue, which was taken in ethyl acetate and washed with water, brine, dried and evaporated under vacuum to give the crude sulfonamide which was purified by column chromatography to provide the desired compound 292.

Example 70: Preparation of Compound 106

The sulfonamide 292 was dissolved in a 1:1 mixture of TFA: DCM and the reaction mixture was stirred at room temperature for 24 h. Solvents were removed and the residue purified by column chromatography to provide compound 106. Mass Spectrum (LCMS, ESI Pos.) Calcd. For C24H27N4O5S: 483.0 (M+H), Found 483.0

Scheme 31 illustrates the preparation of compound 107.

Scheme 31

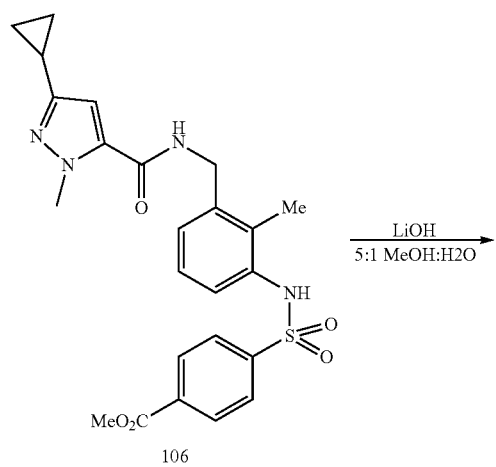

106

-continued

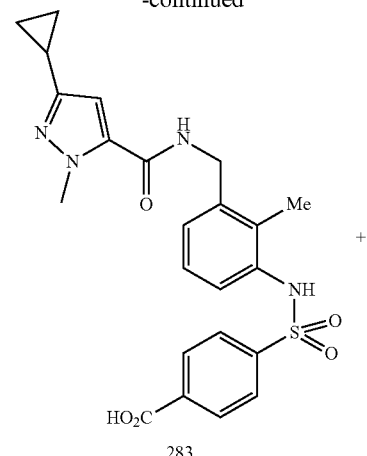

283

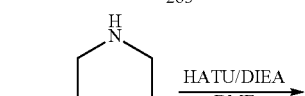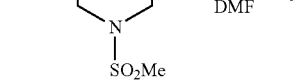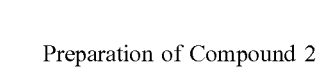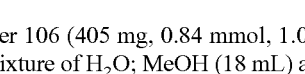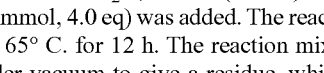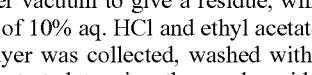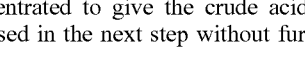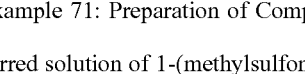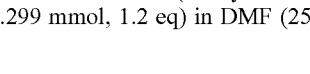

107

Preparation of Compound 293

The ester 106 (405 mg, 0.84 mmol, 1.0 eq) was taken up in a 1:5 mixture of H₂O; MeOH (18 mL) and then LiOH (77 mg, 3.36 mmol, 4.0 eq) was added. The reaction mixture was stirred at 65° C. for 12 h. The reaction mixture was evaporated under vacuum to give a residue, which was stirred in a mixture of 10% aq. HCl and ethyl acetate for 30 min. The organic layer was collected, washed with H₂O (1×), dried and concentrated to give the crude acid 293, which was directly used in the next step without further purification.

Example 71: Preparation of Compound 107

To a stirred solution of 1-(methylsulfonyl)piperazine 242 (49 mg, 0.299 mmol, 1.2 eq) in DMF (25 mL) were added the crude acid 293 (116 mg, 0.249 mmol, 1.0 eq), HATU (114 mg, 0.299 mmol, 1.2 and DIEA (160 mg, 1.245 mmol, 5.0 eq) and the reaction mixture was stirred at RT for 12 h. The reaction mixture was then diluted with EtOAc and washed with 10% aq. HCl (1×), sat. NaHCO$_3$ (1×) and water (3×). The organic layer was collected, dried (MgSO$_4$) and evaporated to give a residue, which was purified by column chromatography (EtOAc/Hexane) to give the amide 107. Mass Spectrum (LCMS, ESI Pos.) Calcd. For C$_{28}$H$_{35}$N$_6$O$_6$S$_2$:615.0 (M$^+$H), Found 615.0.

108

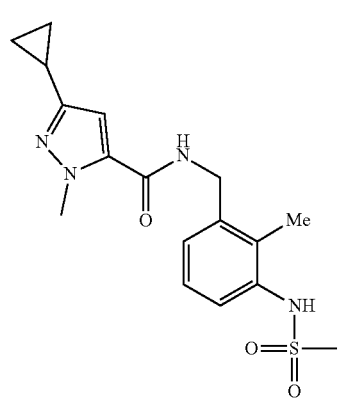

Example 72: Preparation of Compound 108

Compound 108 was prepared using the synthetic procedure used to synthesize compound 106. Methanesulfonyl chloride is commercially available. Mass Spectrum (LCMS, ESI Pos.) Calcd. For C$_{17}$H$_{23}$N$_4$O$_3$S: 363.0 (M$^+$H), Found 363.0.

109

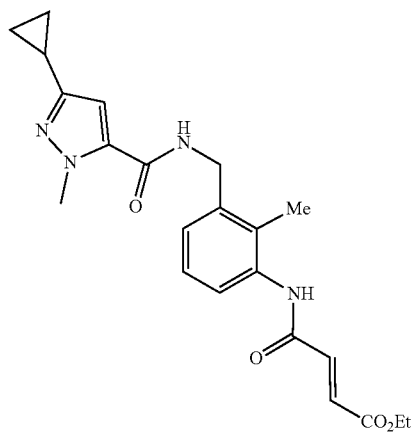

Example 73: Preparation of Compound 109

Compound 109 was prepared using the synthetic procedure used to synthesize compound 106. (E)-Ethyl 4-chloro-4-oxobut-2-enoate is commercially available. Mass Spectrum (LCMS, ESI Pos.) Calcd. For C$_{22}$H$_{27}$N$_4$O$_4$: 411.0 (M$^+$H), Found 411.0.

110

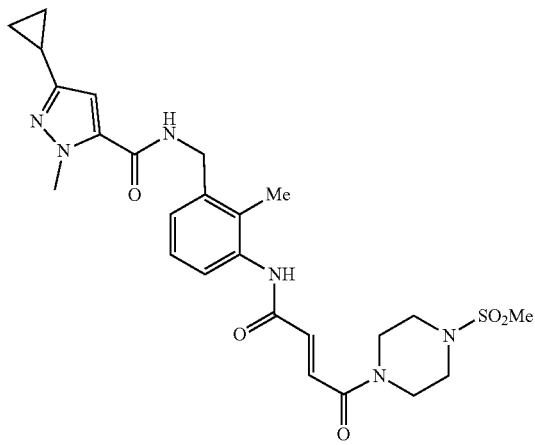

Example 74: Preparation of Compound 110

Compound 110 was prepared from compound 109 following the procedure used to make compound 106. Calcd. For C$_{25}$H$_{33}$N$_6$O$_5$S: 529.0 (M$^+$H), Found 529.0.

Scheme 32 illustrates the preparation of compound 111.

Scheme 32

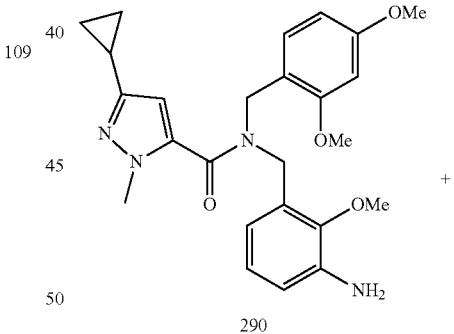

290

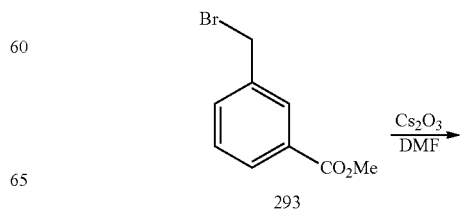

293

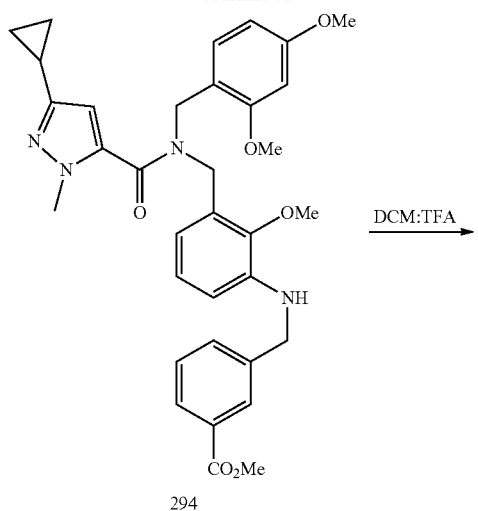

294

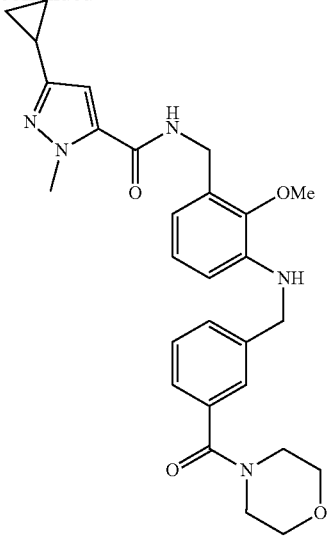

111

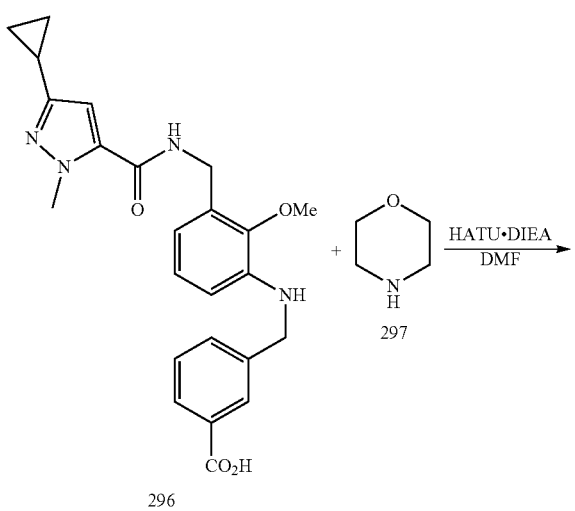

296

Preparation of Compound 294

To a stirred solution of amine 290 (452 mg, 1.04 mmol 1.0 eq) in DMF (10 ml) were added $Cs_2CO_3$ (507 mg, 1.56 mmol, 1.5 eq) and methyl 3-(bromomethyl)benzoate 293 (286 mg, 1.25 mmol, 1.2 eq), and the reaction mixture was stirred at room temperature for 12 hr. The reaction mixture was diluted with ethyl acetate and the organic layer was washed with sat. aqueous $NaHCO_3$ solution, 10% HCl solution, brine, dried and evaporated under vacuum to provide the crude amide 294.

Preparation of Compound 295

The amide was dissolved in a 1:1 mixture of TFA: DCM and the reaction mixture was stirred at room temperature for 24 h. Solvents were removed and the residue purified by column chromatography to provide ester 295. Mass Spectrum (LCMS, ESI Pos.) Calcd. For $C_{25}H_{28}N_4O_4$: 449.0 ($M^+H$), Found 449.0.

Preparation of Compound 296

The ester 295 (376 mg, 0.84 mmol, 1.0 eq) was taken up in a 1:5 mixture of $H_2O$; MeOH (18 mL) and then LiOH (77 mg, 3.36 mmol, 4.0 eq) was added. The reaction mixture was stirred at 65° C. for 12 h. The reaction mixture evaporated under vacuum to give a residue, which was stirred in a mixture of 10% aq. HCl and ethyl acetate for 30 min. The organic layer was collected, washed with $H_2O(1\times)$, dried and concentrated to give the crude acid, which was directly used in the next step without further purification.

Example 75: Preparation of Compound 111

To a stirred solution of morpholine 297 (26 mg, 0.299 mmol, 1.2 eq) in DMF (10 mL) were added the crude acid 296 (108 mg, 0.249 mmol, 1.0 eq), HATU (114 mg, 0.299 mmol, 1.2 eq) and DIEA (160 mg, 1.245 mmol, 5.0 eq). The reaction mixture was stirred at RT for 12 h. The reaction mixture was then diluted with EtOAc and washed with 10% aq. HCl (1×), sat. $NaHCO_3$ (1×) and water (3×). The organic layer was collected, dried (MgSO$_4$) and evaporated to give a residue, which was purified by column chromatography (EtOAc/Hexane) to give the amide 111. Mass Spectrum (LCMS, ESI Pos.) Calcd. For C$_{28}$H$_{34}$N$_5$O$_4$:504.0 (M$^+$H), Found 504.0.

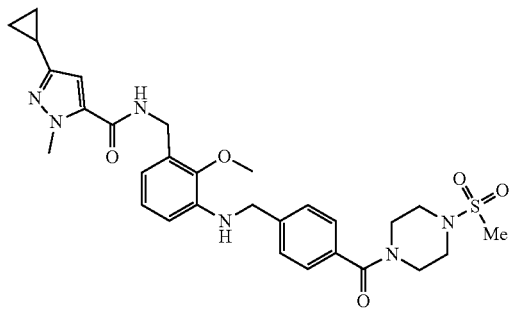

112

Example 76: Preparation of Compound 112

Compound 112 was prepared following the procedure used to prepare compound 111 except that commercially available methyl 4-(chloromethyl)benzoate was used in the initial step and 1-(methylsulfonyl)piperazine was used to acylate the carboxylic acid in the last step.

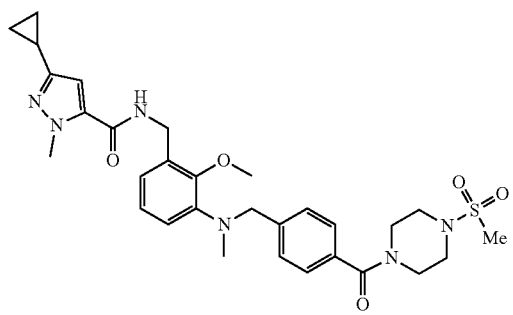

113

Example 77: Preparation of Compound 113

Compound 112 was prepared following the procedure used to prepare compound 111 except that commercially available methyl 4-[(methylamino)methyl]benzoate was used in the initial step and 1-(methylsulfonyl)piperazine was used to acylate the carboxylic acid in the last step.

Scheme 33 illustrates the preparation of compound 114.

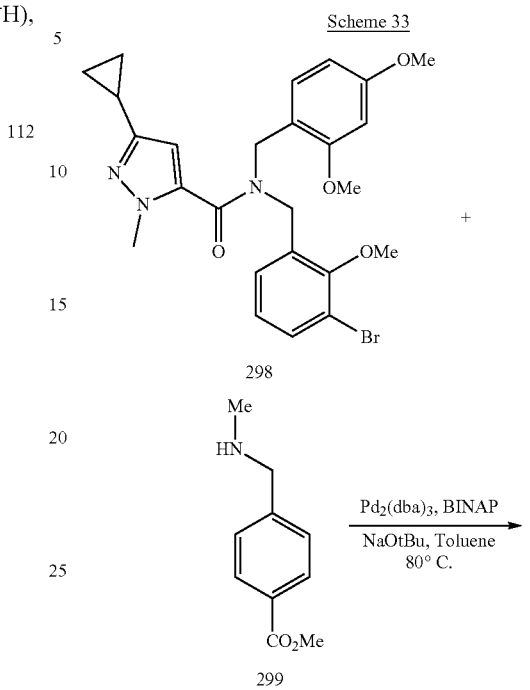

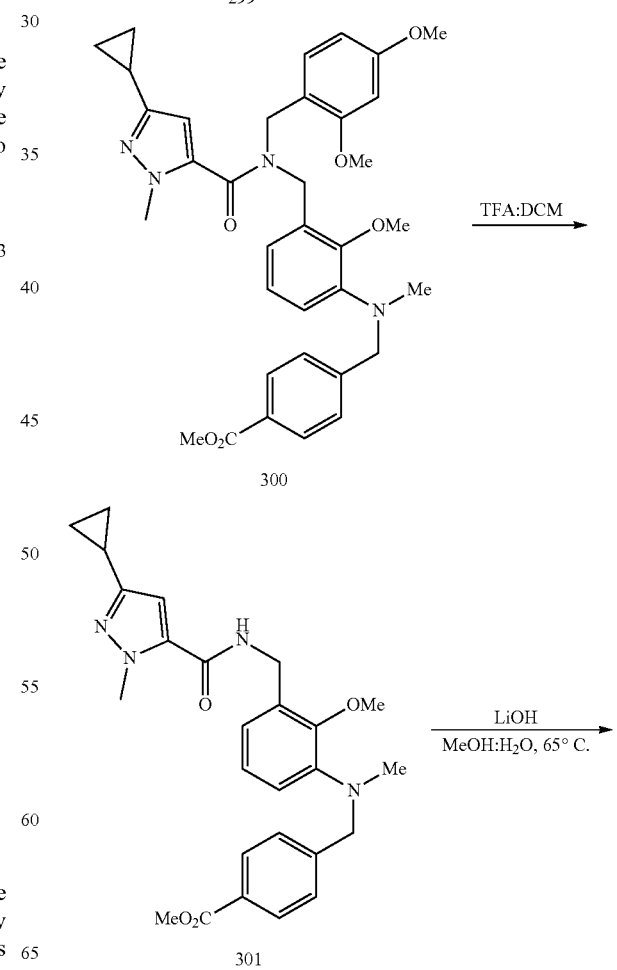

255

-continued

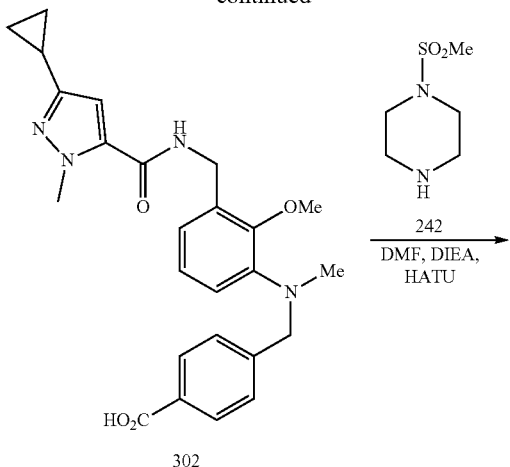

302

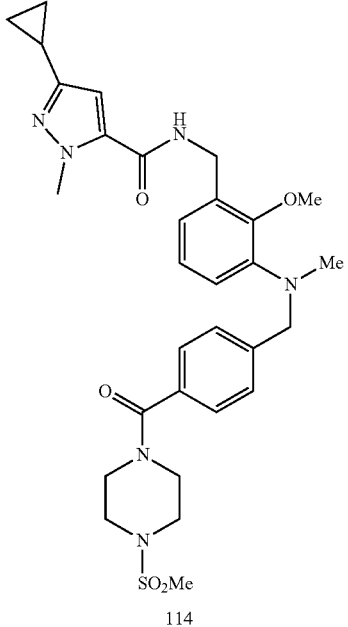

114

Preparation of Compound 300

To a stirred solution of bromide 298 (200 mg, 0.389 mmol 1.0 eq) in toluene (5 ml) was added sodium tert-butoxide (93 mg, 0.9725 mmol, 2.5 eq), methyl 4-[(methylamino)methyl] benzoate 299 (84 mg, 0.466 mmol, 1.2 eq) and BINAP (24 mg, 0.039 mmol, 0.1 eq). The reaction mixture was purged with argon for five min and then tris(dibenzylideneacetone) dipalladium(0) (36 mg, 0.039 mmol, 0.1 eq) was added and the reaction mixture was heated at 80° C. for 6 h. The reaction mixture was evaporated under vacuum to give a residue, which was taken in ethyl acetate and washed with water and brine. The organic layer was dried and evaporated under vacuum to provide the crude product, which was purified by column chromatography to yield the amine 300. Mass Spectrum (LCMS, ESI Pos.) Calcd. For $C_{35}H_{41}N_4O_6$: 613.0 (M$^+$H), Found 613.0.

Preparation of Compound 301

The amine was taken in a 1:1 mixture of TFA: DCM and the reaction mixture was stirred at room temperature for 24

256 h. Solvents were removed and the residue purified by column chromatography to give the ester 310. Mass Spectrum (LCMS, ESI Pos.) Calcd. For $C_{26}H_{31}N_4O_4$:463.0 (M$^+$H), Found 463.0.

Preparation of Compound 302

The ester 301 (388 mg, 0.84 mmol, 1.0 eq) was taken up in a 1:5 mixture of H$_2$O; MeOH (18 mL) and then LiOH (77 mg, 3.36 mmol, 4.0 eq) was added. The reaction mixture was stirred at 65° C. for 12 h. The reaction mixture evaporated under vacuum to give a residue, which was stirred in a mixture of 10% aq. HCl and ethyl acetate for 30 min. The organic layer was collected, washed with H$_2$O(1×), dried and concentrated to give the crude acid 302, which was directly used in the next step without further purification.

Example 78: Preparation of Compound 114

To a stirred solution of 1-(methylsulfonyl)piperazine 242 (49 mg, 0.299 mmol, 1.2 eq) in DMF (25 mL) were added the crude acid (112 mg, 0.249 mmol, 1.0 eq), HATU (114 mg, 0.299 mmol, 1.2 eq) and DIEA (161 mg, 1.245 mmol, 5.0 eq), and the reaction mixture was stirred at RT for 12 h. The reaction mixture was then diluted with EtOAc and washed with 10% aq. HCl (1×), sat. NaHCO$_3$ (1×) and water (3×). The organic layer was collected, dried (MgSO$_4$) and evaporated to give a residue, which was purified by column chromatography (EtOAc/Hexane) to give the amide 114. Mass Spectrum (LCMS, ESI Pos.) Calcd. For $C_{30}H_{39}N_6O_5S$:595.0 (M$^+$H), Found 595.0.

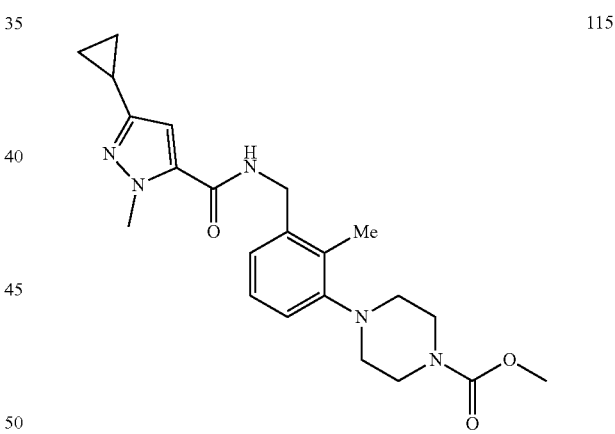

115

Example 79: Preparation of Compound 115

Compound 115 was prepared following the procedure used to prepare compound 111 except that commercially available methyl piperazine-1-carboxylate was used in the initial step. Mass Spectrum (LCMS, ESI Pos.) Calcd. For $C_{22}H_{30}N_5O_3$: 412.0 (M$^+$H), Found 412.0.

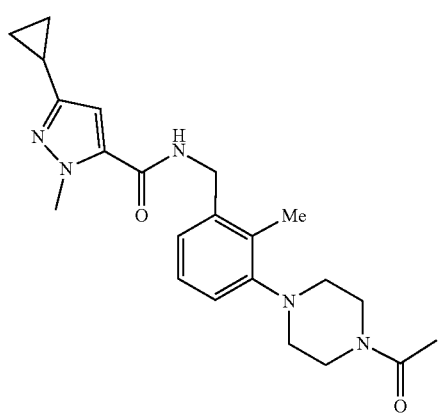

116

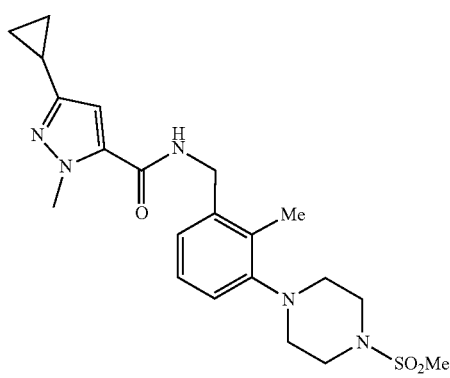

117

Example 80: Preparation of Compound 116

Compound 116 was prepared following the procedure used to prepare compound 111 except that commercially available piperazine-1-carboxylic acid dimethylamide was used in the initial step. Mass Spectrum (LCMS, ESI Pos.) Calcd. For $C_{23}H_{33}N_6O_2$: 425.0 (M$^+$H), Found 425.0.

Example 81: Preparation of Compound 117

Compound 117 was prepared following the procedure used to prepare compound 111 except that commercially available 1-(methylsulfonyl)piperazine was used in the initial step. Mass Spectrum (LCMS, ESI Pos.) Calcd. For $C_{21}H_{30}N_5O_3S$: 432.0 (M$^+$H), Found 432.0.

Example 82: Preparation of Compound 118

Compound 118 was prepared following the procedure used to prepare compound 111 except that commercially available 1-(methylsulfonyl)piperazine was used in the initial step. Mass Spectrum (LCMS, ESI Pos.) Calcd. For $C_{21}H_{30}N_5O_4S$: 448.0 (M$^+$H), Found 448.0.

Scheme 34 illustrates the preparation of compound 119.

-continued

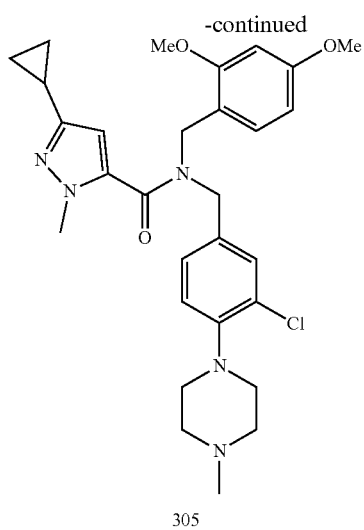

305

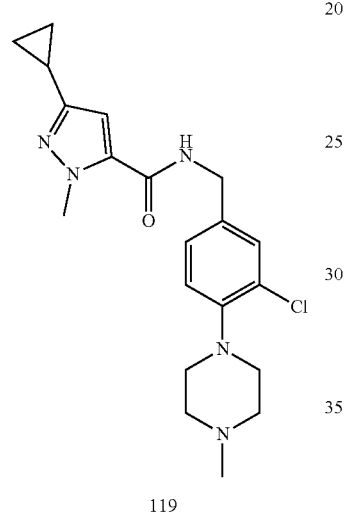

119

Preparation of Compound 305

To a stirred solution of the bromide 303 (500 mg, 0.96 mmol, 1.0 eq) in toluene were added sodium tert-butoxide (230 mg, 2.41 mmol, 2.5 eq) amine 303 (1.2 eq) and BINAP (119 mg, 0.19 mmol, 0.2 eq). The reaction mixture was purged with argon and then added $Pd_2(dba)_3$ (88 mg, 0.096 mmol, 0.1 eq), and the reaction mixture was stirred at 100° C. for 5 h. Toluene was removed under vacuum to give a residue, which was taken in EtOAc and washed with water. The organic layer was dried and evaporated to give a residue, which was purified by column chromatography to yield compound 305. Mass Spectrum (LCMS, ESI Pos.) Calcd. For $C_{29}H_{37}ClN_5O_3$: 539.0 ($M^+H$), Found 539.0

Example 83: Preparation of Compound 119

Compound 305 was taken up in a 1:1 mixture of DCM:TFA and stirred at room temperature for 12 h. Solvents were removed and the residue was purified by column chromatography to give the desired product 119. Mass Spectrum (LCMS, ESI Pos.) Calcd. For $C_{20}H_{27}ClN_5O$: 388.0 ($M^+H$), Found 388.0

Scheme 35 illustrates the preparation of compound 121.

Scheme 35

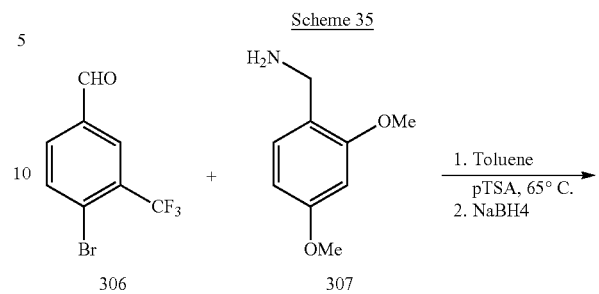

306  307

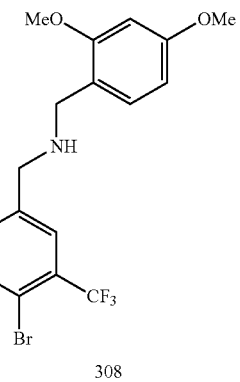

308

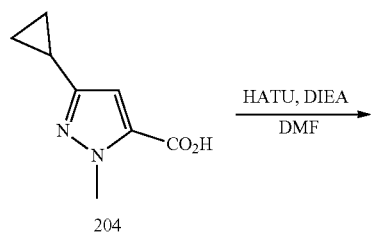

204

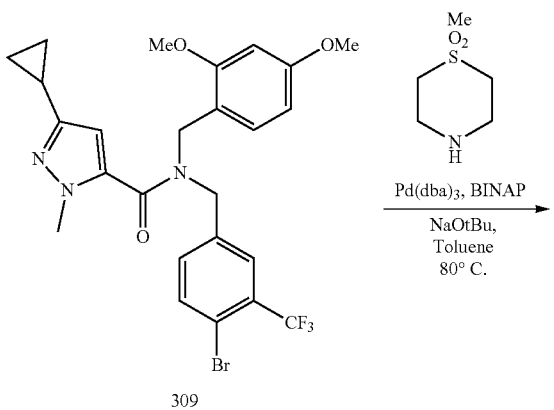

309

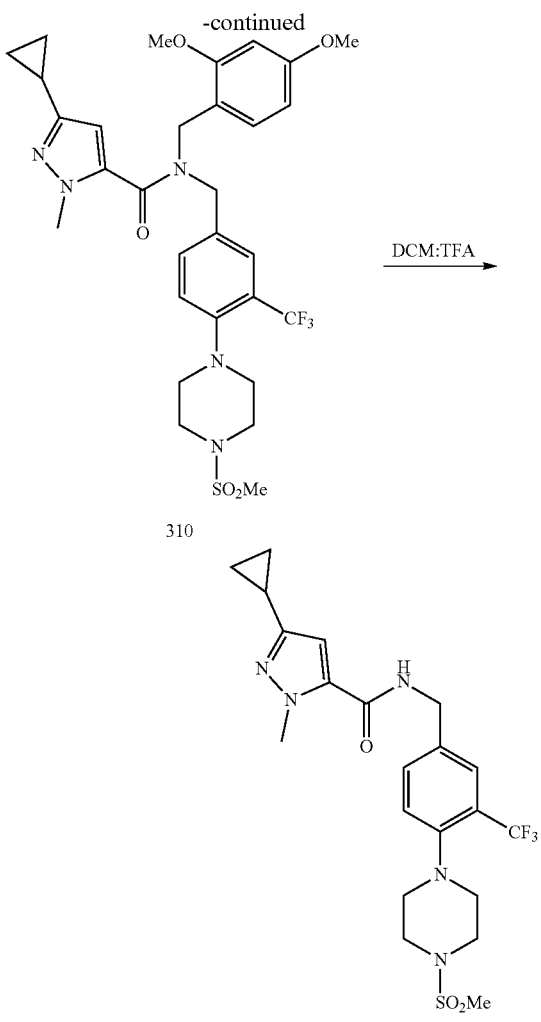

EtOAc and washed with 10% aq. HCl (1×), sat. NaHCO$_3$ (1×) and water (3×). The organic layer was collected, dried (MgSO$_4$) and evaporated to give a residue, which was purified by column chromatography (EtOAc/Hexane) to give compound the desired amide 310. Mass Spectrum (LCMS, ESI Pos.) Calcd. For $C_{25}H_{26}BrF_3N_3O_3$: 553.0 (M$^+$H), Found 553.0.

Preparation of Compound 310

To a stirred solution of bromide 309 (400 mg, 0.724 mmol, 1.0 eq) in toluene (10 ml) was added sodium tert-butoxide (173 mg, 1.81 mmol, 2.5 eq), 1-(methylsulfonyl)piperazine (142 mg, 0.868 mmol, 1.2 eq) 242 and BINAP (45 mg, 0.0724 mmol, 0.1 eq). The reaction mixture was purged with argon for five min and then tris(dibenzylideneacetone)dipalladium(0) (66 mg, 0.0724 mmol, 0.1 eq) was added and the reaction mixture was heated at 80° C. for 6 h. The reaction mixture was evaporated under vacuum to give a residue, which was taken up in ethyl acetate and washed with water and brine. The organic layer was dried and evaporated under vacuum to provide the crude product, which was purified by column chromatography to yield the amide 310. Mass Spectrum (LCMS, ESI Pos.) Calcd. For $C_{30}H_{37}F_3N_5O_5S$:636.0 (M$^+$H), Found 636.0.

Example 84: Preparation of Compound 121

The amide 310 was taken in a 1:1 mixture of TFA: DCM and the reaction mixture was stirred at room temperature for 24 h. Solvents were removed and the residue purified by column chromatography to give compound 121. Mass Spectrum (LCMS, ESI Pos.) Calcd. For $C_{21}H_{27}F_3N_5O_3S$: 486.0 (M$^+$H), Found 486.0.

Preparation of Compound 308

To a solution of 4-bromo-3-(trifluoromethyl)benzaldehyde 306 (653 mg, 2.58 mmol, 1.0 eq) in toluene were added 2,4-dimethoxybenzyl amine 307 (430 mg, 2.58 mmol, 1.0 eq) and catalytic amount of p-toluene sulfonic acid. The reaction mixture was stirred at 65° C. for 24 h. Solvent was removed and the residue was taken in MeOH and cooled in an ice bath. Then sodium borohydride (195 mg, 5.16 mmol, 2.0 eq) was added slowly and the reaction mixture was stirred at RT for 12 h. Solvent was removed and residue was taken in ethyl acetate and then sat. NaHCO$_3$ was added and the mixture was stirred for 1 h. The organic layer was separated, dried (MgSO$_4$) and solvent was removed to give the amine, which was used in the next step without further purification.

Preparation of Compound 309

To a solution of the crude amine 308 (2.58 mmol, 1.0 eq) in DMF (10 mL) were added 3-cyclopropyl-1-methyl-1H-pyrazole-5-carboxylic acid 204 (477 mg, 2.84 mmol, 1.1 eq), HATU (1.18 g, 3.09 mmol, 1.2 eq), and DIEA (1.67 g, 12.95 mmol, 5.0 eq) and the reaction mixture was stirred at RT for 12 h. The reaction mixture was then diluted with

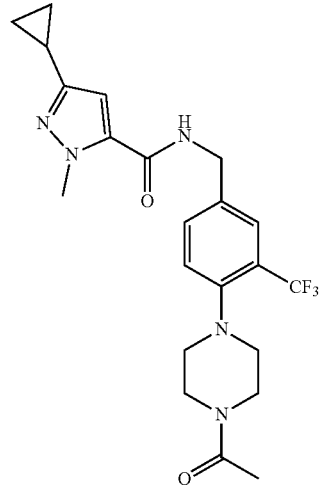

Example 85: Preparation of Compound 122

Compound 122 was prepared following the procedure used to prepare compound 120 except that commercially available 1-(acetyl)piperazine was used in the initial step. Mass Spectrum (LCMS, ESI Pos.) Calcd. For $C_{22}H_{27}F_3N_5O_2$: 450.0 (M$^+$H), Found 450.0.

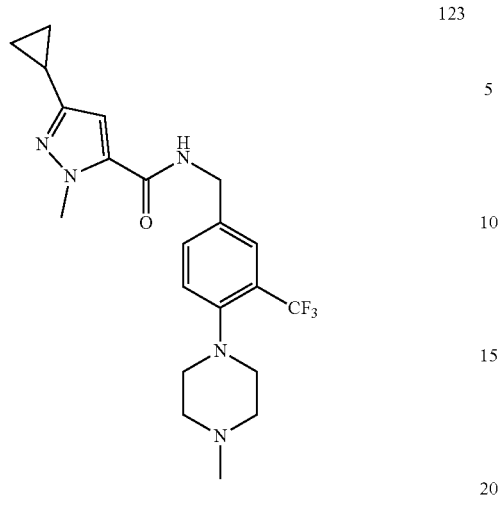

123

Example 86: Preparation of Compound 123

Compound 123 was prepared following the procedure used to prepare compound 120 except that commercially available 1-(methyl)piperazine was used in the initial step. Mass Spectrum (LCMS, ESI Pos.) Calcd. For $C_{21}H_{27}F_3N_5O$: 422.0 (M$^+$H), Found 422.0.

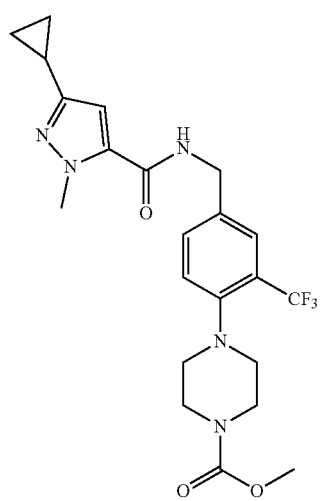

124

Example 87: Preparation of Compound 124

Compound 124 was prepared following the procedure used to prepare compound 120 except that commercially available methyl piperazine-1-carboxylate was used in the initial step. Mass Spectrum (LCMS, ESI Pos.) Calcd. For $C_{22}H_{27}F_3N_5O_3$: 466.0 (M$^+$H), Found 466.0.

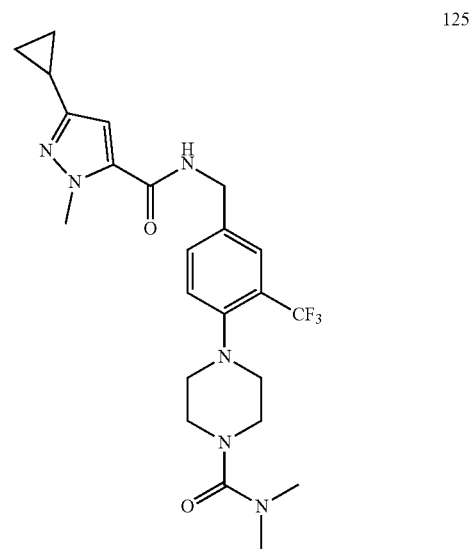 [SMILES: CN(C)C(=O)N1CCN(c2ccc(CNC(=O)c3cc(C4CC4)nn3C)cc2C(F)(F)F)CC1]

125

Example 88: Preparation of Compound 125

Compound 125 was prepared following the procedure used to prepare compound 120 except that commercially available piperazine-1-carboxylic acid dimethylamide was used in the initial step. Mass Spectrum (LCMS, ESI Pos.) Calcd. For $C_{23}H_{30}F_3N_6O_2$: 479.0 (M$^+$H), Found 479.0, Scheme 36 illustrates the preparation of compound 126.

Scheme 36

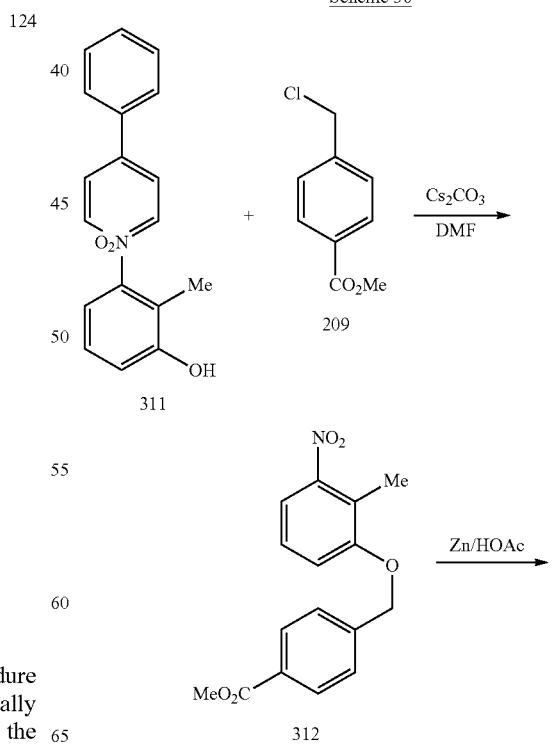

265
-continued

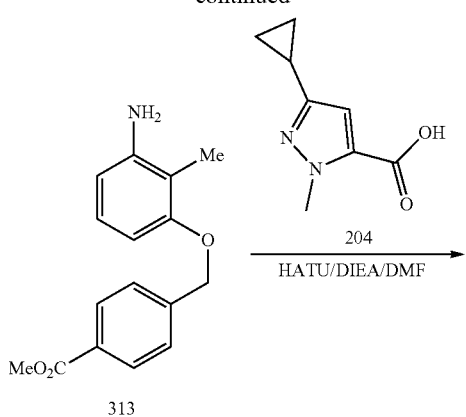

313

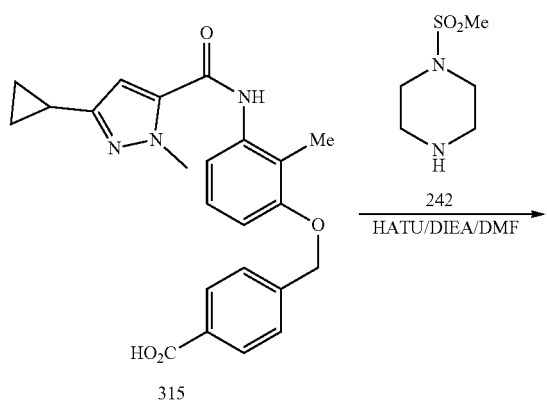

266
-continued

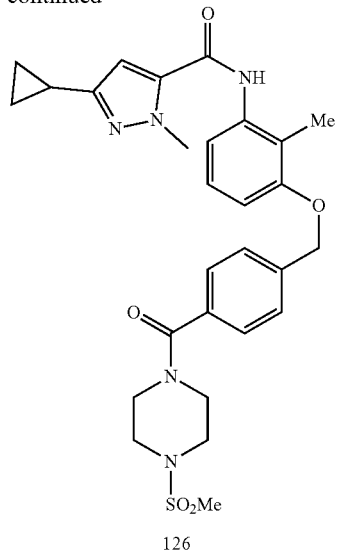

126

Preparation of Compound 312

To a stirred solution of compound 2-methyl-3-nitrophenol 311 (100 mg, 0.653 mmol, 1.0 eq) in DMF (10 ml) were added $Cs_2CO_3$ (318 mg, 0.98 mmol, 1.5 eq) and methyl 4-(chloromethyl)benzoate 209 (181 mg 0.98 mmol, 1.5 eq) and the reaction mixture was stirred at RT for 12 h. The reaction mixture was diluted with water and extracted with ethyl acetate (3×). The combined organic layer was washed with water, brine and dried over $NaSO_4$ and evaporated under vacuum to get a residue, which was purified by column chromatography to give the desired alkylation product 312.

Preparation of Compound 313

To a stirred solution of the nitro compound (150 mg, 0.498 mmol 1.0 eq) in acetic acid (10 ml) was added zinc powder (48 mg, 0.74 mmol, 1.5 eq) and the reaction mixture was stirred at room temperature for 12 hrs. Water was added to the reaction mixture and the reaction mixture was extracted with ethyl acetate (3×). The combined organic layers were washed with water, brine, dried and evaporated under vacuum to provide the crude amine 313, which was used in the next step without further purification.

Preparation of Compound 314

To a solution of the crude amine 313 (105 mg, 0.43 mmol, 1.0 eq) in DMF (10 mL) were added 3-cyclopropyl-1-methyl-1H-pyrazole-5-carboxylic acid 204 (77 mg, 0.464 mmol, 1.2 eq), HATU (220 mg, 0.58 mmol, 1.5 eq), and DIEA (250 mg, 1.93 mmol, 5.0 eq) and the reaction mixture was stirred at RT for 12 h. The reaction mixture was then diluted with EtOAc and washed with 10% aq. HCl (1×), sat. $NaHCO_3$ (1×) and water (3×). The organic layer was collected, dried ($MgSO_4$) and evaporated to give a residue, which was purified by column chromatography (EtOAc/Hexane) to give compound the desired ester 314. Mass Spectrum (LCMS, ESI Pos.) Calcd. For $C_{24}H_{26}N_3O_4$: 420.0 ($M^+H$), Found 420.0.

Preparation of Compound 315

The ester 314 (120 mg, 0.576 mmol, 1.0 eq) was taken up in a 1:5 mixture of $H_2O$; MeOH (18 mL) and then LiOH (48 mg, 1.14 mmol, 4.0 eq) was added. The reaction mixture was stirred at 65° C. for 12 h. The reaction mixture evaporated under vacuum to give a residue, which was stirred in a mixture of 10% aq. HCl and ethyl acetate for 30 min. The organic layer was collected, washed with $H_2O$ (1×), dried and concentrated to give the crude acid 315, which was directly used in the next step without further purification.

Example 89: Preparation of Compound 126

To a stirred solution of 1-(methylsulfonyl)piperazine 242 (49 mg, 0.299 mmol, 1.2 eq) in DMF (15 mL) were added the crude acid 315 (101 mg, 0.249 mmol, 1.0 eq), HATU (114 mg, 0.299 mmol, 1.2 eq) and DIEA (161 mg, 1.245 mmol, 5.0 eq), and the reaction mixture was stirred at RT for 12 h. The reaction mixture was then diluted with EtOAc and washed with 10% aq. HCl (1×), sat. $NaHCO_3$ (1×) and water (3×). The organic layer was collected, dried ($MgSO_4$) and evaporated to give a residue, which was purified by column chromatography (EtOAc/Hexane) to give the amide 126. Mass Spectrum (LCMS, ESI Pos.) Calcd. For $C_{28}H_{34}N_5O_5S$:552.0 ($M^+H$), Found 552.0.

Scheme 36 illustrates the preparation of compound 127.

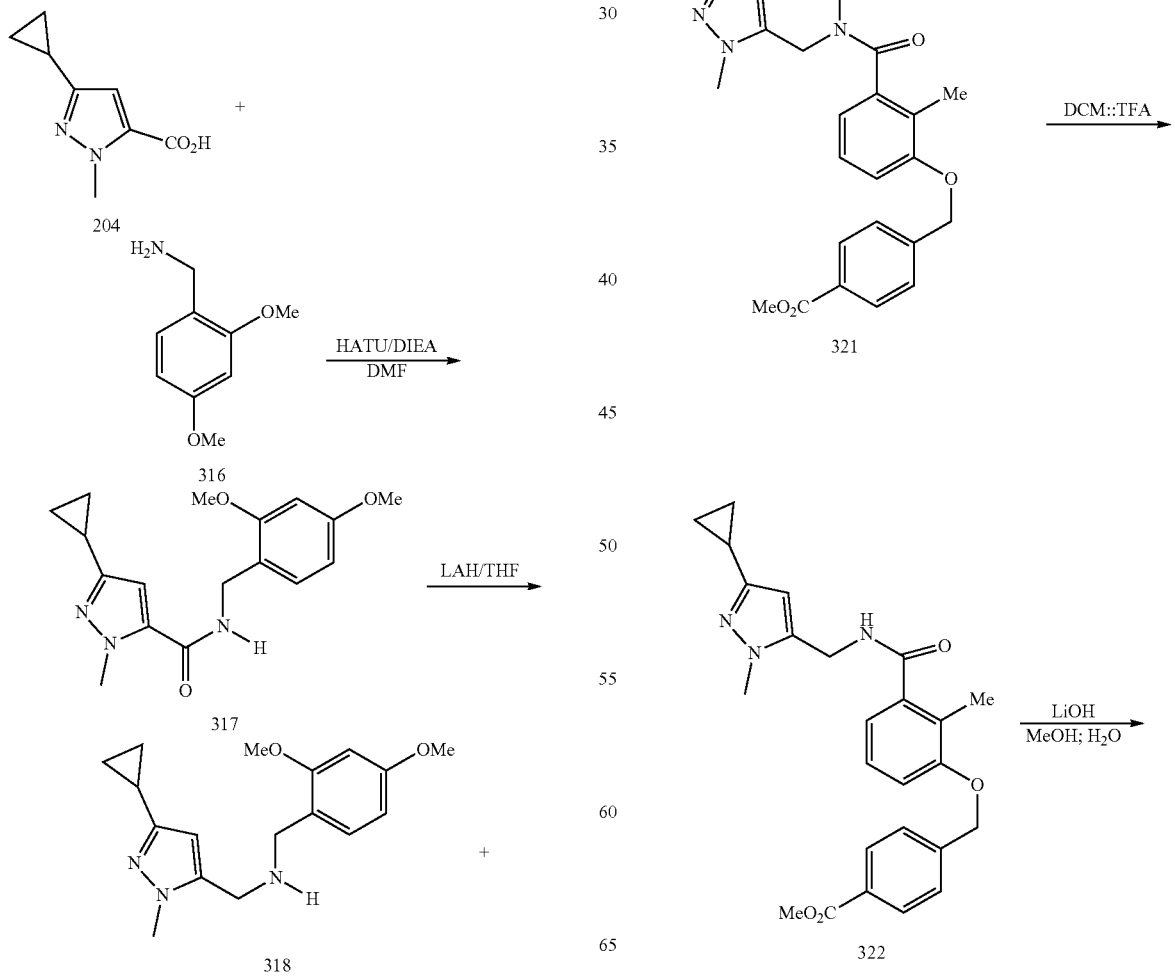

-continued

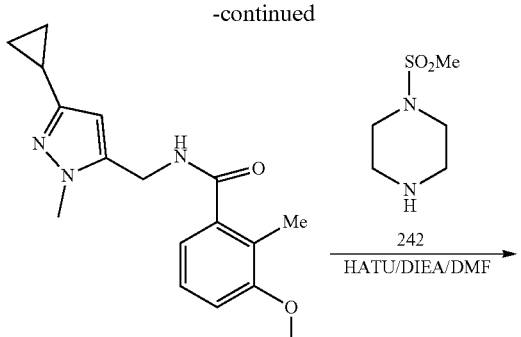

323

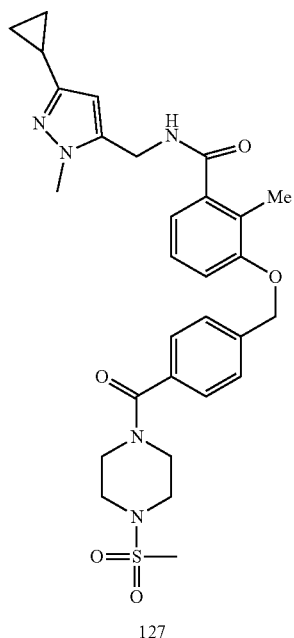 [SMILES: Cc1c(OCc2ccc(C(=O)N3CCN(S(C)(=O)=O)CC3)cc2)cccc1C(=O)NCc1cc(C2CC2)nn1C]

127

Preparation of Compound 317

To a solution of 2,4-dimethoxybenzylamine 319 (547 mg, 3.27 mmol, 1.1 eq) in DMF (10 mL) were added 3-cyclopropyl-1-methyl-1H-pyrazole-5-carboxylic acid 204 (500 mg, 2.97 mmol, 1.0 eq), DIEA (1.92 g, 14.85 mmol, 5.0 eq) and HATU (1.35 g, 3.56 mmol, 1.2 eq) and the reaction mixture was stirred at RT for 12 h. The reaction mixture was then diluted with EtOAc and washed with 10% aq. HCl (1×), sat. NaHCO₃ (1×) and water (3×). The organic layer was collected, dried (MgSO₄) and evaporated to give a residue, which was purified by column chromatography (EtOAc/Hexane) to give compound the desired amide 317. Mass Spectrum (LCMS, ESI Pos.) Calcd. For $C_{17}H_{22}N_3O_3$: 316.0 (M⁺H), Found 316.0.

Preparation of Compound 320

To a solution of the amide 317 (200 mg, 0.635 mmol, 1.0 eq) in THF at 0° C. was slowly added 2M solution of lithium aluminum hydride solution in THF (0.65 mL, 1.27 mmol). The reaction mixture was stirred at room temperature for 12 h. The reaction mixture was cooled at 0° C. and then 0.048 mL water, 0.048 mL of 15% NaOH and 0.15 mL of water were added. The reaction mixture was then extracted with ethyl acetate (3×). The combined organic layers were dried and evaporated to give crude amine 318, which was used in the next step without further purification.

Preparation of Compound 321

To a solution of the crude amine 318 (0.635 mmol 1.0 eq) in DMF (10 mL) were added 3-hydroxy-2-methylbenzoic acid (106 mg, 0.700 mmol, 1.1 eq), DIEA (410 mg, 3.18 mmol, 5.0 eq) and HATU (290 mg, 0.762 mmol, 1.2 eq), and the reaction mixture was stirred at RT for 12 h. The reaction mixture was then diluted with EtOAc and washed with 10% aq. HCl (1×), sat. NaHCO₃ (1×) and water (3×). The organic layer was collected, dried (MgSO₄) and evaporated to give a residue, which was purified by column chromatography (EtOAc/Hexane) to give compound the desired amide 320. Mass Spectrum (LCMS, ESI Pos.) Calcd. For $C_{25}H_{30}N_3O_4$: 436.0 (M⁺H), Found 436.0.

Preparation of Compound 321

To a stirred solution of amide 320 (284 mg, 0.653 mmol, 1.0 eq) in DMF (15 ml) were added Cs₂CO₃ (318 mg, 0.98 mmol, 1.5 eq) and methyl 4-(chloromethyl)benzoate 209 (181 mg 0.98 mmol, 1.5 eq) and the reaction mixture was stirred at RT for 12 h. The reaction mass was diluted with water and extracted with ethyl acetate (3×). The combined organic layers were washed with water, brine and dried over NaSO₄ and evaporated under vacuum to provide a residue, which was purified by column chromatography to give the desired alkylation product 321. Mass Spectrum (LCMS, ESI Pos.) Calcd. For $C_{25}H_{30}N_3O_4$: 436.0 (M⁺H), Found 436.0.

Preparation of Compound 322

The ester was taken in a 1:1 mixture of TFA: DCM and the reaction mixture was stirred at room temperature for 24 h. Solvents were removed and the residue purified by column chromatography to give the desired compound 322. Mass Spectrum (LCMS, ESI Pos.) Calcd. For $C_{25}H_{28}N_3O_4$: 434.0 (M⁺H), Found 434.0

Preparation of Compound 323

The ester 322 (249 mg, 0.576 mmol, 1.0 eq) was taken up in a 1:5 mixture of H₂O:MeOH (18 mL) and then LiOH (48 mg, 1.14 mmol, 4.0 eq) was added. The reaction mixture was stirred at 65° C. for 12 h. The reaction mixture evaporated under vacuum to give a residue, which was stirred in a mixture of 10% aq. HCl and ethyl acetate for 30 min. The organic layer was collected, washed with H₂O(1×), dried and concentrated to give the crude acid, which was directly used in the next step without further purification.

Example 90: Preparation of Compound 127

To a stirred solution of 1-(methylsulfonyl)piperazine 242 (49 mg, 0.299 mmol, 1.2 eq) in DMF (15 mL) were added the crude acid (104 mg, 0.249 mmol, 1.0 eq), DIEA (161 mg, 1.245 mmol, 5.0 eq), and HATU (114 mg, 0.299 mmol, 1.2 eq) and the reaction mixture was stirred at RT for 12 h. The reaction mixture was then diluted with EtOAc and washed with sat. NaHCO₃ (1×), 10% aq. HCl (1×), and water (3×). The organic layer was collected, dried (MgSO₄) and evaporated to give a residue, which was purified by column chromatography (EtOAc/Hexane) to give the amide 127. Mass Spectrum (LCMS, Pos.) Calcd. For $C_{29}H_{36}N_5O_5S$: 566.0 ($M^+H$), Found 566.0.

Scheme 37 illustrates the preparation of compound 128.

Scheme 37

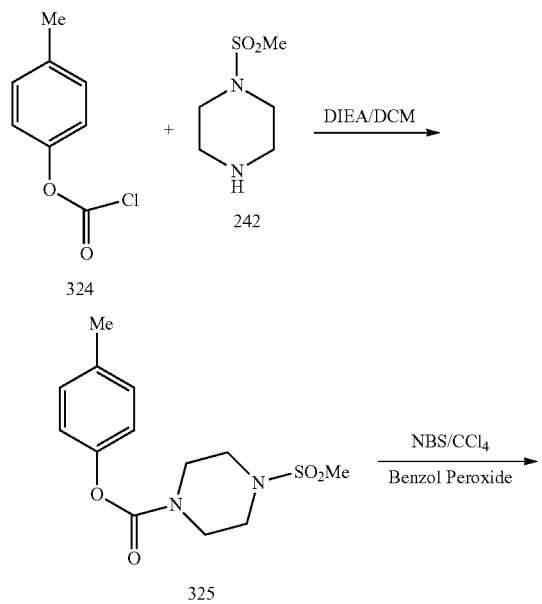

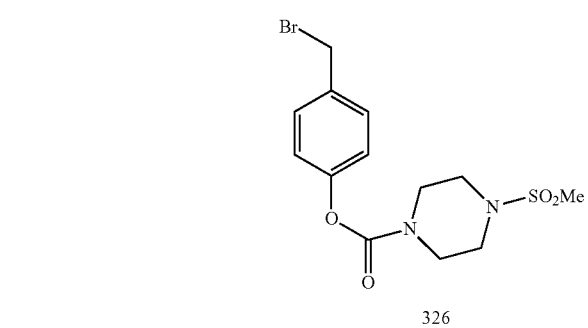

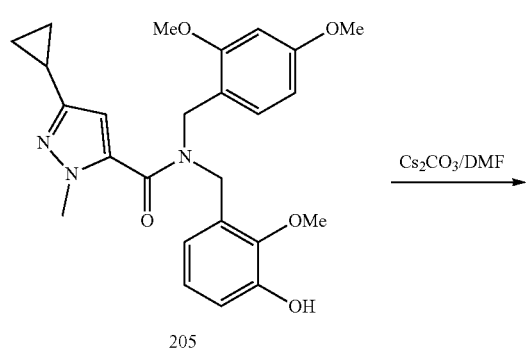

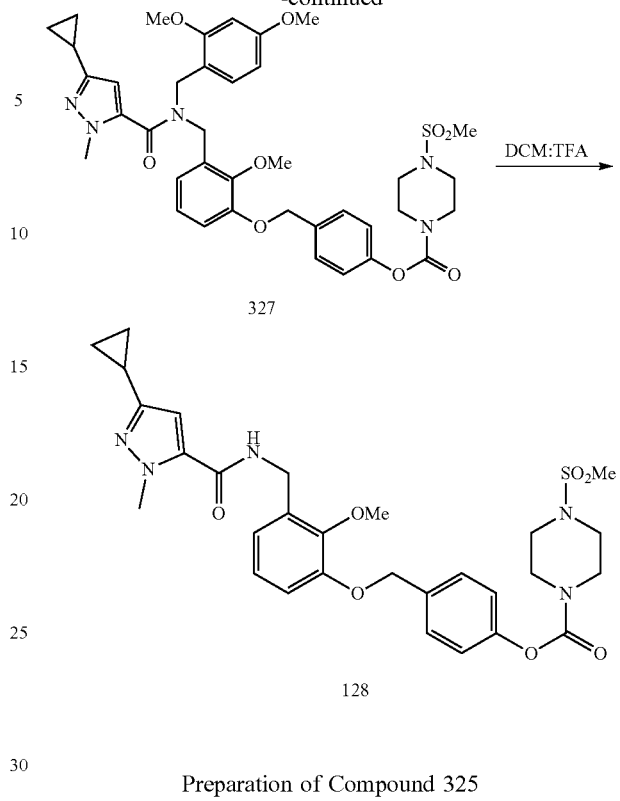

Preparation of Compound 325

To a stirred solution of 1-(methylsulfonyl)piperazine 242 (500 mg, 3.04 mmol, 1 eq) in DCM (10 ml) at 0° C. were added DIEA (590 mg, 4.57 mmol, 1.5 eq), DMAP (32.7 mg, 0.304 mmol 0.1 eq) and p-tolyl chloroformate (570 mg, 3.34 mmol 1.1 eq) 324 and the reaction mixture was stirred at RT for 12 h. The reaction mixture was then diluted with DCM and quenched with sat. $NaHCO_3$ solution. The reaction mixture was extracted with DCM (2×) and the combined organic layer was washed with water, brine, dried ($Na_2SO_4$) and evaporated under vacuum to give a residue, which was purified by column chromatography to give the carbamate 325. Mass Spectrum (LCMS, ESI Pos.) Calcd. For $C_{13}H_{19}N_2O_4S$:299.0 ($M^+H$), Found 299.0.

Preparation of Compound 326

To a stirred solution of the carbamate 325 (200 mg, 0.670 mmol, 1.0 eq) in CCl4 (15 ml) were added NBS (143 mg, 0.805 mmol 1.2 eq) and benzoyl peroxide (19 mg, 0.081 mmol 0.1 eq) and the reaction mixture was heated at reflux for 12 h. The reaction mixture was filtered via a pad of celite and evaporated to give a residue, which was purified by column chromatography to give the desired bromide 326. Mass Spectrum (LCMS, ESI Pos.) Calcd. For $C_{13}H_{18}BrN_2O_4S$:378.0 ($M^+H$), Found 378.0.

Preparation of Compound 327

To a stirred solution of compound 205 (100 mg, 0.222 mmol, 1.0 eq) in DMF (10 ml) were added $Cs_2CO_3$ (108 mg, 0.333 mmol, 1.5 eq) and the bromide 326 (87 mg 0.222 mmol, 1.0 eq) and the reaction mixture was stirred at RT for 12 h. The reaction mixture was diluted with water and extracted with ethyl acetate (3×). The combined organic layers were washed with water, brine and dried over $NaSO_4$ and evaporated under vacuum to provide a residue, which was purified by column chromatography to give the desired alkylation product 327.

Example 91: Preparation of Compound 128

The crude alkylation product 327 was taken up in a 1:1 mixture of DCM: TFA and the reaction mixture was stirred at room temperature for 12 h. Solvents were evaporated under vacuum to give a residue, which was purified by column chromatography to give the desired product compound 128. Mass Spectrum (LCMS, ESI Pos.) Calcd. For $C_{29}H_{36}N_5O_7S$:598.0 ($M^+H$), Found 598.0.

Example 92: Preparation of Compound 129

Compound 129 was prepared following the procedure used to prepare compound 127 except that commercially available p-tolyl isocyanate was used in the first step. Mass Spectrum (LCMS, ESI Pos.) Calcd. For $C_{29}H_{37}N_6O_6S$: 597.0 ($M^+H$), Found 597.0.

Scheme 38 illustrates the preparation of compound 130.

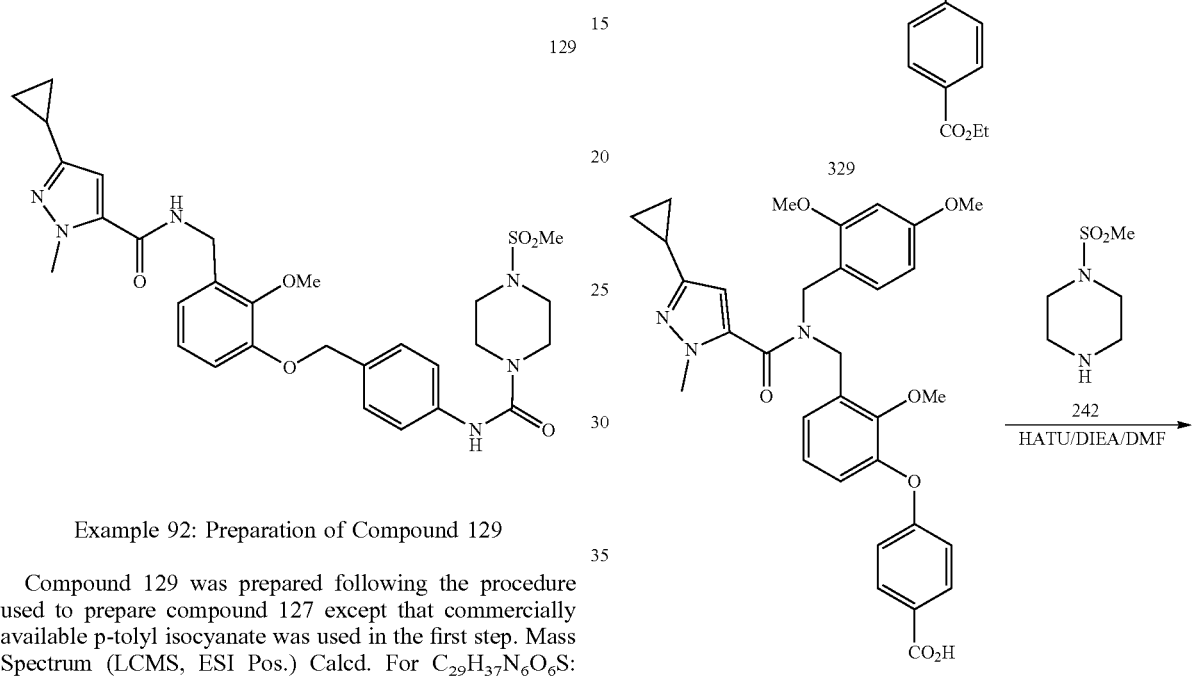

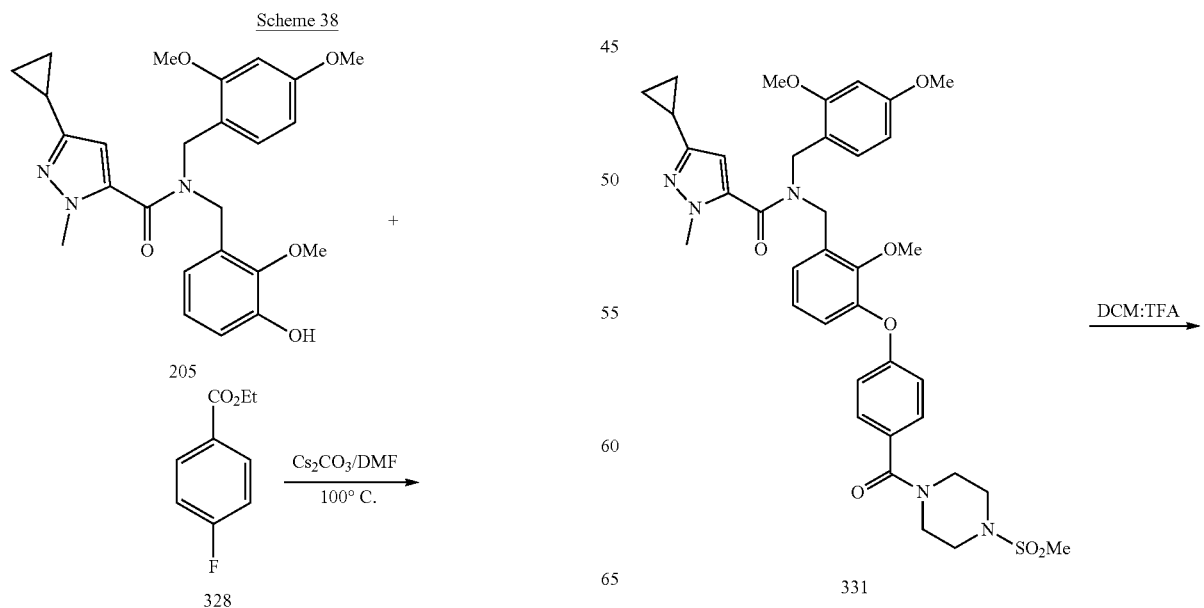

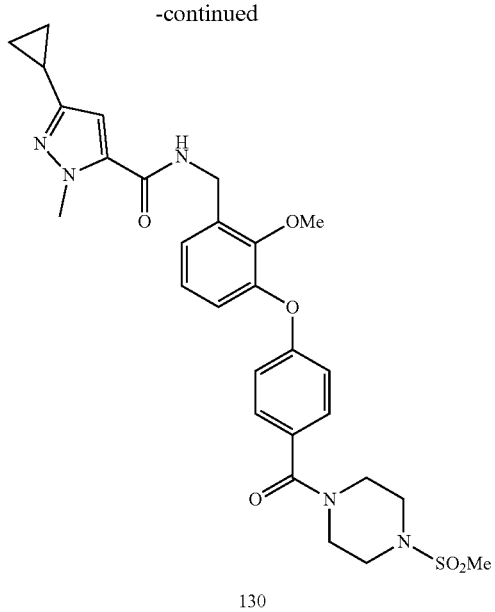

130

Preparation of Compound 329

To a stirred solution of compound 205 (200 mg, 0.442 mmol, 1.0 eq) in DMF (15 ml) were added Cs$_2$CO$_3$ (216 mg, 0.640 mmol, 1.5 eq) and methyl 4-fluorobenzoate 328 (89 mg 0.531 mmol, 1.2 eq) and the reaction mixture was heated at 100° C. for 12 h. The reaction mixture was diluted with water and extracted with ethyl acetate (3×). The combined organic layers were washed with water, brine and dried over NaSO$_4$ and evaporated under vacuum to get a residue, which was purified by column chromatography to give the desired product 329. Mass Spectrum (LCMS, ESI Pos.) Calcd. For C$_{34}$H$_{38}$N$_3$O$_7$: 600.0 (M$^+$H), Found 600.0.

Preparation of Compound 330

The ester 329 (100 mg, 0.166 mmol 1.0 eq) was taken in a 1:5 mixture of H$_2$O: MeOH (12 mL) and then LiOH (28 mg, 0.667 mmol, 4.0 eq) was added. The reaction mixture was stirred at 65° C. for 12 h. The reaction mixture evaporated under vacuum to give a residue, which was stirred in a mixture of 10% aq. HCl and ethyl acetate for 30 min. The organic layer was collected, washed with H$_2$O (1×), dried and concentrated to give the crude acid, which was directly used in the next step without further purification.

Preparation of Compound 331

To a stirred solution of 1-(methylsulfonyl)piperazine (33 mg, 0.199 mmol, 1.2 eq) in DMF (15 mL) were added the crude acid (0.166 mmol, 1.0 eq), DIEA (107 mg, 0.83 mmol, 5.0 eq), and HATU (76 mg, 0.199 mmol, 1.2 eq) and the reaction mixture was stirred at RT for 12 h. The reaction mixture was then diluted with EtOAc and washed with sat. NaHCO$_3$ (1×), 10% aq. HCl (1×), and water (3×). The organic layer was collected, dried (MgSO$_4$) and evaporated to give 331.

Example 93: Preparation of Compound 130

Amide 331 which was taken up in a 1:1 mixture of DCM: TFA and stirred at room temperature for 12 h. Solvents were evaporated to provide a residue, which was purified by column chromatography (EtOAc/Hexane) to give the desired product 130. Mass Spectrum (LCMS, ESI Pos.) Calcd. For C$_{28}$H$_{34}$N$_5$O$_6$S: 568.0 (M$^+$H), Found 568.0.

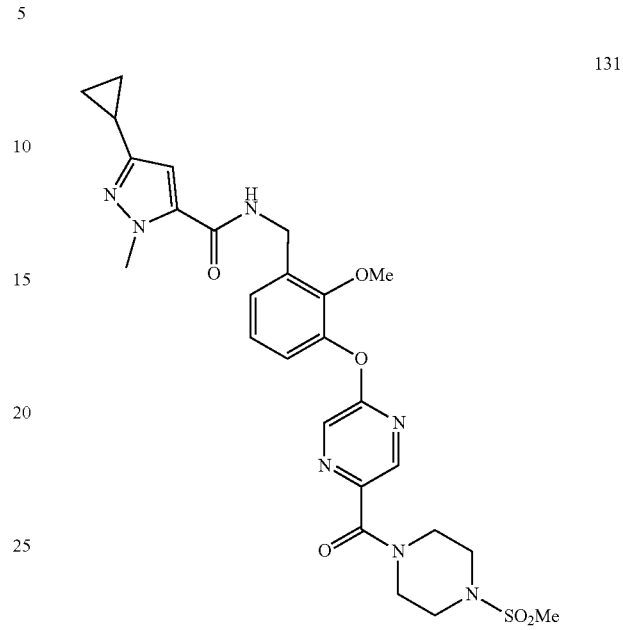

131

Example 94: Preparation of Compound 131

Compound 131 was prepared following the procedure used to prepare compound 130 except that commercially available methyl 5-chloropyrazine-2-carboxylate was used in the first step. Mass Spectrum (LCMS, ESI Pos.) Calcd. For C$_{26}$H$_{32}$N$_7$O$_6$S: 570.0 (M$^+$H), Found 570.0.

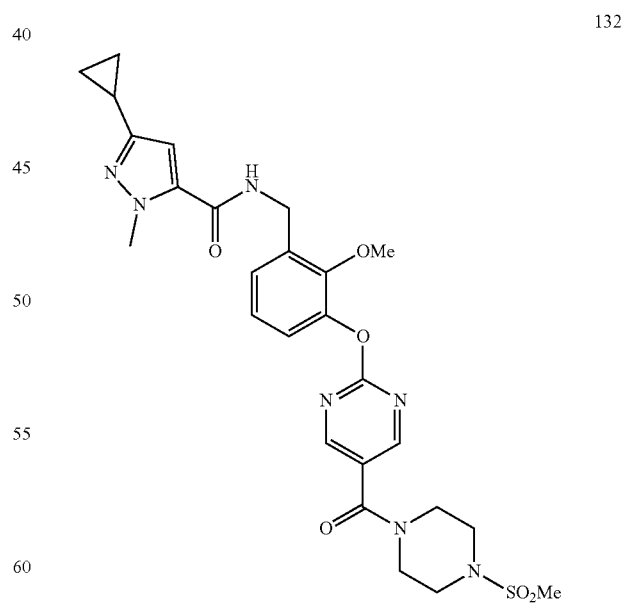

132

Example 95: Preparation of Compound 132

Compound 132 was prepared following the procedure used to prepare compound 130 except that commercially available methyl 2-chloropyrimidine-5-carboxylate was used in the first step. Mass Spectrum (LCMS, ESI Pos.) Calcd. For $C_{26}H_{32}N_7O_6S$: 570.0 (M+H), Found 570.0.

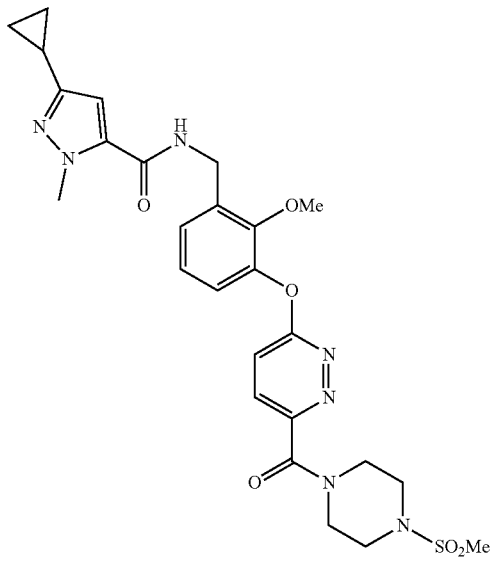

133

Example 96: Preparation of Compound 133

Compound 133 was prepared following the procedure used to prepare compound 130 except that commercially available methyl 6-chloropyridazine-3-carboxylate was used in the first step. Mass Spectrum (LCMS, ESI Pos.) Calcd. For $C_{26}H_{32}N_7O_6S$: 570.0 (M+H), Found 570.0.

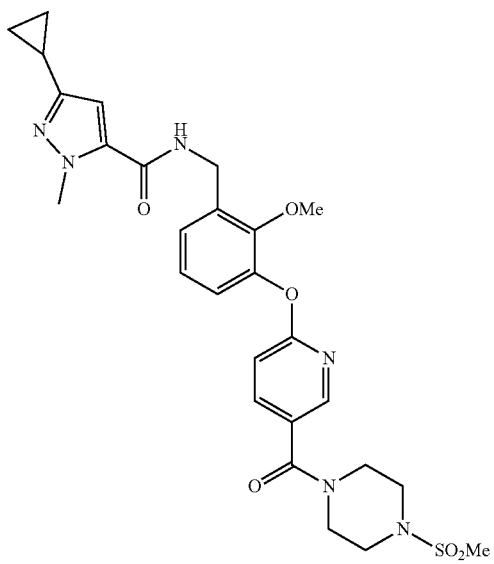

134

Example 97: Preparation of Compound 134

Compound 134 was prepared following the procedure used to prepare compound 130 except that commercially available methyl 6-chloronicotinate was used in the first step. Mass Spectrum (LCMS, ESI Pos.) Calcd. For $C_{27}H_{33}N_6O_6S$: 569.0 (M+H), Found 569.0.

General Procedure for the Preparation of Hetero Aromatic Alkyl Bromides To a stirred solution of the methyl heteroaromatic compound (1.0 eq) in CCl4 were added NBS (1.2 eq) and benzoyl peroxide (0.1 eq) and the reaction mixture was heated at reflux for 12 h. The reaction mixture was filtered via a pad of celite and evaporated to give a residue, which was purified by column chromatography to give the desired bromide. Bromides prepared include, for example,

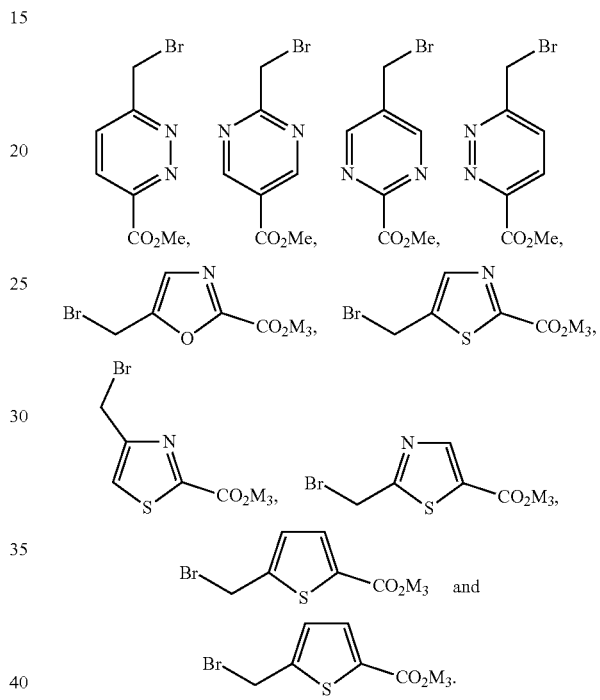

The above bromides were used to prepare heteroaromatic analogs of compound 9 such as compounds 135 to 144 using procedures analogous to those used to prepare compound 9.

Scheme 39 illustrates the preparation of compound 145.

Scheme 39

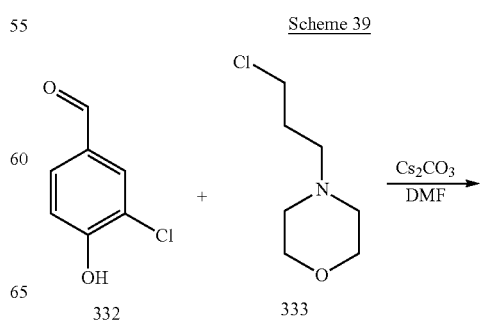

332                    333

-continued

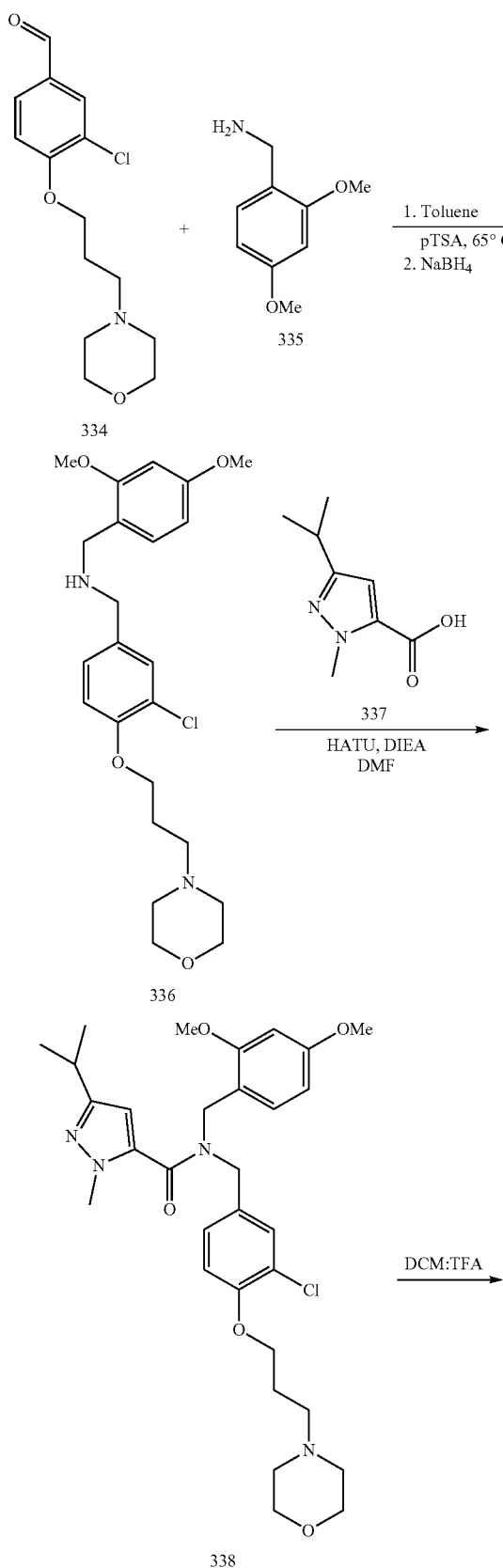

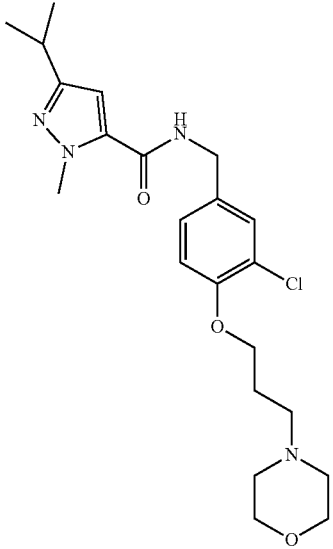

145

Preparation of Compound 334

To a stirred solution of 3-chloro-4-hydxoxy benzaldehyde 332 (1.0 g, 6.41 mmol, 1.0 eq) in DMF (20 mL) were added Cs₂CO₃ (5.22 g 16.02 mmol, 2.5 eq) and of 4-(3-chloropropyl) morpholine 333 (1.56 g, 9.61 mmol, 1.5 eq) and the reaction mixture was stirred at room temperature for 24 h. The reaction mixture was diluted with water and extracted with ethyl acetate (3×). The combined organic layers were washed with water (3×), brine (1×) dried and evaporated under vacuum to yield a crude residue, which was purified by the column chromatography to provide aldehyde 334.

Preparation of Compound 336

To a stirred solution of the aldehyde 334 (800 mg, 2.82 mmol, 1.0 eq) in toluene (15 mL) were added 2,4-dimethoxy benzylamine 335 (0.51 g, 3.10 mmol, 1.1 eq) and catalytic amount of p-toluenesulfonic acid and the reaction mixture was stirred at 65° C. for 24 h. Solvent was removed under vacuum to give a crude imine, which was used directly in the next step. To a stirred solution of the crude imine (1.00 g, 2.31 mmol, 1.0 eq) in MeOH (20 mL) at 0° C. was slowly added NaBH₄ (0.18 g, 3.46 mmol, 1.5 eq). The reaction mixture was stirred at room temperature for 5 h. Solvent was evaporated to yield a solid, which was taken up in ethyl acetate and saturated sodium bicarbonate solution was added. The reaction mixture was stirred for an hour. The organic layer was washed with brine, dried and evaporated under vacuum to give a crude amine 336, which was used in the next step without further purification.

Preparation of Compound 338

To a stirred solution of the crude amine 336 (0.20 g, 0.45 mmol, 1.0 eq) in DMF (10 ml) were added DIEA (290 mg, 2.25 mmol, 5.0 eq), and 3-isopropyl-1-methyl-1H-pyrazole-5-carboxylic acid 337 337 (83 mg, 0.495 mmol, 1.1 eq) and HATU (256 mg, 0.68 mmol, 1.5 eq) and the reaction mixture was stirred at RT for 12 h. The reaction diluted with water and extracted with ethyl acetate (2×). The combined organic Example 98: Preparation of Compound 145

The crude ether 338 was taken up in a 1:1 mixture of DCM and TFA and stirred at room temperature for 12 h. Solvents were evaporated to give a residue, which was purified by column chromatography to provide the desired product 145. Mass Spectrum (LCMS, ESI Pos.) Calcd. For $C_{22}H_{32}ClN_4O_3$: 435.0 (M$^+$H), Found 435.0.

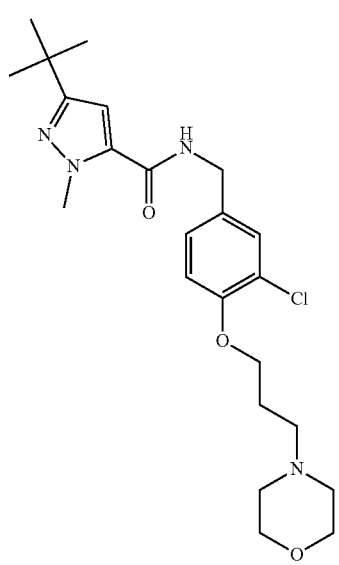

146

Example 99: Preparation of Compound 146

Compound 146 was prepared following the procedure used to prepare compound 145 except that commercially available 3-tert-Butyl-1-methylpyrazole-5-carboxylic acid was used to acylate the amine intermediate. Mass Spectrum (LCMS, ESI Pos.) Calcd. For $C_{23}H_{34}ClN_4O_3$: 449.0 (M$^+$H), Found 449.0.

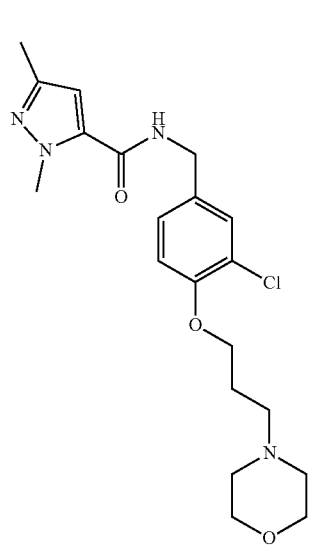

147

Example 100: Preparation of Compound 147

Compound 147 was prepared following the procedure used to prepare compound 145 except that commercially available 1,3-dimethyl-1H-pyrazole-5-carboxylic acid was used to acylate the amine intermediate. Mass Spectrum (LCMS, ESI Pos.) Calcd. For $C_{23}H_{34}ClN_4O_3$: 449.0 (M$^+$H), Found 449.0.

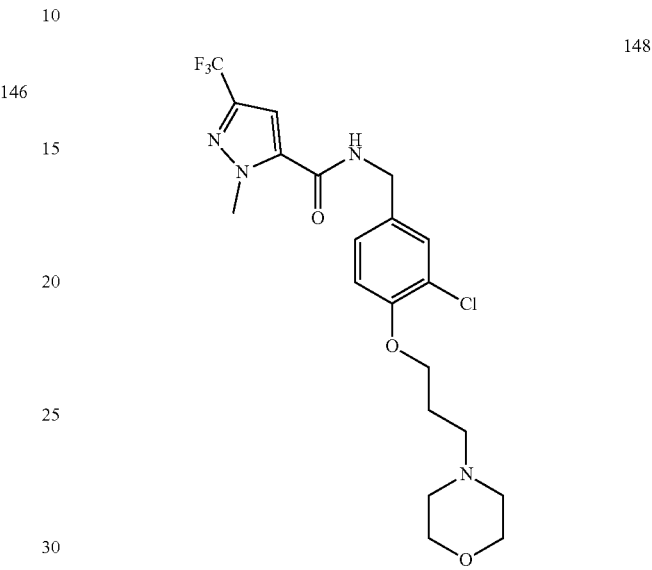

148

Example 101: Preparation of Compound 148

Compound 148 was prepared following the procedure used to prepare compound 145 except that commercially available 3-triflouromethyl-1-methylpyrazole-5-carboxylic acid was used to acylate the amine intermediate. Mass Spectrum (LCMS, ESI Pos.) Calcd. For $C_{20}H_{28}ClN_4O_3$: 407.0 (M$^+$H), Found 407.0.

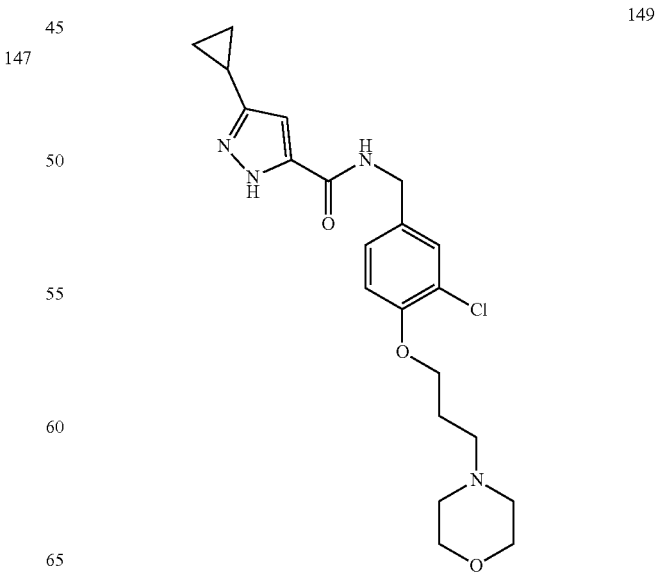

149

Example 102: Preparation of Compound 149

Compound 149 was prepared following the procedure used to prepare compound 145 except that commercially available 3-cyclopropyl-1-methylpyrazole-5-carboxylic acid was used to acylate the amine intermediate. Mass Spectrum (LCMS, ESI Pos.) Calcd. For $C_{21}H_{28}ClN_4O_3$: 419.0 (M$^+$H), Found 419.0.

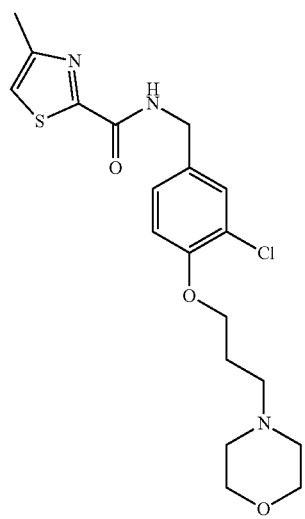

150

Example 103: Preparation of Compound 150

Compound 150 was prepared following the procedure used to prepare compound 145 except that commercially available 4-methylthiazole-2-carboxylic acid was used to acylate the amine intermediate. Mass Spectrum (LCMS, ESI Pos.) Calcd. For $C_{19}H_{25}ClN_3O_3S$: 410.0 (M$^+$H), Found 410.01.

151

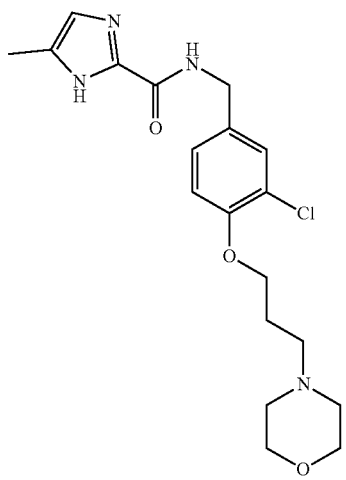

Example 104: Preparation of Compound 151

Compound 151 was prepared following the procedure used to prepare compound 145 except that commercially available 5-methyl-1H-imidazole-2-carboxylic acid was used to acylate the amine intermediate. Mass Spectrum (LCMS, ESI Pos.) Calcd. For $C_{19}H_{26}ClN_4O_3$: 393.0 (M$^+$H), Found 393.0.

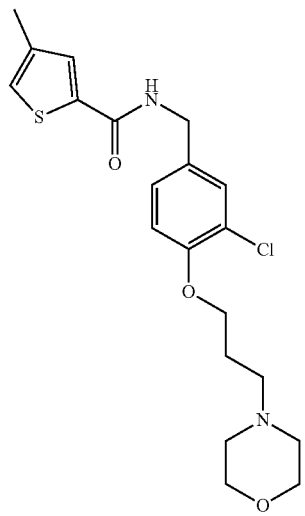

152

Example 105: Preparation of Compound 152

Compound 152 was prepared following the procedure used to prepare compound 145 except that commercially available 4-methylthiophene-2-carboxylic acid was used to acylate the amine intermediate. Mass Spectrum (LCMS, ESI Pos.) Calcd. For $C_{20}H_{26}ClN_2O_3S$: 409.0 (M$^+$H), Found 409.0.

153

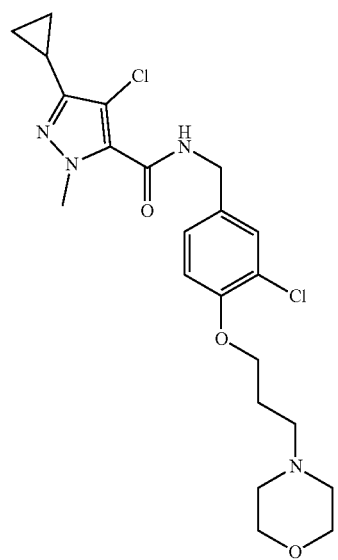

Example 106: Preparation of Compound 153

Compound 153 was prepared following the procedure used to prepare compound 145 except that commercially available 4-chloro-3-cyclopropyl-1-methyl-1H-pyrazole-5-

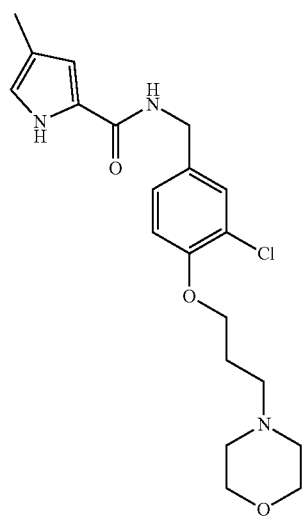

Example 107: Preparation of Compound 154

Compound 154 was prepared following the procedure used to prepare compound 145 except that commercially available 4-methylpyrrole-2-carboxylic acid was used to acylate the amine intermediate. Mass Spectrum (LCMS, ESI Pos.) Calcd. For $C_{20}H_{27}ClN_3O_3$: 392.0 (M$^+$H), Found 392.0.

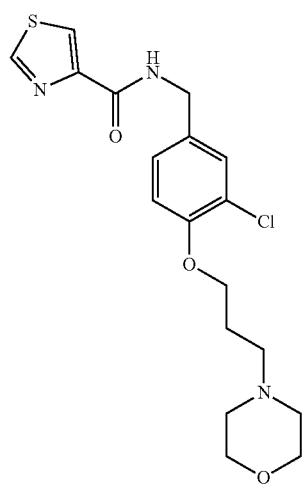

Example 108: Preparation of Compound 155

Compound 155 was prepared following the procedure used to prepare compound 145 except that commercially available thiazole-4-carboxylic acid was used to acylate the amine intermediate. Mass Spectrum (LCMS, ESI Pos.) Calcd. For $C_{18}H_{23}ClN_3O_3S$: 396.0 (M$^+$H), Found 396.0.

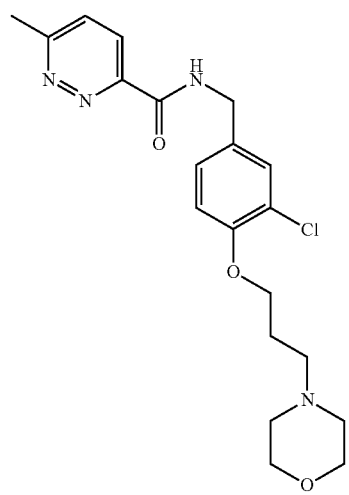

Example 109: Preparation of Compound 156

Compound 156 was prepared following the procedure used to prepare compound 145 except that commercially available 6-methylpyridazine-3-carboxylic acid was used to acylate the amine intermediate. Mass Spectrum (LCMS, ESI Pos.) Calcd. For $C_{20}H_{26}ClN_4O_3$: 405.0 (M$^+$H), Found 405.0.

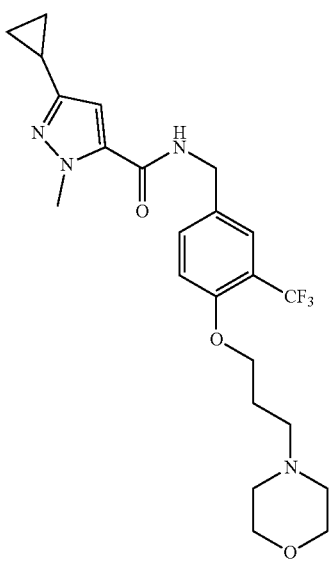

Example 110: Preparation of Compound 157

Compound 157 was prepared following the procedure used to prepare compound 145 except that commercially available 4-hydroxy-3-(trifluoromethyl) benzaldehyde was used in the first step and commercially available 3-cyclopropyl-1 h-pyrazole-5-carboxylic acid was used to acylate the amine intermediate. Mass Spectrum (LCMS, ESI Pos.) Calcd. For $C_{23}H_{33}N_4O_4$: 429.0 (M$^+$H), Found 429.0.

158

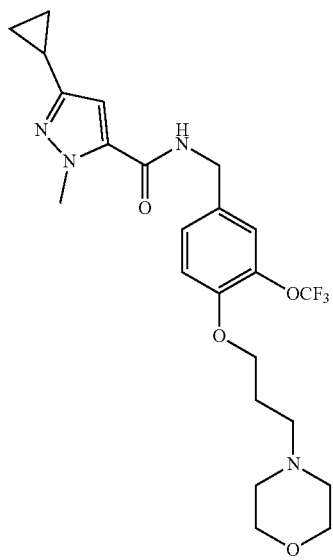

Example 111: Preparation of Compound 158

Compound 158 was prepared following the procedure used to prepare compound 145 except that commercially available 4-hydroxy-3-(trifluoromethoxy)benzaldehyde was used in the first step and commercially available 3-cyclopropyl-1h-pyrazole-5-carboxylic acid was used to acylate the amine intermediate. Mass Spectrum (LCMS, ESI Pos.) Calcd. For $C_{23}H_{30}F_3N_4O_4$: 483.0 (M$^+$H), Found 483.0.

159

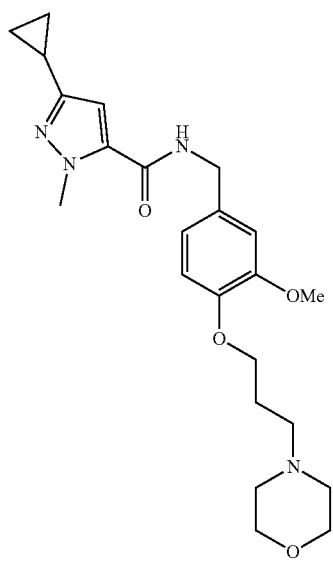

Example 112: Preparation of Compound 159

Compound 159 was prepared following the procedure used to prepare compound 145 except that commercially available 4-hydroxy-3-(methoxy)benzaldehyde was used in the first step and commercially available 3-cyclopropyl-1h-pyrazole-5-carboxylic acid was used to acylate the amine intermediate. Mass Spectrum (LCMS, ESI Pos.) Calcd. For $C_{23}H_{33}N_4O_4$: 429.0 (M$^+$H), Found 429.0.

Scheme 40 illustrates the preparation of compound 160.

Scheme 40

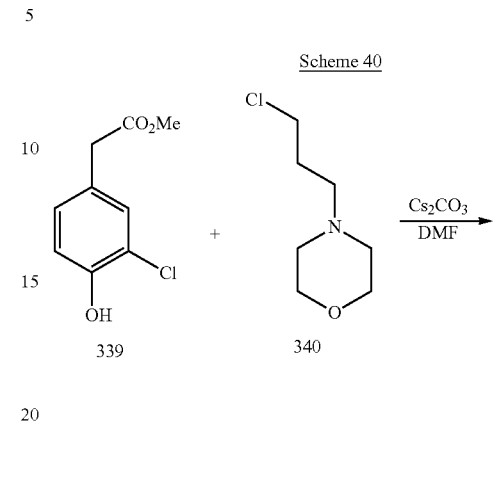

339   340

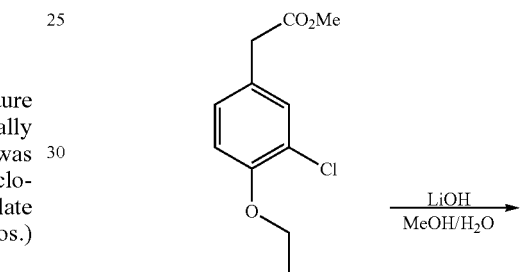

341

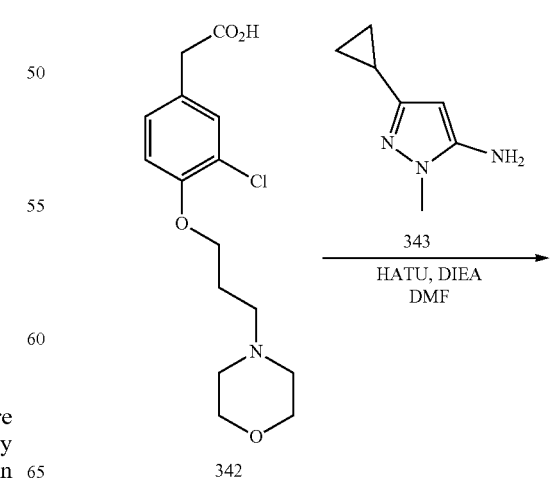

342

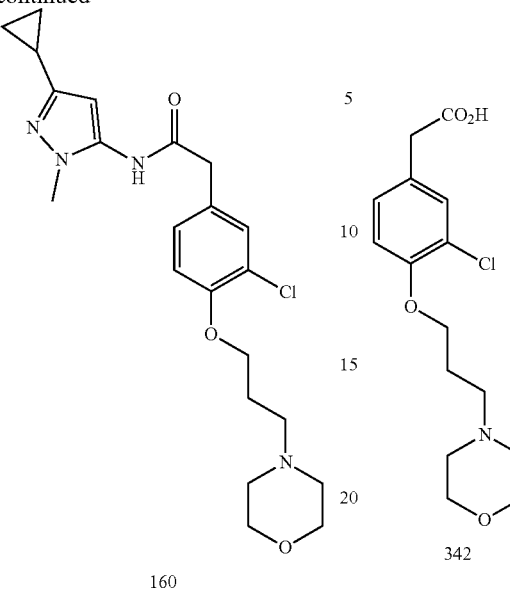

160

Scheme 41 illustrates the preparation of compound 161.

Scheme 41

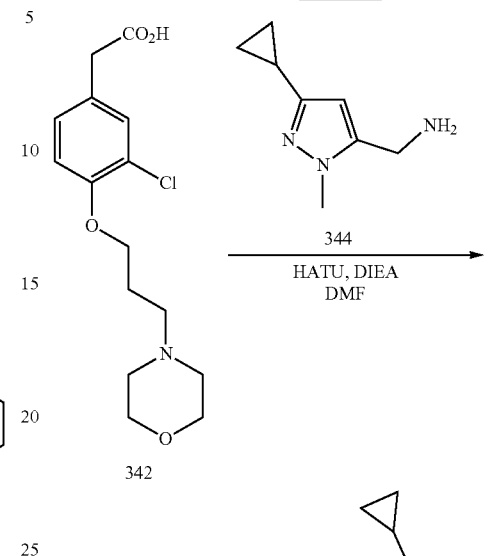

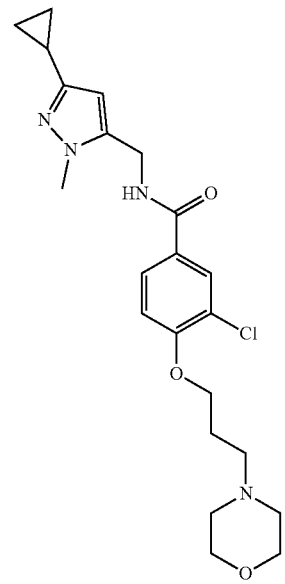

161

Preparation of Compound 341

To a stirred solution of methyl 2-(3-chloro-4-hydroxyphenyl)acetate 339 (100 mg, 0.50 mmol, 1.0 eq) in DMF (5 mL) were added $Cs_2CO_3$ (407 mg, 1.25 mmol, 2.5 eq) and 4-(3-chloropropyl)morpholine 340 (122 mg, 0.75 mmol, 1.5 eq) and the reaction mixture was stirred at room temperature for 24 h. The reaction mixture was diluted with water and extracted with ethyl acetate (3×). The combined organic layers were washed with water (3×), brine, dried and evaporated under vacuum to give a crude residue, which was purified by column chromatography to yield the desired product 341. Mass Spectrum (LCMS, ESI Pos.) Calcd. For $C_{16}H_{23}ClNO_4$: 328.0 ($M^+H$), Found 328.0.

Preparation of Compound 342

To a stirred solution of the ester 341 (100 mg, 0.305 mmol, 1.0 eq) in a 5:1 mixture of methanol: water (6 ml) was added LiOH (15 mg, 0.61 mmol, 2.0 eq) and the reaction mixture was stirred at room temperature for 12 h. Solvent was removed to give the crude acid 342, which was directly used in the next step.

Example 112: Preparation of Compound 160

To a stirred solution of the crude acid 342 (0.305 mmol, 1.0 eq) in DMF (5 mL) were added 3-cyclopropyl-1-methyl-1 h-pyrazol-5-amine 343 (50 mg, 0.366 mmol, 1.2 eq), DIEA (197 mg, 1.525 mmol, 5.0 eq) and HATU (139 mg, 0.366 mmol, 1.2 eq), and the reaction mixture was stirred at room temperature. The reaction mixture was diluted with ethyl acetate and washed with water (2×), brine, dried and evaporated under vacuum to give the crude amide, which was purified by preparative column chromatography to give the desired product 160. Mass Spectrum (LCMS, ESI Pos.) Calcd. For $C_{22}H_{30}ClN_4O_3$: 433.0 ($M^+H$), Found 433.0.

Example 113: Preparation of Compound 161

To a stirred solution of the crude acid 342 (0.305 mmol, 1.0 eq) in DMF (5 mL) were added (3-cyclopropyl-1-methyl-1H-pyrazol-5-yl) methanamine 344 (55 mg, 0.366 mmol, 1.2 eq), DIEA (197 mg, 1.525 mmol, 5.0 eq) and HATU (139 mg, 0.366 mmol, 1.2 eq), and the reaction mixture was stirred at room temperature. The reaction mixture was diluted with ethyl acetate and washed with water (2×), brine, dried and evaporated under vacuum to give the crude amide, which was purified by preparative column chromatography to give the desired product 161. Mass Spectrum (LCMS, ESI Pos.) Calcd. For $C_{22}H_{30}ClN_4O_3$: 433.0 ($M^+H$), Found 433.0.

Scheme 42 illustrates the preparation of compound 162.

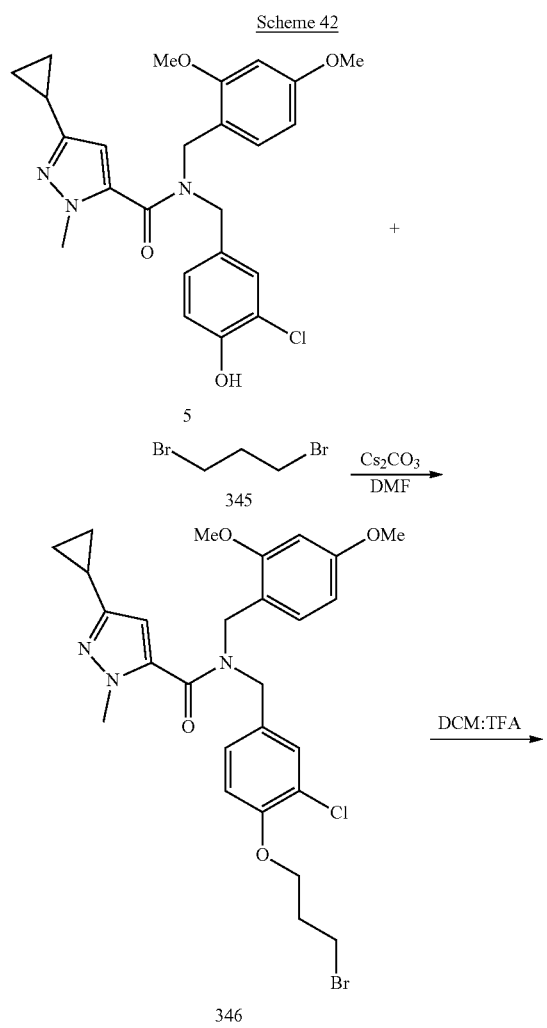

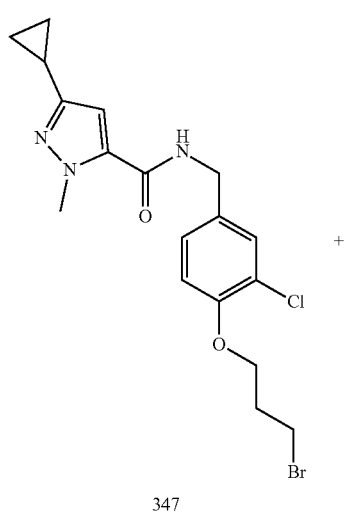

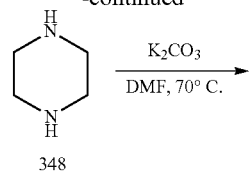

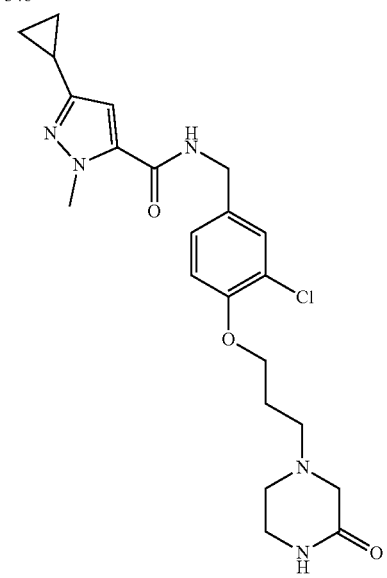

Preparation of Compound 346

To a solution of compound 5 (5.0 g, 11.0 mmol 1.0 eq) in DMF (30 mL) were added cesium carbonate (7.2 g, 22.0 mmol, 2.0 eq) and 1,3-dibromopropane 345 (4.40 g, 22.0 mmol, 2.0 eq) and the reaction mixture was stirred at room temperature for 24 h. The reaction mixture was diluted with ethyl acetate and washed with water (3×). The organic layer was dried (MgSO$_4$) and evaporated to give a residue, which was purified by column chromatography (Hexane/EtOAc) to give the bromide 348. Mass Spectrum (LCMS, ESI Pos.) Calcd. For $C_{27}H_{32}BrClN_3O_4$: 577.0 (M$^+$H), Found 577.0

Preparation of Compound 347

The bromide 348 was taken up in a 1:1 mixture of DCM:TFA and stirred for 12 h. Solvents were removed under vacuum to give a crude residue, which was purified by column chromatography to give the desired bromide 347. Mass Spectrum (LCMS, ESI Pos.) Calcd. For $C_{18}H_{22}BrClN_3O_2$: 427.0 (M$^+$H), Found 427.0

Example 114: Preparation of Compound 162

To a stirred solution of the bromide 347 (185 mg, 0.434 mmol, 1.0 eq) in DMF (10 mL) were added DIEA (224 mg, 1.74 mmol, 4.0 eq) and piperazin-2-one 348 (65 mg, 0.651 mmol, 1.5 eq) and the reaction mixture was stirred at 70° C. for 24 h. The reaction mixture was diluted with ethyl acetate and washed with water (4×). The organic layer was collected, dried and solvent was removed to give a crude residue, which was purified by column chromatography (DCM/MeOH) to give the desired compound 162. Mass Spectrum (LCMS, ESI Pos.) Calcd. For $C_{22}H_{29}ClN_5O_3$: 446.0 (M$^+$H), Found 446.0

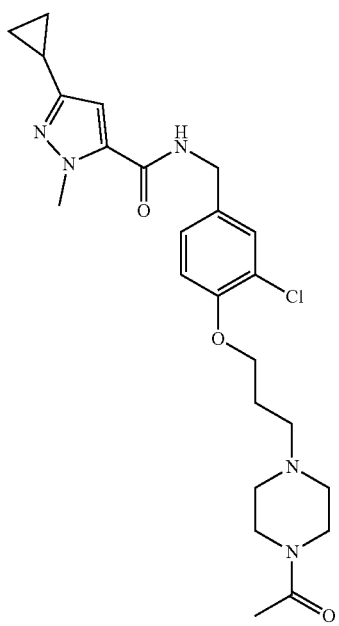

163

Example 115: Preparation of Compound 163

Compound 163 was prepared following the procedure used to prepare compound 162 except that commercially available 1-acetylpiperazine was used to alkylate the bromide 347. Mass Spectrum (LCMS, ESI Pos.) Calcd. For $C_{24}H_{33}ClN_5O_3$: 475.0 (M$^+$H), Found 475.0.

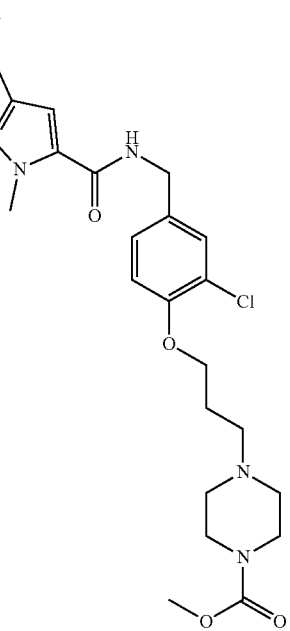

164

Example 116: Preparation of Compound 164

Compound 164 was prepared following the procedure used to prepare compound 162 except that commercially available methyl piperazine-1-carboxylate was used to alkylate the bromide 347. Mass Spectrum (LCMS, ESI Pos.) Calcd. For $C_{24}H_{33}ClN_5O_4$: 490.0 (M$^+$H), Found 490.0.

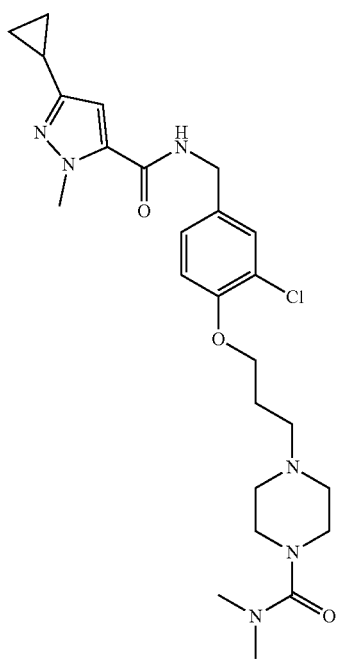

165

Example 117: Preparation of Compound 165

Compound 165 was prepared following the procedure used to prepare compound 162 except that commercially available N,N-dimethylpiperazine-1-carboxamide was used to alkylate the bromide 347. Mass Spectrum (LCMS, ESI Pos.) Calcd. For $C_{25}H_{36}ClN_6O_3$: 504.0 (M$^+$H), Found 504.0.

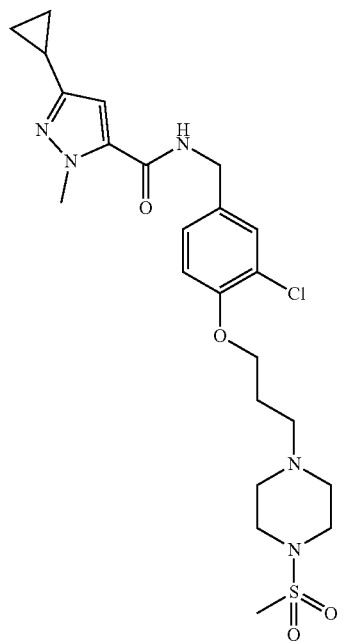

166

Example 118: Preparation of Compound 166

Compound 166 was prepared following the procedure used to prepare compound 162 except that commercially available 1-methanesulfonylpiperazine was used to alkylate the bromide 347. Mass Spectrum (LCMS, ESI Pos.) Calcd. For $C_{23}H_{33}ClN_5O_4S$: 510.0 (M⁺H), Found 510.0.

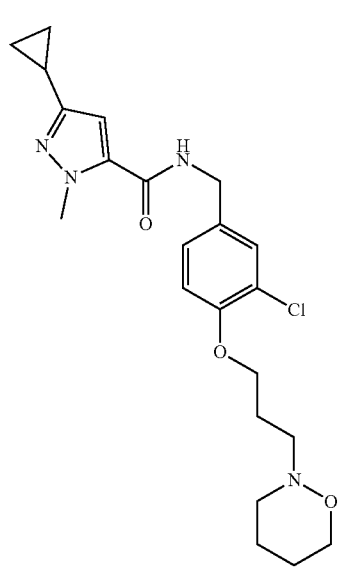

167

Example 119: Preparation of Compound 167

Compound 167 was prepared following the procedure used to prepare compound 162 except that commercially available 1,2-oxazinane hydrochloride was used to alkylate the bromide 347. Mass Spectrum (LCMS, ESI Pos.) Calcd. For $C_{22}H_{30}ClN_4O_3$: 433.0 (M⁺H), Found 433.0.

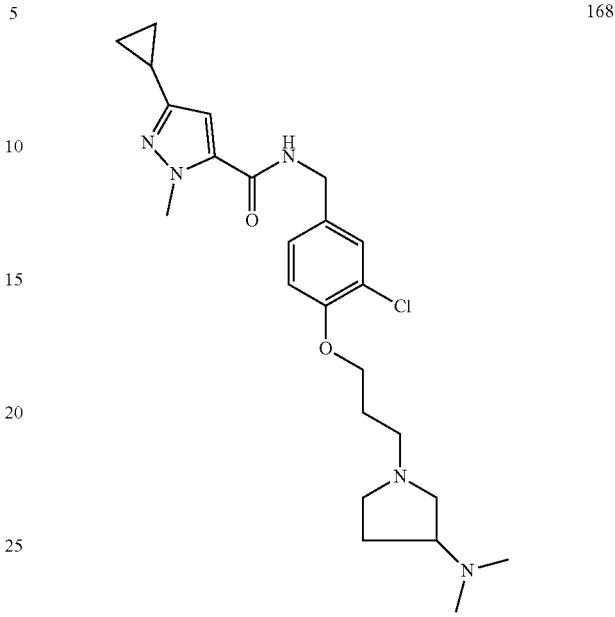

168

Example 120: Preparation of Compound 168

Compound 168 was prepared following the procedure used to prepare compound 162 except that commercially available N,N-dimethylpyrrolidin-3-amine was used to alkylate the bromide 347. Mass Spectrum (LCMS, ESI Pos.) Calcd. For $C_{24}H_{35}ClN_5O_2$: 461.0 (M⁺H), Found 461.0.

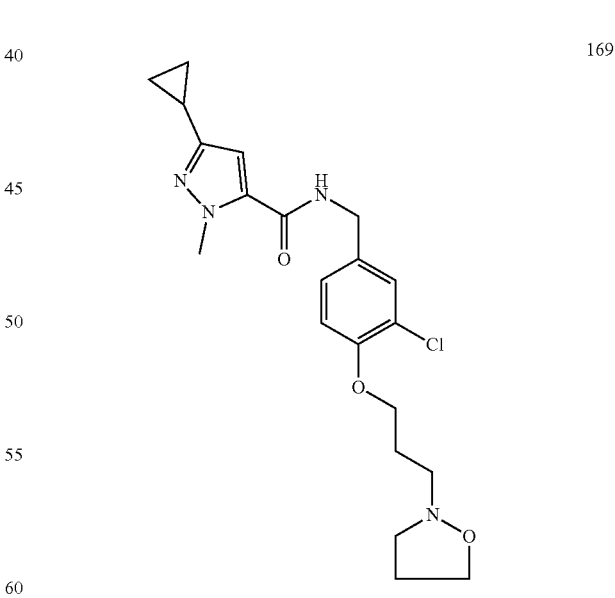

169

Example 121: Preparation of Compound 169

Compound 169 was prepared following the procedure used to prepare compound 162 except that commercially available isoxazolidine was used to alkylate the bromide 347. Mass Spectrum (LCMS, ESI Pos.) Calcd. For C$_{21}$H$_{28}$ClN$_4$O$_3$: 419.0 (M$^+$H), Found 419.0.

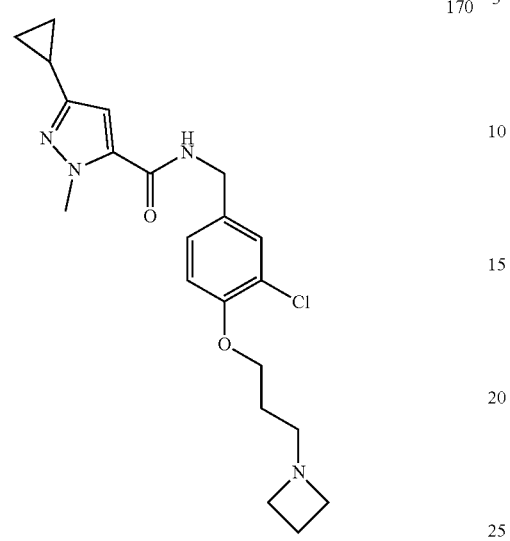

170

Example 122: Preparation of Compound 170

Compound 170 was prepared following the procedure used to prepare compound 162 except that commercially available azetidine was used to alkylate the bromide 347. Mass Spectrum (LCMS, ESI Pos.) Calcd. For C$_{21}$H$_{27}$ClN$_4$O$_2$: 403.0 (M$^+$H), Found 403.0.

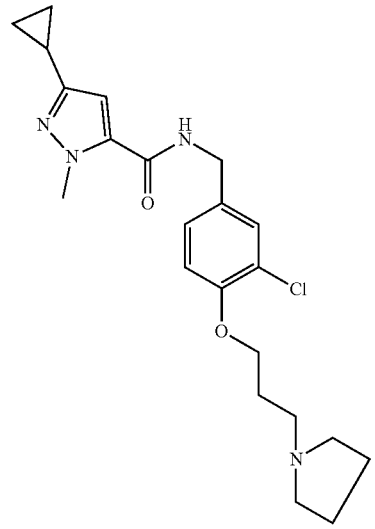

171

Example 123: Preparation of Compound 171

Compound 171 was prepared following the procedure used to prepare compound 162 except that commercially available pyrrolidine was used to alkylate the bromide 347. Mass Spectrum (LCMS, ESI Pos.) Calcd. For C$_{21}$H$_{27}$ClN$_4$O$_2$: 403.0 (M$^+$H), Found 403.0.

Scheme 43 illustrates the preparation of compound 172.

Scheme 42

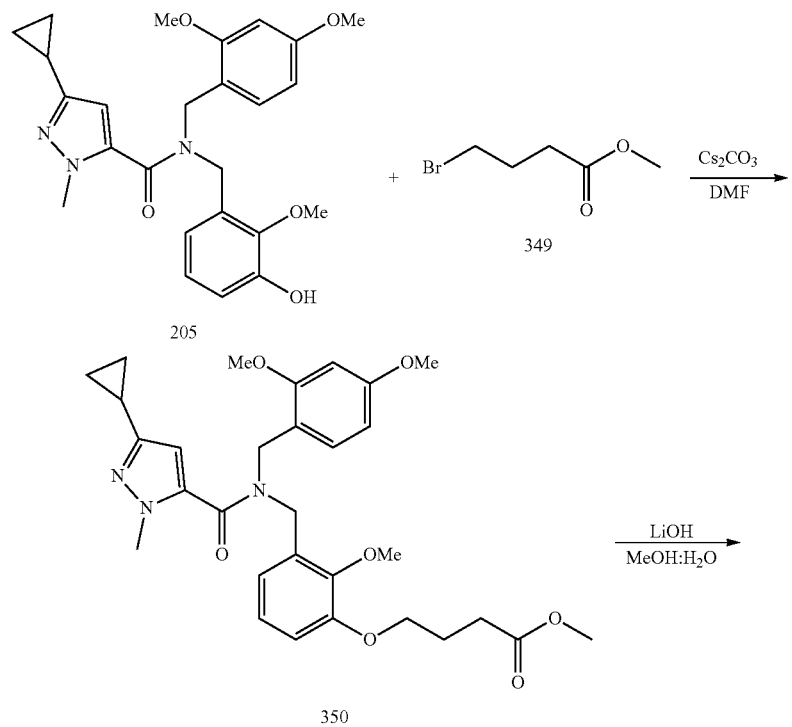

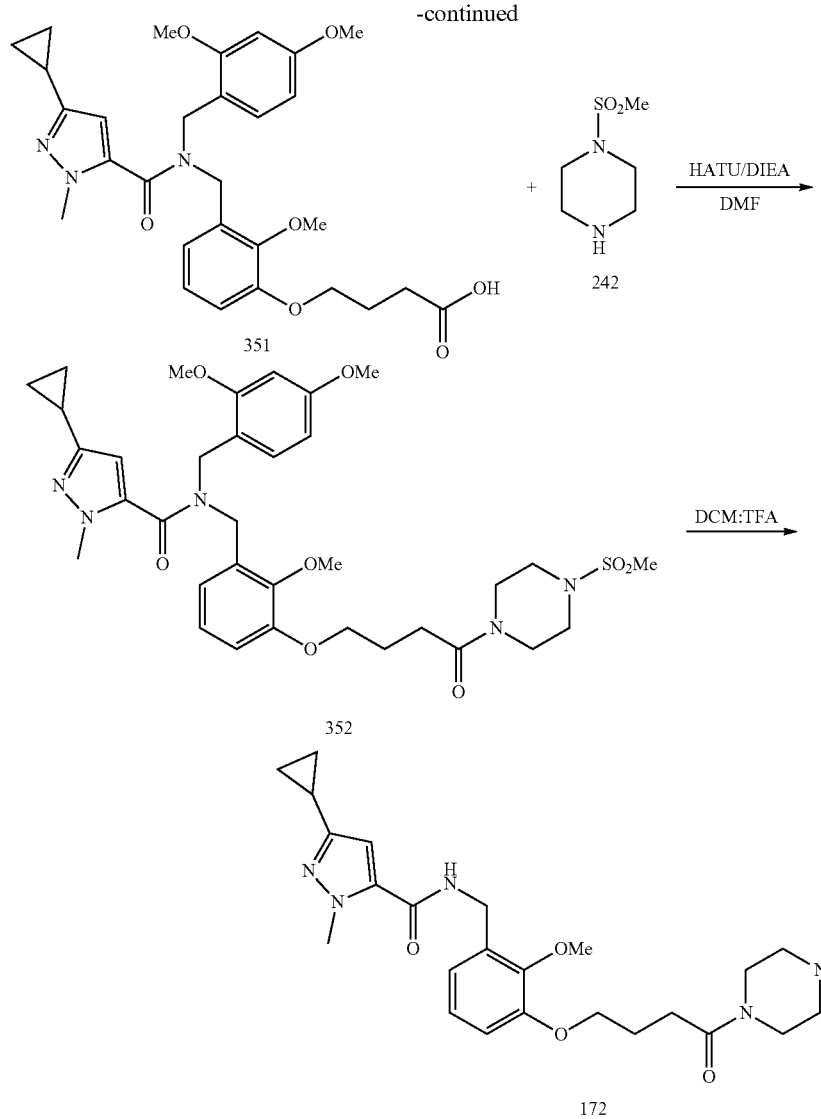

Preparation of Compound 350

To a stirred solution of compound 205 (200 mg, 0.44 mmol, 1.0 eq) in DMF (10 mL), were added Cs$_2$CO$_3$ (360 mg, 1.10 mmol 2.5 eq) and methyl 4-bromobutanoate 349 (0.120 g, 0.66 mmol, 1.50 eq) and the reaction mixture stirred at RT for 24 h. The reaction mixture was diluted with water and extracted with EtOAc (2×). The combined organic layers were washed with water (2×), brine, dried and evaporated under vacuum to provide the crude product, which was purified by column chromatography to yield 350.

Preparation of Compound 351

To a stirred solution of the ester 350 (180 mg, 0.29 mmol, 1.0 eq) in a 5:1 mixture of MeOH:H$_2$O (12 mL) was added LiOH (34 mg, 0.72 mmol, 2.5 eq) and the reaction mixture was stirred at room temperature for 6 h. The solvents were evaporated to give a residue, which was neutralized with aq. 10% HCl and then extracted with ethyl acetate (2×). The combined organic layers were dried and evaporated under vacuum to give the crude acid 352, which was used in the next step without further purification.

Preparation of Compound 352

To a stirred solution of the crude acid 351 (150 mg, 0.27 mmol, 1.0 eq) in DMF (10 mL) were added 1-(methylsulfonyl)piperazine (38 mg, 0.23 mmol, 1.1 eq), DIEA (90 mg, 0.69 mmol, 2.5 eq) and HATU (159 mg, 0.41 mmol, 1.5 eq), and the reaction mixture was stirred at room temperature for 12 h. The reaction mixture was diluted with EtOAc and the organic layer was washed with sat. NaHCO$_3$, 10% HCl and brine. The organic layer was then dried and evaporated under vacuum to give the crude amide 352.

Example 124: Preparation of Compound 172

The crude amide 352 was taken up in a 1:1 mixture of DCM:TFA and stirred for 12 h. Solvents were removed to give a residue which was then purified by column chromatography yield compound 172. Mass Spectrum (LCMS, ESI Pos.) Calcd. For C$_{25}$H$_{36}$N$_5$O$_6$S: 534.0 (M$^+$H), Found 534.0.

Scheme 44 illustrates a general procedure for preparation of amines 353.

Scheme 44

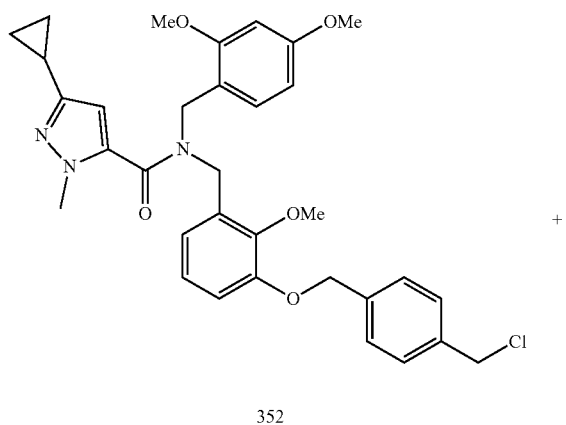

352

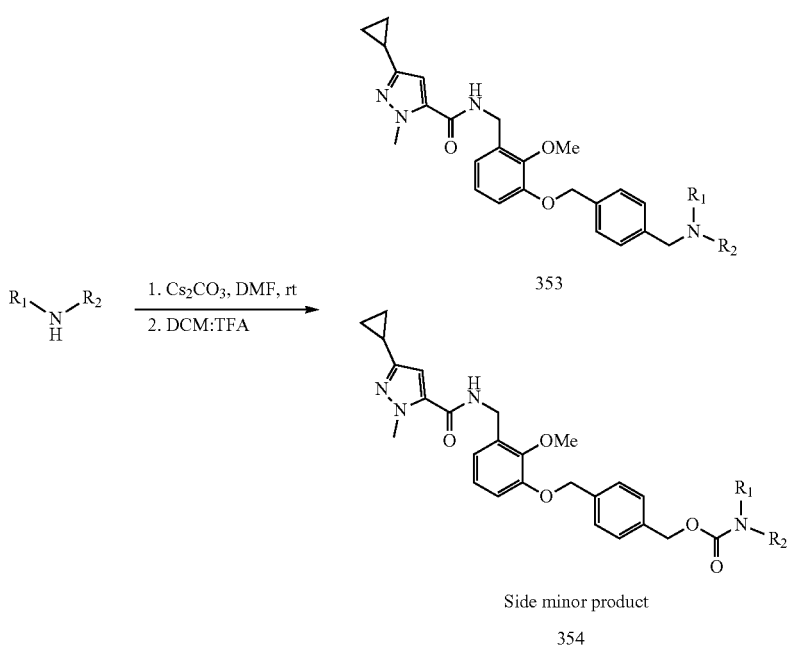

General Procedure for the Preparation Amines of 353

To a solution of compound 7 (200 mg, 0.34 mmol) in DMF (10.0 mL) were added $Cs_2CO_3$ (332 mg, 1.02 mmol, 3.0 eq) and a secondary amine 8 (0.68 mmol, 2.0 eq) and the reaction mixture was stirred at 60° C. for 18 h. The reaction mixture was diluted with ethyl acetate and washed with water (3×). The organic layer was collected, dried and evaporated to give a viscous liquid, which was purified by column chromatography to provide intermediate 353.

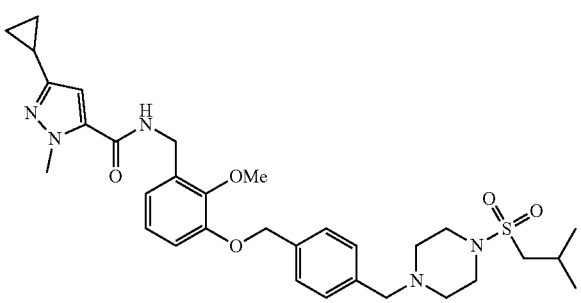

19

Example 125: Preparation of Compound 19

Prepared following the general procedure for the preparation of amines 353. Mass Spectrum (LCMS, ESI Pos.) Calcd. For $C_{29}H_{35}F_2N_4O_3$:525.0 (M$^+$H), Found 525.0.

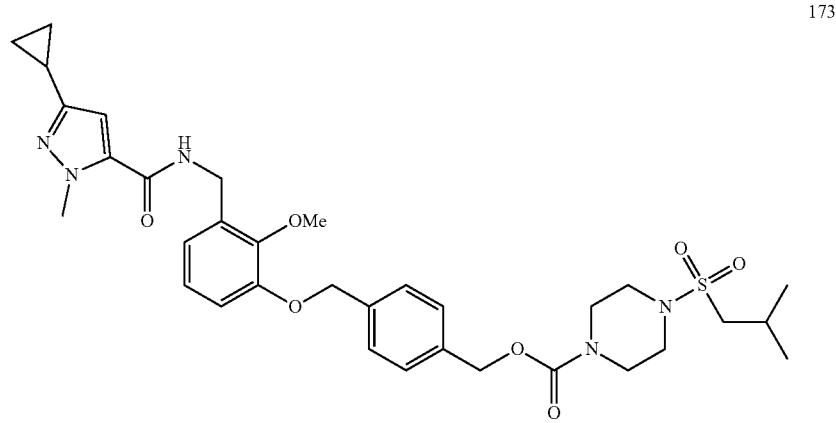 [SMILES: COc1c(CNC(=O)c2cc(C3CC3)nn2C)cccc1OCc1ccc(COC(=O)N2CCN(S(=O)(=O)CC(C)C)CC2)cc1]

173

Example 126: Preparation of Compound 173

Prepared following the general procedure for the preparation of amines 353. Mass Spectrum (LCMS, ESI Pos.) Calcd. For $C_{33}H_{44}N_5O_7S$:654.0 (M$^+$H), Found 654.0.

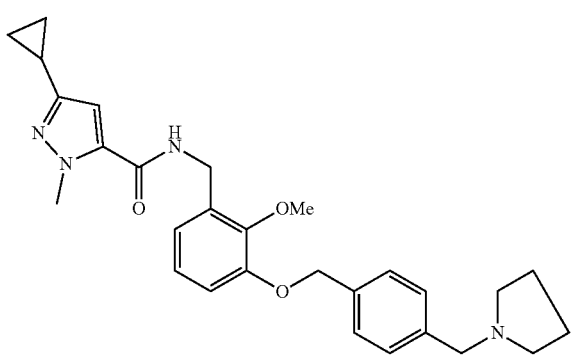

18

Example 127: Preparation of Compound 18

Prepared following the general procedure for the preparation of amines 353. Mass Spectrum (LCMS, ESI Pos.) Calcd. For $C_{28}H_{35}N_4O_3$:475.0 (M$^+$H), Found 475.0.

174

Example 128: Preparation of Compound 174

Prepared following the general procedure for the preparation of amines 353. Mass Spectrum (LCMS, ESI Pos.) Calcd. For $C_{31}H_{38}N_5O_6$:576.0 (M$^+$H), Found 576.0.

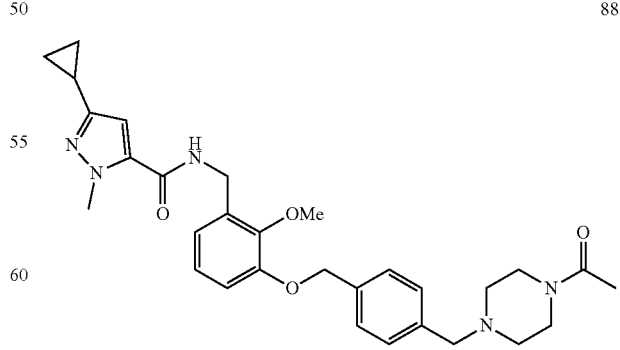

88

Prepared following the general procedure for the preparation of amines 353. Mass Spectrum (LCMS, ESI Pos.) Calcd. For $C_{30}H_{35}N_5O_4$:532.0 (M$^+$H), Found 532.0.

Scheme 45 illustrates a general procedure for preparation of 3,4 analogs 35

Scheme 45

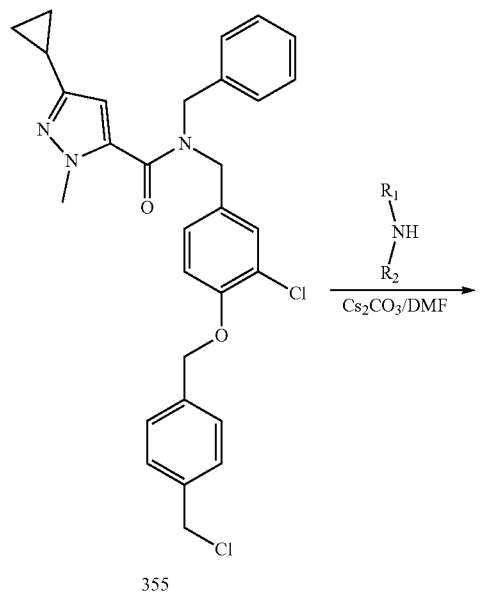

355

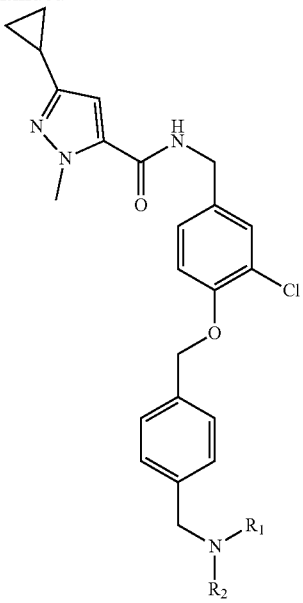

357

To a solution of chloride 355 (181 mg, 0.34 mmol) in DMF (10.0 mL) were added $Cs_2CO_3$ (332 mg, 1.02 mmol, 3.0 eq) and a secondary amine 8 (0.68 mmol, 2.0 eq) and the reaction mixture was stirred at 60° C. for 18 h. The reaction mixture was diluted with ethyl acetate and washed with water (3×). Organic layer was collected, dried and evaporated to give a viscous liquid, which was purified by column chromatography to give amine 356. The crude amine 356 was taken up in a 1:1 mixture of DCM: TFA and stirred for 12 h. Solvents were removed to give a residue which was then purified by column chromatography to yield intermediate 357.

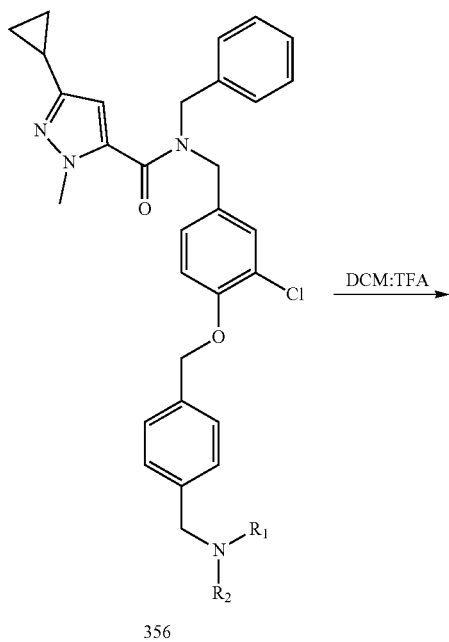

356

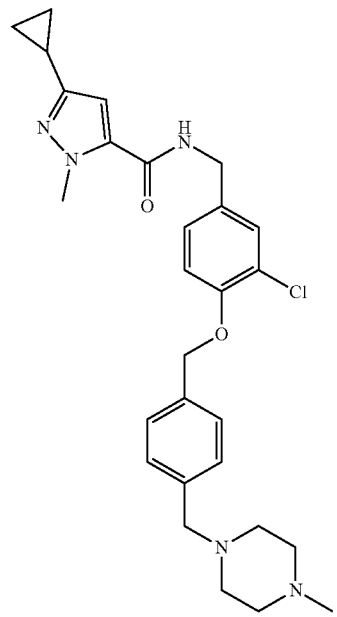

175

Example 129: Preparation of Compound 175

Prepared following the general procedure for the preparation of amines 353. Mass Spectrum (LCMS, ESI Pos.) Calcd. For $C_{28}H_{35}ClN_5O_2$:509.0 ($M^+H$), Found 509.0

Infectious Assay Protocol

MDCK cells were infected with FLUV at MOI=0.01 or MRC-5 cells were infected with huCoV229e at MOI=0.01 and vehicle or drug added at a final concentration of 1 uM, 100 nM, 25 nM or 6.25 nM. 48 hrs post infection medium was collected and centrifuged at 100 kxrpm/24 min in TL100.2 tabletop ultracentrifuge rotor and the supernatant was aspirated. Pelleted material was resuspended in loading buffer and analyzed by SDS-PAGE followed by transfer to 0.2u PVDF and western blotting for FLUV or CoV nucleoprotein, respectively, as described previously (Selvarajah et al., www.biorxiv.org/content/10.1101/2021.01.17.426875v1). Spread of infection was determined by quantified intensity of the full-length nucleoprotein band (FLUV, 55 kDa; CoV; 42 kDa) with uninfected and infected, vehicle-treated samples as negative and positive controls and with a known active compound

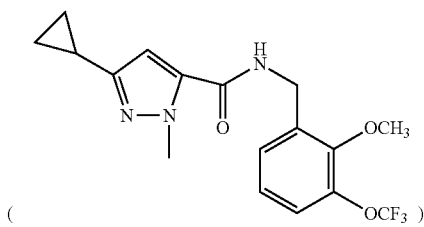 [SMILES: COc1c(CNC(=O)c2cc(C3CC3)nn2C)cccc1OC(F)(F)F]

as an internal positive control, previously validated by plaque assay and TCID50.

The results of the infective assay protocol are shown for select compounds in Table 2 below.

| Compound # | Assay Result EC50/EC90 (nM) |
| --- | --- |
| 1 | <25 |
| 2 | <25 |
| 3 | <25 |
| 4 | <25 |
| 5 | <25 |
| 6 | <25 |
| 7 | <25 |
| 8 | <25 |
| 9 | <10 |
| 10 | <12 |
| 11 | <4 |
| 12 | <20 |
| 16 | 4 |
| 17 | <4 |
| 18 | <20 |
| 19 | <20 |
| 20 | <20 |
| 21 | <20 |
| 24 | <4 |
| 26 | <25 |
| 27 | <80 |
| 28 | <48 |

Efficacy Testing:

MRC-5 cells were seeded at 10,000 cells per well the day prior to infection in 96-well black plates with clear bottoms (Costar 3603). The following day, cells were infected with recombinant Nipah virus expressing ZsGreen fluorescence protein (rNiV-ZsG) at multiplicity of infection 0.01 with ~100 50% tissue culture infectious dose ($TCID_{50}$). Levels of rNiV-ZsG replication were measured at 72 hour post-infection based on mean ZsGreen fluorescence signal intensity ($418_{ex}/518_{em}$) using a Biotek HID1 Synergy instrument (Aglilent). Fluorescence signal intensity assayed in DMSO-treated, virus-infected cells were set as 100% ZsGreen fluorescence. Concentrations of compound that inhibited 50% of the green fluorescence signal ($EC_{50}$) were calculated from dose response data fitted to the mean value of experiments performed for each concentration in the 10-point, 3-fold dilution series using a 4-parameter non-linear logistic regression curve with variable slope using GraphPad Prism 9 (GraphPad Software, La Jolla, CA, USA). Reference: Lo, M. K., Nichol, ST., Spiropoulou, C. F., 2014. Evaluation of luciferase and GFP-expressing Nipah viruses for rapid quantitative antiviral screening, Antiviral Res. 106, 53-60)

Toxicity Testing:

Cell viability was assayed on MRC-5 cells in minimum essential medium supplemented with 5 mM glucose using Alamar Blue HS reagent (Thermofisher) according to manufacturer's recommendations, with fluorescence ($560_{ex}/590_{cm}$) measured at 72 hours post-compound treatment after 4 hours of incubation with reagent. Fluorescence levels (indicative of resazurin reduction as a surrogate marker of cell viability) assayed in DMSO-treated, uninfected cells were set as 100% cell viability. Dose response curves were fitted to the mean value of experiments performed for each concentration in the 10-point, 3-fold dilution series using a 4-parameter non-linear logistic regression curve with variable slope. All Alamar Blue assays were conducted in 96-well black plates with clear bottoms. Concentrations of compound that inhibited 50% of the fluorescence signal ($CC_{50}$) were calculated from dose response data fitted to the mean value of experiments performed for each concentration in the 10-point, 3-fold dilution series using a 4-parameter non-linear logistic regression curve with variable slope using GraphPad Prism 9 (GraphPad Software, La Jolla, CA, USA).

The results of the efficacy testing and toxicity testing are shown for select compounds in Table 3 below.

| Compound | MRC-5 EC50 (uM) | MRC-5 CC50 (uM) |
|---|---|---|
| 19 | 0.01458 | >5 |
| 173 | 0.02388 | >5 |
| 17 | 0.02973 | >5 |
| 18 | 0.1241 | >5 |
| 174 | 0.1292 | >5 |
| 88 | 0.144 | >5 |
| 8 | 0.1938 | >5 |
| 175 | 0.1999 | >5 |
| 23 | 0.3235 | >5 |
| 9 | 0.508 | >5 |
| 13 | 0.6284 | >5 |
| 94 | 1.055 | >5 |
| 80 | 1.444 | >5 |
| 113 | 1.496 | >5 |
| 91 | 1.665 | >5 |
| 128 | 2.236 | >5 |
| 118 | 3.85 | >5 |
| 133 | 6.316 | >5 |
| 63 | 6.82 | >5 |
| 128 | 6.947 | >5 |
| 96 | 16.07 | >5 |
| 92 | 16.73 | >5 |
| 127 | 20 | >5 |

What is claimed is:
1. A compound having the structure:

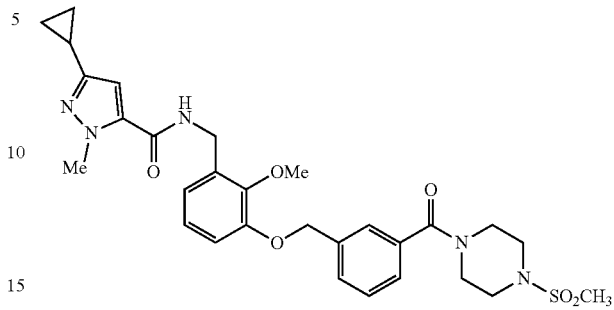

or pharmaceutically acceptable salts, hydrates or solvates thereof.

2. A pharmaceutical composition comprising the compound of claim 1 and a pharmaceutically acceptable vehicle.

3. A method of treating an influenza infection in a patient comprising administering to the patient in need thereof the compound of claim 1.

4. A method of treating an influenza infection in a patient comprising administering to the patient in need thereof the pharmaceutical composition of claim 1.

5. A method of treating a coronavirus infection in a patient comprising administering to the patient in need thereof the compound of claim 3.

6. A method of treating a coronavirus infection in a patient comprising administering to the patient in need thereof the pharmaceutical composition of claim 1.

* * * * *